United States Patent
Askary et al.

(10) Patent No.: US 11,421,273 B2
(45) Date of Patent: Aug. 23, 2022

(54) IN SITU READOUT OF DNA BARCODES

(71) Applicant: California Institute of Technology, Pasadena, CA (US)

(72) Inventors: Amjad Askary, Pasadena, CA (US); Michael B. Elowitz, Los Angeles, CA (US); Mark W. Budde, Arcadia, CA (US); Carlos Lois, South Pasadena, CA (US); Luis Sanchez Guardado, Pasadena, CA (US); Long Cai, Pasadena, CA (US); James Linton, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 193 days.

(21) Appl. No.: 16/701,087

(22) Filed: Dec. 2, 2019

(65) Prior Publication Data
US 2020/0172968 A1 Jun. 4, 2020

Related U.S. Application Data

(60) Provisional application No. 62/936,307, filed on Nov. 15, 2019, provisional application No. 62/774,754, filed on Dec. 3, 2018.

(51) Int. Cl.
| | | |
|---|---|---|
| *C12Q 1/6874* | (2018.01) | |
| *G01N 1/30* | (2006.01) | |
| *C12Q 1/6876* | (2018.01) | |
| *C12Q 1/6818* | (2018.01) | |

(52) U.S. Cl.
CPC ......... *C12Q 1/6874* (2013.01); *C12Q 1/6818* (2013.01); *C12Q 1/6876* (2013.01); *G01N 1/30* (2013.01)

(58) Field of Classification Search
CPC .................. C12Q 1/682; C12Q 1/6841; C12Q 2525/301; C12Q 2537/155; C12Q 2543/10; C12Q 2543/101; C12Q 1/6874; C12Q 1/6818; C12Q 1/6876; C12N 9/22; C12N 310/20; C12N 15/00; G01N 1/30
See application file for complete search history.

(56) References Cited

U.S. PATENT DOCUMENTS

| | | | |
|---|---|---|---|
| 2012/0190835 A1* | 7/2012 | Pierce | C12Q 1/682 536/23.1 |
| 2014/0073520 A1 | 3/2014 | Cai et al. | |
| 2015/0148239 A1 | 5/2015 | Peter et al. | |
| 2015/0167003 A1* | 6/2015 | Naldini | A61P 11/06 435/354 |
| 2015/0267251 A1 | 9/2015 | Cai et al. | |
| 2016/0289740 A1 | 10/2016 | Fu et al. | |
| 2019/0094115 A1* | 3/2019 | Bhakdi | C11D 3/2065 |

OTHER PUBLICATIONS

Askary et al., Nat.Biotechnol. 38(1): 66-75, January (Year: 2020).*
Alemany et al., "Whole-organism clone tracing using single-cell sequencing,"Nature 2018, 556, 108-112.
Askary et al., "In situ readout of DNA barcodes and single base edits facilitated by in vitro transcription," Nature Biotechnology 2020, 38(1), 66-75.
Baker et al., "Transneuronal Regulation of Tyrosine Hxdroxylase Expression in Olfactory Bulb of Mouse and Rat," The Journal of Neuroscience 1983, 3(1), 69-78.
Bhang et al., "Studying clonal dynamics in response to cancer therapy using high complexity barcoding," Nature Medicine 2015, 21(5), 440-448.
Biddy et al., "Single-cell mapping of lineage and identity in direct reprogramming," Nature 2018, 564(7735), 219-224.
Boutros et al., "Microscopy-Based High-Content Screening," Cell 2015, 163, 1314-1325.
Cai et al., "Improved tools for the Brainbow toolbox," Nature Methods 2013, 10(6), 540-547.
Chan et al., "Molecular recording of mammalian embryogenesis," bioRxiv 2018, 384925, in 32 pages. https://doi.org/10.1101/384925.
Chen et al., "A Barcoding Strategy Enabling Higher-Throughput Library Screening by Microscopy," ACS Snyth. Biol. 2015, 4, 1205-1216.
Chen et al., "Spatially resolved, highly multiplexed RNA profiling in single cells," Science 2015, 348(6233), aaa6090, 1-36.
Chen et al., "Efficient in situ barcode sequencing using padlock probe-based BaristaSeq," Nucleic Acids Research 2018, 46(4), e22, 1-10.
Choi et al., "Programmable in situ amplification for multiplexed imaging of mRNA expression," Nat Biotechnol. 2010, 28(11), 1208-1212.
Choi et al., "Mapping a multiplexed zoo of mRNA expression," Development 2016, 143, 3632-3637.
Choi et al., "Third-generation in situ hybridization chain reaction: multiplexed, quantitative, sensitive, versatile, robust," Development 2018, 145, 1-10.
Cong et al., "Multiplex Genome Engineering Using CRISPR/Cas Systems," Science 2013, 339(6121), 819-823.
Ding et al., "Constitutive splicing and economies of scale in gene expression," Nat. Struct. Mol. Biol. 2019, 26, 424-432.
Dixit et al., "Perturb-Seq: Dissecting Molecular Circuits with Scalable Single-Cell RNA Profiling of Pooled Genetic Screens," Cell 2016, 167, 1853-1866.
Doench et al., "Optimized sgRNA design to maximize activity and minimize off-target effects of CRISPR-Cas9," Nat Biotechnol. 2016, 34(2), 184-191.

(Continued)

*Primary Examiner* — Cynthia B Wilder
(74) *Attorney, Agent, or Firm* — Sheppard, Mullin, Richter & Hampton LLP

(57) ABSTRACT

Disclosed herein include systems, methods, compositions, and kits for in situ readout of barcodes, such as DNA barcodes. Barcode constructs containing a promoter (e.g., a phage promoter) that is inactive in live cells can be integrated in the genomes of cells. Cells can be fixed, and phage RNA polymerase can be used for transcription of the barcode to RNA transcripts. The RNA transcripts can be detected using, for example, fluorescent imaging and used to determine barcode sequences.

30 Claims, 35 Drawing Sheets
(33 of 35 Drawing Sheet(s) Filed in Color)
Specification includes a Sequence Listing.

(56) References Cited

OTHER PUBLICATIONS

Emanuel et al., "High-throughput, image-based screening of pooled genetic variant libraries," Nat Methods. 2017, 14(12), 1159-1162.
Eng et al., "Transcriptome-scale super-resolved imaging in tissues by RNA seqFISH+," Nature 2019, 568(7751), 235-239.
Faedo et al., "Developmental expression of the T-box transcription factor T-bet/Tbx21 during mouse embryogenesis," Mechanisms of Development 2002, 116, 157-160.
Farzadfard et al., "Single-Nucleotide-Resolution Computing and Memory in Living Cells," bioRxiv 2018, 263657, in 51 pages, https://doi.org/10.1101/263657.
Farzadfard et al., "Emerging applications for DNA writers and molecular recorders," Science 2018, 361, 870-875.
Feldman et al., "Pooled optical screens in human cells," bioRxiv 2018, 383943, in 23 pages. https://doi.org/10.1101/383943.
Freida et al., "Synthetic recording and in situ readout of lineage information in single cells," Nature 2017, 541, 107-111.
Gaudelli et al., "Programmable base editing of A•T to G•C in genomic DNA without DNA cleavage," Nature 2017, 551 (7681), 464-471.
Gehrke et al., "An APOBEC3A-Cas9 base editor with minimized bystander and off-target activities," Nat Biotechnol. 2018, 36(10), 977-982.
Hamburger et al., "A Series of Normal Stages in the Development of the Chick Embryo," J. Morphol. 1951, 88, 49-92.
International Search Report and Written Opinion dated Mar. 20, 2020 in PCT Patent Application No. PCT/US2019/064071.
Kalhor et al., "Rapidly evolving homing CRISPR barcodes," Nat Methods. 2017, 14(2), 195-200.
Kalhor et al., "Developmental barcoding of whole mouse via homing CRISPR," Science 2018, 361(6405), 1-27.
Ke et al., "In situ sequencing for RNA analysis in preserved tissue and cells," Nature Methods 2013, 10(9), 857-860.
Kebschull et al., "High-Throughput Mapping of Single-Neuron Projections by Sequencing of Barcoded RNA," Neuron 2016, 91, 975-987.
Kebschull et al., "Cellular barcoding: lineage tracing, screening and beyond," Nature Methods 2018, 15, 871-879.
Komor et al., "Improved base excision repair inhibition and bacteriophage Mu Gam protein yields C:G-to-T:A base editors with higher efficiency and product purity," Sci. Adv. 2017, 3(eaao4774), 1-9.
Komor et al., "Programmable editing of a target base in genomic DNA without double-stranded DNA cleavage," Nature 2016, 533(7603), 420-424.
Lee et al., "Highly multiplexed subcellular RNA sequencing in situ,"Science 2014, 343(6177), 1360-1363.
Levesque et al., "Visualizing SNVs to quantify allele-specific expression in single cells," Nat Methods. 2013, 10(9), 865-867.
Li et al., "Base editing with a Cpf1—cytidine deaminase fusion," Nature Biotechnology 2018, 36(4), 324-327.
Li et al., "Aligning sequence reads, clone sequences and assembly contigs with BWA-MEM," arXiv [q-bio.GN] 2013, 1-3.
Listgarten et al., "Prediction of off-target activities for the end-to-end design of CRISPR guide RNAs," Nature Biomedical Engineering 2, 38-47.
Livet et al., "Transgenic strategies for combinatorial expression of fluorescent proteins in the nervous system," Nature 2007, 450, 56-62.
Lois et al., "Germline Transmission and Tissue-Specific Expression of Transgenes Delivered by Lentiviral Vectors," Science 2002, 295(5556), 868-872.
Lois et al., "Long-Distance Neuronal Migration in the Adult Mammalian Brain," Science 1994, 264(5162), 1145-1148.
Lu et al., "Tracking single hematopoietic stem cells in vivo using high-throughput sequencing in conjunction with viral genetic barcoding," Nature Biotechnology 2011, 29(10), 928-933.

Marras et al., "High-fidelity amplified FISH for the detection and allelic discrimination of single mRNA molecules," PNAS 2019, 116(28), 13921-13926.
Mathews et al., "Expanded Sequence Dependence of Thermodynamic Parameters Improves Prediction of RNA Secondary Structure," J. Mol. Biol. 1999, 288, 911-940.
McKenna et al., "Whole organism lineage tracing by combinatorial and cumulative genome editing," Science 2016, 353(6298), aaf7907, 1-27.
Mitra et al., "Fluorescent in situ sequencing on polymerase colonies," Analytical Biochemistry 2003, 320, 55-65.
Moffitt et al., "High-throughput single-cell gene-expression profiling with multiplexed error-robust fluorescence in situ hybridization," PNAS 2016, 113(39), 11046-11051.
Naik et al., "Diverse and heritable lineage imprinting of early haematopoietic progenitors," Nature 2013, 496, 229-232.
Pei et al., "Polylox barcoding reveals haematopoietic stem cell fates realized in vivo," Nature 2017, 548(7668), 456-460.
Press et al., "Numerical Recipes in C: The Art of Scientific Computing," Cambridge University Press 1992, in 1,018 pages.
Raj et al., "Imaging individual mRNA molecules using multiple singly labeled probes," Nature Methods 2008, 5(10), 877-879.
Raj et al., "Simultaneous single-cell profiling of lineages and cell types in the vertebrate brain," Nat Biotechnol. 2018, 36(5), 442-450.
Rees et al., "Base editing: precision chemistry on the genome and transcriptome of living cells," Nature Reviews Genetics 2018, 19, 770-788.
Rouhanifard et al., "ClampFISH detects individual nucleic-acid molecules using click chemistry based amplification," Nat Biotechnol. 2019, 1-17.
Santalucia, "A unified view of polymer, dumbbell, and oligonucleotide DNA nearest-neighbor thermodynamics," Proc. Natl. Acad. Sci. USA 1998, 95, 1460-1465.
Satija et al., "Spatial reconstruction of single-cell gene expression," Nat Biotechnol. 2015, 33(5), 495-502.
Schindelin et al., "Fiji: an open-source platform for biological-image analysis," Nature Methods 2012, 9, 676-682.
Shah et al., "Single-molecule RNA detection at depth by hybridization chain reaction and tissue hydrogel embedding and clearing," Development 2016, 143, 2862-2867.
Shah et al., "seqFISH Accurately Detects Transcripts in Single Cells and Reveals Robust Spatial Organization in the Hippocampus," Neuron 2017, 94, 752-758.
Shah et al., "Dynamics and Spatial Genomics of the Nascent Transcriptome by Intron seqFISH," Cell 2018, 174, 363-376.
Sousa et al., "T7 RNA Polymerase," Progress in Nucleic Acid Research and Molecular Biology 2003, 73, 1-41.
Spanjaard et al., "Simultaneous lineage tracing and cell-type identification using CRISPR/Cas9-induced genetic scars," Nat Biotechnol. 2018, 36(5), 469-473.
Sternberg et al., "Exquisite Sequence Selectivity with Small Conditional RNAs,"Nano Lett. 2014, 14, 4568-4572.
Symmons et al., "Allele-specific RNA imaging shows that allelic imbalances can arise in tissues through transcriptional bursting," bioRxiv2018, 386359, in 49 pages, https://doi.org/10.1101/386359.
Tang et al., "Rewritable multi-event analog recording in bacterial and mammalian cells," Science 2018, 360(6385), 1-23.
Vieregg et al., "Selective Nucleic Acid Capture with Shielded Covalent Probes," J. Am. Chem. Soc. 2013, 135, 9691-9699.
Walsh et al., "Widespread Dispersion of Neuronal Clones Across Functional Regions of the Cerebral Cortex," Science 1992, 255(5043), 434-440.
Wang et al., "Three-dimensional intact-tissue sequencing of single-cell transcriptional states," Science 2018, 1-18.
Weinreb et al., "Lineage tracing on transcriptional landscapes links state to fate during differentiation," bioRxiv2018, 467886, in 40 pages, https://doi.org/10.1101/467886.
Weistein et al., "DNA microscopy: Optics-free spatio-genetic imaging by a stand-alone chemical reaction," bioRxiv 2018, 471219, in 41 pages. https://doi.org/10.1101/471219.
Wu et al., "Continuously Tunable Nucleic Acid Hybridization Probes," Nat Methods 2015, 12(12), 1191-1196.

(56) References Cited

OTHER PUBLICATIONS

Zheng et al., "Massively parallel digital transcriptional profiling of single cells," Nature Communications 2017, 8(14049), 1-12.
Lee et al., "Fluorescent in situ sequencing (FISSEQ) of RNA for gene expression profiling in intact cells and tissues," Nat Protoc 2015, 10, 442-458.

* cited by examiner

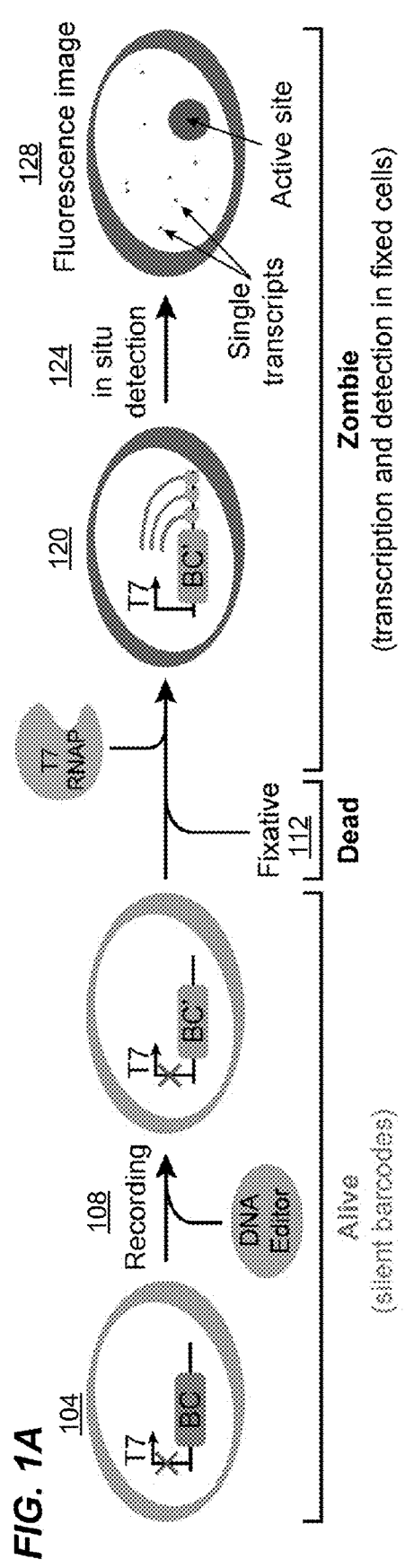
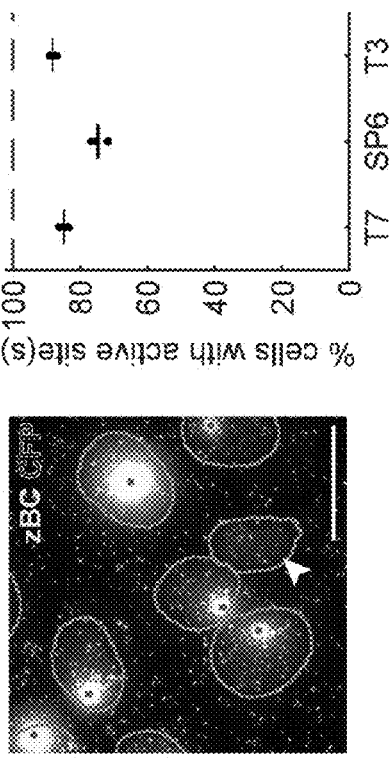
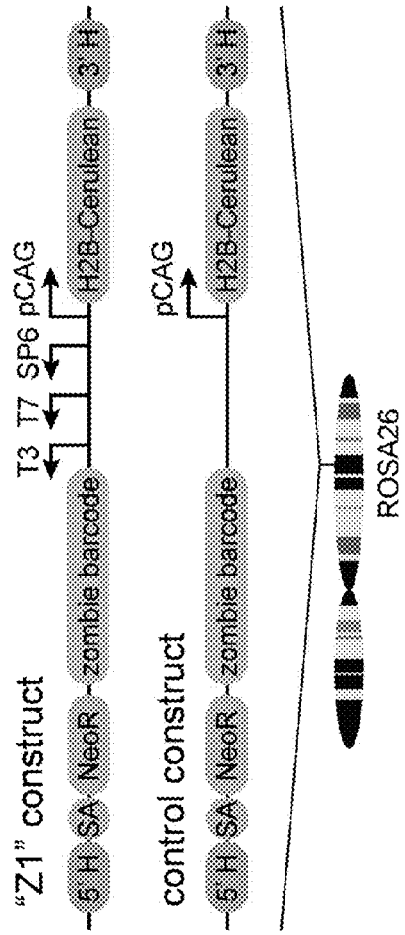
FIG. 1A
FIG. 1B
FIG. 1D

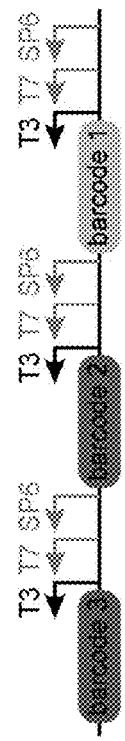
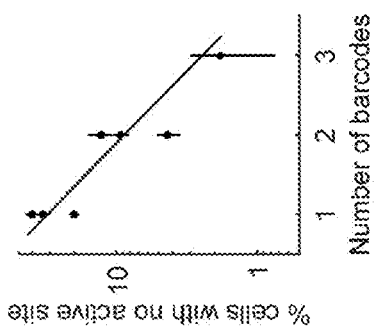
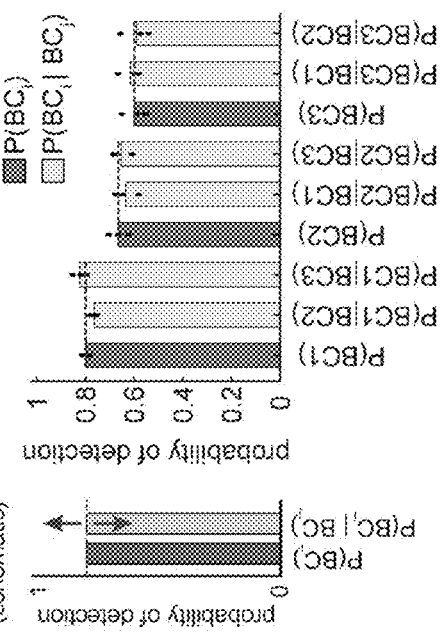
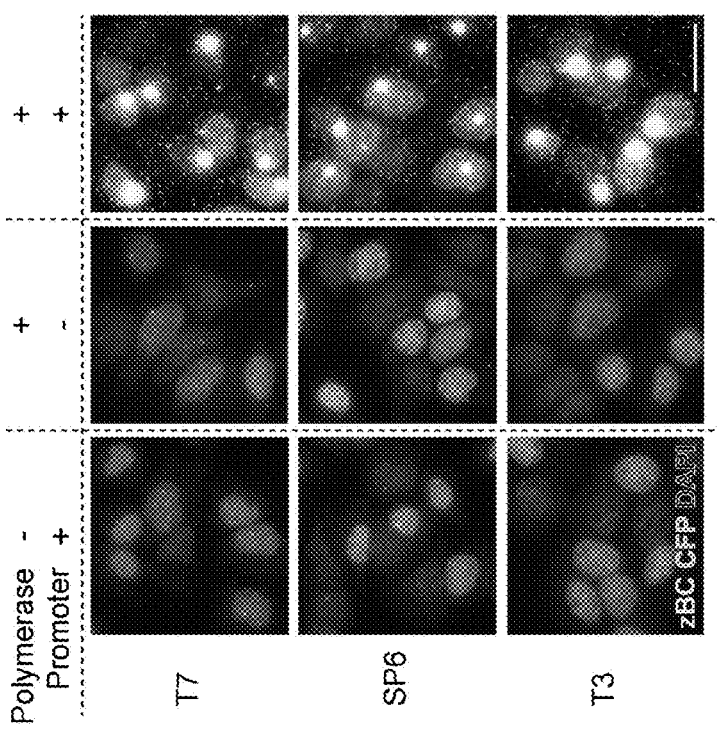
FIG. 1C
FIG. 1E
"Z3" construct
FIG. 1F
FIG. 1G

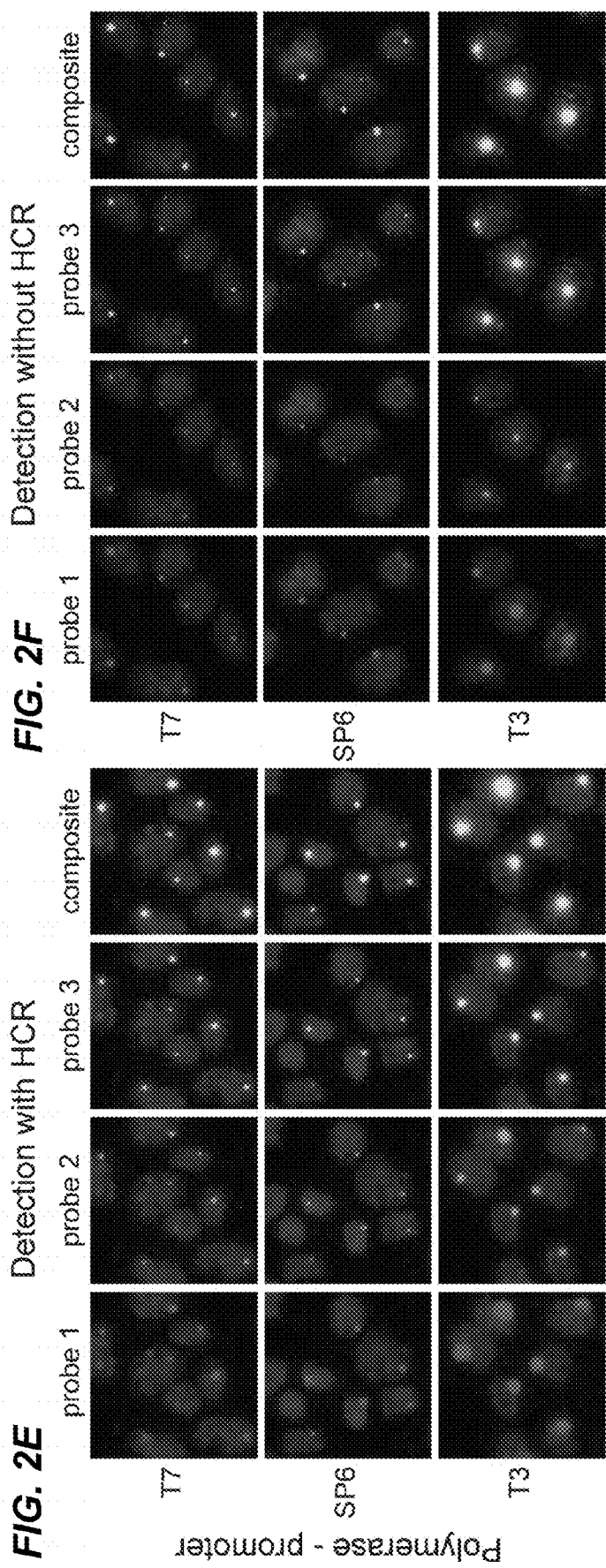

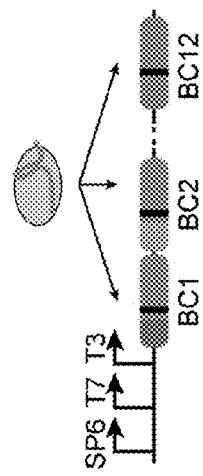
FIG. 4B Design 1: independent addressing
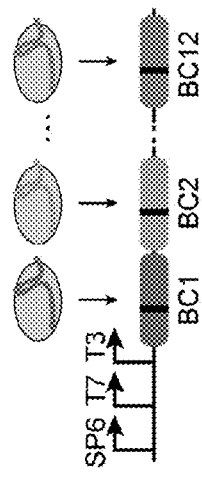
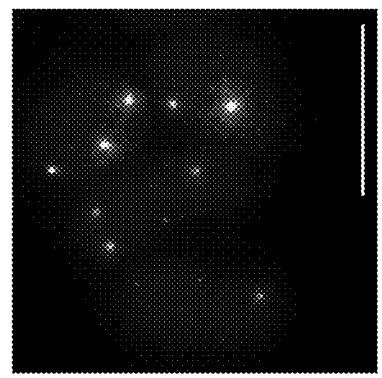
FIG. 4C
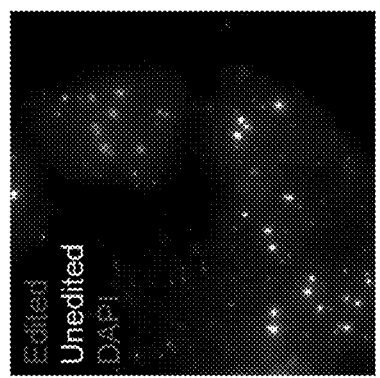
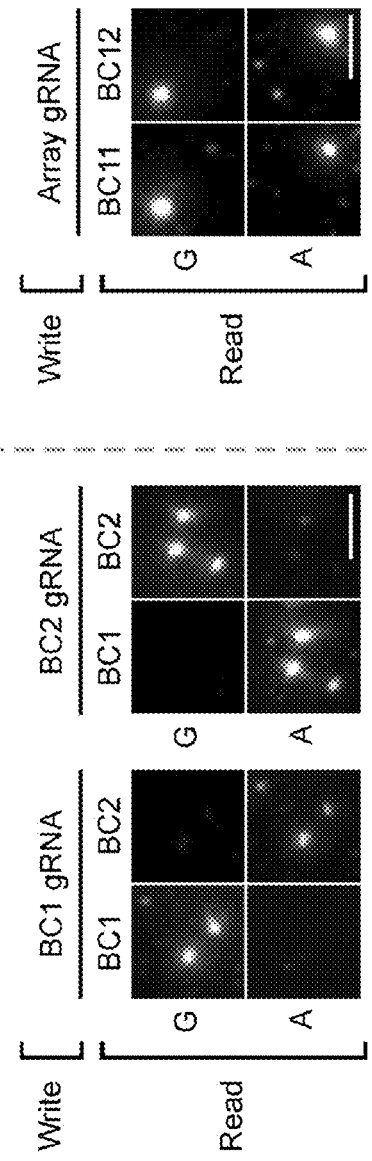
FIG. 4D

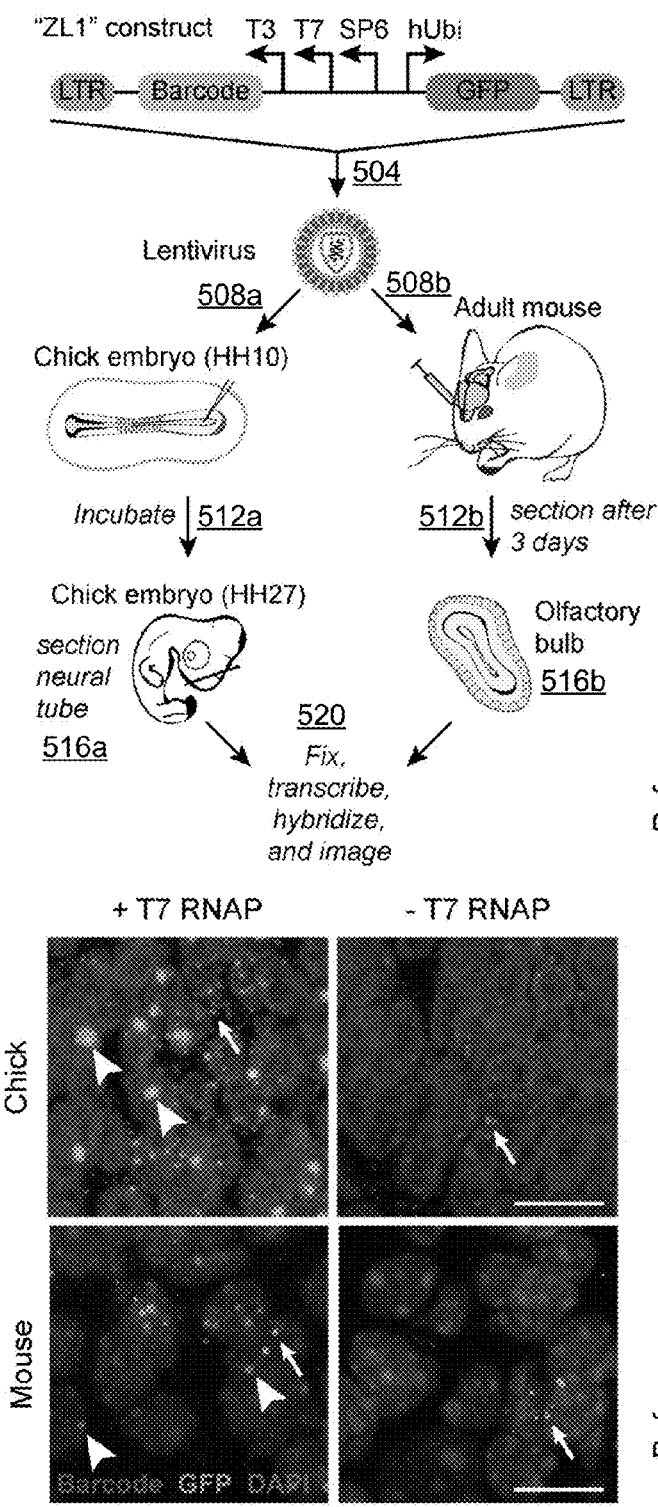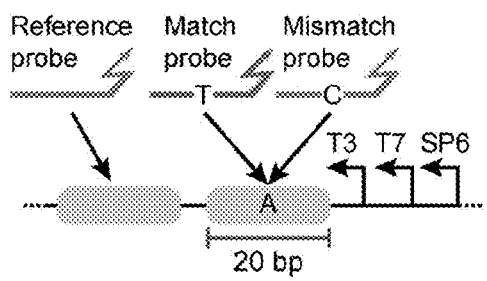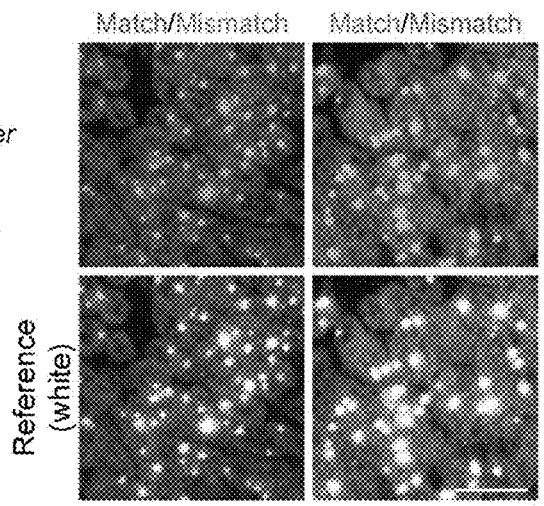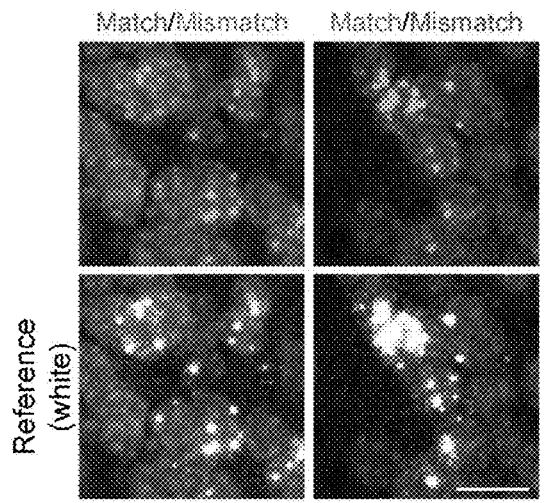
FIG. 5A
FIG. 5B
FIG. 5C
FIG. 5D
FIG. 5E Scatter plots of ln(intensity) for lentivirus pair 1 (hyb 1)

Numbers indicate dot count

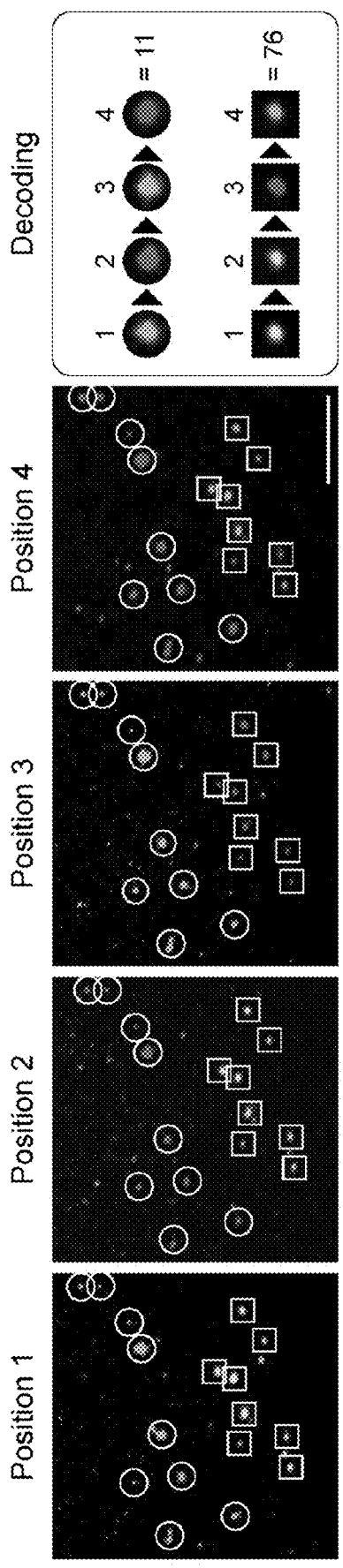
FIG. 6C
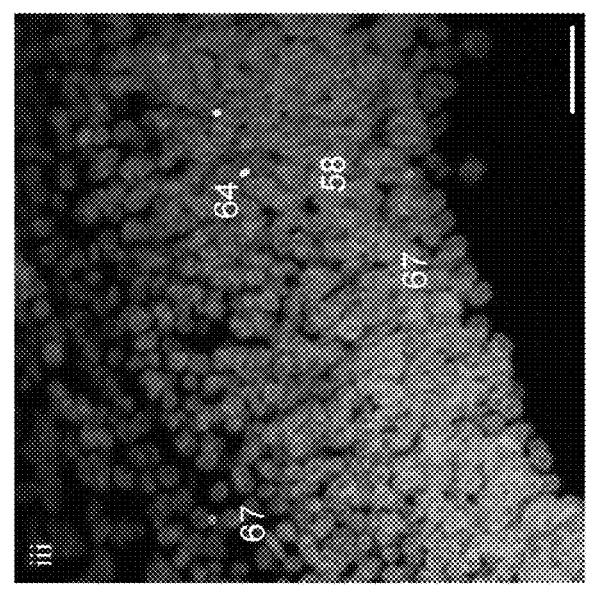
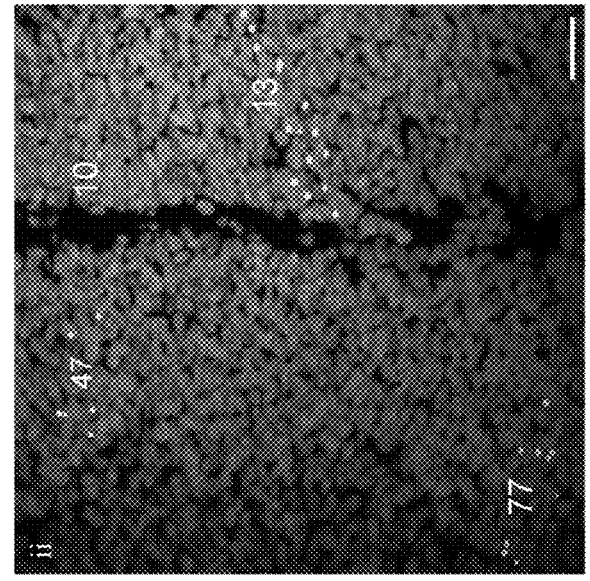
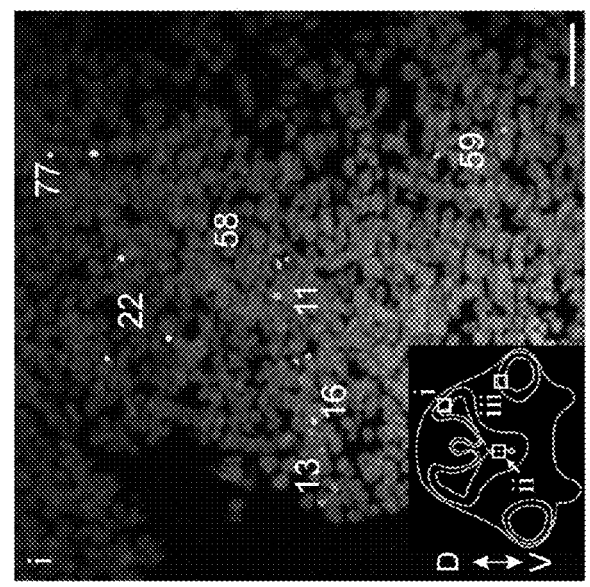
FIG. 6D
Distinct barcode combinations are labeled in arbitrary colors; no relation to colors in C.

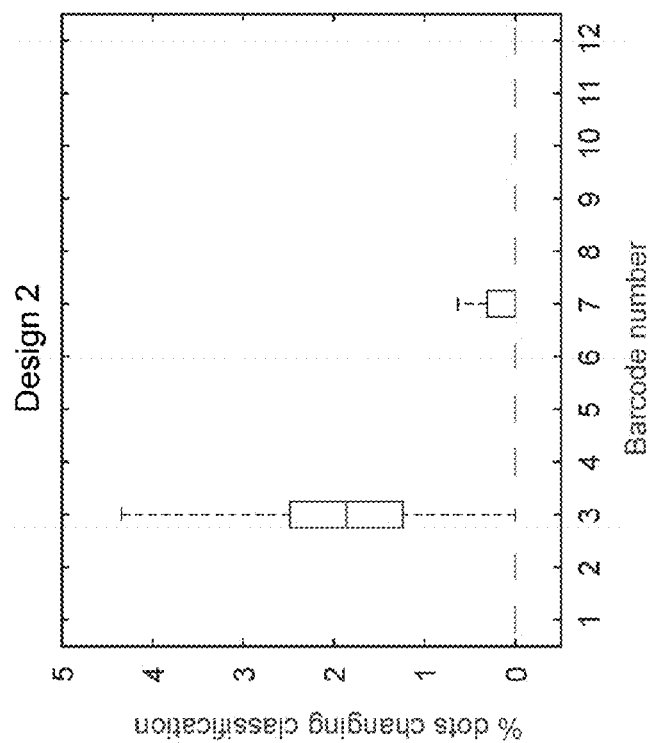
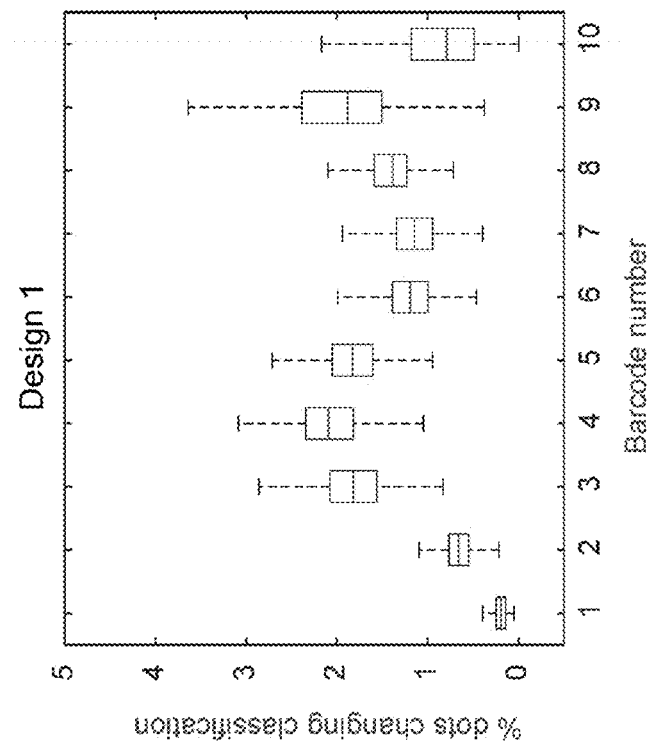
FIG. 15

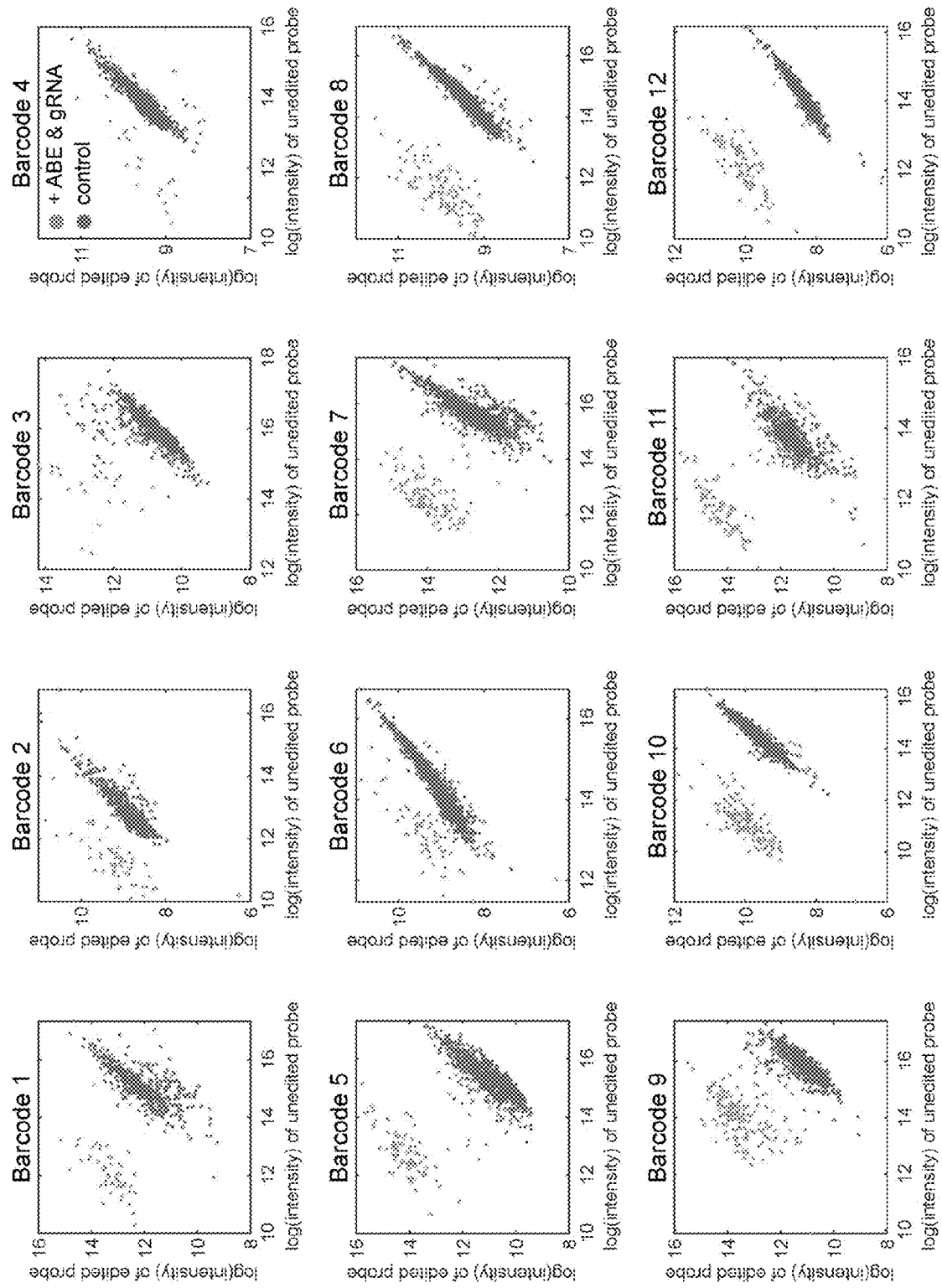
FIG. 17A  Design 2: negative control versus cells transfected with ABE and gRNA

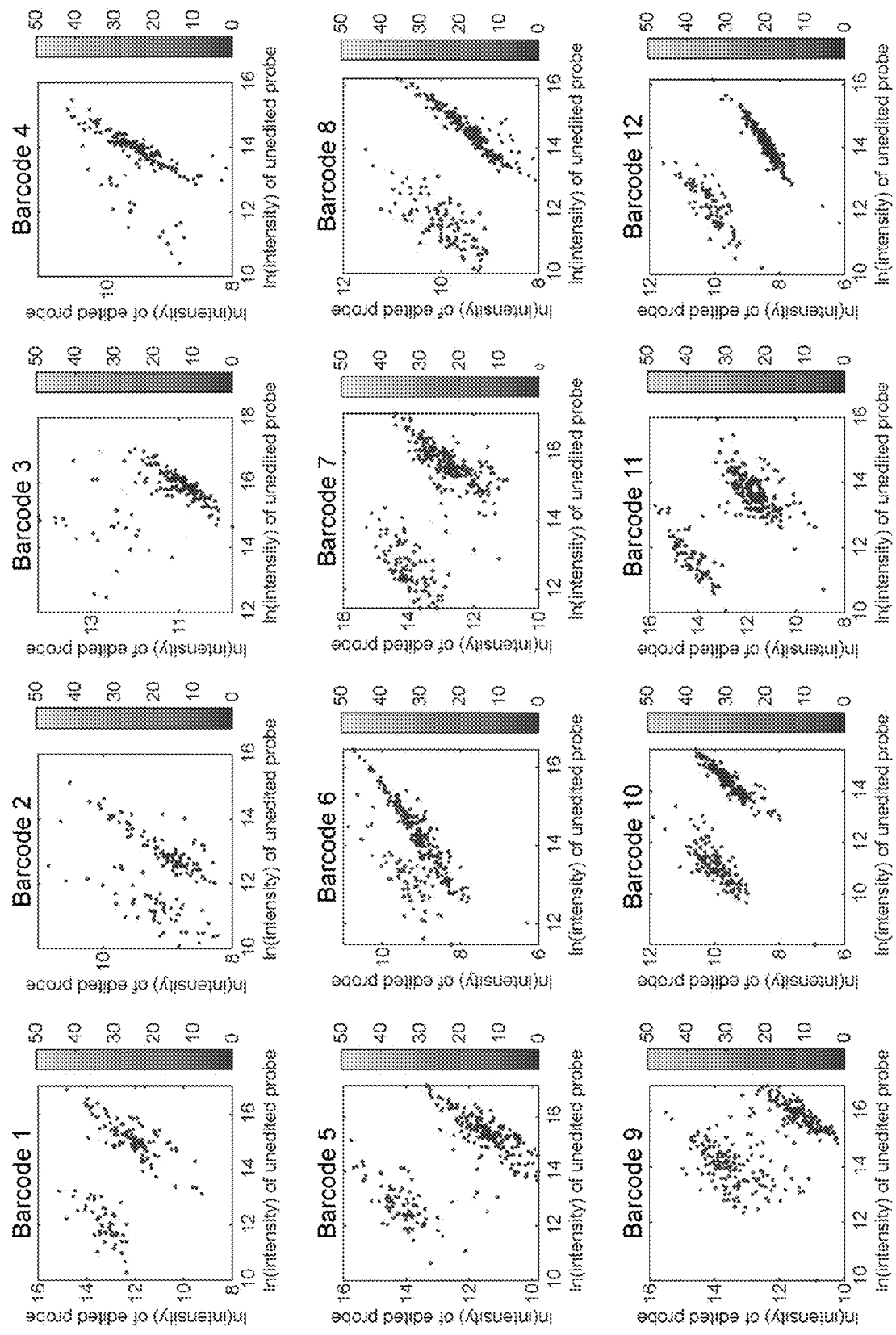
FIG. 17B  Design 2: frequency of classification change upon bootstrap resampling (%)

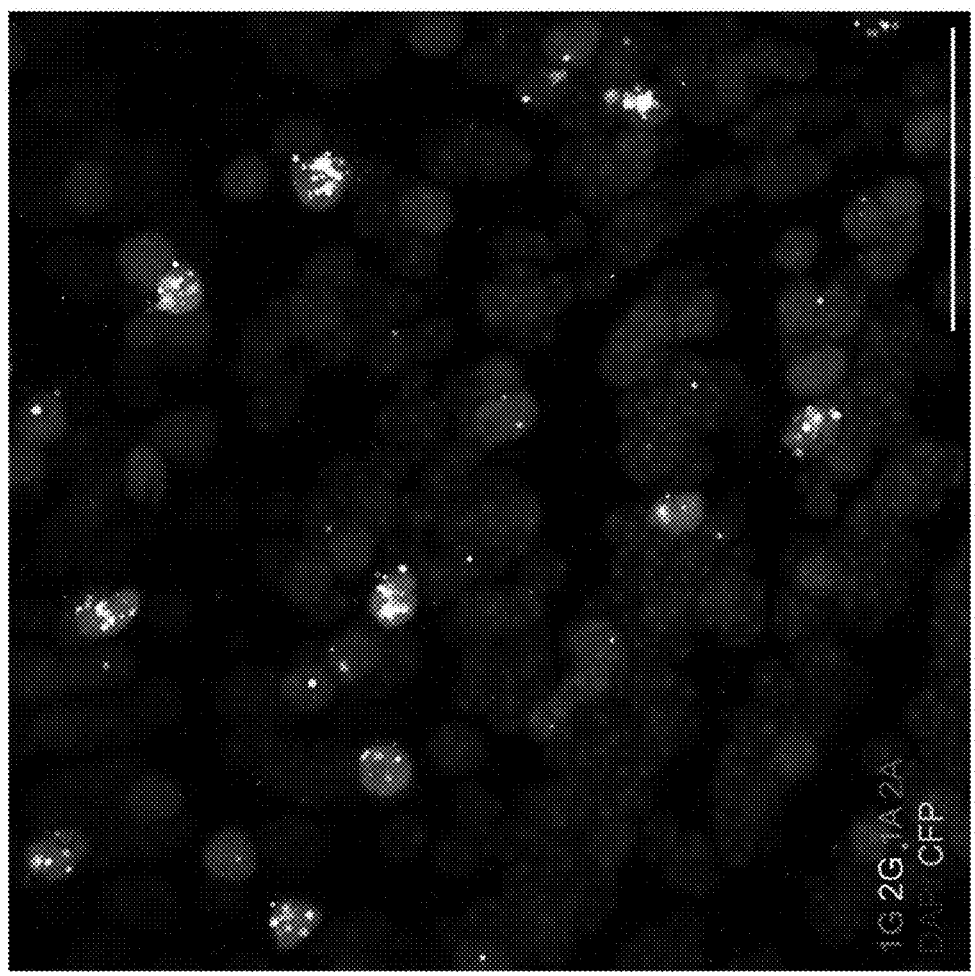
FIG. 20B
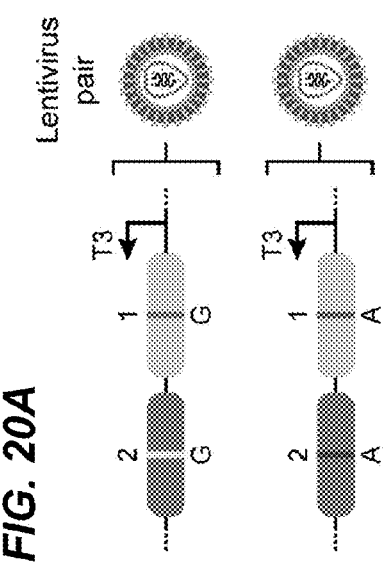
FIG. 20A
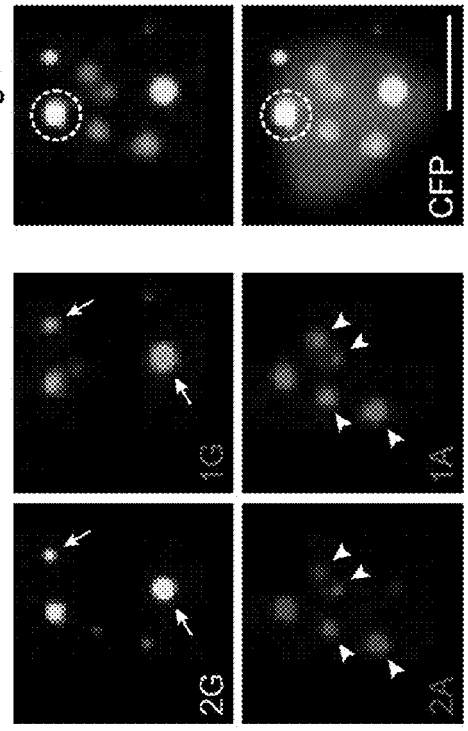
FIG. 20C
FIG. 20D

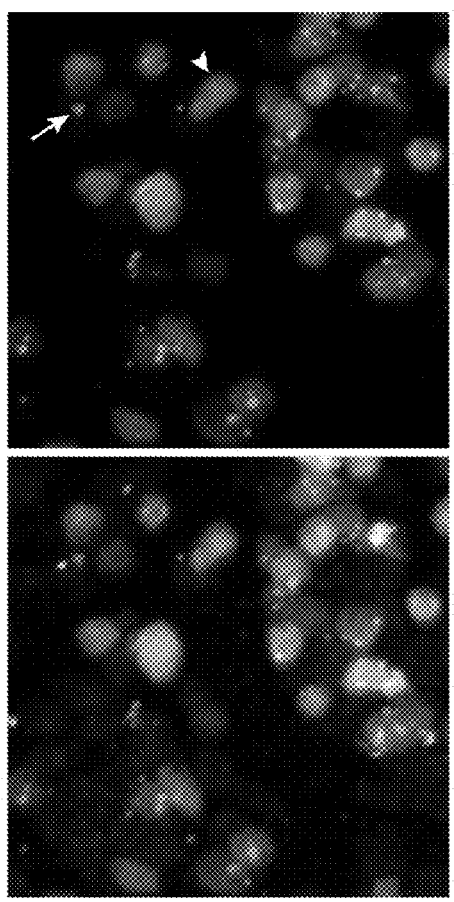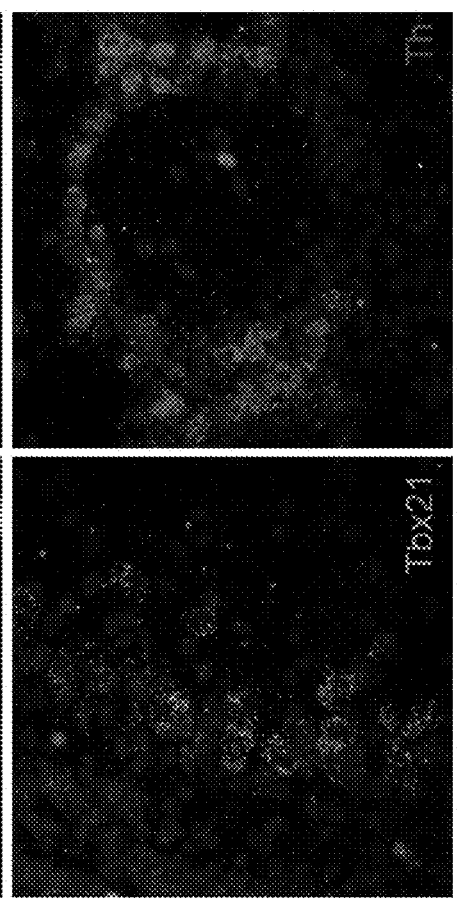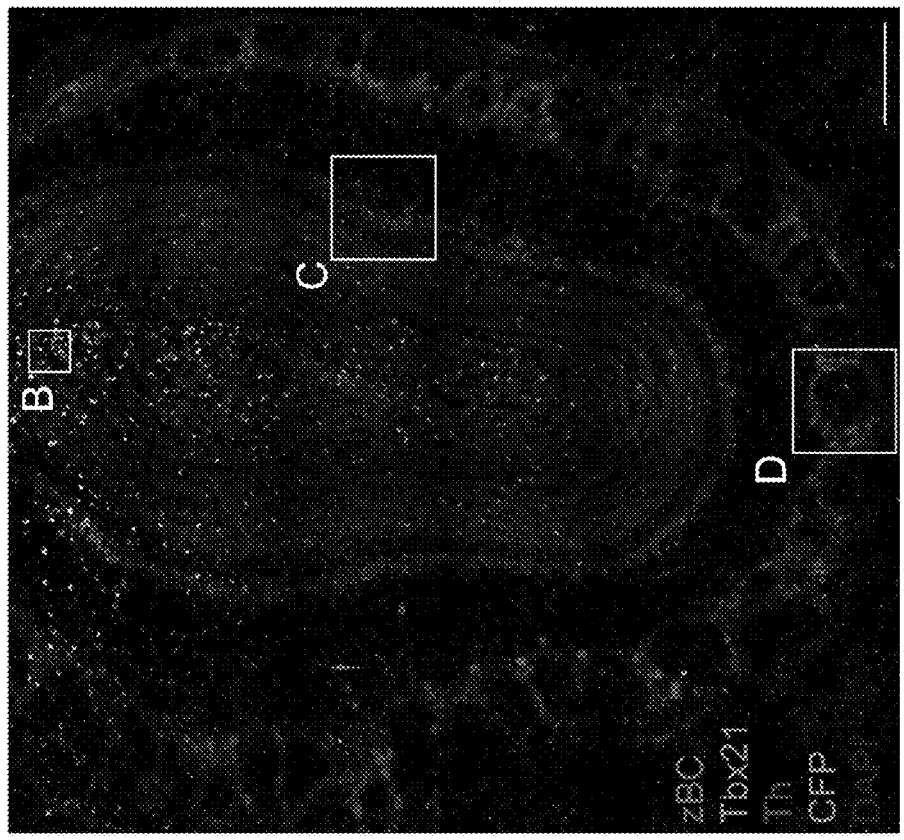
FIG. 22B2
FIG. 22D
FIG. 22B1
FIG. 22C
FIG. 22A

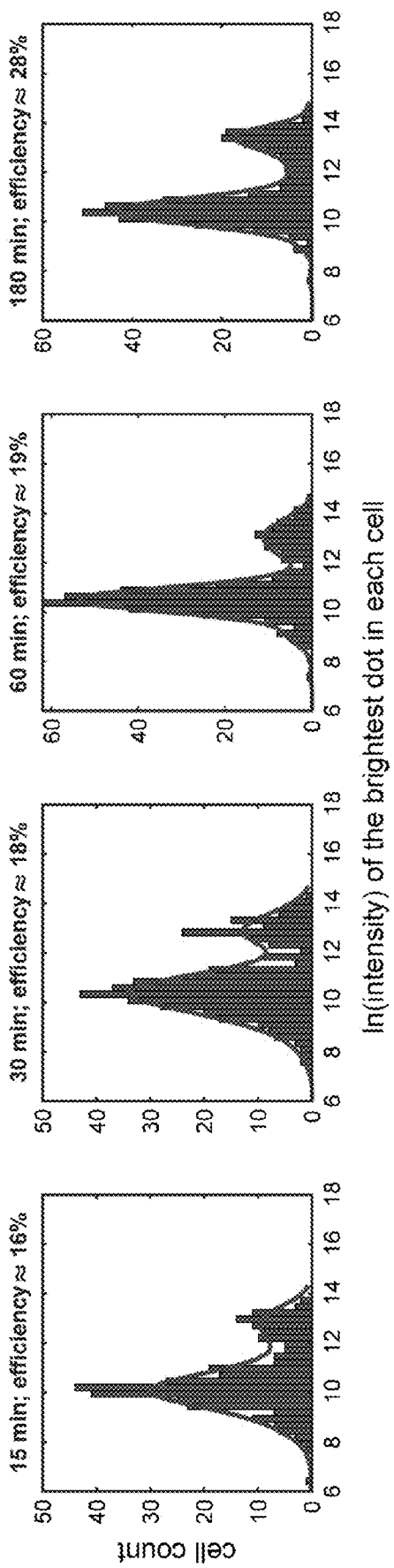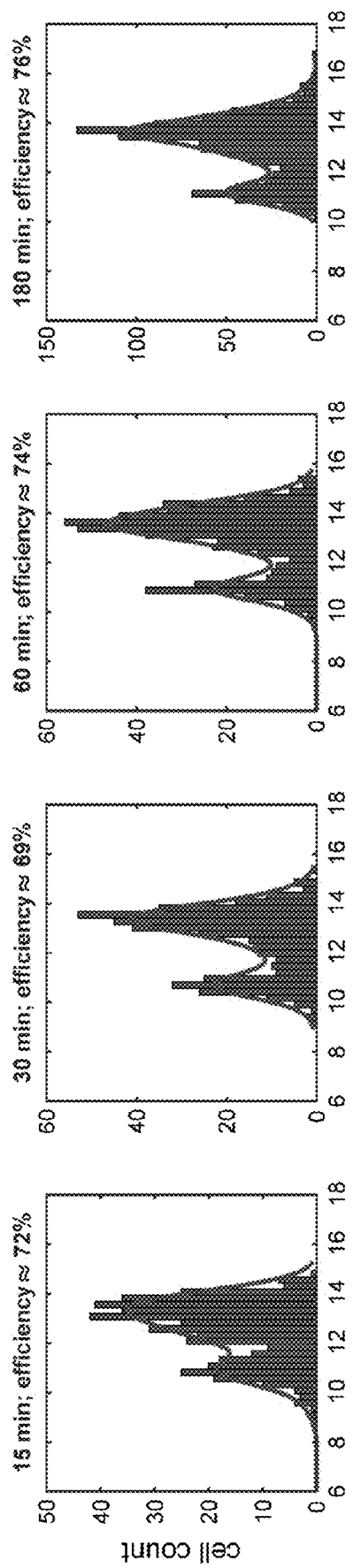
FIG. 24

IN SITU READOUT OF DNA BARCODES

RELATED APPLICATIONS

The present application claims priority under 35 U.S.C. § 119(e) to U.S. Provisional Application No. 62/774,754, filed Dec. 3, 2018, and U.S. Provisional Application No. 62/936,307, filed Nov. 15, 2019. The content of each of these related applications is incorporated herein by reference in its entirety.

STATEMENT REGARDING FEDERALLY SPONSORED R&D

This invention was made with government support under Grant No. MH116508 awarded by the National Institutes of Health. The government has certain rights in the invention.

REFERENCE TO SEQUENCE LISTING

The present application is being filed along with a Sequence Listing in electronic format. The Sequence Listing is provided as a file entitled 30KJ-302413-US_Sequence-Listing, created Nov. 26, 2019, which is 133 kilobytes in size. The information in the electronic format of the Sequence Listing is incorporated herein by reference in its entirety.

BACKGROUND

Field

The present disclosure relates generally to the field of barcoding cells, for example in situ readout of barcodes.

Description of the Related Art

Barcodes transcribed in living cells can be detected in cells. Detecting barcode expression across a diverse population of living cells can be challenging, for example, due to stochastic silencing, bursty expression, and unintended cell-type dependent promoter activity. Barcodes with large differences can be detected. There is a need to eliminate barcode expression in living cells and to detect single nucleotide variations in barcodes.

SUMMARY

Disclosed herein include embodiments of systems, methods, compositions, and kits for determining barcode sequences in situ. In some embodiments, the method of determining barcode sequences in situ comprises: providing a plurality of cells each comprising a barcode polynucleotide with a barcode sequence. The method can comprise: fixing the plurality of cells using a fixative to generate a plurality of fixed cells. The method can comprise: generating a plurality of barcode molecules comprising the barcode sequence of the barcode polynucleotide in each of the plurality of fixed cells. The method can comprise: contacting the plurality of fixed cells with a plurality of detection probes each comprising a barcode binding sequence and an initiator sequence, thereby each of the plurality of barcode molecules comprising the barcode sequence of the barcode polynucleotide in the fixed cell hybridizes to a detection probe, of the plurality of detection probes, comprising the barcode binding sequence reverse complementary to the barcode sequence, or a portion thereof. The method can comprise: contacting the plurality of fixed cells with pairs of amplifier probes, wherein the amplifier probes of each pair of amplifier probes comprise an identical fluorophore, thereby a first amplifier probe of a pair of amplifier probes hybridizes to (i) the initiator sequence of a detection probe of the plurality of detection probes hybridized to a barcode molecule in a fixed cell of the plurality of fixed cells and (ii) a second amplifier probe of the pair of amplifier probes. The method can comprise: detecting the fluorophore, or fluorescence thereof, of the pair of amplifier probes with the first amplifier probe hybridized to the detection probe hybridized to the barcode molecules in each of the plurality of fixed cells using fluorescence imaging. The method can comprise: determining the barcode sequence in each of the plurality of fixed cells using the fluorophore detected, wherein the fluorophore detected indicates the barcode sequence of the barcode polynucleotide in the one or more fixed cells.

In some embodiments, thereby the barcode sequence of each of the plurality of barcode molecules hybridizes to the barcode binding sequence of the detection probe that is reverse complementary to the barcode sequence of the barcode molecule. In some embodiments, contacting the plurality of fixed cells with the plurality of detection probes comprises: contacting the plurality of fixed cells with detection probe molecules of each of the plurality of detection probes, thereby each of the plurality of barcode molecules comprising the barcode sequence of the barcode polynucleotide in the fixed cell hybridizes to a detection probe molecule of the detection probe comprising the barcode binding sequence reverse complementary to the barcode sequence, or a portion thereof. In some embodiments, four, or at least two, detection probes of the plurality of detection probes comprise (i) barcode binding sequences that differ at one position and (ii) different initiator sequences.

In some embodiments, different pairs of amplifier probes comprise different fluorophores, and optionally the different fluorophores are spectrally distinct. In some embodiments, thereby a first amplifier probe molecule of the first amplifier probe of the pair of amplifier probes hybridizes to (i) a detection probe molecule of the detection probe hybridized to the barcode molecule in the fixed cell and (ii) a second amplifier probe molecule of the second amplifier probe of the pairs of amplifier probes, and first amplifier probe molecules of the first amplifier probe of the pair of amplifier probes hybridize to second amplifier probe molecules, comprising the second amplifier probe molecule hybridized to the first amplifier probe molecule, of the second amplifier probe of the pairs of amplifier probes in a chain reaction. In some embodiments, at least 10 first amplifier probe molecules hybridize to at least 10 second amplifier probe molecules in the chain reaction.

In some embodiments, (1) a first amplifier probe of the pair of amplifier probes comprises: (1a) a first amplifier probe subsequence reverse complementary to a first subsequence of the initiator sequence of the detection probe of the plurality of detection probes, (1b) a second amplifier probe subsequence reverse complementary to a second subsequence of the initiator sequence, (1c) a third amplifier probe subsequence, and (1d) a fourth amplifier probe subsequence comprising the second subsequence of the initiator sequence, and/or (2) a second amplifier probe of the pair of amplifier probes comprises: (2a) a first amplifier probe subsequence comprising a reverse complementary sequence of the third amplifier probe subsequence of the first amplifier probe, (2b) a second amplifier probe subsequence comprising the second amplifier probe subsequence, (2c) a third amplifier probe subsequence comprising the first subsequence of the initiator sequence, and (2d) a fourth amplifier probe subsequence comprising the second subsequence of the initiator sequence. In some embodiments, contacting the plurality of fixed cells with the pairs of amplifier probes comprises contacting the plurality of fixed cells with the pairs of amplifier probes each comprising the first amplifier probe and the second amplifier probe with hairpin structures formed by the second amplifier probe subsequence hybridizing with fourth amplifier probe subsequence of the first amplifier probe and by the second amplifier probe subsequence hybridizing with the fourth amplifier probe subsequence of the second amplifier probe. In some embodiments, thereby (1a) the first amplifier probe subsequence, of the first amplifier probe, reverse complementary to a first subsequence of the initiator sequence and (1b) the second amplifier probe subsequence, of the first amplifier probe, reverse complementary to a second subsequence of the initiator sequence of (1) the first amplifier probe hybridize to the first subsequence and the second subsequence, respectively, of the initiator sequence, respectively, and (1c) the third amplifier probe subsequence and (1d) the fourth amplifier probe subsequence of the second amplifier probe hybridize to (2a) the first amplifier probe subsequence and (2b) the fourth amplifier probe subsequence of the second amplifier probe, respectively.

Disclosed herein include embodiments of a method of determining barcode sequences in situ. In some embodiments, the method comprises: providing a plurality of cells each comprising a barcode polynucleotide with a barcode sequence. The method can comprise: fixing the plurality of cells using a fixative to generate a plurality of fixed cells. The method can comprise: generating a plurality of barcode molecules comprising the barcode sequence of the barcode polynucleotide in each of the plurality of fixed cells. The method can comprise: contacting the plurality of fixed cells with a plurality of detection probes each comprising a barcode binding sequence and an initiator sequence, thereby each of the plurality of barcode molecules comprising the barcode sequence of the barcode oligonucleotide in the fixed cell hybridizes to a detection probe, of the plurality of detection probes, comprising the barcode binding sequence reverse complementary to the barcode sequence, or a portion thereof. The method can comprise: contacting the plurality of fixed cells with a plurality of first amplifier probes each comprising a different fluorophore, thereby a first amplifier probe of the plurality of first amplifier probes hybridizes to (i) the initiator sequence of a detection probe of the plurality of detection probes hybridized to a barcode molecule in a fixed cell of the plurality of fixed cells. The method can comprise: detecting the fluorophore, or fluorescence thereof, of the first amplifier probe hybridized to the detection probe hybridized to the barcode molecules in each of the plurality of fixed cells using fluorescence imaging. The method can comprise: determining the barcode sequence in each of the plurality of fixed cells using the fluorophore detected, wherein the fluorophore detected indicates the barcode sequence of the barcode polynucleotide in the one or more fixed cells.

Disclosed herein include embodiments of a method of determining barcode sequences in situ. In some embodiments, the method comprises: providing a plurality of cells each comprising a barcode polynucleotide with a barcode sequence. The method can comprise: fixing the plurality of cells using a fixative to generate a plurality of fixed cells. The method can comprise: generating a plurality of barcode molecules comprising the barcode sequence of the barcode polynucleotide in each of the plurality of fixed cells. The method can comprise: contacting the plurality of fixed cells with a plurality of detection probes each comprising a barcode binding sequence and a fluorophore, thereby each of the plurality of barcode molecules comprising the barcode sequence of the barcode oligonucleotide in the fixed cell hybridizes to a detection probe, of the plurality of detection probes, comprising the barcode binding sequence reverse complementary to the barcode sequence of the barcode polynucleotide. The method can comprise: detecting the fluorophore, or fluorescence thereof, of the detection probe hybridized to the barcode molecules in each of the plurality of fixed cells using fluorescence imaging. The method can comprise: determining the barcode sequence in each of the plurality of fixed cells using the fluorophore detected, wherein the fluorophore detected indicates the barcode sequence of the barcode polynucleotide in the one or more fixed cells.

Disclosed herein include embodiments of a method of determining barcode sequences in situ. In some embodiments, the method comprises: providing a plurality of cells each comprising a barcode polynucleotide with a barcode sequence. The method can comprise: fixing cells of the plurality of cells using a fixative to obtain a plurality of fixed cells. The method can comprise: generating, for each of one or more fixed cells of the plurality of fixed cells, a plurality of barcode molecules comprising the barcode sequence of the barcode polynucleotide in the fixed cell. The method can comprise: contacting each of the one or more fixed cells with a plurality of detection probes each comprising a barcode binding sequence. In some embodiments, thereby (i) one, at least one, or each of the plurality of barcode molecules comprising the barcode sequence of the oligonucleotide in the fixed cell hybridizes to a detection probe of the plurality of detection probes comprising the barcode binding sequence reverse complementary to the barcode sequence, or a portion thereof, and (ii) the detection probe is associated with a fluorophore. The method can comprise: detecting the fluorophore, or fluorescence thereof, associated with the detection probe hybridized to the one, at least one, or each barcode molecule in each of the one or more fixed cells using fluorescence imaging. The fluorophore, associated with the detection probe hybridized to the barcode molecule comprising the barcode sequence of the barcode polynucleotide in the fixed cell, detected can indicate the barcode sequence of the barcode polynucleotide in the fixed cell.

In some embodiments, contacting each of the one or more fixed cells with the plurality of detection probes comprises: contacting each of the one or more fixed cells with the plurality of detection probes each comprising the barcode binding sequence and an initiator sequence, thereby one, at least one, or each of the plurality of barcode molecules comprising the barcode sequence of the oligonucleotide in the fixed cell hybridizes to a detection probe of the plurality of detection probes comprising the barcode binding sequence reverse complementary to the barcode sequence, or a portion thereof. Contacting each of the one or more fixed cells with the plurality of detection probes can comprise: contacting each of the one or more fixed cells with pairs of amplifier probes, wherein the amplifier probes of each pair of amplifier probes comprise an identical fluorophore, thereby a first amplifier probe of a pair of amplifier probes hybridizes to (i) the initiator sequence of a detection probe of the plurality of detection probes hybridized to a barcode molecule in the fixed cell and (ii) a second amplifier probe of the pair of amplifier probes.

In some embodiments, the initiator sequence is about 40 nucleotides in length. In some embodiments, two, or different, pairs of amplifier probes comprise different fluorophores, and optionally wherein the two, or different, fluorophores are spectrally distinct. In some embodiments, thereby a first amplifier probe molecule of the first amplifier probe of the pair of amplifier probes hybridize to (i) a detection probe molecule of the detection probe hybridized to the barcode molecule in the fixed cell and (ii) a second amplifier probe molecule of the second amplifier probe of the pairs of amplifier probes, and first amplifier probe molecules of the first amplifier probe of the pair of amplifier probes hybridize to second amplifier probe molecules, comprising the second amplifier probe molecule hybridized to the first amplifier probe molecule, of the second amplifier probe of the pairs of amplifier probes in a chain reaction. At least 10 first amplifier probe molecules can hybridize to at least 10 second amplifier probe molecules in the chain reaction.

In some embodiments, (1) a first amplifier probe of the pair of amplifier probes comprises: (1a) a first amplifier probe subsequence reverse complementary to a first subsequence of the initiator sequence of the detection probe of the plurality of detection probes, (1b) a second amplifier probe subsequence reverse complementary to a second subsequence of the initiator sequence, (1c) a third amplifier probe subsequence, and (1d) a fourth amplifier probe subsequence comprising the second subsequence of the initiator sequence. In some embodiments, (2) a second amplifier probe of the pair of amplifier probes comprises: (2a) a first amplifier probe subsequence comprising a reverse complementary sequence of the third amplifier probe subsequence of the first amplifier probe, (2b) a second amplifier probe subsequence comprising the second amplifier probe subsequence, (2c) a third amplifier probe subsequence comprising the first subsequence of the initiator sequence, and (2d) a fourth amplifier probe subsequence comprising the second subsequence of the initiator sequence. Contacting the plurality of fixed cells with the pairs of amplifier probes can comprise contacting the plurality of fixed cells with the pairs of amplifier probes each comprising the first amplifier probe and the second amplifier probe with hairpin structures formed by the second amplifier probe subsequence hybridizing with fourth amplifier probe subsequence of the first amplifier probe and by the second amplifier probe subsequence hybridizing with the fourth amplifier probe subsequence of the second amplifier probe.

In some embodiments, said detecting comprises detecting the fluorophore of the first amplifier probe hybridized to the initiator sequence of the detection probe hybridized to the barcode molecule in the fixed cell and the fluorophore of the second amplifier probe of the pair of amplifier probes comprising the first amplifier probe.

In some embodiments, contacting each of the one or more fixed cells with the plurality of detection probes comprises: contacting each of the one or more fixed cells with the plurality of detection probes each comprising the barcode binding sequence and an initiator sequence, thereby one, at least one, or each of the plurality of barcode molecules comprising the barcode sequence of the oligonucleotide in the fixed cell hybridizes to a detection probe of the plurality of detection probes comprising the barcode binding sequence reverse complementary to the barcode sequence, or a portion thereof. Contacting each of the one or more fixed cells with the plurality of detection probes can comprise: contacting each of the one or more fixed cells with a plurality of first amplifier probes each comprising a different fluorophore, thereby a first amplifier probe of the plurality of first amplifier probes hybridizes to the initiator sequence of a detection probe of the plurality of detection probes hybridized to a barcode molecule in the fixed cell.

In some embodiments, two, or different, first amplifier probes of the plurality of first amplifier probes comprise different fluorophores. In some embodiments, thereby a first amplifier probe molecule of the first amplifier probe of the plurality of first amplifier probes hybridizes to a detection probe molecule of the detection probe hybridized to the barcode molecule in the fixed cell. In some embodiments, said detecting comprises detecting the fluorophore of the first amplifier probe hybridized to the initiator sequence of the detection probe hybridized to the barcode molecule in the fixed cell.

In some embodiments, contacting each of the one or more fixed cells with the plurality of detection probes comprises: contacting each of the one or more fixed cells with the plurality of detection probes each comprising the barcode binding sequence and a fluorophore, thereby one, at least one, or each of the plurality of barcode molecules comprising the barcode sequence of the oligonucleotide in the fixed cell hybridizes to a detection probe of the plurality of detection probes comprising the barcode binding sequence reverse complementary to the barcode sequence, or a portion thereof, and the fluorophore. In some embodiments, said detecting comprises detecting the fluorophore of the detection probe hybridized to the barcode molecule in the fixed cell.

In some embodiments, a genome of one, at least one, or each cell of the plurality of cell comprises the barcode polynucleotide with the barcode sequence. In some embodiments, providing the plurality of cells comprises: integrating the barcode polynucleotide into a genome of one, at least one, or each of the plurality of cells. Integrating the barcode polynucleotide can comprise: integrating the barcode polynucleotide into the genome of one, at least one, or each of the plurality of cells at a specific site of the genome. The specific site can be a ROSA26 locus. In some embodiments, said integrating occurs about 12 days prior to said fixing.

In some embodiments, integrating the barcode polynucleotide into the genome of one, at least one, or each of the plurality of cells comprises: transfecting the cell with a donor plasmid comprising the barcode polynucleotide, a sequence thereof, a subsequence thereof, of a reverse complementary sequence of any of the preceding. Transfecting the cell with the donor plasmid can comprise: transfecting the cell with the donor plasmid and a plasmid capable of expressing Cas9 and/or a guide ribonucleic acid (gRNA) for integrating the barcode polynucleotide into the genome of one, at least one, or each of the plurality of cells at the specific site of the genome.

In some embodiments, integrating the barcode polynucleotide comprises: integrating the barcode polynucleotide into the genome of one, at least one, or each of the plurality of cells using a viral vector. The viral vector can comprise a polynucleotide comprising the barcode polynucleotide, a sequence thereof, a subsequence thereof, or a reverse complementary sequence of any of the proceeding. The viral vector can comprise a retrovirus, a lentivirus, an adenovirus, an adeno-associated virus, or a combination thereof. Integrating the barcode polynucleotide can comprise: injecting the viral vector into an organism or a tissue of the organism. The organism can be a mammal.

In some embodiments, the barcode polynucleotide comprises at least one promoter upstream of the barcode sequence. The at least one promoter can comprise three promoters. The at least one promoter can be a phage promoter. The at least one promoter can comprise a bacteriophage T3 promoter, a bacteriophage T7 promoter, a bacteriophage SP6 promoter, or a combination thereof. The at least one promoter can be inactive in one, at least one, or each live cell of the plurality of cells. The at least one promoter can be active in one, at least one, or each of the plurality of fixed cells.

In some embodiments, the barcode polynucleotide of one, at least one, or each of the plurality of cells comprises, for example, about 12 barcode sequences. The barcode sequences can be downstream of at least one promoter. Two of the barcode sequences can be downstream of different promoters, optionally wherein the different promoters comprise an identical promoter sequence. Two or more of the barcode sequences can have an identical length. The 12 barcode sequences can be different. The 12 barcode sequences can each be selected from a different set comprising four, or at least two, possible barcode sequences, and the possible barcode sequences of each set of possible barcode sequences can differ at one position. A combination of the 12 barcode sequences can be selected from about 16 million, or about 500000, possible combinations of 12 barcode sequences. The barcode sequences can be separated from one another by at least about 7 nucleotides.

In some embodiments, the barcode sequence is selected from a set comprising four, or at least two, possible barcode sequences. The possible barcode sequences from the set of possible barcode sequences differ at one position, for example position 7 of the barcode sequence. The possible barcode sequences can comprise adenine (A) nucleobase, guanine (G) nucleobase, or cytosine (C) nucleobase at the one position. The barcode sequence can be 20 nucleotides in length. The barcode polynucleotides of at least two cells of the plurality of cells can comprise an identical barcode sequence. The barcode polynucleotides of at least two cells of the plurality of cells can comprise different barcode sequences. The at least two cells can be cells of a cell type, cells of a cell subtype, and/or cells of an identical lineage. The at least two cells can be cells of different cell types, cells of different cell subtypes, and/or cells of different lineages. A first cell of the at least two cells can be a cell of interest, and/or wherein a second cell of the at least two cells is not a cell of interest. The first cell can be a cancer cell, and/or the second cell is a normal cell.

In some embodiments, the polynucleotide comprises a constitutively active promoter upstream of a marker gene. The at least one promoter and the constitutively active promoter can have divergent orientations. The marker gene can comprise a gene of a fluorescent protein, and optionally wherein the fluorescent protein comprises a green fluorescent protein, a yellow fluorescent protein, a cyan fluorescent protein, or a combination thereof.

In some embodiments, the fixative comprises a non-cross-linking fixative, a precipitating fixative, a denaturing fixative or a combination thereof. The fixative can comprise methanol and acetic acid. The ratio of methanol and acetic acid in the non-cross-linking fixative can be from about 10:1 (v/v) to about 1:10 (v/v). The fixative can comprise from about 5% acetic acid in methanol to about 75% acetic acid in methanol. Fixing the cells can comprise: fixing the cells without using a cross-linking fixative. The plurality of fixed cells can comprise dead cells.

In some embodiments, the method comprises: fixing fixed cells of the plurality of fixed cells using a second fixative to obtain a plurality of second fixed cells. Contacting each of the one or more fixed cells can comprise: contacting each of the one or more second fixed cells with a plurality of detection probes each comprising a barcode binding sequence, thereby (i) one, at least one, or each of the plurality of barcode molecules comprising the barcode sequence of the oligonucleotide in the second fixed cell hybridizes to a detection probe of the plurality of detection probes comprising the barcode binding sequence reverse complementary to the barcode sequence, or a portion thereof, and (ii) the detection probe is associated with a fluorophore. Detecting the fluorophore, or fluorescence thereof can comprise: detecting the fluorophore, or fluorescence thereof, associated with the detection probe hybridized to the one, at least one, or each barcode molecule in each of the one or more second fixed cells using fluorescence imaging, and wherein the fluorophore, associated with the detection probe hybridized to the barcode molecule comprising the barcode sequence of the barcode polynucleotide in the second fixed cell, detected indicates the barcode sequence of the barcode polynucleotide in the second fixed cell. The second fixative can comprise a cross-linking fixative. The second fixative can comprise formaldehyde.

In some embodiments, one, at least one, or each of the plurality of cells comprises no barcode molecule. Generating the plurality of barcode molecules can comprise: transcribing the barcode polynucleotide in each of the plurality of fixed cell to generate the plurality of barcode molecules comprising the barcode sequence of the barcode polynucleotide in the fixed cell. Transcribing the barcode polynucleotide can comprise: transcribing the barcode polynucleotide in each of the plurality of fixed cell to generate the plurality of barcode molecules comprising the barcode sequence of the barcode polynucleotide in the fixed cell using a phage RNA polymerase. The phage RNA polymerase can comprise a bacteriophage T3 RNA polymerase, a bacteriophage T7 RNA polymerase, a bacteriophage SP6 RNA polymerase, or a combination thereof. The plurality of barcode molecules comprises at least 100 barcode molecules comprising the barcode sequence of the barcode polynucleotide in each of the plurality of fixed cells.

In some embodiments, thereby the barcode sequence of each of the plurality of barcode molecules hybridizes to the barcode binding sequence of the detection probe that is reverse complementary to the barcode sequence of the barcode molecule. In some embodiments, contacting the plurality of fixed cells with the plurality of detection probes comprises: contacting each of the one or more fixed cells with detection probe molecules of each of the plurality of detection, thereby (i) one, at least one, or each of the plurality of barcode molecules comprising the barcode sequence of the oligonucleotide in the fixed cell hybridizes to a detection probe molecule of the detection probe of the plurality of detection probes comprising the barcode binding sequence reverse complementary to the barcode sequence, or a portion thereof, and (ii) the detection probe molecule of the detection probe is associated with a fluorophore.

In some embodiments, four, or at least two, detection probes of the plurality of detection probes comprise the barcode binding sequences that differ at one position. In some embodiments, four, or at least two, detection probes of the plurality of detection probes comprise (i) barcode binding sequences that differ at one position and (ii) different initiator sequences. The four, or at least two, detection probes can have an identical concentration. The concentration of one, at least one, or each of the four, or at least two, detection probes can be about 4 nM. One, at least one, or each of the plurality of barcode molecules comprising the barcode sequence of the oligonucleotide in the fixed cell can hybridize to one of the four, or at least two, detection probes comprising the barcode binding sequence reverse complementary to the barcode sequence, or a portion thereof, not the remaining three, or at least one, detection probe(s).

In some embodiments, the plurality of detection probes comprises 12 sets of detection probes, wherein each of the sets of detection probes comprises four, or at least two, detection probes with barcode binding sequences that differ at one position and are reverse complementary to possible barcode sequences of one of the sets of possible barcode sequences. The detection probes of one of the sets of detection probes can comprise different initiator sequences. Said contacting and said detecting comprises: iteratively, contacting each of the one or more fixed cells with a different set of detection probes each comprising a barcode binding sequence, thereby (i) one, at least one, or each of the plurality of barcode molecules comprising the barcode sequence of the oligonucleotide in the fixed cell hybridizes to a detection probe of the set of detection probes comprising the barcode binding sequence reverse complementary to the barcode sequence, or a portion thereof, and (ii) the detection probe is associated with a fluorophore; and detecting the fluorophore associated with the detection probe hybridized to the one, at least one, or each barcode molecule in each of the one or more fixed cells using fluorescence imaging. A combination of the fluorophores associated with detection probes hybridized to the barcode molecule comprising the barcode sequence of the barcode polynucleotide in the fixed cell, detected can indicate the barcode sequence of the barcode polynucleotide in the fixed cell. The method can comprise: removing the detection probe hybridized to the one, at least one, or each barcode molecule in each of the one or more fixed cells. Said removing can comprise: digesting the detection probe hybridized to the one, at least one, or each barcode molecule in each of the one or more fixed cells using DNase.

In some embodiments, the method comprises: determining the barcode sequence in each of the one or more fixed cells using the fluorophore, associated with the detection probe hybridized to the barcode molecule comprising the barcode sequence of the barcode polynucleotide in the fixed cell, detected. In some embodiments, the method comprises: determining lineages of, and/or a clonal relationship between, two or more fixed cells of the plurality of fixed cells using the barcode sequence of the barcode polynucleotide in each of the two or more fixed cells. In some embodiments, the method comprises: determining a spatial relationship of two or more fixed cells of the plurality of fixed cells; and correlating the barcode sequences of the barcode polynucleotide in each of the two or more fixed cells with a spatial relationship of the two or more fixed cells. The two or more cells can be cells of different cell types or cell subtypes. The two or more cells can be cells of an identical cell type or cell subtype.

In some embodiments, the method comprises: staining nuclei of the plurality of fixed cells; and identifying nuclei of the plurality of fixed cells based on the nuclei stained, wherein said detecting comprises: detecting the fluorescence of the fluorophore, associated with the detection probe hybridized to the barcode molecule comprising the barcode sequence of the barcode polynucleotide in the fixed cell, in the nucleus of the cell identified.

In some embodiments, the method comprises: base editing the barcode sequence of the barcode polynucleotide in one, at least one, or each of the plurality of cells. In some embodiments, said base editing comprises: base editing the barcode sequence of the barcode polynucleotide in one, at least one, or each of the plurality of cells at the one position that the possible barcode sequences from the set of possible barcode sequences are different. In some embodiments, said base editing comprises: adenine (A)-to-guanine (G) base editing and/or cytosine (C)-to-thymine (T) base editing.

In some embodiments, said base editing comprises: base editing using a base editor and a guide ribonucleic acid (gRNA) targeting a gRNA targeting sequence of the barcode polynucleotide, and wherein the gRNA targeting sequence comprises the barcode sequence, or a portion thereof, of the barcode polynucleotide. The gRNA targeting sequence is 20 nucleotides in length. The barcode sequence and the gRNA targeting sequence of the barcode polynucleotide can completely overlap. The barcode sequence and the gRNA targeting sequence of the barcode polynucleotide can overlap by 11 nucleotides. The barcode polynucleotide can comprise a Protospacer Adjacent Motif (PAM), and optionally the PAM is downstream of the gRNA targeting sequence. The base editor can comprise an adenine base editor (ABE) and/or a cytosine base editor (CBE). Said base editing can comprise: introducing a plasmid capable of expressing the base editor and the gRNA into one or more of the plurality of cells. Said introducing can comprise: introducing the plasmid capable of expressing the base editor and the gRNA into the one or more cells using transient transfection.

In some embodiments, said base editing comprises base editing the barcode sequence of the barcode polynucleotide in one, at least one, or each of the plurality of cells at one or more predetermined time points. In some embodiments, said base editing comprises base editing the barcode sequence of the barcode polynucleotide in one, at least one, or each of the plurality of cells at an edit rate, optionally wherein the edit rate is predetermined, optionally wherein the edit rate is about 1% to about 100% edit per unit time, and optionally the edit rate is about 1% to 100% edit per cell per cell division cycle.

In some embodiments, the method comprises: determining gene expression in one, at least one, or each of the plurality of cells. In some embodiments, the method comprises: correlating the gene expression of two or more fixed cells of the plurality of fixed cells with the lineages of, the clonal relationship between, and/or the spatial relationship of, the two or more fixed cells.

In some embodiments, the plurality of cells is from a sample comprising a cell culture, a tissue, an organ, an embryo, an organism, a section thereof. In some embodiments, the plurality of cells is from a sample comprising an in vivo sample and/or an in vitro sample. In some embodiments, the plurality of cells comprises one or more tumor cells, one or more immune cells, one or more epithelial cells, one or more nervous cells, one or more blood cells, one or more bone cells, one or more fat cells, one or more muscle cells, and/or one or more sex cells. In some embodiments, the plurality of cells comprises one or more stem cells, one or more progenitor cells, and/or one or more mature cells. In some embodiments, two, at least two, or each of the plurality of cells are cultured under an identical condition. In some embodiments, two, at least two, or each of the plurality of cells are cultured under different conditions. The identical condition or each of the different conditions can comprise a genetic perturbation, an environmental perturbation, or a combination thereof.

Disclosed herein include embodiments of a plurality of compositions for determining barcode sequences in situ. In some embodiments, the plurality of compositions comprises: a plurality of cells each comprising a barcode polynucleotide with a barcode sequence, of any method or embodiment disclosed herein. The plurality of compositions can comprise: (a) a donor plasmid comprising the barcode polynucleotide, a sequence thereof, a subsequence thereof, or a reverse complementary sequence of any of the proceeding, the barcode polynucleotide comprising at least one barcode sequence, (b) a plasmid capable of expressing Cas9 and/or a guide ribonucleic acid (gRNA) for integrating the barcode polynucleotide into the genome, and/or (c) a viral vector for integrating the barcode polynucleotide into each of the plurality of cells, of any method or embodiment disclosed herein. The viral vector can comprise a polynucleotide comprising the barcode polynucleotide, a sequence thereof, a subsequence thereof, or a reverse complementary sequence of any of the proceeding. The plurality of compositions can comprise: a fixative, of any method or embodiment disclosed herein. The plurality of compositions can comprise: a polymerase of any method or embodiment disclosed herein. The plurality of compositions can comprise: a plurality of detection probes of any method or embodiment disclosed herein. The plurality of compositions can comprise: pairs of amplifier probes, or a plurality of first amplifier probes, of any method or embodiment disclosed herein.

Disclosed herein include embodiments of a kit. In some embodiments, the kit comprises: a plurality of compositions disclosed herein. The kit can comprise: instructions for using the plurality of compositions for determining barcode sequences in situ, high throughput screening, analyzing clonal dynamics and heterogeneity in a tumor or tumors, immunology, or developmental biology, and/or lineage or event recording.

Disclosed herein include embodiments of a method comprising using a plurality of compositions or a kit disclosed herein for: high throughput screening, analyzing clonal dynamics and heterogeneity in a tumor or tumors, immunology, or developmental biology, and/or lineage or event recording.

Details of one or more implementations of the subject matter described in this specification are set forth in the accompanying drawings and the description below. Other features, aspects, and advantages will become apparent from the description, the drawings, and the claims. Neither this summary nor the following detailed description purports to define or limit the scope of the inventive subject matter.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1A-1G. Phage RNA polymerases enable in situ readout of DNA barcodes without in vivo expression.

FIG. 1A. Workflow for analysis of Zombie barcodes (left to right). First, barcode constructs containing a phage promoter, such as T7, that is inactive in live cells, are integrated in the genome at 104. Second, and optionally, base editors or other DNA modifying enzymes (brown) can alter barcode sequence to increase barcode diversity at 108. Third, cells are fixed at 112 and phage RNA polymerase (pink) is added at 116. This enables transcription of the barcode to RNA (gray lines) at 120. RNA transcripts can be detected in situ at 124, using for example, fluorescent imaging at 128. RNA transcripts accumulate at the active site (large red dot), and also diffuse away from it (small red dots represent individual transcripts).

FIG. 1B. The Z1 construct was engineered to contain a barcode downstream of T3, T7, and SP6 phage promoters, and to express H2B-Cerulean fluorescent protein (CFP) in living cells from a divergently oriented mammalian promoter. Z1 was stably integrated in mouse ES cells at the ROSA26 locus (single integration per genome). This line was compared to a similar cell line containing the control construct lacking phage promoters. FIG. 1C. Polyclonal control cells and Z1 cells (columns) were imaged with or without the indicated phage polymerases (rows). HCR was used to detect barcode RNA (zBC). Nuclei were visualized by native fluorescence of H2B-CFP (cyan) as well as DAPI staining (blue). Barcode transcripts appear only in Z1 cells with phage polymerase (yellow dots, right column). The experiment was independently repeated twice with similar results. Scale bar is 25 µm.

FIG. 1D. In monoclonal cultures, active sites can be detected in most cells (image). Nuclei (blue) and active sites (yellow) are segmented automatically (green outlines and red dots, respectively). One cell in this field of view does not show any active site (arrowhead). Scale bar is 25 µm. Percentages of cells with detectable active sites for each polymerase are shown on the right. Horizontal lines indicate the mean of replicates (n=3 biologically independent samples). Total of 3916 cells were analyzed, with at least 420 cells for each replicate.

FIG. 1E. The Z3 construct encodes three 900 bp barcodes, each expressed from a distinct set of phage promoters. This construct was integrated at ROSA26, transcribed using T3 RNA polymerase, and imaged in all three color channels. T7 and SP6 promoters are shaded gray because they are not used in FIG. 1F and FIG. 1G. Sizes of elements are not drawn to scale.

FIG. 1F. Schematic: Assuming independence, the conditional probability of detecting barcode i in a cell, given detection of another barcode (j), should equal the overall probability of barcode i detection, with deviations signifying either synergy (green arrow) or interference (red arrow) between barcodes. Bar plot: for Z3, the conditional probability analysis shows independent detection events for all three barcodes. Bars indicate mean of 3 replicates (points).

FIG. 1G. Fraction of Z3 cells with no detectable active sites declines with the number of barcodes analyzed, consistent with independent expression of different phage promoters in the same cell. Thus, detection efficiency can be increased with additional barcode copies. Dots represent the mean for different barcodes or barcode combinations and black vertical lines show the range over three replicates. Blue line indicates the exponential fit. Total of 564 cells were analyzed for plots in F and G.

FIGS. 2A-2H. Reliable detection of short barcodes.

FIG. 2A. Short probes (colored lines) target 20 bp regions of the larger Z1 barcode sequence and can be detected in distinct fluorescence channels. These probes also contain distinct 40 bp initiator sequences for multi-channel HCR analysis. Local accumulation of transcripts at the active site effectively amplifies signal and enables detection, even with a single probe per target site.

FIG. 2B. Z1 cells were treated with each polymerase (rows) and imaged in three channels (columns) after detection with individual fluorescently labeled probes (colors matching those in FIG. 2A). Final column shows composite images. The barcode in Z1 cells is integrated site-specifically at the ROSA26 locus. The experiment was independently repeated three times with similar results. Scale bar is 25 µm.

FIG. 2C. Signal from each individual probe can be detected in the majority of the cells by single molecule Fluorescence In Situ Hybridization (smFISH) or hybridization chain reaction (HCR). Plot shows the percentage of Z1 cells with active sites detected using a single 20 bp probe. Dots are color-coded based on probe identity. n=3 biologically independent samples. Lines show the average efficiency over three probes and three replicates.

Figure 2A:
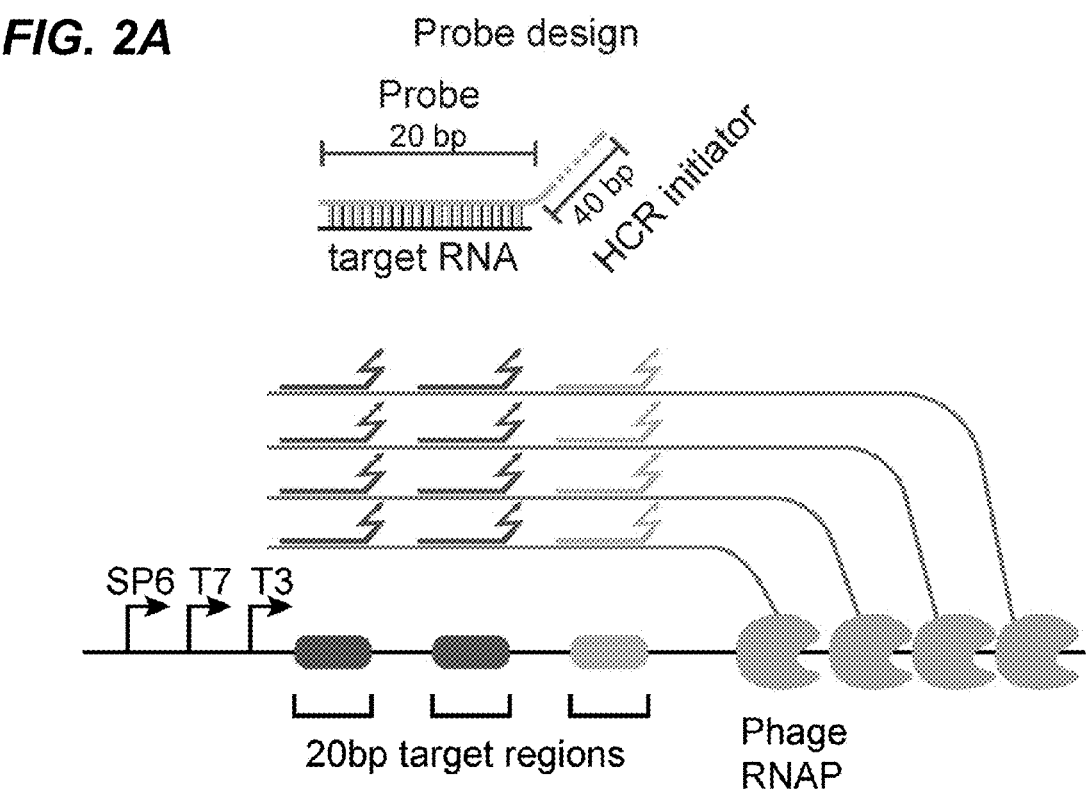
Figure 2B:
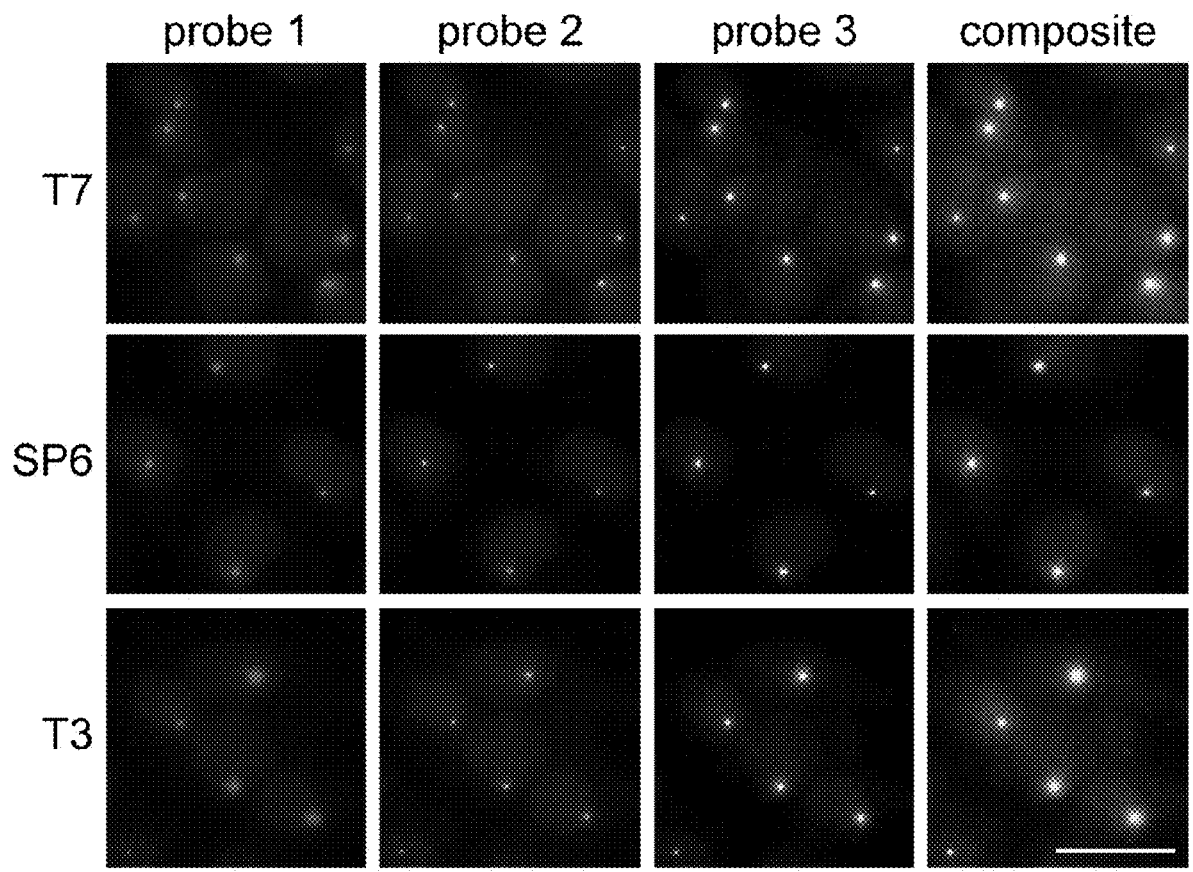
Figure 2C:
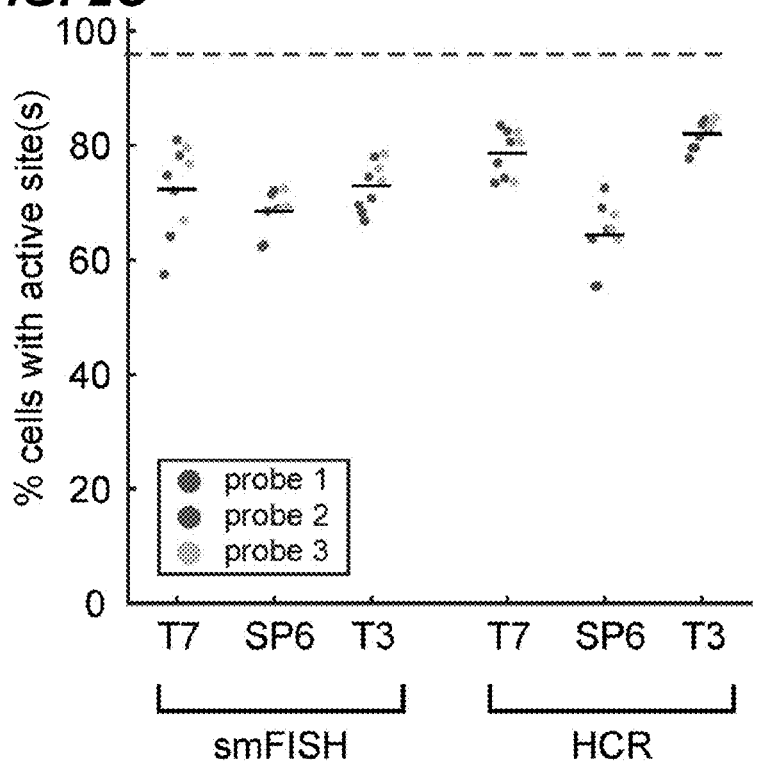
Figure 2D:
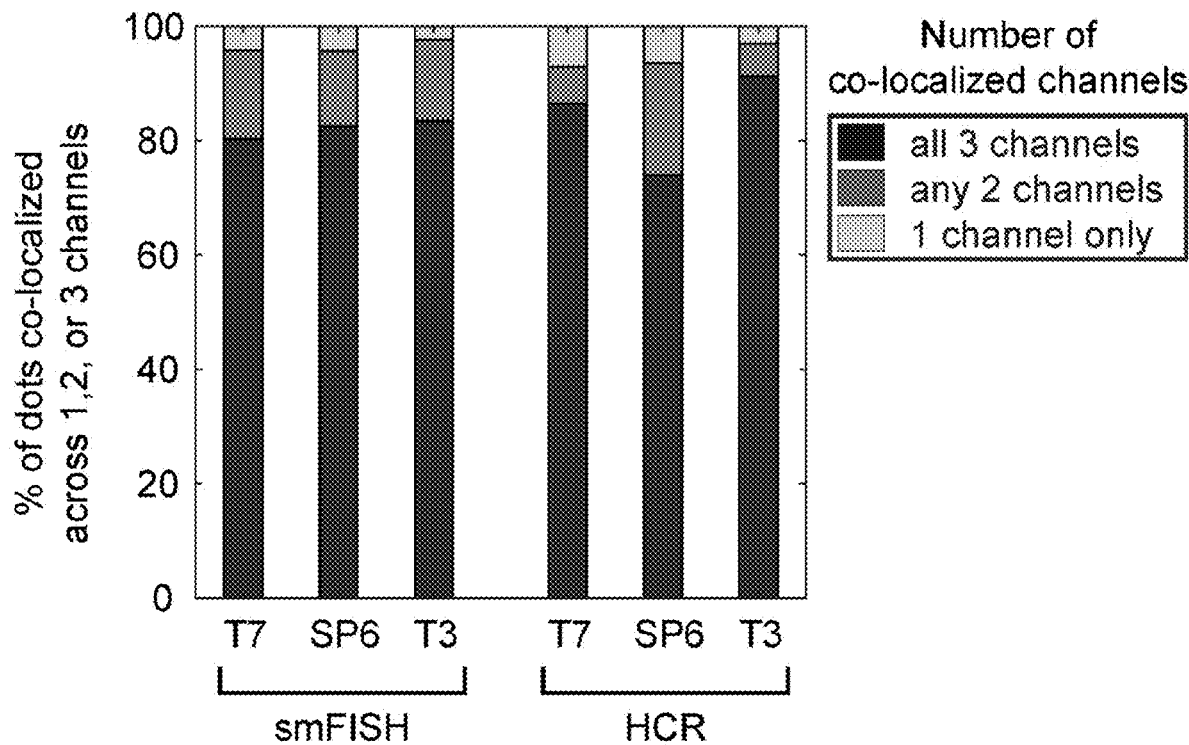

FIG. 2D. Colocalization analysis shows that the majority of dots colocalize in multiple channels, indicating the reliability of single probe detection. For each condition, gray shades indicate fractions of dots that are detected in only 1 channel or co-detected in 2 or 3 channels. Data from three biologically independent samples are combined in each condition. For plots in C and D, total of 5097 cells were analyzed, with at least 669 cells for each condition.

FIG. 2E. Z1 cells were treated with each polymerase (rows), imaged following HCR in three channels (columns).

FIG. 2F. Phage transcripts can be detected without HCR amplification. Images show same treatment as in FIG. 2B, except with only a single HCR hairpin, preventing HCR amplification. Images in FIG. 2B and FIG. 2C are scaled to different intensity ranges.

Figure 2H:
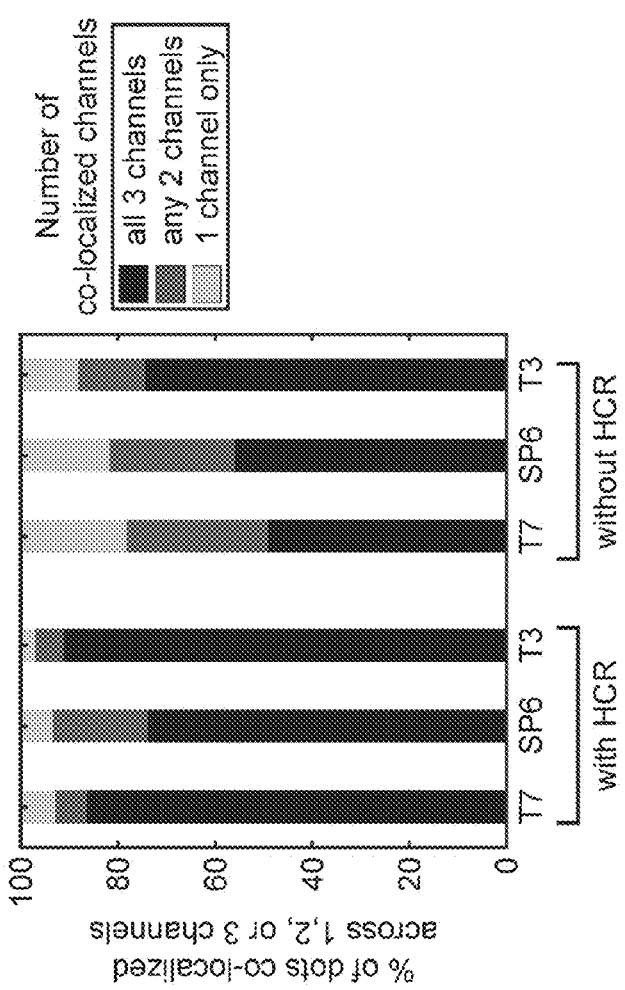
Figure 2G:
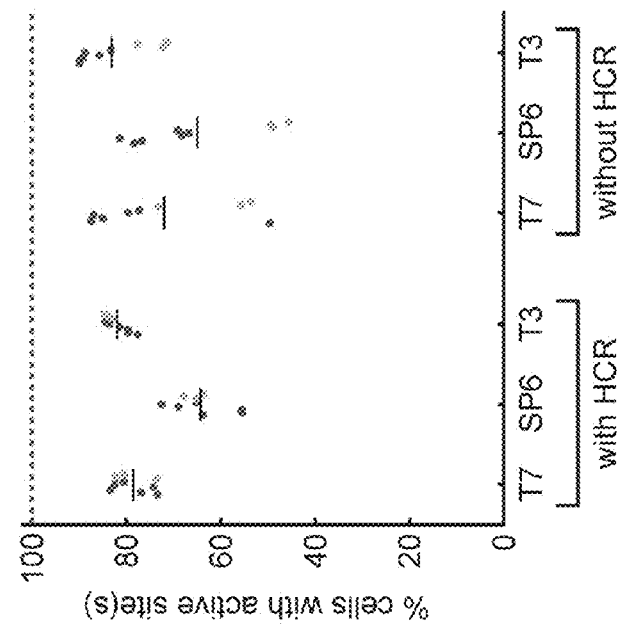

FIG. 2G. Detection efficiency for individual dots is comparable with or without HCR (Wilcoxon rank sum test, p>0.4). The percentage of Z1 cells with active sites detected using a single 20 bp probe. Dots are color-coded based on the probe identity. Lines show the average efficiency over three probes and three replicates.

FIG. 2H. Co-localization analysis shows greater overlap between channels with HCR. For each condition, gray shades indicate fractions of dots that are detected in 1, 2, or all 3 channels. In rare cases, two dots from the same channel were detected in one active site, mainly due to the proximity of the active sites. These dots were excluded from the analysis.

FIGS. 3A-3D. Probe competition accurately discriminates single nucleotide variants.

Figure 3A:
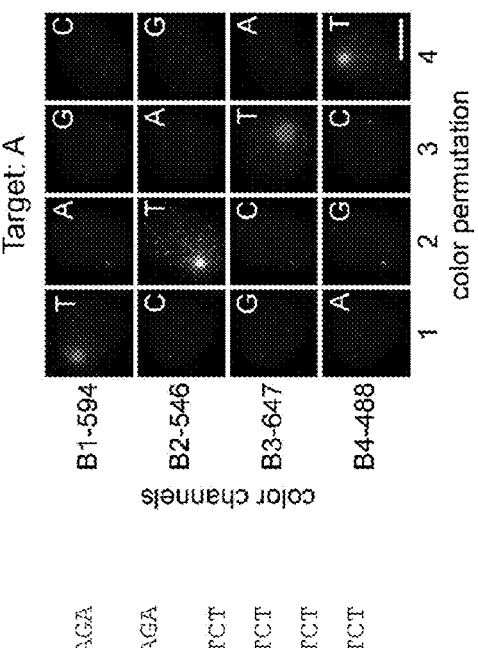

FIG. 3A. Perfect match probes outcompete those with a single mismatch when an equimolar mixture of all 4 probe variants is used. This feature can be used to detect SNVs in situ.

Figure 3B:
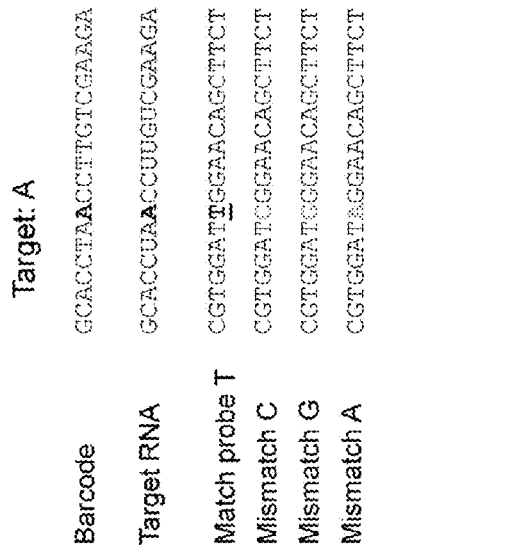

FIG. 3B. Sequences of barcode, target RNA, and probes with SNV position indicated in bold underline (match) and brown (mismatch).

Figure 3C:
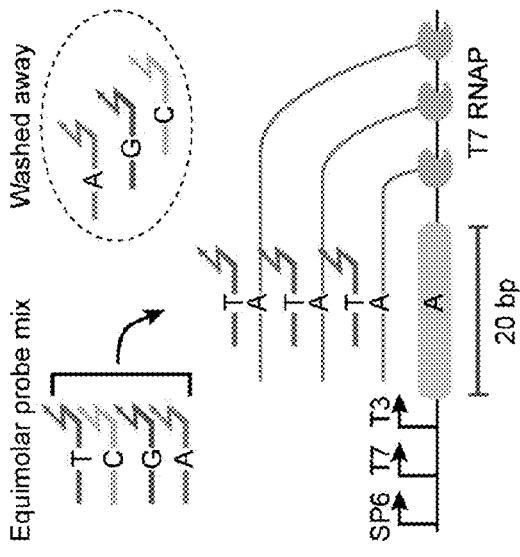

FIG. 3C. Representative images of Z1 cells showing detection of the correct target nucleotide in the barcode (see FIG. 3D for quantification of the results and FIG. 12 for representative images of other target nucleotides). All images were acquired under the same conditions and displayed with identical processing parameters for each channel (row). Each column represents one experiment in which four probes with a SNV and orthogonal HCR initiators (B1-4) were mixed and hybridized to the sample with the indicated color permutation. Letters indicate the probe variant in each image. HCR initiator and the fluorescence channel used for each probe are shown next to the rows. The barcode in Z1 cells is integrated site specifically in ROSA26 locus. Scale bar is 10 μm.

Figure 3D:
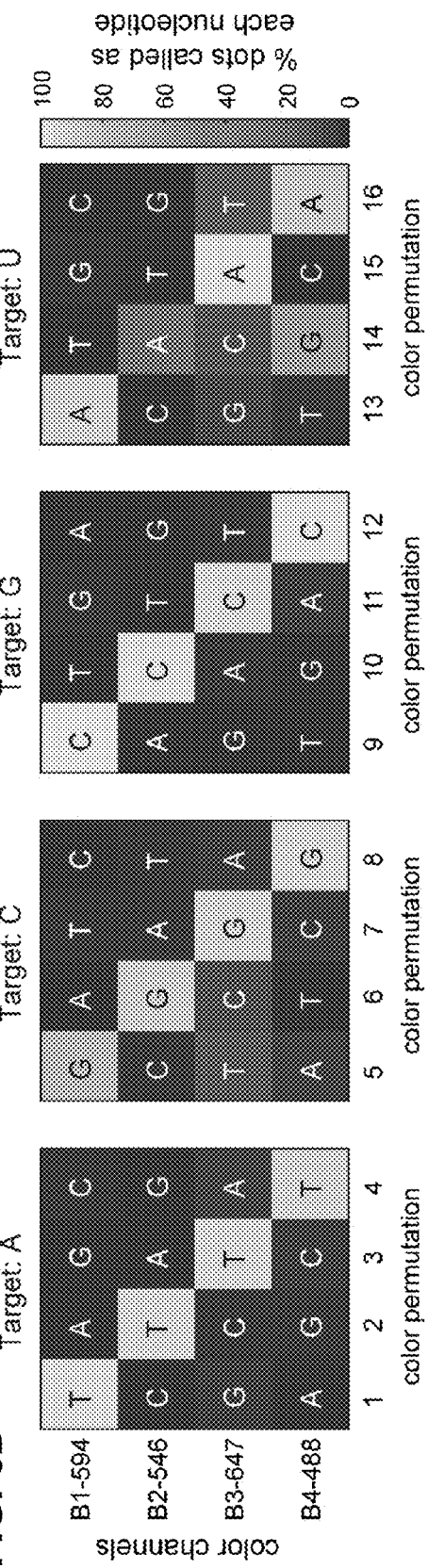

FIG. 3D. Probe competition can detect all four target nucleotides. Each matrix represents SNV analysis with four distinct color permutations, as in FIG. 3C, with the indicated target nucleotide at distinct positions. For targeting U (rightmost matrix), one permutation (14) is ambiguous due to wobble base pairing, but others (e.g. 15) provide accurate discrimination. Color scale represents the percentage of dots in which the indicated color channel has the highest rank of normalized brightness (see Methods). Total of 4009 cells were analyzed, with at least 135 cells for each color permutation.

FIGS. 4A-4F. CRISPR base edits can be read out in situ.

Figure 4A:
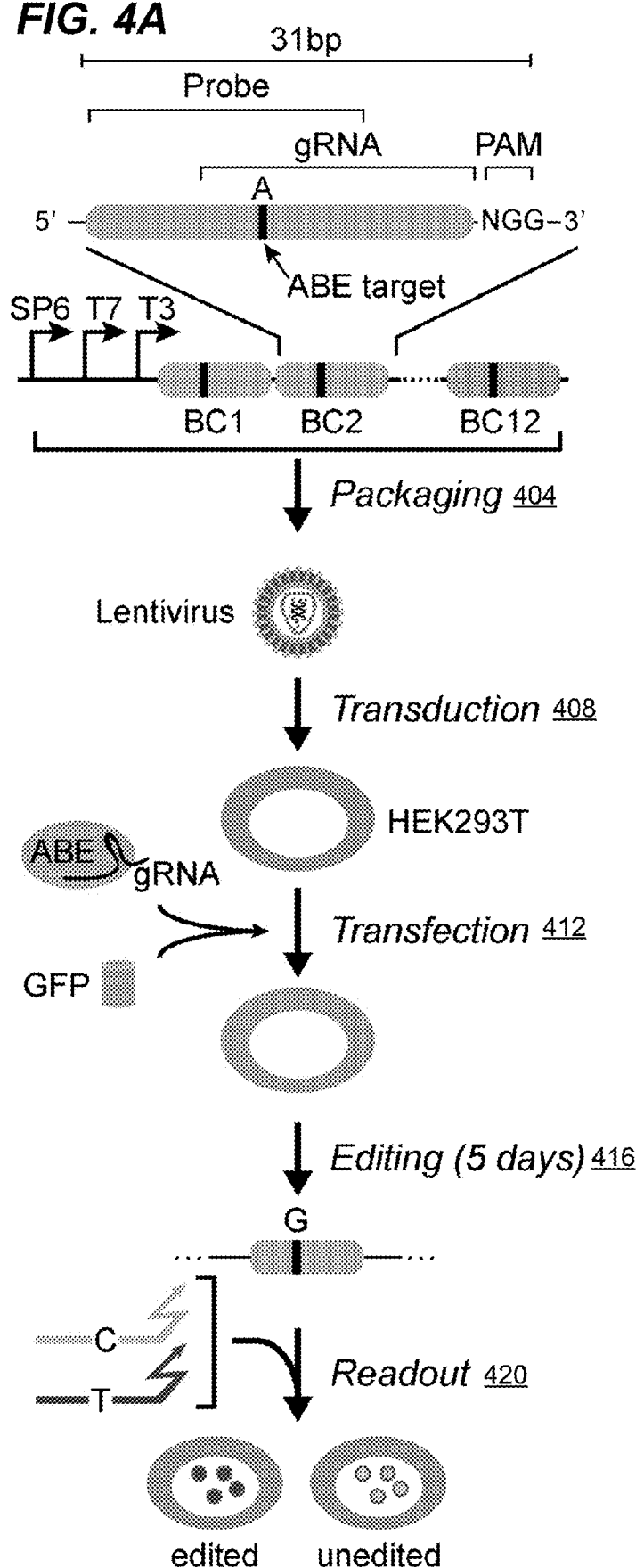

FIG. 4A. Arrays of 12 barcodes were designed so that, in each barcode, a single base pair (black vertical line) can be targeted by the adenine base editor (ABE) and a gRNA. The barcode arrays were packaged in lentivirus at 404 and transduced into HEK293T cells at 408. ABE7.10, gRNA, and a fluorescent co-transfection marker (e.g., GFP), were transiently delivered as DNA into the cells at 412, and editing was allowed to occur for 5 days at 416. Finally, cells were fixed, treated with T3 RNA polymerase and read out by competing probes for original (orange) and edited (red) base variants at 420.

FIG. 4B. Two designs of the memory array. Design 1 allows each barcode to be edited independently by a distinct gRNA, whereas all barcodes in design 2 are targeted by the same gRNA, providing more memory states for an individual gRNA. In both designs, the state of each individual barcode can be readout in situ, using Zombie.

FIG. 4C. Representative images, for design 1 (left) and design 2 (right), showing a mixture of edited (red) and unedited (yellow) active sites. Since barcodes are delivered by lentiviral transduction, cells can carry multiple copies of the barcode in their genome. The experiment was independently repeated twice with similar results. Scale bar is 10 μm.

FIG. 4D. Each barcode in design 1 (left) can be addressed independently using its corresponding gRNA. 2×2 matrices show results of targeting distinct barcodes. Edits are seen at the targeted barcode but not the adjacent non-targeted barcode. In contrast, design 2 gRNA (right) can edit all barcodes. The experiment was independently repeated twice with similar results. Scale bar is 3 μm.

Figure 4E:
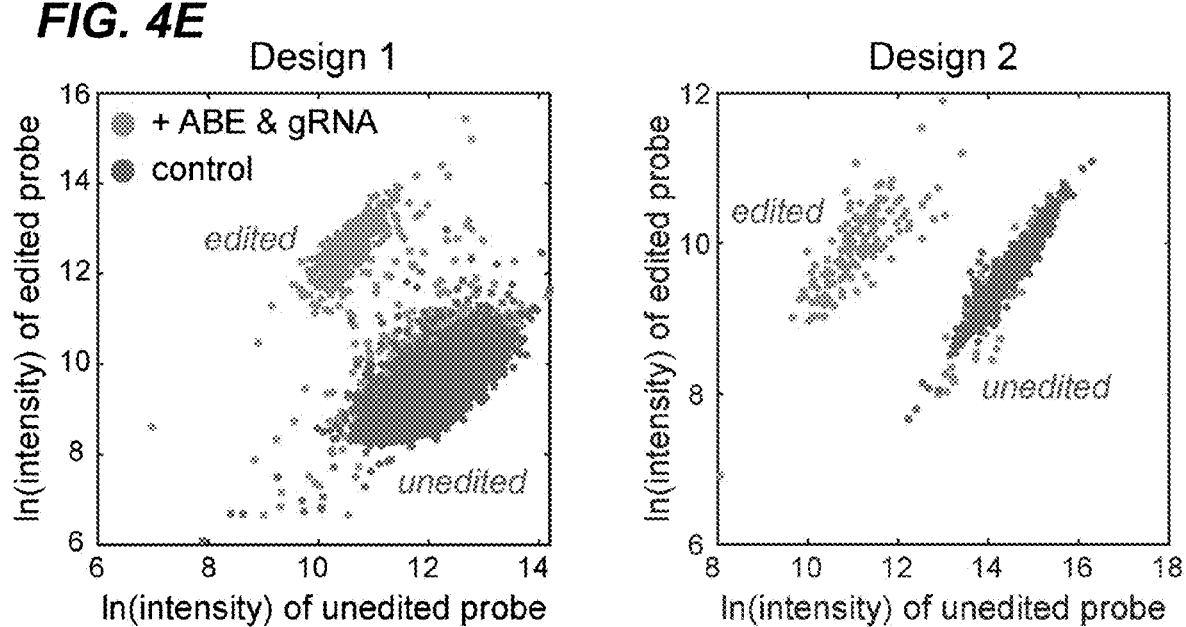

FIG. 4E. Analysis of Barcode 1, Design 1 (left) and Barcode 10, Design 2 (right). Dots can be classified into distinct edited and unedited groups based on the signal intensity in edited and unedited channels. Scatter plots show the natural log of the intensity in edited versus unedited channels. Data from negative control samples (blue) are plotted on top of points from samples which received both ABE7.10 and gRNA plasmids. See FIGS. 16-17 for all barcodes in both designs.

Figure 4F:
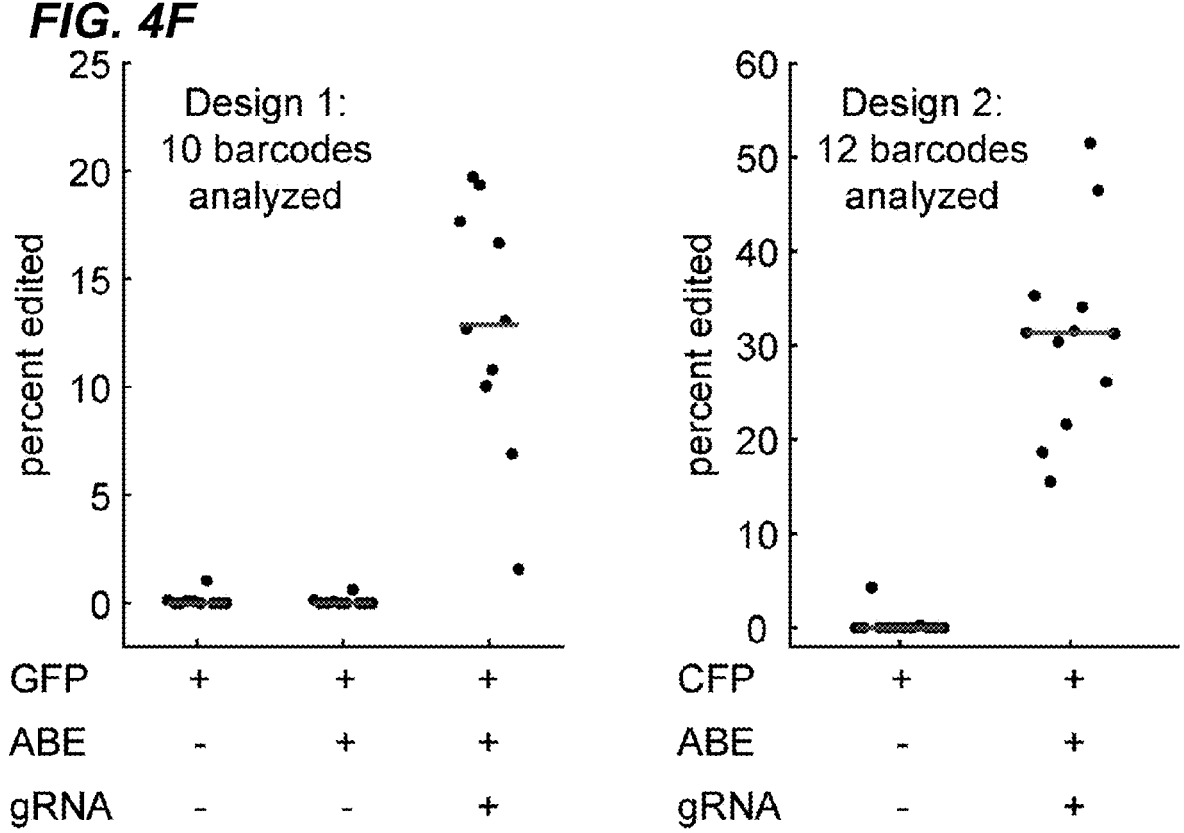

FIG. 4F. Edits are detected when both ABE and gRNA are present. Each point represents one barcode, red lines show the median. Without ABE and barcode-specific gRNA, only a very small fraction of active sites are mis-identified as edited, indicating low false positive rates across barcodes. Note that editing rates differ among barcodes (vertical scatter). On average 1357 and 383 active sites were analyzed for each barcode at each condition, for design 1 and 2, respectively.

FIGS. 5A-5H. Zombie can detect barcodes and discriminate single nucleotide variants in chick embryo and adult mouse brain.

FIG. 5A. The ZL1 construct includes a barcode downstream of phage promoters and a human Ubiquitin C promoter (hUbi) controlling GFP expression to allow identification of transduced cells. ZL1 was packaged in lentivirus at 504 and injected into the olfactory bulb of a 3-month old mouse at 508a or chick neural tube at embryonic stage HH10 at 508b. Chick embryos were incubated for 3 days post-transduction, until stage HH27, at 512a and then frozen and sectioned for analysis of the neural tube at 516a. Mouse brains were frozen and sectioned 3 days post-transduction at 512b to analyze olfactory bulb at 516b. Both samples were then fixed, treated with T7 RNA polymerase, probed, and imaged at 520.

FIG. 5B. In coronal sections through the diencephalon of chick embryos, distinct active sites (arrowheads) were observed with, but not without, transcription by T7 RNA polymerase. Similarly, Zombie active sites could also be detected, in a T7 dependent manner, in the granular cell layer of the olfactory bulb (arrowheads). Although the expression of GFP, detected by HCR, was sparse (arrows), the injection site could still be identified. All experiments were repeated on at least 3 sections with similar results. (C) To test for detection of single base pair mismatches in mouse and chicken tissue sections, samples were hybridized with match and mismatch probes (pink and green, respectively). A reference probe independently identified the active sites.

FIGS. 5D-5E. In both chicken and mouse samples, fluorescent signal at active sites was dominated by the match probe, regardless of channel assignments (columns). Match probes also co-localized with reference channels (bottom rows), indicating competition between match and mismatch probes does not reduce overall detection efficiency. All experiments were repeated on at least 3 sections with similar results. Since barcodes are delivered by lentiviral injection, cells can carry multiple copies of the barcode in their genome. Scale bars are 10 µm.

Figure 5F:
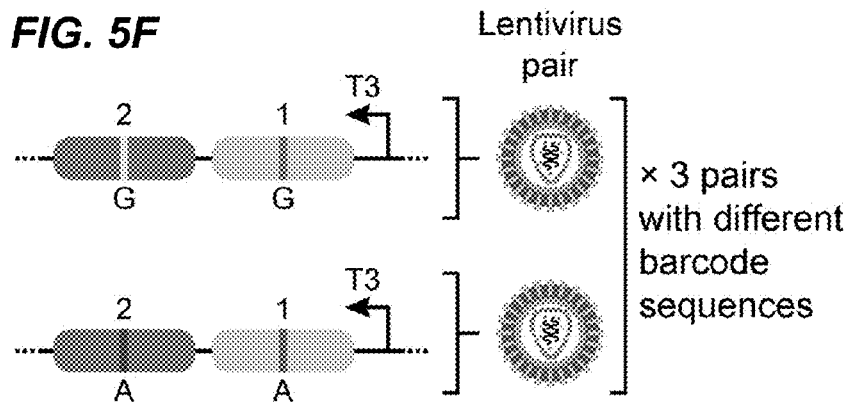

FIG. 5F. Pairs of barcoded lentiviral vectors were used to further assess the SNV detection capability in vivo. Each virus contains two distinct 20 bp barcodes, denoted by 1 and 2. Within a pair, viruses have variants of these barcodes that differ with each other at only one base pair (A or G). A mix of three viral pairs, with different barcode sequences but the same SNV arrangement, was co-injected in the mouse olfactory bulb and read out in three rounds of hybridization and imaging, 12 days post-transduction.

Figure 5G:
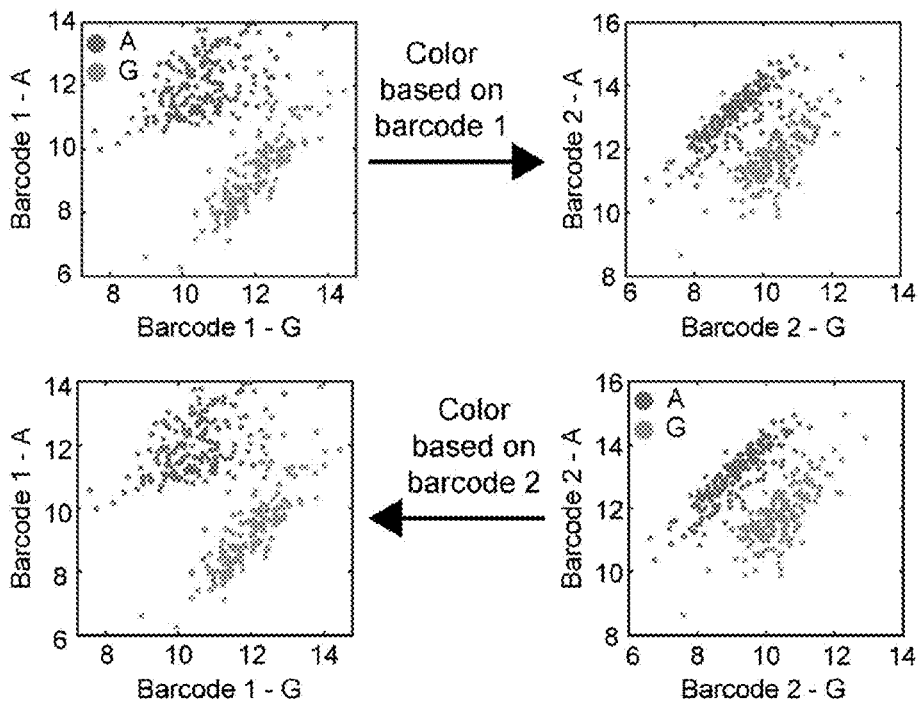

FIG. 5G. Scatter plots showing natural log of signal intensity for two variants (A and G) of two barcodes (1 and 2) for lentivirus pair 1 (see FIG. 19 for the other pairs). Each point represents one active site. The points are color coded based on their barcode 1 state (top) or barcode 2 state (bottom) to show the concordance between the detected state of two barcodes.

Figure 5H:
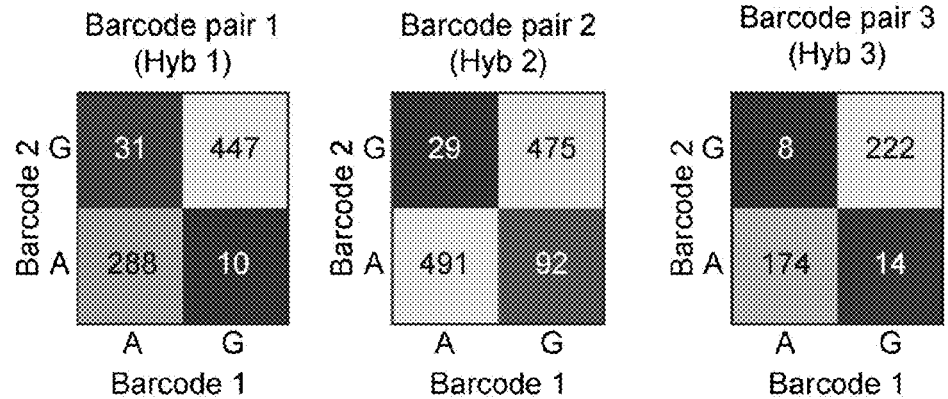

FIG. 5H. In all pairs, the majority of active sites are classified as either A or G for both barcodes. Data are combined from two biological replicates.

FIGS. 6A-6D. In situ readout of a combinatorial barcode library.

Figure 6B:
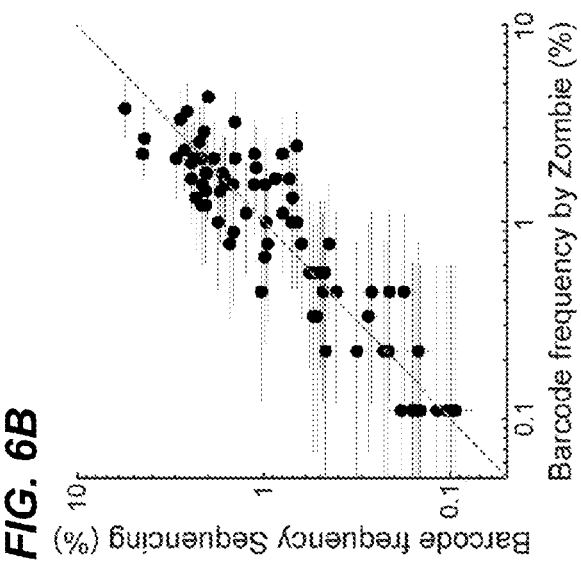
Figure 6A:
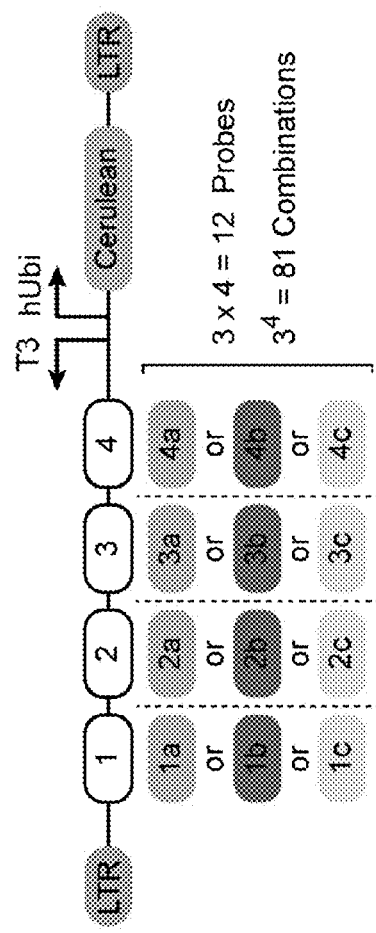

FIG. 6A. A combinatorial lentiviral library in which each of 4 positions can take one of three distinct position-specific 20 bp barcodes to generate 81 possible barcode combinations. The viruses also encode Cerulean downstream of hUbi promoter.

FIG. 6B. The frequency at which barcode combinations are detected in situ, in transduced HEK293T cells, is consistent with the frequency measured by next generation sequencing. Each point represents one barcode combination. 906 active sites were analyzed by Zombie. Error bars are 95% binomial confidence intervals, calculated using Clopper-Pearson method. Since the number of observations by imaging (906 active sites) is lower than the sequencing read count (102056 aligned reads), the horizontal error bars are wider than the vertical ones.

FIG. 6C. Detection of two clones of cells, labeled by two barcode combinations, in a coronal section of chick neural tube. Maximum intensity projected images corresponding to variants in each barcode position are merged in 3 color channels (cyan, magenta, and yellow, corresponding to A). Dots that do not appear consistently in all rounds are excluded from the analysis.

FIG. 6D. Examples of cells in developing chick cortex (i), pallidum (ii), and retina (iii) labeled with various barcode combinations (arbitrary colors). The inset shows the approximate location of the panels on a drawing of a coronal section through chick neural tube and indicates dorsal (D) and ventral (V) directions. For FIGS. 6C and 6D, two embryos were analyzed. 39 out of 81 barcode combinations were identified in one embryo by analyzing 44 images acquired from 10 sections. In the other embryo, 20 distinct barcode combinations were identified in 11 images acquired from 6 consecutive sections. Scale bars are 25 m.

FIGS. 7A-7D. Zombie active sites are only found in the cells where they are made, whereas the individual transcripts can diffuse away and be detected in cells other than their cell of origin.

Figure 7A:
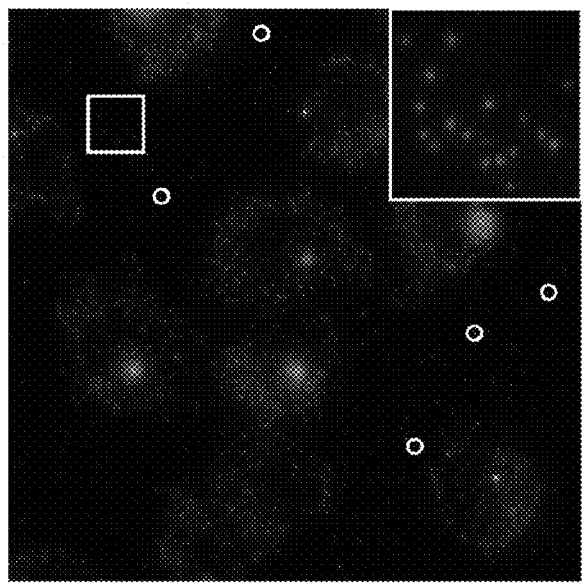

FIG. 7A. Co-culture of mES-Z1 cells with non-transgenic parental cells. Active sites are only found in CFP+ cells. However, small diffraction limited dots are found in all cells including the non-transgenic ones.

Figure 7B:

FIG. 7B. Same image as A, but with blue and cyan channels turned off for better visibility of the barcode signal. A few examples of individual barcode transcripts are marked by circles. The inset shows a magnified and contrast adjusted view of a CFP negative cell, marked by the square, which contains some small barcode dots, indicating diffusion of individual RNA molecules from the cells in which they are produced.

Figure 7C:
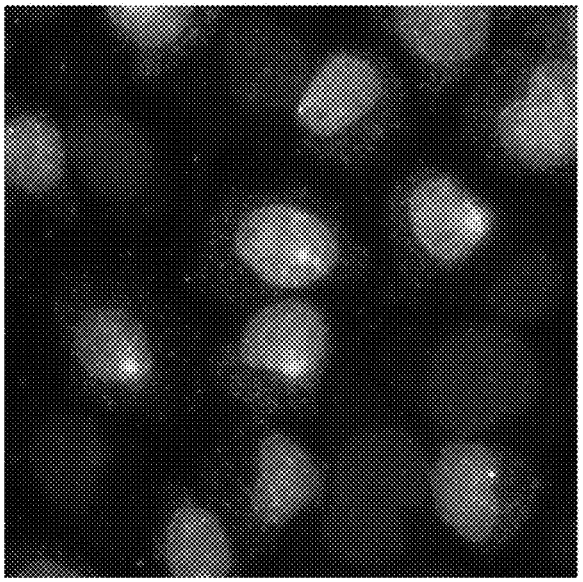

FIG. 7C. In the absence of any transgenic cells, background non-specific signal is low. Indicating that the signal observed in the presence of transgenic cells is not non-specific HCR amplification.

Figure 7D:
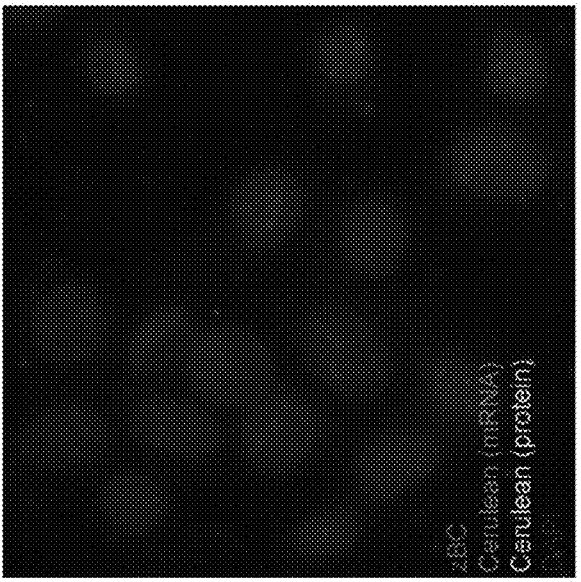

FIG. 7D. Same image as FIG. 7C, but with blue and cyan channels turned off to make the lack of small dots more evident. The experiments were independently repeated three times with similar results. Scale bar is 25 m.

Figure 8:
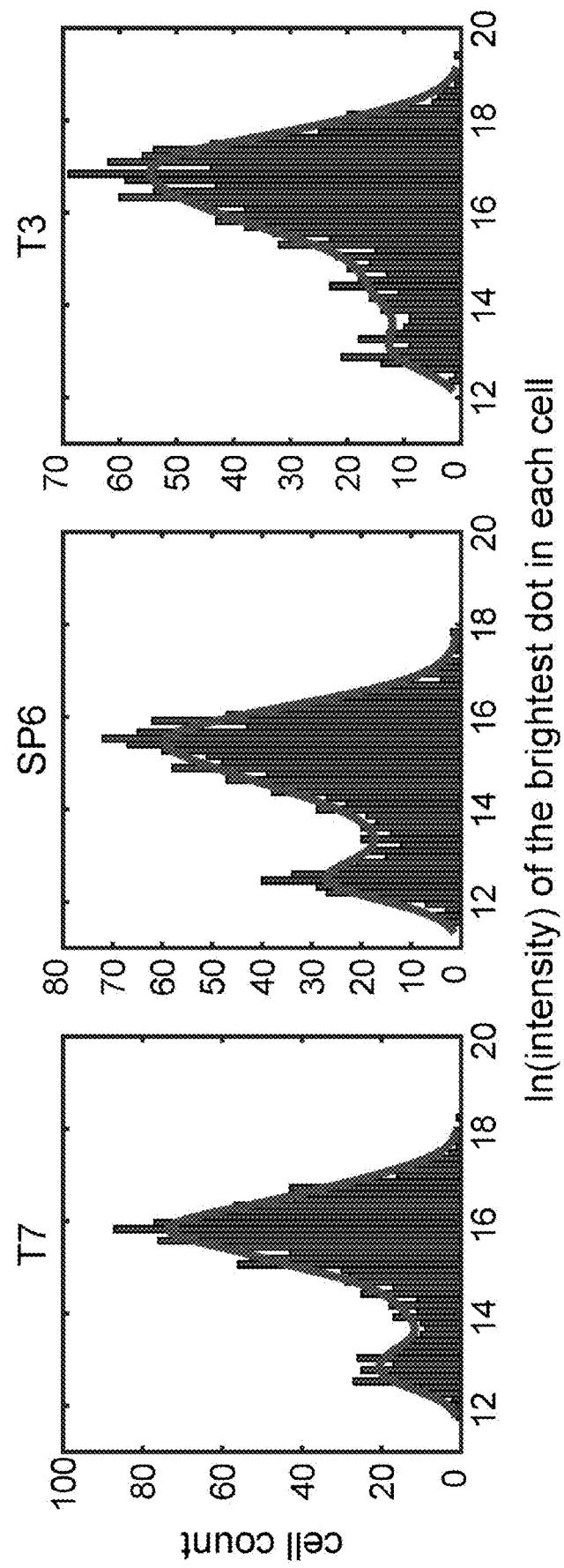

FIG. 8. Histogram of intensity for the brightest dot in each cell shows bimodal distribution, consistent with presence or absence of active sites in the cells.

Figure 9:
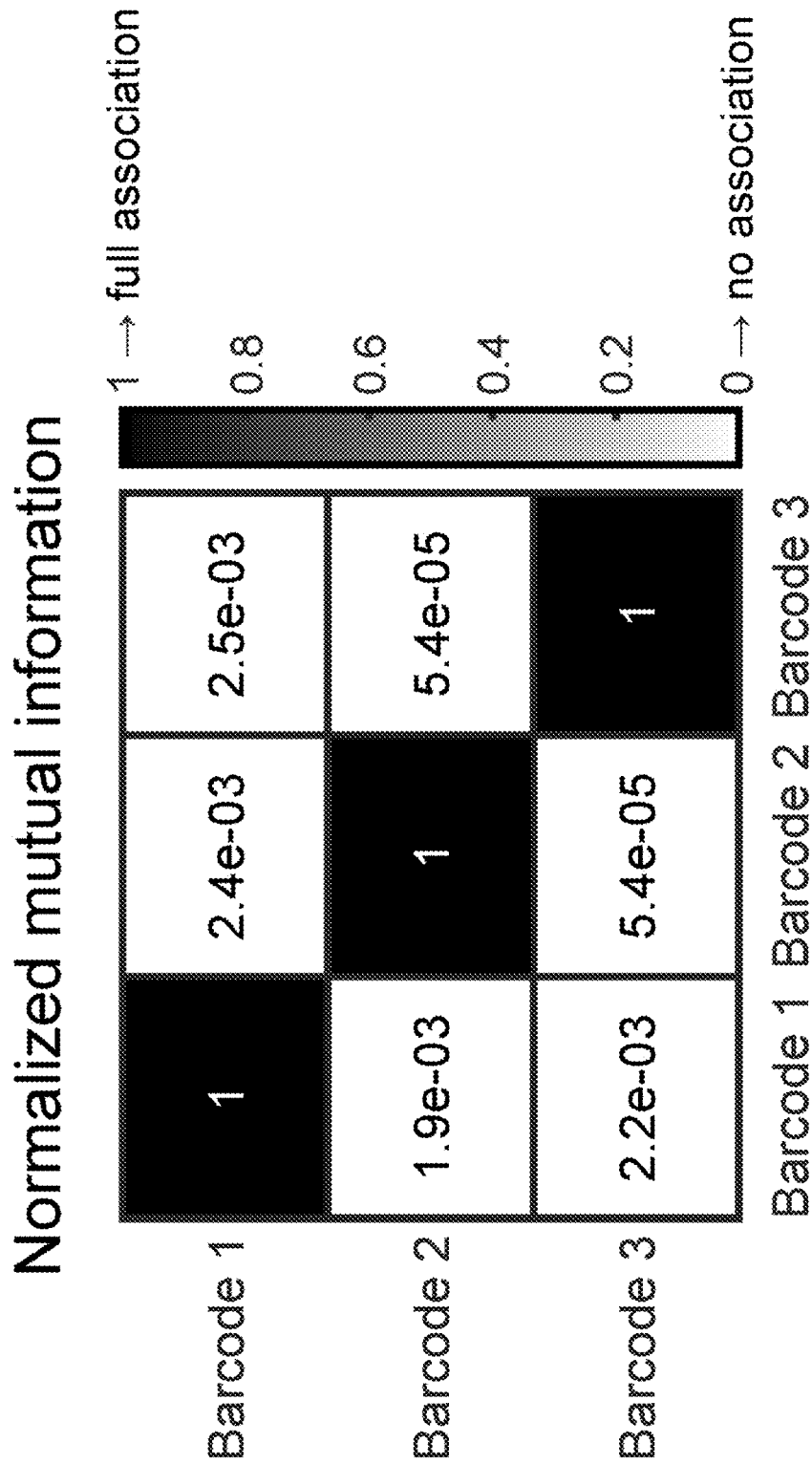

FIG. 9. Mutual information analysis of pairwise correlations between Z3 barcodes. Diagonal elements are set to 1 by definition. Off-diagonal elements represent normalized mutual information (i.e. uncertainty coefficient) between detection of indicated barcode pairs. Low values are consistent with independent detection. For each pair of barcodes, detecting one at a given site does not significantly alter the probability of detection of the other (chi-square test, p>0.1). Total of 564 cells were analyzed.

Figure 10:
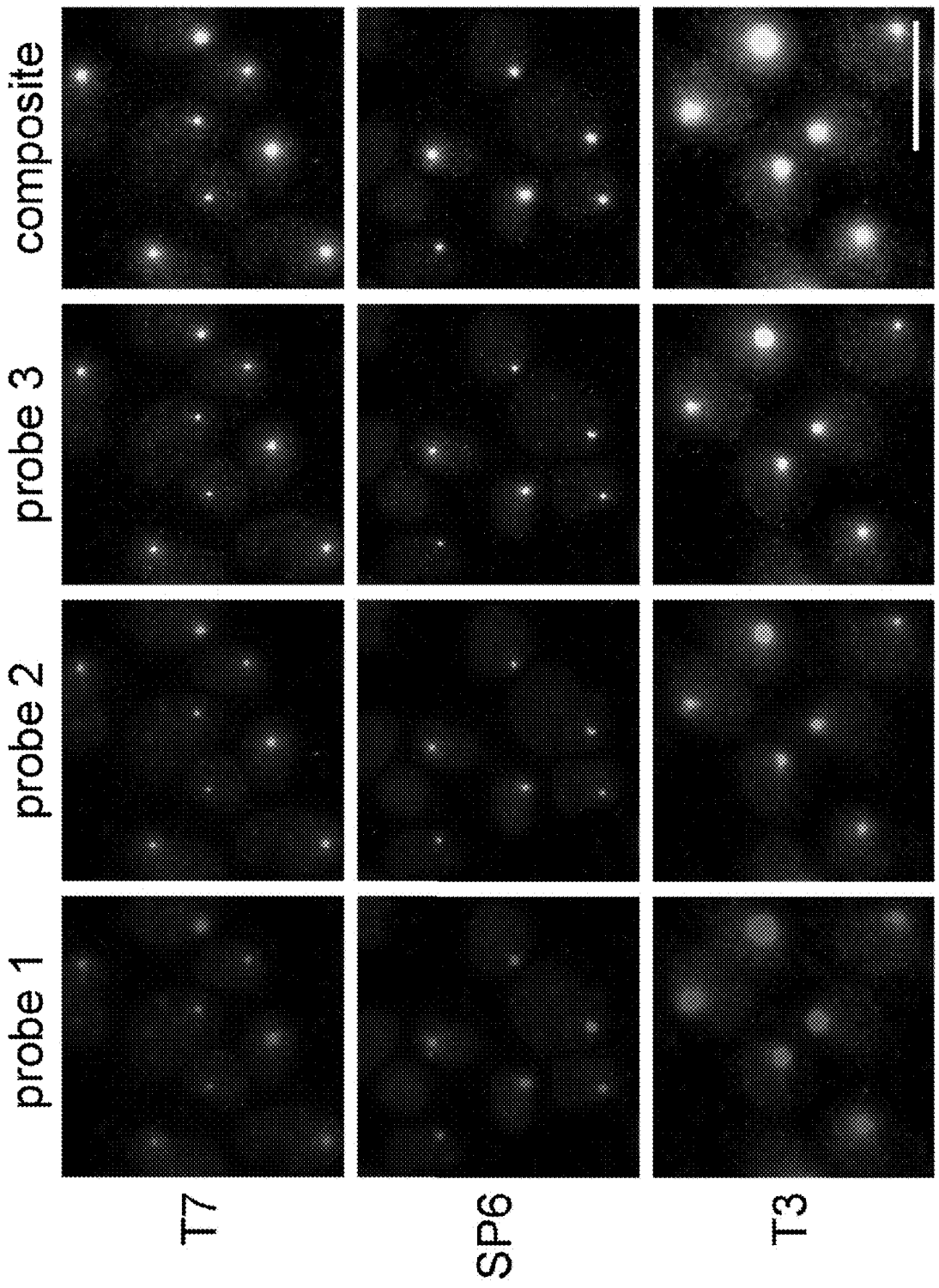

FIG. 10. Reliable detection of 20 bp targets with individual HCR probes. Images show same treatment as in FIG. 2B, except with HCR amplification. Images are scaled to different intensity ranges compared to FIG. 2B. The experiment was independently repeated three times with similar results. Scale bar is 25 µm.

Figure 11:
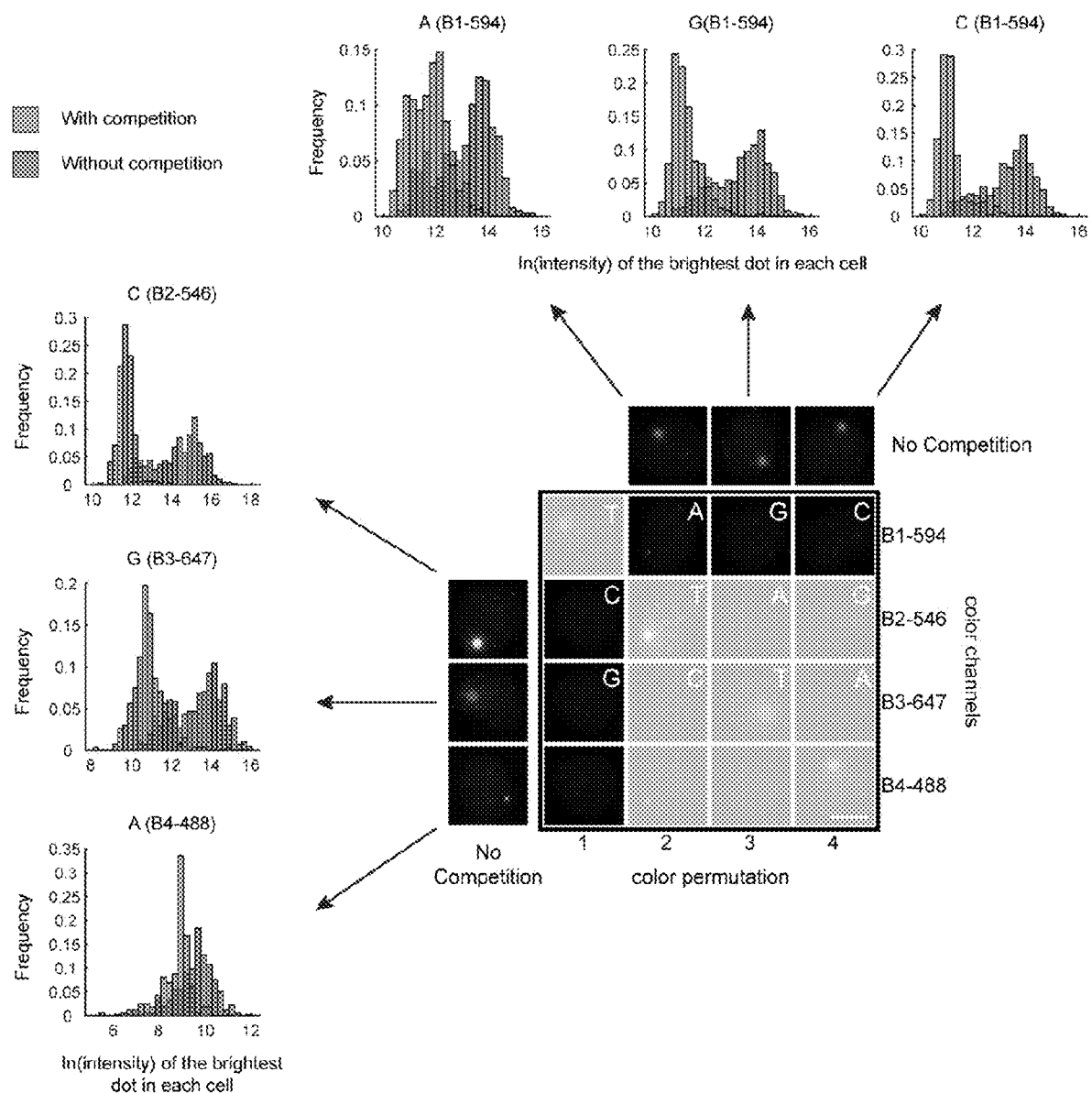

FIG. 11. In the absence of competition, probes with a single mismatch can bind to their targets in the active site and generate significant fluorescent signal. The signal from probes with a single mismatch (A, G, or C) is minimal when they are hybridized together with a match probe (T) in an equimolar mixture (FIG. 3C, reproduced here in the box with the panels not relevant to the current experiment shaded). However, when hybridized individually, without competition, they generate considerable signal in the active sites. Representative images are shown outside the box, next to their corresponding condition. All images were acquired and processed under the same conditions for each channel. Histograms show the distribution of signal intensity (natural log of the intensity of the brightest dot in each cell) for the mismatch probes in the presence and absence of competition. Total of 2374 cells were analyzed for the no competition conditions, with at least 295 cells for each condition.

The bimodal distributions, in the absence of competition, reflect a subset of cells with bright active sites. This background signal is largely reduced in the presence of competition. These results suggest that probe competition is necessary for discrimination of single nucleotide variants.

Figure 12:
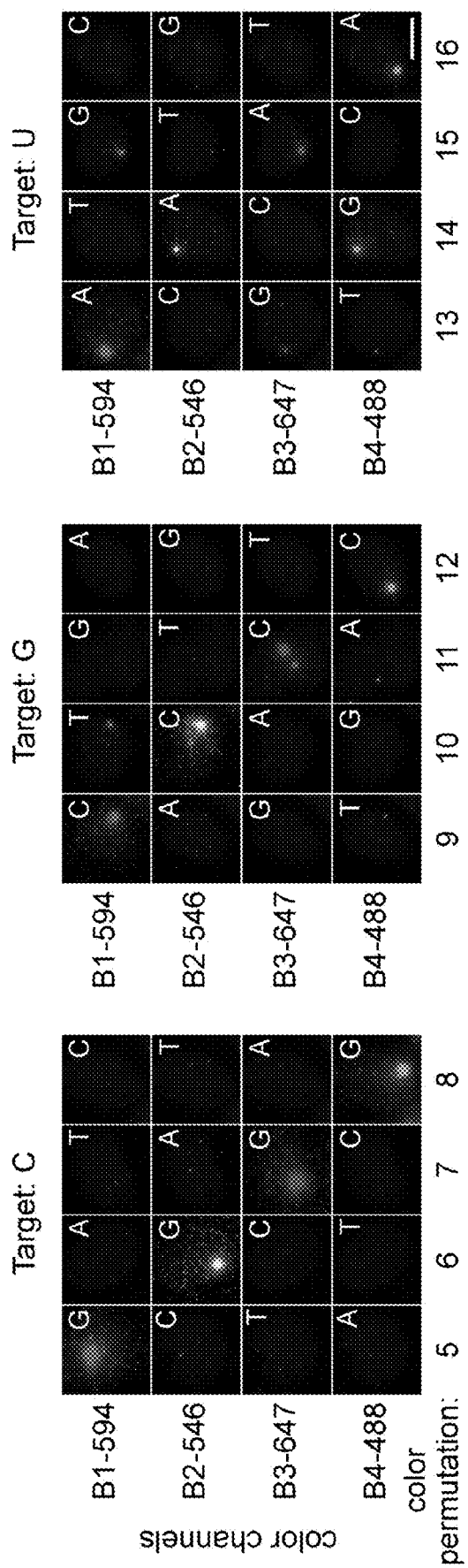

FIG. 12. Representative images showing discrimination based on a single nucleotide mismatch. All images are acquired under the same conditions, and brightness for each channel is adjusted identically across all the images. Each column represents one experiment in which four probes with a single nucleotide variation and orthogonal HCR initiators (B1, B2, B3, and B4) were mixed and hybridized to the sample. The identity of the variable nucleotide is shown by the letter on the panels. HCR initiators and the fluorescent channels used for each probe are shown next to the rows. See FIG. 3D for quantification of the results. Scale bar is 10 am.

Figure 13:
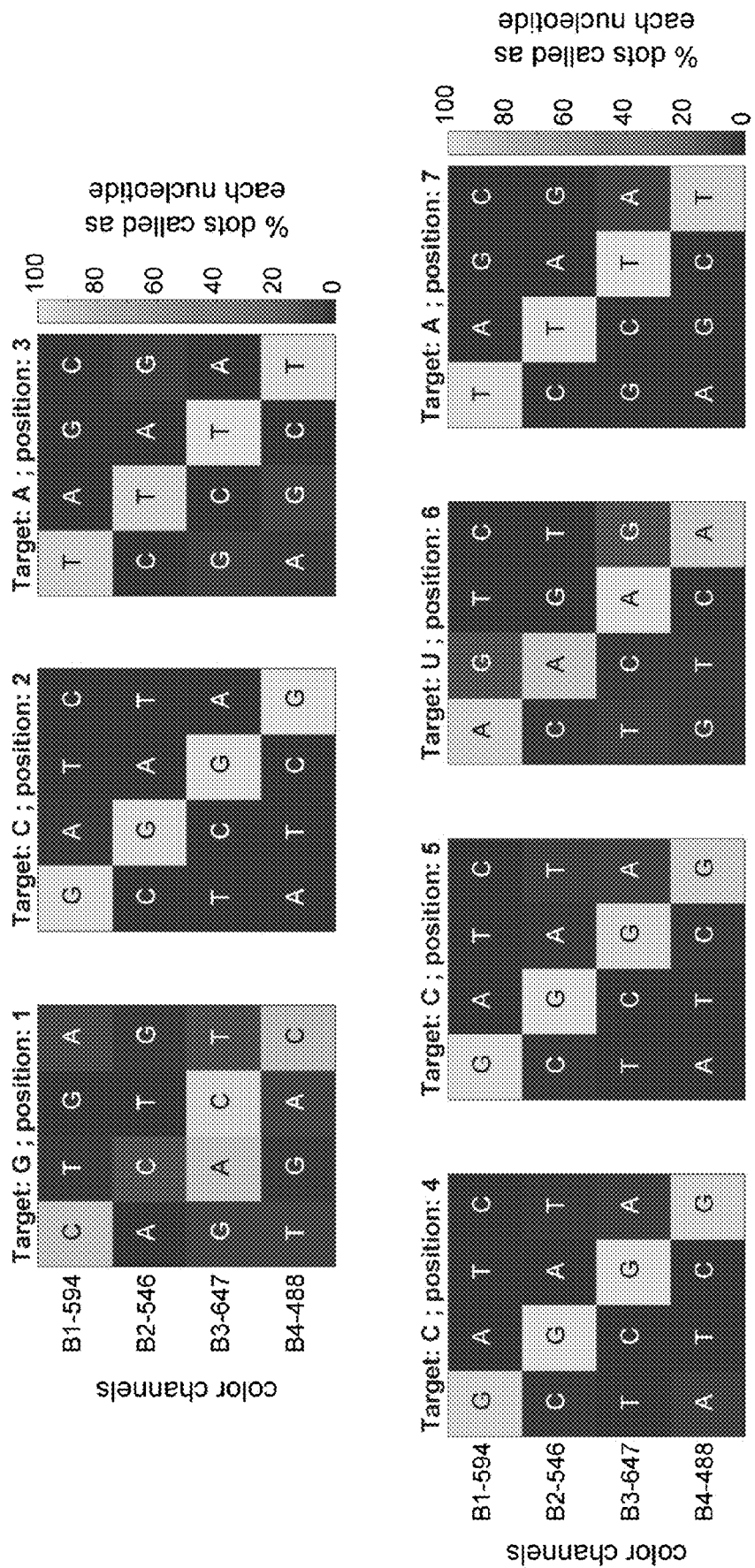

FIG. 13. SNV detection is robust to the position of the variant base pair in the barcode sequence. Matrices represent SNV analysis, as in FIG. 3D, with four distinct color permutations, with the indicated target nucleotide at positions 1 through 7 (starting from the 5' end of the probe). Accurate discrimination can be achieved for positions 2 to 7. Even position 1 provides discrimination ability. Total of 9364 cells were analyzed, with at least 234 cells for each permutation.

Figure 14:
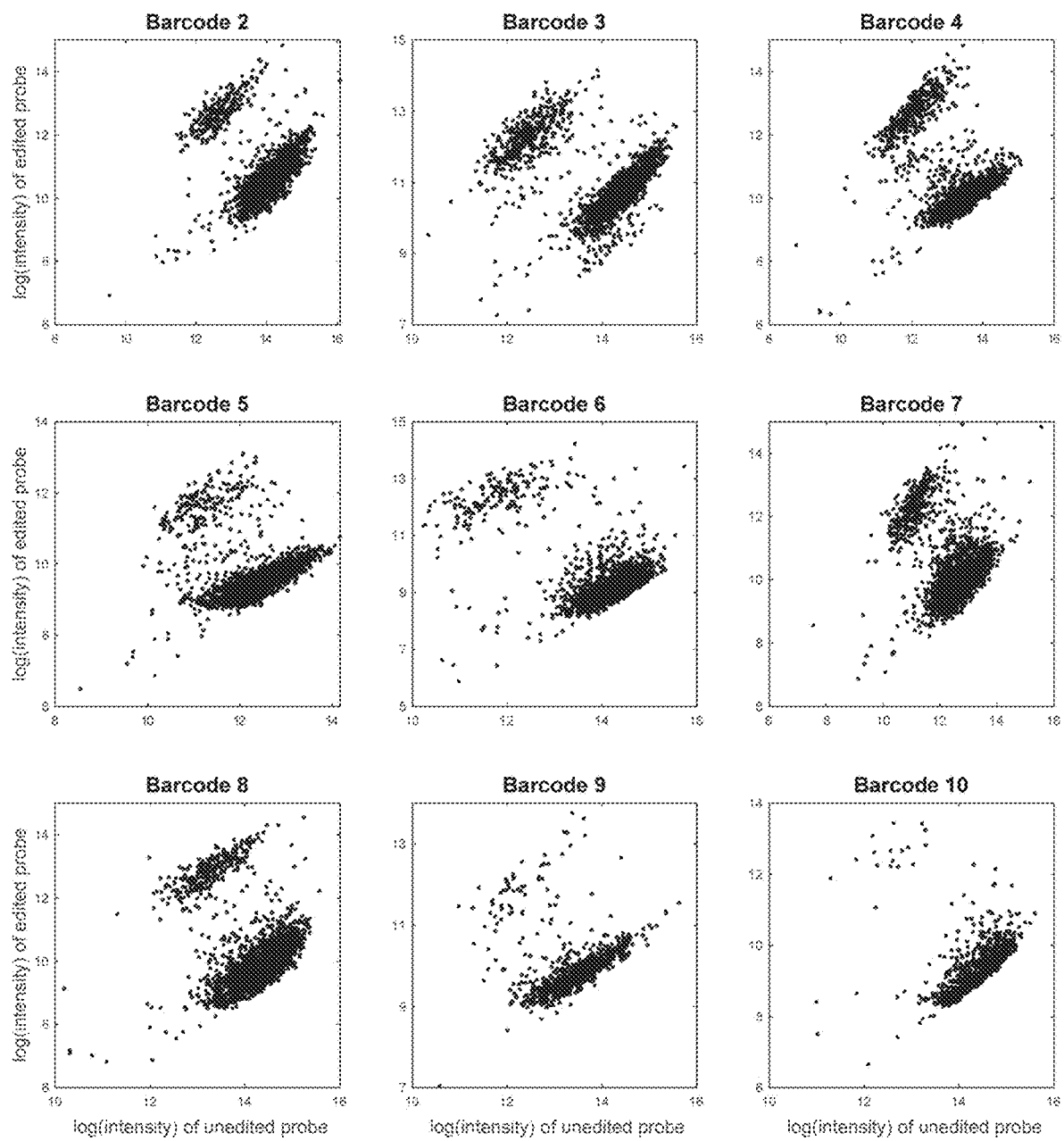

FIG. 14. Edited and unedited barcodes can be distinguished based on the signal intensity of the competing probes. The barcodes in the synthetic memory unit can be edited upon transfection with ABE and their corresponding gRNA. For each active site, signal intensity of probes detecting edited versus unedited state was quantified. The scatter plots show two distinct groups for each barcode, representing the edited and unedited states.

FIG. 15. Bootstrap analysis of active site classification. For each barcode, boxplots show the fraction of active sites that were classified differently when the data were resampled with replacement. The central red line in each box indicates the median, across 5000 bootstrap rounds, and the bottom and top edges of the box indicate the 25th and 75th percentiles, respectively. The whiskers extend to the most extreme data points not considered outliers. Red lines at zero, in design 2, indicate that no dots changed their classification.

Figure 16A:
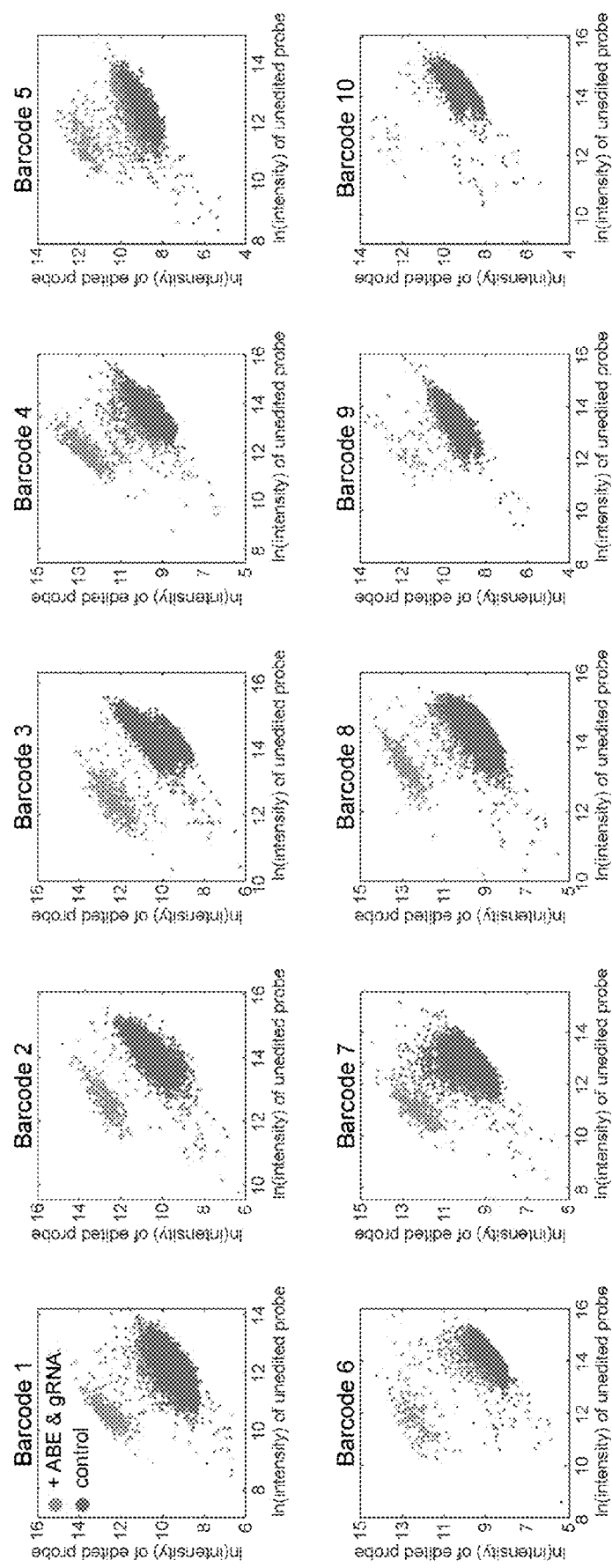
Figure 16B:
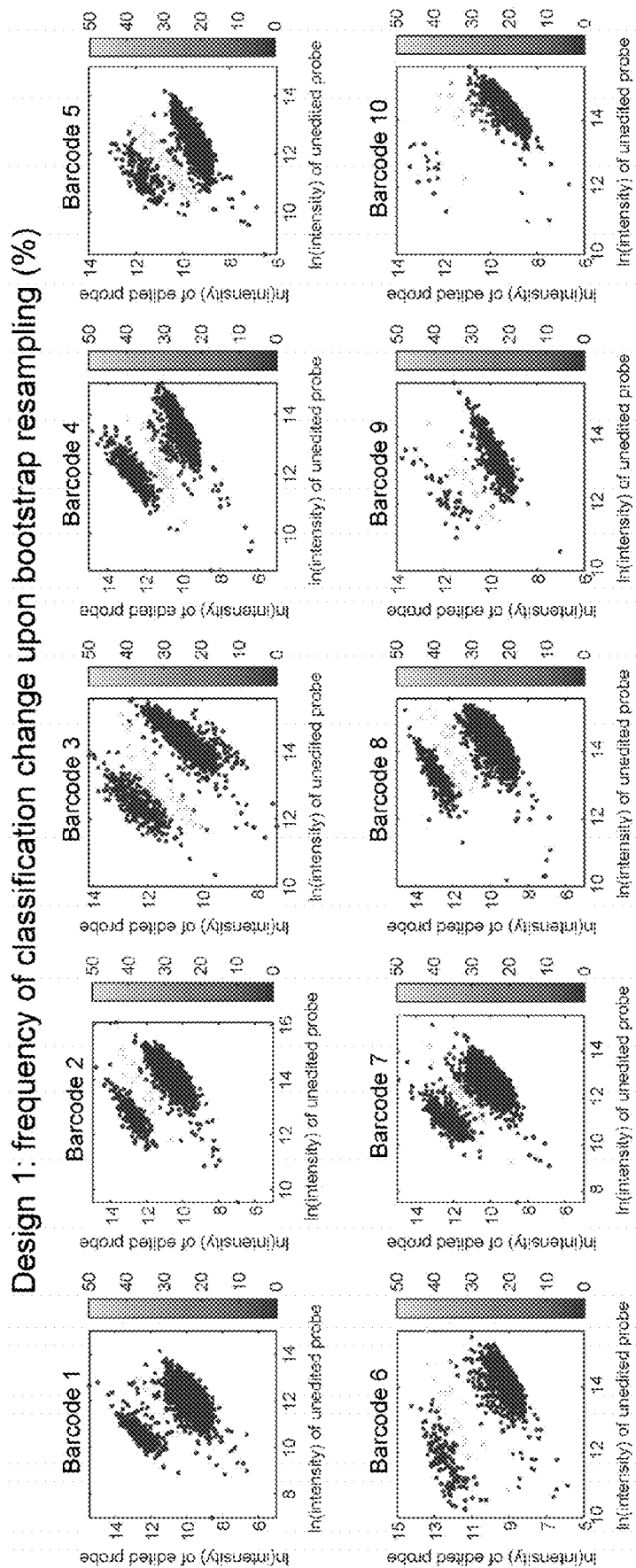

FIGS. 16A-16B. Design 1 barcodes can be classified based on signal intensity in edited and unedited channels.

FIG. 16A. Scatter plots show natural log of signal intensity in the edited (y-axis) versus unedited (x-axis) channels for each barcode. Negative controls lacking ABE and gRNA (blue) are superimposed on samples transfected with all components (orange). Edited (upper orange cloud) and unedited (lower blue cloud) active sites are broadly distinguishable.

FIG. 16B. Natural log of signal intensity in edited versus unedited channels color coded based on the frequency (%) by which classification of each dot, as edited or unedited, is changed across 5000 rounds of bootstrap resampling. All points here are from samples transfected with GFP, ABE, and the gRNA of the specified barcode.

FIGS. 17A-17B. Design 2 barcodes can be classified based on signal intensity in edited and unedited channels.

FIG. 17A. Scatter plots show natural log of signal intensity in the edited (y-axis) versus unedited (x-axis) channels for each barcode. Negative controls lacking ABE and gRNA (blue) are superimposed on samples transfected with all components (orange). Edited (upper orange cloud) and unedited (lower blue cloud) active sites are broadly distinguishable.

FIG. 17B. Natural log of signal intensity in edited versus unedited channels color coded based on the frequency (%) by which classification of each dot, as edited or unedited, is changed across 5000 rounds of bootstrap resampling. All points here are from samples transfected with CFP, ABE, and the gRNA of the specified barcode.

Figure 18:
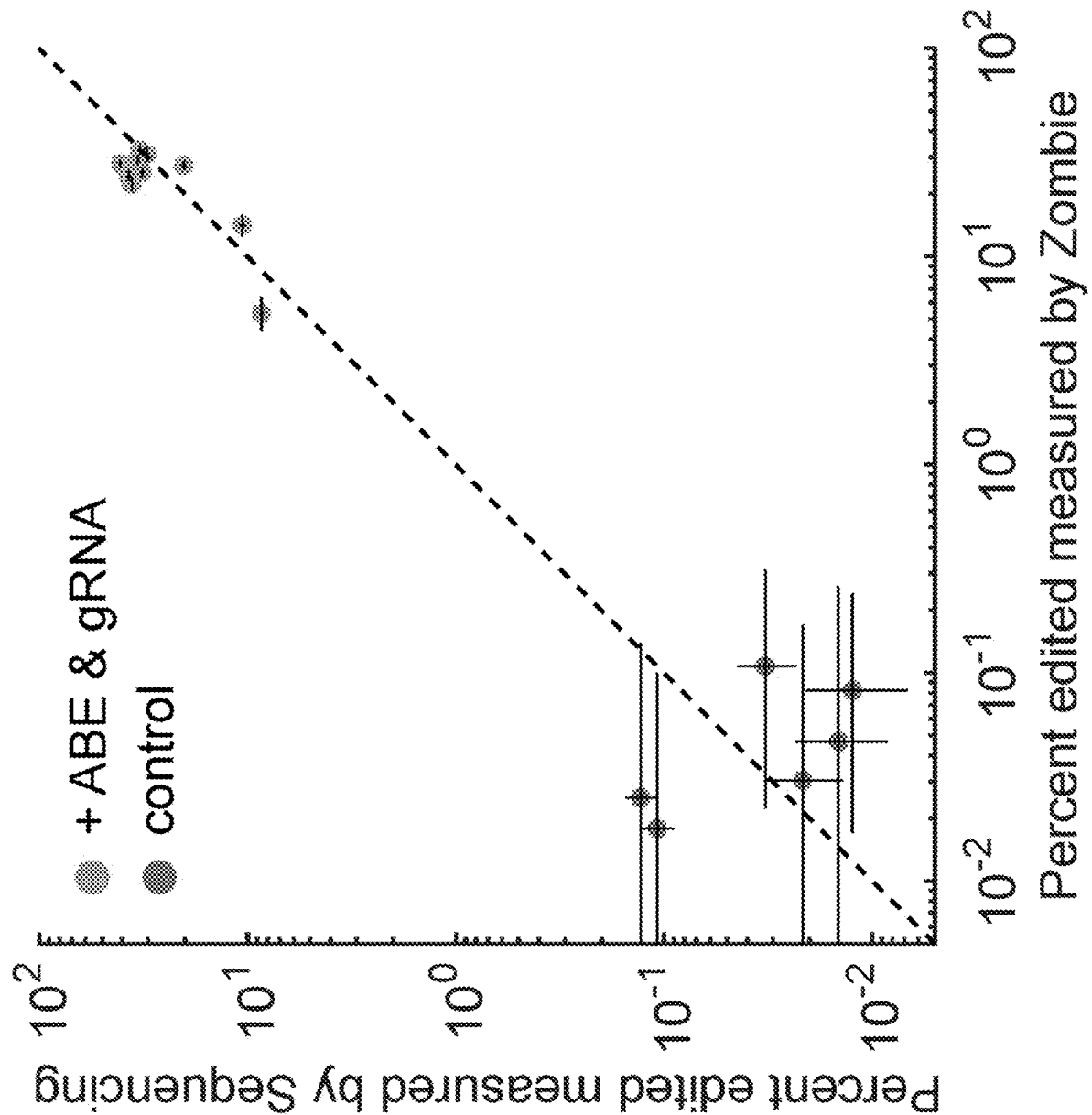

FIG. 18. Edit frequencies measured by Zombie are similar to those measured by next generation sequencing. HEK293T cells containing multiple integrations of lentivirally delivered design 1 memory array were transiently transfected with plasmids for ABE7.10, a barcode specific gRNA, and CFP (orange points). As negative control, a separate group with CFP but not ABE7.10 and gRNA was also transfected (blue points). 5 days after transfection, some cells from each group were analyzed by Zombie, similar to FIGS. 4A-4F, and the rest were analyzed by next generation sequencing (see methods). No edits by Zombie was detected in four negative control samples (not plotted). Error bars are 95% binomial confidence intervals, calculated using Clopper-Pearson method. Number of active sites analyzed by Zombie were 4251, 1237, 2910, 3466, 4883, 3742, 3095, 2465, 1501, and 1991 for barcodes 1 through 10, respectively, in ABE and gRNA positive condition (orange) and 3650, 3293, 4496, 5508, 5347, 3986, 5605, 5020, 2790, and 2142 for barcodes 1 through 10, respectively, in the control condition (blue).

Figure 19:
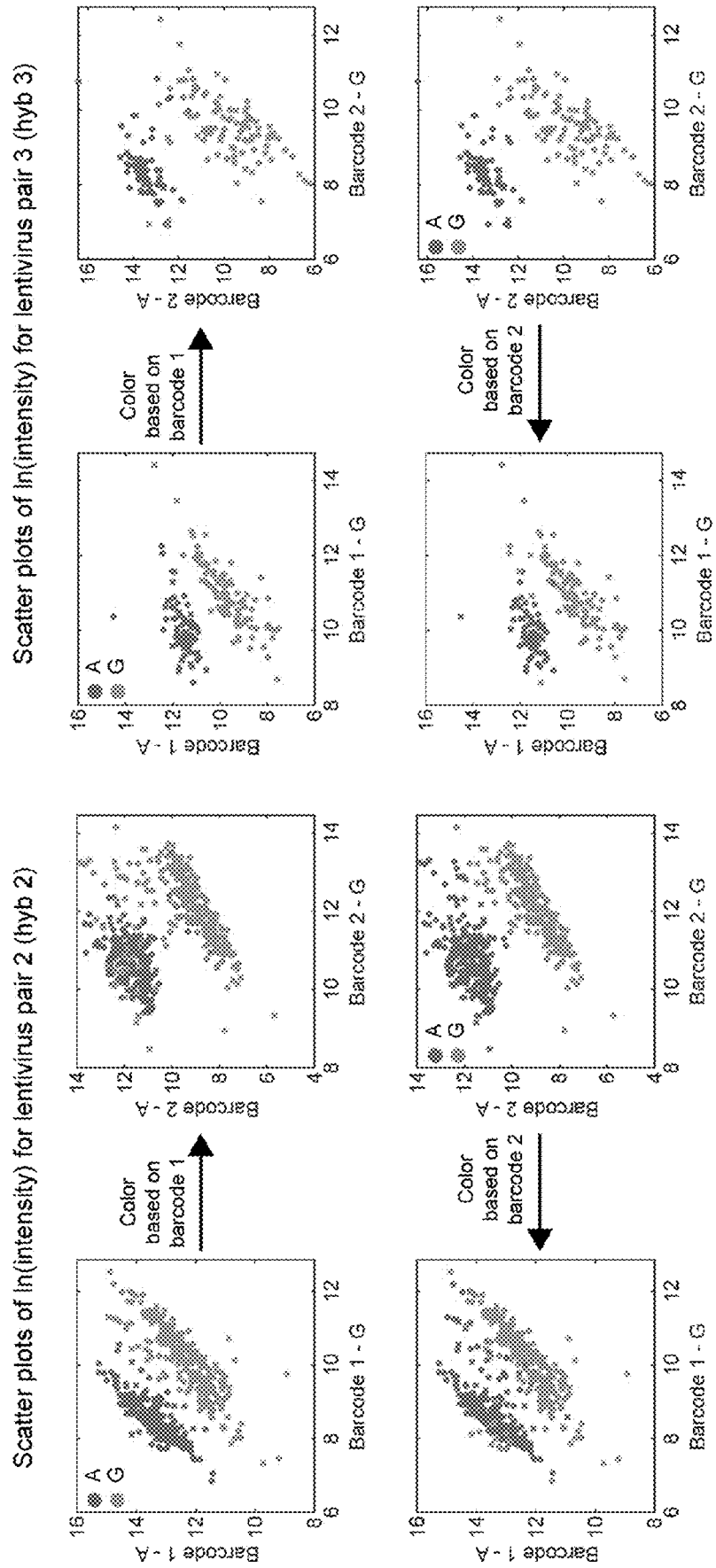

FIG. 19. Zombie accurately discriminates barcodes with single nucleotide variations in mouse brain tissue. Scatter plots showing natural log of signal intensity for two variants (A and G) of two barcodes (1 and 2), as in FIG. 5G, for lentivirus pairs 2 (left) and 3 (right). Each point represents one active site. The experiment was performed on brain sections from two mice. Biological duplicates showed similar results.

FIGS. 20A-20D. Overlapping barcode integration sites can result in underestimation of Zombie SNV detection accuracy in mouse brain sections.

FIG. 20A. Correlation between two SNVs engineered in the same virus can be used to estimate SNV detection accuracy in tissue samples transduced by the viral mix (Schematic reproduced from FIG. 5F). The lentivirus pairs are designed so that each active site incorporates either an A in both barcodes 1 and 2, or a G in both barcodes.

FIG. 20B. Maximum intensity projection of a confocal stack shows transduced cells in a section of mouse olfactory bulb. Scale bar is 50 μm.

FIG. 20C. Injection of lentivirus mix into the olfactory bulb can result in the integration of multiple viral genomes, containing different barcodes, in the same cell. Imaging reveals multiple "GG" (arrows) and "AA" (arrowheads) integration sites in the same cell, which permit accurate classification.

FIG. 20D. In some cases, integration sites for two virus pairs overlap in the nucleus (dashed circle), leading to an erroneous SNV call. Upper and lower images are identical overlays of the four images in FIG. 20C, but the lower image also includes CFP fluorescence in gray. The experiment was repeated on two biologically independent samples with similar results. Scale bar is 5 μm.

Figure 21:
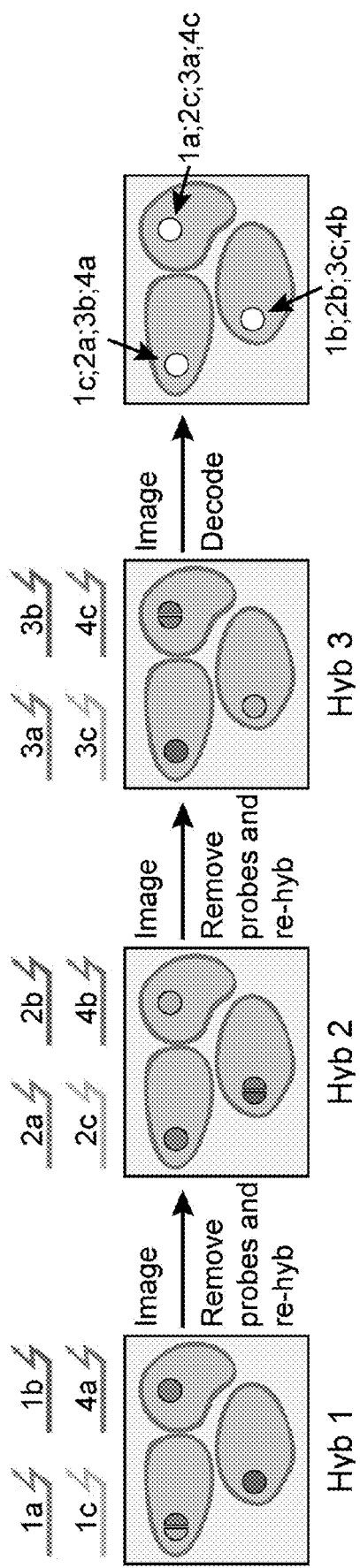

FIG. 21. In situ readout of a viral library with 81 combinations in three rounds of hybridization and imaging. In each round, tissue sections were analyzed using 4 probes, in distinct fluorescence channels, corresponding to three variants in one of the barcode positions 1, 2, or 3 and one variant in position 4 (see FIG. 6A for the design of the library). As a result, in each round, some active sites were visualized in two channels (shown as semi-circles in this illustration).

Information from images of all three rounds was then combined to decode the identity of each active site.

FIGS. 22A-22D. Zombie barcode detection is compatible with in situ detection of endogenous gene expression in tissue sections.

FIG. 22A. Maximum projected confocal images of an olfactory bulb section are tiled to show a larger field of view. The barcode was delivered by injection of a lentivirus that also expresses H2B-Cerulean under human UbiC promoter. Expression of Tbx21 and Tyrosine hydroxylase (Th) was visualized by HCR Fluorescence In Situ Hybridization (FISH). CFP is detected based on its native fluorescence, without any further staining.

FIG. 22B 1-22B2. Although there is a correlation between expression of CFP and detection of Zombie active sites, there are instances of cells with low or no CFP that have an active site (arrow), as well as those that show CFP expression but no active site (arrowhead). Without being bound to any particular theory, it is believed that the former is caused by lack of expression of CFP from the integrated viral genome (e.g., due to silencing) and the latter is indicative of imperfect barcode detection efficiency.

FIG. 22C-22D. magnified views showing Tbx21 (green) and Th (red) endogenous mRNA detected by HCR in two orthogonal channels. Four biological replicates showed similar results. scale bar is 200 µm.

Figure 23:
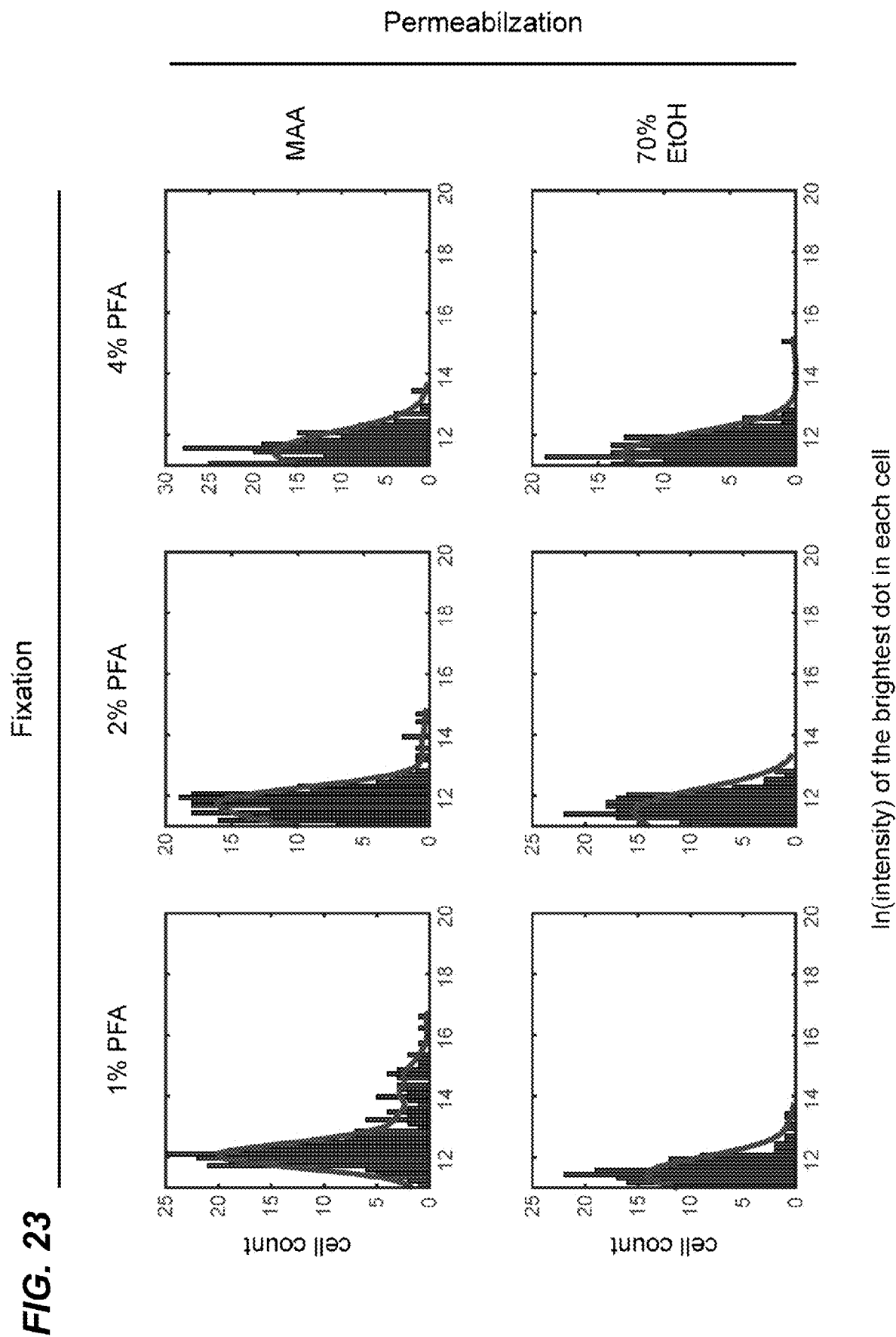

FIG. 23. Formaldehyde (PFA) fixation prior to in situ transcription results in a drastic decrease in detection efficiency. Histogram of intensity of the brightest dot in each cell is shown for different fixation and permeabilization conditions. Fraction of cells with active sites decreases significantly when cells are fixed by 1% PFA and permeabilized by 3:1 mixture of methanol and acetic acid (MAA). Fixation by 2 and 4% PFA leads to almost complete lack of Zombie active site in cells. For this reason, PFA fixation is not used prior to in situ transcription.

FIG. 24. Effect of transcription time and fixation on detection efficiency. Increasing transcription time from 15 min to 3 hours has a modest effect on transcription efficiency. However, fixing with MAA (3:1 mix of methanol and acetic acid) increases efficiency considerably compared to fixing with 100% methanol.

Figure 25:
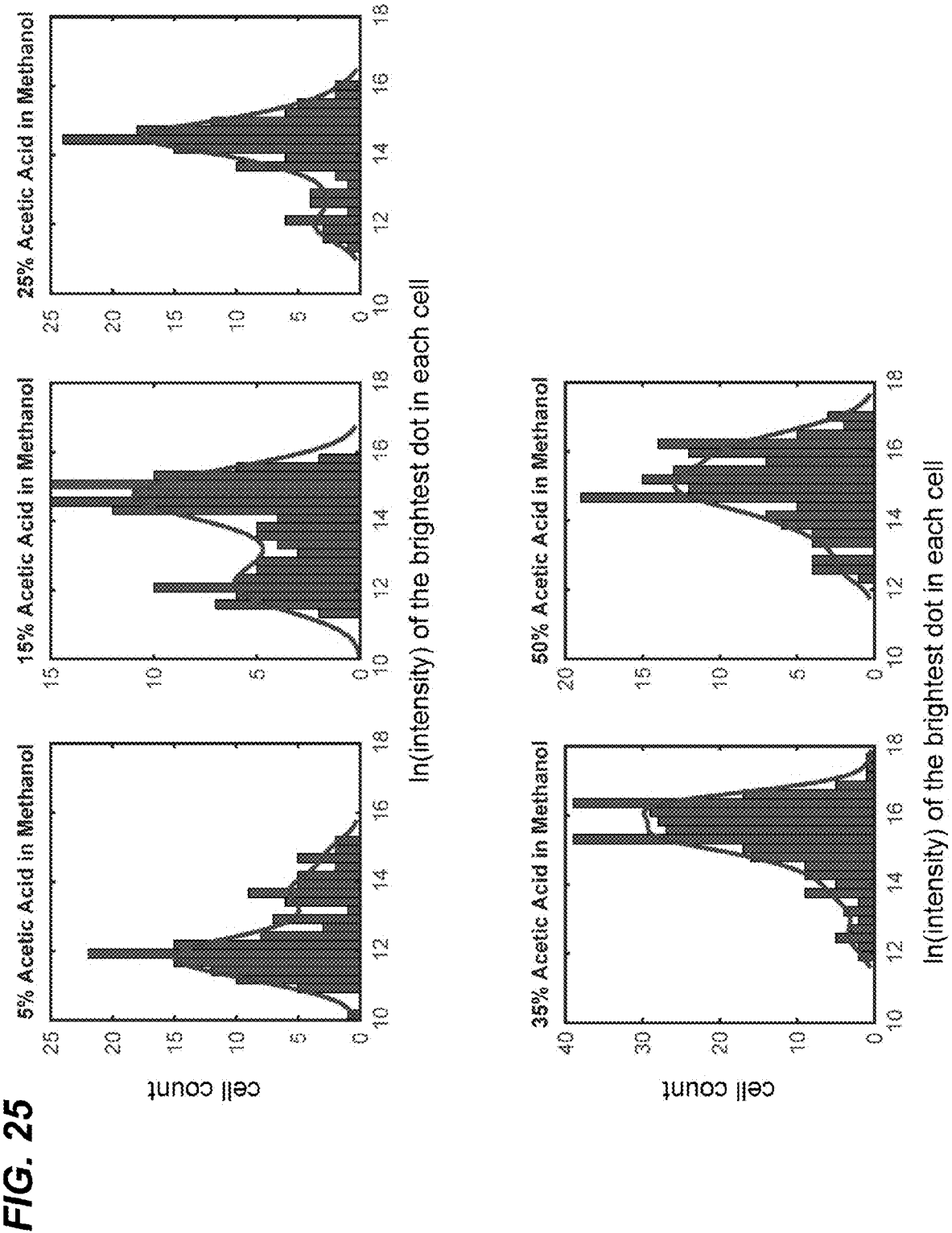

FIG. 25. The ratio of acetic acid to methanol in the fixation step prior to in situ transcription affects detection efficiency. Histogram of intensity of the brightest dot in each cell is shown for different acetic acid to methanol ratios. 25% acetic acid in methanol was used herein for fixation. A modest gain in efficiency can be obtained by increasing acetic acid to 35 or 50 percent.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein and made part of the disclosure herein.

All patents, published patent applications, other publications, and sequences from GenBank, and other databases referred to herein are incorporated by reference in their entirety with respect to the related technology.

Molecular barcoding technologies that uniquely identify single cells are hampered by limitations in barcode measurement. Readout by sequencing does not preserve the spatial organization of cells in tissues, whereas imaging methods preserve spatial structure but are less sensitive to barcode sequence. A system for image-based readout of short (20 bp) DNA barcodes is disclosed herein. In this system, referred to herein as Zombie, the spatial location and sequence of DNA barcodes can be detected with high sensitivity in fixed tissues. Phage RNA polymerases can transcribe engineered barcodes in fixed cells. The resulting RNA can be subsequently detected by fluorescent in situ hybridization. Using competing match and mismatch probes, Zombie can accurately discriminate single-nucleotide differences in the barcodes. Zombie can allow in situ readout of dense combinatorial barcode libraries and single-base mutations produced by CRISPR base editors without requiring barcode expression in live cells. Zombie can function across diverse contexts, including cell culture, chick embryos, and adult mouse brain tissue. The ability to sensitively read out compact and diverse DNA barcodes by imaging will facilitate a broad range of barcoding and genomic recording strategies.

Disclosed herein include embodiments of a method of determining barcode sequences in situ. In some embodiments, the method comprises: providing a plurality of cells each comprising a barcode polynucleotide with a barcode sequence. The method can comprise: fixing cells of the plurality of cells using a fixative to obtain a plurality of fixed cells. The method can comprise: generating, for each of one or more fixed cells of the plurality of fixed cells, a plurality of barcode molecules comprising the barcode sequence of the barcode polynucleotide in the fixed cell. The method can comprise: contacting each of the one or more fixed cells with a plurality of detection probes each comprising a barcode binding sequence. In some embodiments, thereby (i) one, at least one, or each of the plurality of barcode molecules comprising the barcode sequence of the oligonucleotide in the fixed cell hybridizes to a detection probe of the plurality of detection probes comprising the barcode binding sequence reverse complementary to the barcode sequence, or a portion thereof, and (ii) the detection probe is associated with a fluorophore. The method can comprise: detecting the fluorophore, or fluorescence thereof, associated with the detection probe hybridized to the one, at least one, or each barcode molecule in each of the one or more fixed cells using fluorescence imaging. The fluorophore, associated with the detection probe hybridized to the barcode molecule comprising the barcode sequence of the barcode polynucleotide in the fixed cell, detected can indicate the barcode sequence of the barcode polynucleotide in the fixed cell.

Disclosed herein include embodiments of a plurality of compositions for determining barcode sequences in situ. In some embodiments, the plurality of compositions comprises: (1) a plurality of cells each comprising a barcode polynucleotide with a barcode sequence, (2a) a donor plasmid comprising the barcode polynucleotide, a sequence thereof, a subsequence thereof, or a reverse complementary sequence of any of the proceeding, the barcode polynucleotide comprising at least one barcode sequence, (2b) a plasmid capable of expressing Cas9 and/or a guide ribonucleic acid (gRNA) for integrating the barcode polynucleotide into the genome, and/or (2c) a viral vector for integrating the barcode polynucleotide into each of the plurality of cells, a polynucleotide comprising the barcode polynucleotide, a sequence thereof, a subsequence thereof, or a reverse complementary sequence of any of the proceeding, (3) a fixative, (4) a plurality of detection probes, and/or (5) pairs of amplifier probes, or a plurality of first amplifier probes, of any method or embodiment disclosed herein. Disclosed herein include embodiments of a kit. In some embodiments, the kit comprises: a plurality of compositions disclosed herein. The kit can comprise: instructions for using the plurality of compositions for determining barcode sequences in situ, high throughput screening, analyzing clonal dynamics and heterogeneity in a tumor or tumors, immunology, or developmental biology, and/or lineage or event recording.

Disclosed herein include embodiments of a method comprising using a plurality of compositions or a kit disclosed herein for: high throughput screening, analyzing clonal dynamics and heterogeneity in a tumor or tumors, immunology, or developmental biology, and/or lineage or event recording.

Definitions

Unless defined otherwise, technical and scientific terms used herein have the same meaning as commonly understood by one of ordinary skill in the art to which the present disclosure belongs. See, e.g., Singleton et al., Dictionary of Microbiology and Molecular Biology 2nd ed., J. Wiley & Sons (New York, N.Y. 1994); Sambrook et al., Molecular Cloning, A Laboratory Manual, Cold Spring Harbor Press (Cold Spring Harbor, N.Y. 1989). For purposes of the present disclosure, the following terms are defined below.

In Situ Readout of Barcodes

Molecular recording systems help the study of development and disease by allowing reconstruction of dynamic, single-cell developmental histories from end-point measurements. In these systems, individual cells actively record information within their genome by continuous editing of uniquely identifiable engineered genomic target sites, or 'barcodes'. Multiple methods that use CRISPR/Cas9 or site-specific recombinases to produce barcode diversity have now been developed, including the use of CRISPR base editors, in which catalytically impaired Cas9 is fused to deaminases and other enzymes to target mutations to specific nucleotides without generating double stranded breaks.

In these approaches, readout of barcode edits is most often done by sequencing, which is sensitive to single nucleotide variations and can be performed at high throughput. However, sequencing-based approaches disrupt spatial organization of cells within tissues, and often recover information only from a minority of cells. The ability to accurately and efficiently read out single cell barcode edits in situ would link dynamic developmental history with spatial multicellular organization that is essential for the function of many biological systems.

Nucleic acids can be detected in situ, including using strategies for combinatorially encoding a large diversity of transcripts, techniques for amplifying signal from single mRNA molecules, and approaches for in situ sequencing. Barcodes transcribed in living cells can be detected prior to fixation. However, ensuring detectable barcode expression across a diverse population of living cells can be challenging due to stochastic silencing, bursty expression, and unintended cell-type dependent promoter activity. Eliminating the need for expression in living cells could therefore simplify the design of barcode systems. In addition, some methods only detect large scale differences in target sequence and therefore cannot access single nucleotide variations. For example, recording can be based on detection of large-scale barcode deletions. Thus, there is a need for a simple and effective strategy for discriminating barcode edits in fixed tissues.

Disclosed herein includes an in situ detection method that is sensitive to single nucleotide edits and can be applied in diverse organismal contexts. In some embodiments, it uses well-characterized RNA polymerases from the bacteriophages T3, T7, and SP6 to transcribe genomically integrated barcodes in fixed cells, producing an amplified RNA product that can then be detected using single molecule FISH (smFISH) or Hybridization Chain Reaction (HCR). Phage polymerases are known to be efficient and specific for their target promoters, but have not been applied in fixed cells previously. Because the method is based on 'waking up' otherwise transcriptionally 'dead' (silent) barcodes in fixed cells, it is referred to herein as "Zombie" for 'Zombie is Optical Measurement of Barcodes by In situ Expression'. As disclosed herein, Zombie can efficiently detect short (20 bp) barcodes, accurately discriminates single nucleotide variants (SNVs), and detects edits made by base editors, without requiring endogenous expression in some embodiments. These capabilities allow for compact virally delivered combinatorial barcode libraries, and various recording applications. Furthermore, the simplicity and robustness of this system enables it to function not only in cell culture but also in tissues, organs, and/or organisms, for example chick embryos and adult mouse brain tissues.

As disclosed herein, phage RNA polymerases can enable imaging-based barcode readout in individual fixed cells, producing easily detectable fluorescent dots localized to transcriptional sites (See FIGS. 1A-1G for examples). Transcription can enable detection of 20 bp barcodes (See FIGS. 2A-2D for examples) with discrimination of single nucleotide variants using competing probes (See FIGS. 3A-3D for examples). This capability can further enable recovery of edits made by a CRISPR base editor in live cells (See FIGS. 4A-4F for examples). The system can be versatile, for example, operating not only in cell culture but also in chick embryos and adult mouse brain tissue (See FIGS. 5A-5H for examples) and can therefore be suitable for in vivo barcoding applications (See FIGS. 6A-6D for example). Zombie can allow high density barcoding and recording with in situ readout.

Concatenating multiple 20 bp barcodes, as in FIGS. 6A-6D, can enable combinatorial libraries of distinct barcodes, for example, using a modest library of 81 barcodes. In some embodiments, the same design can be scaled up to produce an exponential increase in coding capacity. For example, an array of 12 barcode positions, with 3 barcode variants per position, is expected to achieve a potential barcode diversity of 531,441 variants, similar to that used in sequencing-based barcoding applications, while requiring only 240 bp of sequence and 9 rounds of imaging for read-out (An error correcting coding scheme would require additional hybridization rounds). Coding capacity can be further expanded by inserting multiple arrays at distinct, spatially resolvable genomic sites.

The kits, compositions, methods and systems disclosed herein can enable viral barcoding with imaging readout. In viral barcoding, cells are labeled at a single time-point or, more recently, at multiple time-points, to enable subsequent identification of their descendants. Viral barcoding methods have been used in the study of hematopoietic development, neurobiology, and cancer. They have also enabled new high-throughput screening approaches. However, the methods so far predominantly relied on sequencing for readout of virally delivered barcodes. Diverse combinatorial libraries of short Zombie-readable barcodes enable simultaneous recovery of lineage, cell fate, and spatial organization in diverse settings, including development, regeneration, and cancer. Similarly, Zombie can facilitate multiplexed high-throughput screening, in which cellular phenotypes are assayed by imaging and connected to genetic or environmental perturbations that are identified by barcodes.

One non-limiting exemplary application of Zombie is to enable improved recording systems with image-based readout. In the previously described MEMOIR recording system, Cas9 stochastically and continuously edited ~1 kb barcoded memory elements over multiple cell cycles. These edits resulted in large scale sequence deletions, providing only a single binary memory state per kilobase of sequence. By contrast, in situ readout of base edits could provide a much higher memory density. Additionally, by circumventing the need for barcode expression in living cells, the method and system disclosed herein can avoid issues with burstiness in expression and stochastic silencing, And thus enable a more powerful imaging-based recording system, while maintaining compatibility with subsequent transcriptome readout, e.g. by sequential Fluorescence In Situ Hybridization (seqFISH), in the same cells.

Currently available methods and systems suffer from a general tradeoff between sequencing-based approaches that provide high throughput single nucleotide level readout but no spatial context and imaging approaches that preserve spatial information but lack the sensitivity of sequencing. Recent work has begun to bridge this gap in both directions. The in situ barcode readout method and system disclosed herein allow imaging-based detection with sensitivity and scalability comparable to sequencing, and thus can facilitate imaging-based barcoding, recording, and other applications currently dominated by sequencing.

Determining Barcode Sequences in Situ

Disclosed herein include embodiments of a method of determining barcode sequences in situ. In some embodiments, the method comprises: providing a plurality of cells each comprising a barcode polynucleotide with a barcode sequence (e.g., at 104 in FIG. 1). The method can comprise: fixing cells of the plurality of cells using a fixative to obtain a plurality of fixed cells (e.g., at 112 in FIG. 1). The method can comprise: generating, for each of one or more fixed cells of the plurality of fixed cells, a plurality of barcode molecules comprising the barcode sequence of the barcode polynucleotide in the fixed cell (e.g., at 120 in FIG. 1 after adding a polymerase, such as a phage polymerase at 116 in FIG. 1). The method can comprise: contacting each of the one or more fixed cells with a plurality of detection probes each comprising a barcode binding sequence (e.g., at 124 in FIG. 1; see FIG. 2A for a non-limiting exemplary schematic illustration of a detection probe design). In some embodiments, thereby (i) one, at least one, or each of the plurality of barcode molecules comprising the barcode sequence of the oligonucleotide in the fixed cell hybridizes to a detection probe of the plurality of detection probes comprising the barcode binding sequence reverse complementary to the barcode sequence, or a portion thereof, and (ii) the detection probe is associated with a fluorophore (See FIG. 3A for a non-limiting exemplary schematic illustration). The method can comprise: detecting the fluorophore, or fluorescence thereof, associated with the detection probe hybridized to the one, at least one, or each barcode molecule in each of the one or more fixed cells using fluorescence imaging (e.g., at 128 in FIG. 1; see FIGS. 1D, 1C, 2B, 2E, 2F, and 3C for non-limiting exemplary composite fluorescent images). The fluorophore, associated with the detection probe hybridized to the barcode molecule comprising the barcode sequence of the barcode polynucleotide in the fixed cell, detected can indicate the barcode sequence of the barcode polynucleotide in the fixed cell.

Detecting Barcodes Using Hybridization Chain Reaction

In some embodiments, contacting each of the one or more fixed cells with the plurality of detection probes comprises: contacting each of the one or more fixed cells with the plurality of detection probes each comprising the barcode binding sequence and an initiator sequence (See FIG. 2A for an example). In some embodiments, thereby one, at least one, or each of the plurality of barcode molecules comprising the barcode sequence of the oligonucleotide in the fixed cell hybridizes to a detection probe of the plurality of detection probes comprising the barcode binding sequence reverse complementary to the barcode sequence, or a portion thereof (See FIG. 3A for an example). Contacting each of the one or more fixed cells with the plurality of detection probes can comprise: contacting each of the one or more fixed cells with pairs of amplifier probes (e.g., pairs of chain reaction probes). The amplifier probes of each pair of amplifier probes can comprise an identical fluorophore. In some embodiments, thereby a first amplifier probe of a pair of amplifier probes hybridizes to (i) the initiator sequence of a detection probe of the plurality of detection probes hybridized to a barcode molecule in the fixed cell and (ii) a second amplifier probe of the pair of amplifier probes.

Amplification.

In some embodiments, the initiator sequence is about 40 nucleotides in length. The length of the initiator sequence can be different in different implementations. In some embodiments, the initiator sequence can be, can be about, can be at least, or can be at most, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or a number or a range between any two of these values, nucleotides in length.

In some embodiments, two, or different, pairs of amplifier probes comprise different fluorophores. The two, or different, fluorophores can be spectrally distinct. In some embodiments, thereby a first amplifier probe molecule of the first amplifier probe of the pair of amplifier probes hybridize to (i) a detection probe molecule of the detection probe hybridized to the barcode molecule in the fixed cell and (ii) a second amplifier probe molecule of the second amplifier probe of the pairs of amplifier probes, and first amplifier probe molecules of the first amplifier probe of the pair of amplifier probes hybridize to second amplifier probe molecules, comprising the second amplifier probe molecule hybridized to the first amplifier probe molecule, of the second amplifier probe of the pairs of amplifier probes in a chain reaction. First amplifier probe molecules and second amplifier probe molecules not in the chain reaction (e.g., first amplifier probe molecules not hybridized to second amplifier probe molecules, or second amplifier probe molecules not hybridized to first amplifier probe molecules) can be removed (e.g., washed away).

The number of first amplifier probe molecules and the number of second amplifier probe molecules in the chain reaction can be different in different implementations. For example, at least 10 first amplifier probe molecules can hybridize to at least 10 second amplifier probe molecules in the chain reaction. In some embodiments, the number of first amplifier probe molecules hybridized to the second amplifier probe molecules, the number of second amplifier probe molecules hybridized to the first amplifier probe molecules, or the total number of first and second amplifier probe molecules in the chain reaction, can be, can be about, can be at least, or can be at most, 1, 2, 3, 4, 5, 6, 7, 8, 9, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 2000, 3000, 4000, 5000, 6000, 7000, 8000, 9000, 10000, or a number or a range between any two of these values.

In some embodiments, (1) a first amplifier probe of the pair of amplifier probes comprises (1a) a first amplifier probe subsequence that is reverse complementary to a first subsequence of the initiator sequence of the detection probe of the plurality of detection probes. The first amplifier probe can comprise (1b) a second amplifier probe subsequence that is reverse complementary to a second subsequence of the initiator sequence. The first amplifier probe can comprise (1c) a third amplifier probe subsequence. The first amplifier probe can comprise (1d) a fourth amplifier probe subsequence comprising the second subsequence of the initiator sequence. In some embodiments, (2) a second amplifier probe of the pair of amplifier probes comprises (2a) a first amplifier probe subsequence comprising a reverse complementary sequence of the third amplifier probe subsequence of the first amplifier probe. The second amplifier probe can comprise (2b) a second amplifier probe subsequence comprising the second amplifier probe subsequence. The second amplifier probe can comprise (2c) a third amplifier probe subsequence comprising the first subsequence of the initiator sequence. The second amplifier probe can comprise (2d) a fourth amplifier probe subsequence comprising the second subsequence of the initiator sequence. Contacting the plurality of fixed cells with the pairs of amplifier probes can comprise contacting the plurality of fixed cells with the pairs of amplifier probes each comprising the first amplifier probe and the second amplifier probe with hairpin structures formed by the second amplifier probe subsequence hybridizing with fourth amplifier probe subsequence of the first amplifier probe and by the second amplifier probe subsequence hybridizing with the fourth amplifier probe subsequence of the second amplifier probe.

Barcode Readout.

In some embodiments, said detecting comprises detecting the fluorophore of the first amplifier probe hybridized to the initiator sequence of the detection probe hybridized to the barcode molecule in the fixed cell and the fluorophore of the second amplifier probe of the pair of amplifier probes comprising the first amplifier probe (See FIGS. 2B and 2E for a non-limiting exemplary composite fluorescent image).

Detecting Barcodes without Hybridization Chain Reaction

In some embodiments, contacting each of the one or more fixed cells with the plurality of detection probes comprises: contacting each of the one or more fixed cells with the plurality of detection probes each comprising the barcode binding sequence and an initiator sequence. In some embodiments, thereby one, at least one, or each of the plurality of barcode molecules comprising the barcode sequence of the oligonucleotide in the fixed cell hybridizes to a detection probe of the plurality of detection probes comprising the barcode binding sequence reverse complementary to the barcode sequence, or a portion thereof. Contacting each of the one or more fixed cells with the plurality of detection probes can comprise: contacting each of the one or more fixed cells with a plurality of first amplifier probes each comprising a different fluorophore. In some embodiments, thereby a first amplifier probe of the plurality of first amplifier probes hybridizes to the initiator sequence of a detection probe of the plurality of detection probes hybridized to a barcode molecule in the fixed cell.

In some embodiments, two, or different, first amplifier probes of the plurality of first amplifier probes comprise different fluorophores. In some embodiments, thereby a first amplifier probe molecule of the first amplifier probe of the plurality of first amplifier probes hybridizes to a detection probe molecule of the detection probe hybridized to the barcode molecule in the fixed cell. In some embodiments, said detecting comprises detecting the fluorophore of the first amplifier probe hybridized to the initiator sequence of the detection probe hybridized to the barcode molecule in the fixed cell (See FIG. 2F for a non-limiting exemplary composite fluorescent image).

Detecting Barcodes Using Single Molecule FISH

In some embodiments, contacting each of the one or more fixed cells with the plurality of detection probes comprises: contacting each of the one or more fixed cells with the plurality of detection probes each comprising the barcode binding sequence and a fluorophore, thereby one, at least one, or each of the plurality of barcode molecules comprising the barcode sequence of the oligonucleotide in the fixed cell hybridizes to a detection probe of the plurality of detection probes comprising the barcode binding sequence reverse complementary to the barcode sequence, or a portion thereof, and the fluorophore. In some embodiments, said detecting comprises detecting the fluorophore of the detection probe hybridized to the barcode molecule in the fixed cell.

Barcode Construct and Integration

Barcode Genomic Integration

In some embodiments, a genome of one, at least one, or each cell of the plurality of cell comprises the barcode polynucleotide with the barcode sequence. In some embodiments, providing the plurality of cells comprises: integrating the barcode polynucleotide into a genome of one, at least one, or each of the plurality of cells. Integrating the barcode polynucleotide can comprise: integrating the barcode polynucleotide into the genome of one, at least one, or each of the plurality of cells at a specific site of the genome. The specific site can be a ROSA26 locus, for example.

In some embodiments, said integrating occurs, occurs about, occurs at least, or occurs at most, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days, 42 days, 43 days, 44 days, 45 days, 46 days, 47 days, 48 days, 49 days, 50 days, 51 days, 52 days, 53 days, 54 days, 55 days, 56 days, 57 days, 58 days, 59 days, 60 days, 61 days, 62 days, 63 days, 64 days, 65 days, 66 days, 67 days, 68 days, 69 days, 70 days, 71 days, 72 days, 73 days, 74 days, 75 days, 76 days, 77 days, 78 days, 79 days, 80 days, 81 days, 82 days, 83 days, 84 days, 85 days, 86 days, 87 days, 88 days, 89 days, 90 days, 91 days, 92 days, 93 days, 94 days, 95 days, 96 days, 97 days, 98 days, 99 days, 100 days, 110 days, 120 days, 130 days, 140 day, 150 days, 160 days, 170 days, 180 days, 190 days, 200 days, 210 days, 220 days, 230 days, 240 days, 250 days, 260 days, 270 days, 280 days, 290 days, 300 days, 310 days, 320 days, 330 days, 340 days, 350 days, 1 year, 2 years, 3 years, 4 years, 5 years, 6 years, 7 years, 8 years, 9 years, 10 years, 20 years, 30 years, 40 years, 50 years, 60 years, 70 years, 80 years, 90 years, 100 years, or a number or a range between any two of these values, prior to said fixing.

In some embodiments, integrating the barcode polynucleotide into the genome of one, at least one, or each of the plurality of cells comprises: transfecting the cell with a donor plasmid comprising the barcode polynucleotide, a sequence thereof, a subsequence thereof, of a reverse complementary sequence of any of the preceding. Transfecting the cell with the donor plasmid can comprise: transfecting the cell with the donor plasmid and a plasmid capable of expressing Cas9 and/or a guide ribonucleic acid (gRNA) for integrating the barcode polynucleotide into the genome of one, at least one, or each of the plurality of cells at the specific site of the genome.

In some embodiments, integrating the barcode polynucleotide comprises: integrating the barcode polynucleotide into the genome of one, at least one, or each of the plurality of cells using a viral vector (See FIGS. 4A and 5A for non-limiting exemplary schematic illustrations). The viral vector can comprise a polynucleotide comprising the barcode polynucleotide, a sequence thereof, a subsequence thereof, or a reverse complementary sequence of any of the proceeding. The viral vector can comprise a retrovirus, a lentivirus, an adenovirus, an adeno-associated virus, or a combination thereof. Integrating the barcode polynucleotide can comprise: injecting the viral vector into an organism or a tissue of the organism. The organism can be a mammal.

Promoter

In some embodiments, the barcode polynucleotide comprises at least one promoter upstream (e.g., immediate upstream) of the barcode sequence. The at least one promoter can comprise three promoters. The at least one promoter can be a phage promoter. The at least one promoter can comprise a bacteriophage T3 promoter, a bacteriophage T7 promoter, a bacteriophage SP6 promoter, or a combination thereof. The at least one promoter can be inactive in one, at least one, or each live cell of the plurality of cells. The at least one promoter can be active in one, at least one, or each of the plurality of fixed cells.

The number of promoter(s) upstream (e.g., immediate upstream) of a barcode sequence can be different in different implementations (See FIGS. 1B, 2A, and 3A for examples). In some embodiments, the number of promoter(s) upstream (e.g., immediate upstream) of a barcode sequence can be, can be about, can be at least, or can be at most, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, or a number or a range between any two of these values. The number of barcode sequences under the control of a promoter can be different in different implementations. In some embodiments, the number of barcode sequences under the control of a promoter can be, be about, be at least, or at most, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, or a number or a range between any two of these values. The total number of promoter(s) can be different in different implementations. In some embodiments, the total number of promoter(s) can be, can be about, can be at least, or can be at most, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, or a number or a range between any two of these values.

Barcode Sequences

The length of a barcode sequence can be different in different implementations. In some embodiments, the barcode sequence can be, can be about, can be at least, or can be at most, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, or a number or a range between any two of these values, nucleotides in length.

In some embodiments, the barcode sequence is selected from a set of possible barcode sequences. A set of possible barcode sequences can comprise, comprise about, comprise at least, or comprise at most, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or a range between any two of these values, possible barcode sequences. The possible barcode sequences of each set of possible barcode sequences can differ at one position. The one position can be, for example, position 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100, of the barcode sequence. The possible barcode sequences can comprise adenine (A) nucleobase, guanine (G) nucleobase, or cytosine (C) nucleobase at the one position. The possible barcode sequences can comprise adenine (A) nucleobase, thymine (T) nucleobase, guanine (G) nucleobase, or cytosine (C) nucleobase at the one position. The possible barcode sequences of each set of possible barcode sequences can differ at more than one positions (e.g., 2, 3, 4, 5, 6, 7, 8, 9, or 10, positions).

The barcode sequence of the barcode polynucleotide in a cell can be unique. No cell can comprise a barcode polynucleotide with an identical barcode sequence. At least two cells of the plurality of cells can comprise an identical barcode sequence. In some embodiments, the number of cells comprising barcode polynucleotides with an identical barcode sequence can be, can be about, can be at least, or can be at most, 2, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, 2000, 3000, 4000, 5000, 6000, 7000, 8000, 9000, 10000, or a number or a range between any two of these values.

The barcode polynucleotides of at least two cells of the plurality of cells can comprise different barcode sequences. The at least two cells can be cells of a cell type, cells of a cell subtype, and/or cells of an identical lineage. The at least two cells can be cells of different cell types, cells of different cell subtypes, and/or cells of different lineages. A first cell of the at least two cells can be a cell of interest, and/or a second cell of the at least two cells is not a cell of interest. The first cell can be a cancer cell, and/or the second cell is a normal cell. In some embodiments, the number of cells comprising barcode polynucleotides with different barcode sequences can be, can be about, can be at least, or can be at most, 2, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, 2000, 3000, 4000, 5000, 6000, 7000, 8000, 9000, 10000, or a number or a range between any two of these values.

Marker Gene

In some embodiments, the polynucleotide comprises a constitutively active promoter upstream of a marker gene. The at least one promoter and the constitutively active promoter can have divergent orientations (See FIGS. 1B, 5A, and 6A for examples). The marker gene, the protein encoded by the marker gene, or the expression of any of the proceeding, can be used to identify cells comprising the barcode polynucleotide and/or the barcode sequence. The marker gene can comprise a gene of a fluorescent protein, such as the fluorescent protein comprises a green fluorescent protein (GFP), a yellow fluorescent protein (YFP), a cyan fluorescent protein (CFP), or a combination thereof.

Fixation

In some embodiments, the fixative comprises a non-cross-linking fixative, such as a precipitating fixative (e.g., an alcohol, such as methanol), a denaturing fixative (e.g., a weak acid, such as acetic acid), or a combination thereof. In some embodiments, fixing the cells can comprise: fixing the cells without using a cross-linking fixative. The plurality of fixed cells can comprise dead cells. The plurality of cells can comprise live cells and/or dead cells.

The fixative can comprise methanol (or another alcohol, or another precipitating fixative) and acetic acid (or another weak acid). The ratio of methanol and acetic acid in fixative can be, for example, from about 10:1 (e.g., v/v, w/w, v/w, or w/v) to about 1:10 (e.g. v/v, w/w, v/w, or w/v). In some embodiments, the ratio (e.g., v/v, w/w, v/w, and w/v) of methanol and acetic acid (or any two components in the fixative, such as a precipitating fixative and a denaturing fixative) can be, can be about, can be at least, or can be at most, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1, 60:1, 61:1, 62:1, 63:1, 64:1, 65:1, 66:1, 67:1, 68:1, 69:1, 70:1, 71:1, 72:1, 73:1, 74:1, 75:1, 76:1, 77:1, 78:1, 79:1, 80:1, 81:1, 82:1, 83:1, 84:1, 85:1, 86:1, 87:1, 88:1, 89:1, 90:1, 91:1, 92:1, 93:1, 94:1, 95:1, 96:1, 97:1, 98:1, 99:1, 100:1, or a number or a range between any two of these values. In some embodiments, the ratio (e.g., v/v, w/w, v/w, and w/v) of methanol and acetic acid (or any two components in the fixative, such as a precipitating fixative and a denaturing fixative) can be, can be about, can be at least, or can be at most, 1:2, 1:2, 1:3, 1:4, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, 1:50, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99, 1:100, or a number or a range between any two of these values.

The fixative can comprise, for example, from about 5% acetic acid in methanol to about 75% acetic acid in methanol (e.g., v/v, w/w, v/w, and w/v). The fixative can comprise, comprise about, comprise at least, or comprise at most, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or a number or a range between any two of these values acetic acid in methanol (e.g., v/v, w/w, v/w, and w/v). The fixative can comprise, comprise about, comprise at least, or comprise at most, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or a number or a range between any two of these values, methanol (e.g., v/v, w/w, v/w, and w/v).

In some embodiments, the method comprises: fixing fixed cells of the plurality of fixed cells using a second fixative to obtain a plurality of second fixed cells. Contacting each of the one or more fixed cells can comprise: contacting each of the one or more second fixed cells with a plurality of detection probes each comprising a barcode binding sequence. In some embodiments, thereby (i) one, at least one, or each of the plurality of barcode molecules comprising the barcode sequence of the oligonucleotide in the second fixed cell hybridizes to a detection probe of the plurality of detection probes comprising the barcode binding sequence reverse complementary to the barcode sequence, or a portion thereof, and (ii) the detection probe is associated with a fluorophore. Detecting the fluorophore, or fluorescence thereof can comprise: detecting the fluorophore, or fluorescence thereof, associated with the detection probe hybridized to the one, at least one, or each barcode molecule in each of the one or more second fixed cells using fluorescence imaging. The fluorophore, associated with the detection probe hybridized to the barcode molecule comprising the barcode sequence of the barcode polynucleotide in the second fixed cell, detected can indicate the barcode sequence of the barcode polynucleotide in the second fixed cell. The second fixative can comprise a cross-linking fixative. The second fixative can comprise an aldehyde, such as formaldehyde (e.g., such as 3%-4% formaldehyde in phosphate-buffered saline) and glutaraldehyde.

Barcode Expression

In some embodiments, one, at least one, or each of the plurality of cells (e.g., cells before being fixed with a non-cross-linking fixative) comprises no barcode molecule. Generating the plurality of barcode molecules can comprise: transcribing the barcode polynucleotide in each of the plurality of fixed cell to generate the plurality of barcode molecules comprising the barcode sequence of the barcode polynucleotide in the fixed cell (e.g., at 116 in FIG. 1). Transcribing the barcode polynucleotide can comprise: transcribing the barcode polynucleotide in each of the plurality of fixed cell to generate the plurality of barcode molecules comprising the barcode sequence of the barcode polynucleotide in the fixed cell using a phage RNA polymerase. The phage RNA polymerase can comprise a bacteriophage T3 RNA polymerase, a bacteriophage T7 RNA polymerase, a bacteriophage SP6 RNA polymerase, or a combination thereof.

The plurality of barcode molecules comprises at least 100 barcode molecules comprising the barcode sequence of the barcode polynucleotide in each of the plurality of fixed cells. The number of barcode molecules generated in each cell can be different in different implementations. The number of barcode molecules generated in each cell can be, can be about, can be at least, or can be at most, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, 2000, 3000, 4000, 5000, 6000, 7000, 8000, 9000, 10000, or a number or a range between any two of these values.

Barcode Detection

In some embodiments, thereby the barcode sequence of each of the plurality of barcode molecules hybridizes to the barcode binding sequence of the detection probe that is reverse complementary to the barcode sequence of the barcode molecule (See FIG. 3A for an example). In some embodiments, contacting the plurality of fixed cells with the plurality of detection probes comprises: contacting each of the one or more fixed cells with detection probe molecules of each of the plurality of detection. In some embodiments, thereby (i) one, at least one, or each of the plurality of barcode molecules comprising the barcode sequence of the oligonucleotide in the fixed cell hybridizes to a detection probe molecule of the detection probe of the plurality of detection probes comprising the barcode binding sequence reverse complementary to the barcode sequence, or a portion thereof, and (ii) the detection probe molecule of the detection probe is associated with a fluorophore.

In some embodiments, two, three, or four (or about two, three, or four) detection probes of the plurality of detection probes comprise the barcode binding sequences that differ at one position. In some embodiments, two, three, or four (or about two, three, or four), detection probes of the plurality of detection probes comprise (i) barcode binding sequences that differ at one position and (ii) different initiator sequences. The (about) two, three, or four detection probes can have an identical concentration. One, at least one, or each of the plurality of barcode molecules comprising the barcode sequence of the oligonucleotide in the fixed cell can hybridize to one of the (about) two, three, or four detection probes comprising the barcode binding sequence reverse complementary to the barcode sequence, or a portion thereof, not the remaining (about) one, two, or three, detection probe(s).

The concentration of one, at least one, or each of the (about) two, three, or four detection probes can be different in different implementations, such as about 4 nM. In some embodiments, the concentration of a detection probe can be, can be about, can be at least, or can be at most, 1 nM, 2 nM, 3 nM, 4 nM, 5 nM, 6 nM, 7 nM, 8 nM, 9 nM, 10 nM, 11 nM, 12 nM, 13 nM, 14 nM, 15 nM, 16 nM, 17 nM, 18 nM, 19 nM, 20 nM, 21 nM, 22 nM, 23 nM, 24 nM, 25 nM, 26 nM, 27 nM, 28 nM, 29 nM, 30 nM, 31 nM, 32 nM, 33 nM, 34 nM, 35 nM, 36 nM, 37 nM, 38 nM, 39 nM, 40 nM, 41 nM, 42 nM, 43 nM, 44 nM, 45 nM, 46 nM, 47 nM, 48 nM, 49 nM, 50 nM, 51 nM, 52 nM, 53 nM, 54 nM, 55 nM, 56 nM, 57 nM, 58 nM, 59 nM, 60 nM, 61 nM, 62 nM, 63 nM, 64 nM, 65 nM, 66 nM, 67 nM, 68 nM, 69 nM, 70 nM, 71 nM, 72 nM, 73 nM, 74 nM, 75 nM, 76 nM, 77 nM, 78 nM, 79 nM, 80 nM, 81 nM, 82 nM, 83 nM, 84 nM, 85 nM, 86 nM, 87 nM, 88 nM, 89 nM, 90 nM, 91 nM, 92 nM, 93 nM, 94 nM, 95 nM, 96 nM, 97 nM, 98 nM, 99 nM, 100 nM, or a range between any two of these values.

The plurality of detection probes can comprise a set of detection probes. The set of detection probe can comprise, or comprise about, 2, 3, or 4 detection probes with barcode binding sequences that differ at one position (or more positions) and are reverse complementary to possible barcode sequences of one of the sets of possible barcode sequences. For example, a set of detection probes can comprise 4 detection probes that differ at one position. A barcode sequence can be selected from a set of 4 possible barcode sequences that differ at one position. Each detection probes in the set of detection probes can be reverse complementary to one barcode sequence of the set of possible barcode sequences.

Combinatorial Barcoding

The barcode polynucleotide can comprise different numbers of barcode sequence(s) in different implementations (See FIGS. 4A and 6A for examples). In some embodiments, the barcode polynucleotide of one, at least one, or each of the plurality of cells comprises, comprises about, comprises at least, or comprises at most, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, or a number or a range between any two of these values, barcode sequences.

One or more barcode sequences can be downstream (e.g., immediately downstream) of at least one promoter (e.g., such as 1, 2, 3, 4, 5, 6, 7, 8, 9, or 10 promoters). Two (or more) of the barcode sequences can be downstream of different promoter. The number of barcode sequences downstream of different promoters can be different in different implementations. In some embodiments, the number of barcode sequences downstream of different promoters can be, can be about, can be at least, or can be at most, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, or a number or a range between any two of these values.

The different promoters can comprise an identical promoter sequence or different promoter sequences. The number of different promoters comprising an identical promoter sequence can be different in different implementations. In some embodiments, the number of different promoters comprising an identical promoter sequence can be, can be about, can be at least, or can be at most, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, or a number or a range between any two of these values. The number of different promoters comprising different promoter sequences can be different in different implementations. In some embodiments, the number of different promoters comprising different promoter sequences can be, can be about, can be at least, or can be at most, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, or a number or a range between any two of these values.

The number of barcode sequences having an identical length can be different in different implementations. In some embodiments, the number of barcode sequences having an identical length can be, can be about, can be at least, or can be at most, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, or a number or a range between any two of these values. The number of barcode sequences having different lengths can be different in different implementations. In some embodiments, the number of barcode sequences having different lengths can be, can be about, can be at least, or can be at most, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, or a number or a range between any two of these values.

The number of barcode sequences having different sequences can be different in different implementations. In some embodiments, the number of barcode sequences having different sequences can be, can be about, can be at least, or can be at most, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, or a number or a range between any two of these values. The number of barcode sequences having an identical sequence can be different in different implementations. In some embodiments, the number of barcode sequences having an identical sequence can be, can be about, can be at least, or can be at most, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, or a number or a range between any two of these values.

The barcode sequences of a barcode polynucleotide can each be selected from a different set of possible barcode sequences. A set of possible barcode sequences can comprise, comprise about, comprise at least, or comprise at most, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or a range between any two of these values, possible barcode sequences. The possible barcode sequences of each set of possible barcode sequences can differ at one position. The possible barcode sequences of each set of possible barcode sequences can differ at more than one positions (e.g., 2, 3, 4, 5, 6, 7, 8, 9, or 10, positions).

A combination of the barcode sequences (e.g., 12 barcode sequences) on a barcode polynucleotide can be selected from about 16 million, or about 500000, possible combinations of barcode sequences (e.g., 12 barcode sequences). In some embodiments, a combination of barcode sequences on a barcode polynucleotide can be selected from, from about, from at least, or from at most, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000, 2 million, 3 million, 4 million, 5 million, 6 million, 7 million, 8 million, 9 million, 10 million, 20 million, 30 million, 40 million, 50 million, 60 million, 70 million, 80 million, 90 million, 100 million, or a number or a range between any two of these values, possible combinations of barcode sequences.

Adjacent barcode sequences can be separated from one another by different numbers of nucleotides in different implementations. In some embodiments, adjacent barcode sequences can be separated from one another by, by about, by at least, or by at most, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, or a number or a range between any two of these values, nucleotides.

The plurality of detection probes comprises different sets of detection probes (e.g., 12 sets of detection probes). In some embodiments, the number of set(s) of detection probes in the plurality of detection probes can be, can be about, can be at least, or can be at most, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, or a number or a range between any two of these values.

The detection probes of one of the sets of detection probes can comprise different initiator sequences. Said contacting and said detecting comprises: iteratively, contacting each of the one or more fixed cells with a different set of detection probes each comprising a barcode binding sequence, thereby (i) one, at least one, or each of the plurality of barcode molecules comprising the barcode sequence of the oligonucleotide in the fixed cell hybridizes to a detection probe of the set of detection probes comprising the barcode binding sequence reverse complementary to the barcode sequence, or a portion thereof, and (ii) the detection probe is associated with a fluorophore; and detecting the fluorophore associated with the detection probe hybridized to the one, at least one, or each barcode molecule in each of the one or more fixed cells using fluorescence imaging. A combination of the fluorophores associated with detection probes hybridized to the barcode molecule comprising the barcode sequence of the barcode polynucleotide in the fixed cell, detected can indicate the barcode sequence of the barcode polynucleotide in the fixed cell.

The method can comprise: removing the detection probe hybridized to the one, at least one, or each barcode molecule in each of the one or more fixed cells (e.g., after a round of detection). Said removing can comprise: digesting the detection probe hybridized to the one, at least one, or each barcode molecule in each of the one or more fixed cells using DNase. The number of rounds of detection for detecting the barcode sequences can be different in different implementation. In some embodiments, the number of rounds of detection can be, can be about, can be at least, or can be at most, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, or a number or a range between any two of these values.

Barcode Readout

In some embodiments, the method comprises: determining the barcode sequence in each of the one or more fixed cells using the fluorophore, associated with the detection probe hybridized to the barcode molecule comprising the barcode sequence of the barcode polynucleotide in the fixed cell, detected. In some embodiments, the method comprises: determining lineages of, and/or a clonal relationship between, two or more fixed cells of the plurality of fixed cells (or corresponding cells of the plurality of cells) using the barcode sequence of the barcode polynucleotide in each of the two or more fixed cells (or corresponding cells). In some embodiments, the method comprises: determining a spatial relationship (e.g., in close proximity) of two or more fixed cells of the plurality of fixed cells; and correlating the barcode sequences of the barcode polynucleotide in each of the two or more fixed cells with a spatial relationship (e.g., intermixed spatial relationship) of the two or more fixed cells. The two or more cells can be cells of different cell types or cell subtypes. The two or more cells can be cells of an identical cell type or cell subtype.

Staining

In some embodiments, the method comprises: staining nuclei of the plurality of fixed cells. The method can comprise: identifying nuclei of the plurality of fixed cells based on the nuclei stained. Said detecting can comprise: detecting the fluorescence of the fluorophore, associated with the detection probe hybridized to the barcode molecule comprising the barcode sequence of the barcode polynucleotide in the fixed cell, in the nucleus of the cell identified.

Barcode Editing

In some embodiments, the method comprises: base editing the barcode sequence of the barcode polynucleotide in one, at least one, or each of the plurality of cells (e.g., at 108 in FIG. 1). In some embodiments, said base editing comprises: base editing the barcode sequence of the barcode polynucleotide in one, at least one, or each of the plurality of cells at the one position that the possible barcode sequences from the set of possible barcode sequences are different. In some embodiments, said base editing comprises: adenine (A)-to-guanine (G) base editing and/or cytosine (C)-to-thymine (T) base editing.

In some embodiments, said base editing comprises: base editing using a base editor and a guide ribonucleic acid (gRNA) targeting a gRNA targeting sequence of the barcode polynucleotide. The barcode polynucleotide can comprise a Protospacer Adjacent Motif (PAM). The PAM can be downstream of the gRNA targeting sequence. The base editor can comprise an adenine base editor (ABE) and/or a cytosine base editor (CBE). Said base editing can comprise: introducing a plasmid capable of expressing the base editor and the gRNA into one or more of the plurality of cells (See FIG. 4A for an example). Said introducing can comprise: introducing the plasmid capable of expressing the base editor and the gRNA into the one or more cells using transient transfection.

The gRNA targeting sequence can comprise the barcode sequence, or a portion thereof, of the barcode polynucleotide (See FIG. 4A for an example). Two or more barcode sequences of a barcode polynucleotide can be edited by independently addressing (e.g., the two or more barcode sequences can be edited using two or more gRNA) or by multiplexed addressing (e.g., the two or more barcode sequences can be edited using one gRNA) (See FIG. 4B for an example). The number of barcode sequences of a barcode polynucleotide with an identical gRNA targeting sequence, or different gRNA targeting sequences, can be different in different implementations. In some embodiments, the number of barcode sequences of a barcode polynucleotide with an identical gRNA targeting sequence can be, can be about, can be at least, or can be at most, 2, 3, 4, 5, 6, 7, 8, 8, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, or a number or a range between any two of these values. In some embodiments, the number of barcode sequences of a barcode polynucleotide with different gRNA targeting sequences can be, can be about, can be at least, or can be at most, 2, 3, 4, 5, 6, 7, 8, 8, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, or a number or a range between any two of these values.

The gRNA targeting sequence can have different lengths in different implementations, such as 20 nucleotides in length. In some embodiments, the gRNA targeting sequence can be, can be about, can be at least, or can be at most, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or a range between any two of these values, nucleotides in length.

A memory unit referred to herein can include the barcode sequence and the gRNA targeting sequence of the barcode polynucleotide. The number of memory units on a barcode polynucleotide can be different in different implementations, such as 12. The number of memory unit(s) on a barcode polynucleotide can be, can be about, can be at least, or can be at most, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or a range between any two of these values.

The barcode sequence and the gRNA targeting sequence of the barcode polynucleotide can completely overlap. The barcode sequence and the gRNA targeting sequence of the barcode polynucleotide can overlap by different numbers of nucleotides in different implementations, such as 11 nucleotides. In some embodiments, the barcode sequence and the gRNA targeting sequence of the barcode polynucleotide can overlap by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or a range between any two of these values, nucleotide(s).

In some embodiments, said base editing comprises base editing the barcode sequence of the barcode polynucleotide in one, at least one, or each of the plurality of cells at one or more predetermined time points. The time points can be different in different implementations. In some embodiments, the time point is, is about, is at least, or is at most, 1 hr, 2 hrs, 3 hrs, 4 hrs, 5 hrs, 6 hrs, 7 hrs, 8 hrs, 9 hrs, 10 hrs, 11 hrs, 12 hrs, 13 hrs, 14 hrs, 15 hrs, 16 hrs, 17 hrs, 18 hrs, 19 hrs, 20 hrs, 21 hrs, 22 hrs, 23 hrs, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days, 42 days, 43 days, 44 days, 45 days, 46 days, 47 days, 48 days, 49 days, 50 days, 51 days, 52 days, 53 days, 54 days, 55 days, 56 days, 57 days, 58 days, 59 days, 60 days, 61 days, 62 days, 63 days, 64 days, 65 days, 66 days, 67 days, 68 days, 69 days, 70 days, 71 days, 72 days, 73 days, 74 days, 75 days, 76 days, 77 days, 78 days, 79 days, 80 days, 81 days, 82 days, 83 days, 84 days, 85 days, 86 days, 87 days, 88 days, 89 days, 90 days, 91 days, 92 days, 93 days, 94 days, 95 days, 96 days, 97 days, 98 days, 99 days, 100 days, or a number or a range between any two of these values, days after an event. The event can be, for example, introducing a plasmid capable of expressing the base editor and the gRNA into one or more of the plurality of cells.

In some embodiments, said base editing comprises base editing the barcode sequence of the barcode polynucleotide in one, at least one, or each of the plurality of cells at an edit rate. The edit rate can be predetermined. The edit rate can be different in different implementations, for example, from about 1% to about 100% edit per unit time. In some embodiments, the edit rate is, is about, is at least, or is at most, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or a number or a range between any two of these values, edit per unit time. The edit rate can be, for example, about 1% to 100% edit per cell per cell division cycle. In some embodiments, the edit rate is, is about, is at least, or is at most, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or a number or a range between any two of these values, edit per cell per cell division cycle.

Gene Expression

In some embodiments, the method comprises: determining gene expression (or other -omics data, such as proteomics data, and epigenomics data) in one, at least one, or each of the plurality of cells. Determining the gene expression can comprise: determining the gene expression in one, at least one, or each of the plurality of cells using seqFISH. In some embodiments, the method comprises: correlating the gene expression of two or more fixed cells with the lineages of, the clonal relationship between, and/or the spatial relationship of, the two or more fixed cells. The lineages of, the clonal relationship between, and/or the spatial relationship of, the two or more fixed cells can be determined using the barcode sequences (or combinations of barcode sequences) of the barcodes in the fixed cells. For example, the method can include determining whether cells with similar expression of one or more genes correlate with the lineages of the cells. As another example, the method can include determining whether cells in close proximity have similar expression.

Sample

The plurality of cells can comprise, comprise about, comprise at least, or comprise at most, 2, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, 2000, 3000, 4000, 5000, 6000, 7000, 8000, 9000, 10000, or a number or a range between any two of these values, cells. All cells can be cells of a cell type, of a cell subtype, and/or of an identical lineage. At least two cells can be cells of a cell type, cells of a cell subtype, and/or cells of an identical lineage. In some embodiments, the number of cells of a cell type, of a cell subtype, and/or of an identical lineage can be, can be about, can be at least, or can be at most, 2, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, 2000, 3000, 4000, 5000, 6000, 7000, 8000, 9000, 10000, or a number or a range between any two of these values.

No two cells can be cells of a cell type, of a cell subtype, and/or of an identical lineage. At least two cells can be cells of different cell types, cells of different cell subtypes, and/or cells of different lineages. In some embodiments, the number of cells of different cell types, of different cell subtypes, and/or of different lineages can be, can be about, can be at least, or can be at most, 2, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, 2000, 3000, 4000, 5000, 6000, 7000, 8000, 9000, 10000, or a number or a range between any two of these values.

The plurality of cells can comprise a cell of interest (e.g., a cancer cell) and/or a cell not of interest (e.g., a normal cell). The number of cell(s) of the plurality of cells being cell(s) of interest can be different in different implementations. In some embodiments, the number of cell(s) of the plurality of cells being cell(s) of interest can be, can be about, can be at least, or can be at most, 1, 2, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, 2000, 3000, 4000, 5000, 6000, 7000, 8000, 9000, 10000, or a number or a range between any two of these values. The number of cell(s) of the plurality of cells being cell(s) not of interest can be different in different implementations. In some embodiments, the number of cell(s) of the plurality of cells being cell(s) not of interest can be, can be about, can be at least, or can be at most, 1, 2, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, 2000, 3000, 4000, 5000, 6000, 7000, 8000, 9000, 10000, or a number or a range between any two of these values.

In some embodiments, the plurality of cells is from a sample comprising a cell culture, a tissue, an organ (e.g., the brain), an embryo, an organism (e.g., a mammal), a section thereof. In some embodiments, the plurality of cells is from a sample comprising an in vivo sample and/or an in vitro sample. In some embodiments, the plurality of cells comprises one or more tumor cells, one or more immune cells, one or more epithelial cells, one or more nervous cells, one or more blood cells, one or more bone cells, one or more fat cells, one or more muscle cells, and/or one or more sex cells. In some embodiments, the plurality of cells comprises one or more stem cells, one or more progenitor cells, and/or one or more mature cells. In some embodiments, two, at least two, or each of the plurality of cells are cultured under an identical condition. In some embodiments, two, at least two, or each of the plurality of cells are cultured under different conditions. The number of different conditions can be different in different implementations. In some embodiments, the number of different implementations is, is about, is at last, or is at most, 2, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, or a number or a range between any two of these values. The identical condition or each of the different conditions can comprise a genetic perturbation, an environmental perturbation, or a combination thereof.

Composition & Kit

Disclosed herein include embodiments of a plurality of compositions for determining barcode sequences in situ. In some embodiments, the plurality of compositions comprises: a plurality of cells each comprising a barcode polynucleotide with a barcode sequence disclosed herein. The plurality of compositions can comprise: (a) a donor plasmid comprising the barcode polynucleotide, a sequence thereof, a subsequence thereof, or a reverse complementary sequence of any of the proceeding, the barcode polynucleotide comprising at least one barcode sequence disclosed herein, (b) a plasmid capable of expressing Cas9 and/or a guide ribonucleic acid (gRNA) for integrating the barcode polynucleotide into the genome disclosed herein, and/or (c) a viral vector for integrating the barcode polynucleotide into each of the plurality of cells disclosed herein. The viral vector can comprise a polynucleotide comprising the barcode polynucleotide, a sequence thereof, a subsequence thereof, or a reverse complementary sequence disclosed herein. The plurality of compositions can comprise: a fixative (e.g., a non-cross-linking fixative) disclosed herein. The plurality of compositions can comprise: a polymerase (e.g., a phage polymerase). The plurality of compositions can comprise: a plurality of detection probes (e.g., detection probes conjugated with fluorophores, or detection probes not conjugated with fluorophores) disclosed herein. The plurality of compositions can comprise: pairs of amplifier probes (e.g., pairs of amplifier probes with amplifier probes of a pair conjugated with an identical fluorophore), or a plurality of first amplifier probes disclosed herein.

Disclosed herein include embodiments of a kit. In some embodiments, the kit comprises: a plurality of compositions disclosed herein. The kit can comprise: instructions for using the plurality of compositions for determining barcode sequences in situ, high throughput screening, analyzing clonal dynamics and heterogeneity in a tumor or tumors, immunology, or developmental biology, and/or lineage or event recording.

APPLICATIONS

Disclosed herein include embodiments of a method comprising using a plurality of compositions or a kit disclosed herein for applications including, but are not limited to, high throughput screening, analyzing clonal dynamics and heterogeneity in a tumor or tumors, immunology, or developmental biology, and/or lineage or event recording.

Genetic barcodes are unique DNA sequences that identify individual cells and their descendants. Barcoding are used in diverse biological fields, including immunology, neurobiology, and cancer biology. It has also enabled high throughput screening methods leading to discovery of novel genetic regulators and pharmaceutical perturbations. Dynamic barcoding, in which targeted genomic sequences are continuously modified to generate sequence diversity, has opened up the ability to reconstruct history of cellular events based on information recorded through genomic edits.

Analysis of barcodes has previously been limited to sequencing-based methods. Sequencing approaches provide accurate readout but disrupt the spatial context of cells and, in the case of single cell sequencing methods, typically recover information from a low percentage of cells in a given sample. The ability to read out barcode features and discriminate barcodes using imaging methods would enable identification and analysis of clones, lineages, and recorded genetic information by in situ imaging, without requiring sequencing. It would also be advantageously to enable efficient and straightforward readout of compact barcodes and detection of small changes in the barcode sequence, and be compatible with in situ transcriptional profiling techniques.

Disclosed herein includes compositions, kits, methods and systems based on phage RNA polymerases for imaging-based barcode readout in single cells. Phage polymerases efficiently transcribe barcodes in fixed cells, producing easily detectable fluorescent dots localized to transcriptional sites. Transcription enables detection of, for example, short 20 bp barcodes with discrimination of single nucleotide variants using competing probes. This capability enables recovery of edits made by a CRISPR base editors in living cells. This system, termed Zombie (for "Optical Measurement of Barcodes by In-situ Expression"), is versatile, operating in diverse contexts including cultured cells from various sources, for example human and mouse, and various animal tissues, including chick and mouse tissues. Thus, the method and system disclosed herein can allow high density barcoding and recording with imaging-based readout.

Applications in which the in-situ barcode readout method and system disclosed herein can be used include, but are not limited to:

High throughput screening applications. Cellular phenotypes can be assayed, for example, by imaging and connected to genetic or environmental perturbations that can be identified by barcode sequences. In such applications, large numbers of conditions or perturbations can be analyzed in parallel by in situ imaging rather than sequencing. Also, dynamic phenotypes can be recovered this way by using time-lapse imaging to analyze the temporal dynamics of cellular behaviors, with end-point analysis of barcodes in the same cell.

Analysis of clonal dynamics and heterogeneity in tumors, immunology, and developmental biology. A major question in cancer is the lineage structure of tumors and metastases and its relationship to the spatial organization of the tumor. Sequencing-based barcoding methods have been applied to this problem, but do not preserve spatial organization. The method and system disclosed herein will allow in situ analysis of lineage structure within animal or human tumor contexts for biomedical research and clinical applications. Similar approaches can provide insights into immune system development and tissue development.

Lineage and event recording. Recent work has provided methods for active recording of lineage and event history information in cellular genomes by continuous editing or modification of barcodes over multiple cell division cycles. In particular, "base editors' can be used to modify barcodes by changing single nucleotides. The method and system disclosed herein can enable read out of such single base edits in situ by imaging.

EXAMPLES

Some aspects of the embodiments discussed above are disclosed in further detail in the following examples, which are not in any way intended to limit the scope of the present disclosure.

Experimental Materials and Methods

The following experimental materials and methods were used for Examples 1-5 described below.

Cell Culture

E14 mouse embryonic stem (mES) cells (ATCC cat no. CRL-1821) were cultured in media containing Glasgow's Modified Eagle Medium (GMEM) (Sigma, St. Louis, Mo.), 15% embryonic stem (ES) cell (fetal bovine serum) FBS qualified (Atlanta Biologicals, Norcross, Ga.), 1× Modified Eagle Medium (MEM) Non-Essential Amino Acids (Thermo Fisher Scientific, Canoga Park, Calif.), 1 mM Sodium Pyruvate (Thermo Fisher Scientific, Canoga Park, Calif.), 100M 3-mercaptoethanol (Thermo Fisher Scientific, Canoga Park, Calif.), 1× Penicillin-Streptomycin-L-Glutamine (Thermo Fisher Scientific, Canoga Park, Calif.), and 1000 U/ml Leukaemia Inhibitory Factor (Millipore). Cells were maintained on polystyrene (Falcon) coated with 0.1% gelatin (Sigma, St. Louis, Mo.) at 37° C. and 5% $CO_2$.

HEK293T cells were cultured in 1× Dulbecco's Modified Eagle Medium (DMEM) (Corning, Compton, Calif.), 10% FBS (Corning, Compton, Calif.), 1× Penicillin-Streptomycin-L-Glutamine (Corning, Compton, Calif.), 1 mM Sodium Pyruvate (Corning, Compton, Calif.), and 1×MEM Nonessential Amino Acids (Corning, Compton, Calif.) on polystyrene (Falcon) plates at 37° C. and 5% $CO_2$.

For transient transfections, HEK293T cells were plated in 48-well plates at the density of 125000 cells per well. The next day, cells were transfected with 1.5 μl Lipofectamine 2000 (Thermo Fisher Scientific, Canoga Park, Calif.) according to the manufacturer's instruction. 350 ng of ABE7.10 plasmid, 150 ng of gRNA expression plasmid, and 100 ng of GFP plasmid was used per well. In control wells, ABE7.10 and gRNA plasmids were replaced by pUC19 plasmid (NEB) to maintain the total amount of plasmids transfected at a constant level. Cells were then passaged to 24-well plates the day after transfection.

For in situ detection of barcodes, cells were plated on glass bottom 96-well plates (Cellvis) that were coated with 20 μg/ml laminin-511 (Biolamina) for at least 3 hours at 37° C.

Cell Line Engineering

Sequences of constructs, barcodes, and probes used in the examples below are shown in Tables 1A-1B, 2, 3A-3B, 4A-4D, 5A-5D, and 6A-6B. To create stable polyclonal cell lines, mES cells were cultured in 24-well plates to approximately 70% confluency and co-transfected with 600 ng of donor plasmid (Z1, control, or Z3) and 200 ng of modified pX330 plasmid (Addgene #42230) expressing Cas9 and a gRNA targeting ROSA26 locus (CAGGACAACGCC-CACACACC (SEQ ID NO. 1)). Transfection was performed using Lipofectamine LTX with Plus reagent (Thermo Fisher Scientific, Canoga Park, Calif.) based on the manufacturer's protocol. The cells were then passaged to a 6-well plate the next day and selected with 500 ug/ml Geneticin starting at 2 days after transfection.

TABLE 1A

Sequences of the constructs, barcodes, and/or probes used in Example 1. See FIGS. 1C, 1D, 1F, 1G, and related figures for results.

| Probe target | HCR initiator | Fluorophore | Related figure(s) |
| --- | --- | --- | --- |
| Zi-barcode | B1 | Alexa 546 | FIGS. 1C, 1D, and 8 |
| Cerulean | B3 | Alexa 488 | |
| Cerulean-3'UTR | B2 | Alexa 647 | |
| Z3-barcode1 | B1 | Alexa 488 | FIGS. 1F, 1G, and 9 |
| Z3-barcode2 | B2 | Alexa 647 | |
| Z3-barcode3 | B4 | Alexa 546 | |
| Cerulean | B3 | Alexa 594 | |
| Zi-barcode | B1 | Alexa 647 | FIG. 7 |
| Cerulean | B3 | Alexa 488 | |
| Cerulean-3'UTR | B2 | Alexa 594 | |

Pooled split initiator (v3.0) probes were purchased from Molecular Instruments and used according to their protocol.

TABLE 1B

Sequences of the constructs, barcodes, and/or probes used in Example 1. See FIGS. 1C, 1D, 1F, 1G, and related figures for results.

| Name | Sequence | SEQ ID NO. |
| --- | --- | --- |
| Z1-barcode | taacaggaaacagctatgacgggcccctaggtaagcagtatcttcgacagcttgtctctccagatg ctcttgggccatcttccacatcgtccgtagcagccttggcaatttgccatcactggcaaatacacat aaatccaatgaatacggttaccaccatcacattaccatgcaggtacacagcaagaattgacgttggc atatcacatggtgtaataaccccacttgtgaaacaacccagaataaggtacaaggcggaaatgtcgt cattctaaaataaaaggcatggccaggaatttgtctaataccgggaacttaaattcagcttgaacac cagtcgcaaaaaattcaaagaaagtgattcaggttcgggttcgtggattggaacagcttcttttgtt tcagtgatgagagaatcctcctgtcactcgagaaagaatcaaagaggccaacaacgcagaacaggaa acagctatgacgggcccctaggtaagcagtatcttcgacagcttgtctctccagatgctcttgggc catcttccacatcgtccgtagcagccttggcaatttgccatcactggcaaatacacataaatccaat gaatacggttaccaccatcacattaccatgcaggtacacagcaagaattgacgttggcatatcacat ggtgtaataaccccacttgtgaaacaacccagaataaggtacaaggcggaaatgtcgtcattctaaa ataaaaggcatggccaggaatttgtctaataccgggaacttaaattcagcttgaacaccagtcgcaa aaaattcaaagaaagtgattcaggttcgggttcgtggattggaacagcttcttttgtttcagtgatg agagaatcctcctgtcactcgagaaagaatcaaagaggccaacaa | 2 |
| Z3-barcode1 | taacaggaaacagctatgacgggcccctaggtaagcagtatcttcgacagcttgtctctccagatg ctcttgggccatcttccacatcgtccgtagcagccttggcaatttgccatcactggcaaatacacat aaatccaatgaatacggttaccaccatcacattaccatgcaggtacacagcaagaattgacgttggc atatcacatggtgtaataaccccacttgtgaaacaacccagaataaggtacaaggcggaaatgtcgt cattctaaaataaaaggcatggccaggaatttgtctaataccgggaacttaaattcagcttgaacac cagtcgcaaaaaattcaaagaaagtgattcaggttcgggttcgtggattggaacagcttcttttgtt tcagtgatgagagaatcctcctgtcactcgagaaagaatcaaagaggccaacaacgcagaacaggaa acagctatgacgggcccctaggtaagcagtatcttcgacagcttgtctctccagatgctcttgggc catcttccacatcgtccgtagcagccttggcaatttgccatcactggcaaatacacataaatccaat gaatacggttaccaccatcacattaccatgcaggtacacagcaagaattgacgttggcatatcacat ggtgtaataaccccacttgtgaaacaacccagaataaggtacaaggcggaaatgtcgtcattctaaa ataaaaggcatggccaggaatttgtctaataccgggaacttaaattcagcttgaacaccagtcgcaa aaaattcaaagaaagtgattcaggttcgggttcgtggattggaacagcttcttttgtttcagtgatg agagaatcctcctgtcactcgagaaagaatcaaagaggccaacaa | 3 |

TABLE 1B-continued

Sequences of the constructs, barcodes, and/or probes used in Example 1. See FIGS. 1C, 1D, 1F, 1G, and related figures for results.

| Name | Sequence | SEQ ID NO. |
|---|---|---|
| Z3-barcode2 | taacaggaaacagctatgacgggccccctaggggggttctgacttcttacgaaaatgtggctagcatt ccattctctgacgttcaaagaatcggaataagtcatggtaatggtgggaaatctaatagaagcgact cccataacctccatatttcttggcaaataattctgtctgggttaccgttcacgagccttcagagatc tacgacgtgtagtgggtgggcttgccctccagggtgtagtttgtaattagaatgggatttcctgttt taagtacccaaatacgaaaattgctcttgatgtttaacggctcacttttaagtaaagtttgtgccaa taccgtgcatgggagtaagttattgccaatcttcgagaatttaggcaattttggtatactcaactgg gtctaatatggtggacggaatgatttctcgagaaagaatcaaagaggccaacaacgcagaacaggaa acagctatgacgggccccctaggggggttctgacttcttacgaaaatgtggctagcattccattctct gacgttcaaagaatcggaataagtcatggtaatggtgggaaatctaatagaagcgactcccataacc tccatatttcttggcaaataattctgtctgggttaccgttcacgagccttcagagatctacgacgtg tagtgggtgggcttgccctccagggtgtagtttgtaattagaatgggatttcctgttttaagtaccc aaatacgaaaattgctcttgatgtttaacggctcacttttaagtaaagtttgtgccaataccgtgca tgggagtaagttattgccaatcttcgagaatttaggcaattttggtatactcaactgggtctaatat ggtggacggaatgatttctcgagaaagaatcaaagaggccaacaa | 4 |
| Z3-barcode3 | taacaggaaacagctatgacgggccccctaggcacattgcgtctttataaacttactaaaggttttg gatagttttgaacccattgtttgacgaatattccatattaaaaactctaaaataaaccccagccacc aacatttgaaccagcgttccccccatctccgctgtgatcattctagatctgtattatggcatcgact atgggaatacagggttattctcccattttattgaggtatatggccagttgcgcaacttctttgatga aattttatttgtccgttgcatgattgaaatcctaccagtagttatatatatgtcttttcattgttg tactttggataaagctgcttcttcagaacgctccctactatgctttaaacgcttattttcggaagaa atcatgtgggtcatattttttgcttctcgagaaagaatcaaagaggccaacaacgcagaacaggaa acagctatgacgggccccctaggcacattgcgtctttataaacttactaaaggttttggatagtttt gaacccattgtttgacgaatattccatattaaaaactctaaaataaaccccagccaccaacatttga accagcgttccccccatctccgctgtgatcattctagatctgtattatggcatcgactatgggaata cagggttattctcccattttattgaggtatatggccagttgcgcaacttctttgatgaaattttatt tgtccgttgcatgattgaaatcctaccagtagttatatatatgtcttttcattgttgtactttgga taaagctgcttcttcagaacgctccctactatgctttaaacgcttattttcggaagaaatcatgtgg gtcatattttttgcttctcgagaaagaatcaaagaggccaacaa | 5 |
| Z1 construct | agacacctcgagacccaataaaagatctttattttcattagatctgtgtgttggtttttgtgtgtc tagagtgtgggtgtgggcgttgtcctgcagggggaattgaacaggtgtaaaattggagggacaagact tcccacagattttcggttttgtcgggaagttttttaatagggggcaaataaggaaaatgggaggatag gtagtcatctggggtttatgcagcaaaactacaggttattattgcttgtgatccgcctcggagtat tttccatccgaggtagattaaagacatgctcacccgagttttatactctcctgctgcttgagatccttact acagtatgaaattacagtgtcgcgagttagactatgtaagcagaattttaatcattttttaaagagcc cagtacttcatatccatttctcccgctcctctctgcagcctatcaaaaggtattttagaacactcat tttagccccatttttcatttattatactggcttatccaaccctagacagagcattggcattttccct ttcctgatcttagaagtctgatgactcatgaaaccagacagattaccctgttatccctagaattcag cttgggtaaaaagctatgcgcataggcggtaatacggttatccacagaatcagggggataacgcagga aagaacatgtgagcaaaaggccagcaaaaggcaggaaccgtaaaaaggccgcgttgctggcgtttt tccataggctccgccccctgacgagcatcacaaaaatcgacgctcaagtcagaggtggcgaaaccc gacaggactataaagataccaggcgtttccccctggaagctccctcgtgcgctctcctgttccgacc ctgccgcttaccggatacctgtccgcctttctcccttcgggaagcgtggcgctttctcatagctcac gctgtaggtatctcagttcggtgtaggtcgttcgctccaagctgggctgtgtgcacgaaccccccgt tcagcccgaccgctgcgccttatccggtaactatcgtcttgagtccaacccggtaagacacgactta tcgccactggcagcagccactggtaacaggattagcagagcgaggtatgtaggcggtgctacagagt tcttgaagtggtggcctaactacggctacactagaagaacagtatttggtatctgcgctctgctgaa gccagttaccttcggaaaaagagttggtagctcttgatccggcaaacaaaccaccgctggtagcggt ggtttttttgtttgcaagcagcagattacgcgcagaaaaaaaggatctcaagaagatcctttgatct tttctacggggtctgacgctcagtggaacgaaaactcacgttaagggattttggtcatgagattatc aaaaaggatcttcacctagatccttttaaattaaaagtgaagttttaaatcaatctaaagtatatat gagtaaacttggtctgacagttaccaatgcttaatcagtgaggcacctatctcagcgatctgtctat ttcgttcatccatagttgcctgactccccgtcgtgtagataactacgatacgggagggcttaccatc tggccccagtgctgcaatgataccgcgagatccacgctcaccggctccagatttatcagcaataaac cagccagccggaagggccgagcgcagaagtggtcctgcaactttatccgcctccatccagtctatta attgttgccgggaagctagagtaagtagttcgccagttaatagtttgcgcaacgttgttgccattgc tacaggcatcgtggtgtcacgctcgtcgtttggtatggcttcattcagctccggttcccaacgatca aggcgagttacatgatccccatgttgtgcaaaaagcggttagctccttcggtcctccgatcgttg tcagaagtaagttggccgcagtgttatcactcatggttatggcagcactgcataattctcttactgt catgccatccgtaagatgcttttctgtgactggtgagtactcaaccaagtcattctgagaatagtgt atgcggcgaccgagttgctcttgcccggcgtcaatacgggataataccgcgccacatagcagaactt taaaagtgctcatcattggaaaacgttcttcggggcgaaaactctcaaggatcttaccgctgttgag atccagttcgatgtaacccactcgtgcacccaactgatcttcagcatcttttactttcaccagcgtt tctgggtgagcaaaaacaggaaggcaaaatgccgcaaaaaagggaataagggcgacacggaaatgtt gaatactcatactcttcctttttcaatattattgaagcatttatcagggttattgtctcatgagcgg atacatatttgaatgtatttagaaaaataaacaataggggtgatttaatctgtatcaggggcgtat agtggagcaaagcgaattctaactataacggtcctaaggtagcgaaagccccctcccggccccgcg ccgcagagtctggccgcgcgcccctgcgcaacgtggcaggaagcgcgcgctggggcgggacgggcg agtagggctgagcggtcgcggggcgggtgcaagcacgtttccgacttgagttgcctcaagaggggcg tgctgagccagacctccatcgcgcactccgggggagtggaggggaaggagcgagggctcagttgggctg ttttggaggcaggaagcacttgctctcccaaagtcgctctgagttgttatcagtaagggagctgcag tggagtaggcggggagaaggccgcacccttctccgaggggggagggggagtgttgcaatacctttct | 6 |

TABLE 1B-continued

Sequences of the constructs, barcodes, and/or probes used in Example 1. See FIGS. 1C, 1D, 1F, 1G, and related figures for results.

| Name | Sequence | SEQ ID NO. |
|---|---|---|
| | gggagttctctgctgcctcctggcttctgaggaccgccctgggcctgggagaatcccttcccctct | |
| | tccctcgtgatctgcaactccagtctttctagaagatgggcgggagtcttttgggcaggcttaaagg | |
| | ctaacctggttagggcgcagtagtccagggtttccttgatgatgtcatacttatcctgtcccttttt | |
| | tttccacagctcgcggttgaggacaaactcttcgcggtcttttccagtgttgacaattaatcatcggc | |
| | atagtatatcggcatagtataatacgacaaggtgaggaacgccaccatgattgaacaagatggattg | |
| | cacgcaggttctccggccgcttgggtgggagaggctattcggctatgactgggcacaacagacaatcg | |
| | gctgctctgatgccgccgtgttccggctgtcagcgcagggcgcccggttcttttttgtcaagaccga | |
| | cctgtccggtgccctgaatgaactgcaagacgaggcagcgcggctatcgtggctggccacgacgggc | |
| | gttccttgcgcagctgtgctcgacgttgtcactgaagcgggaagggactggctgctattgggcgaag | |
| | tgccggggcaggatctcctgtcatctcaccttgctcctgccgagaaagtatccatcatggctgatgc | |
| | aatgcggcggctgcatacgcttgatccggctacctgcccattcgaccaccaagcgaaacatcgcatc | |
| | gagcgagcacgtactcggatggaagccggtcttgtcgatcaggatgatctggacgaagagcatcagg | |
| | ggctcgcgccagccgaactgttcgccaggctcaaggcgagcatgcccgacggcgaggatctcgtcgt | |
| | gacccatggcgatgccttgccgaatatcatggtggaaaatggccgcttttctggattcatcgac | |
| | tgtggccggctgggtgtggcggaccgctatcaggacatagcgttggctacccgtgatattgctgaag | |
| | agcttggcggcgaatgggctgaccgcttcctcgtgctttacggtatcgccgctcccgattcgcagcg | |
| | catcgccttctatcgccttcttgacgagttcttctgatgtacaagtaaagcggccgcgactctagat | |
| | cataatcagccataccacatttgtagaggttttacttgctttaaaaaacctcccacacctcccctg | |
| | aacctgaaacataaaatgaatgcaattgttgttgttaacttgttattgcagcttataatggttaca | |
| | aataaagcaatagcatcacaaatttcacaaataaagcatttttttcactgcattctagttgtggttt | |
| | gtccaaactcatcaatgtatcttaggtctcgcgtactgtaggtcctttcagcaaaaaaccctcaag | |
| | acccgtttagaggccccaagggggttatgctagtattgctcaggcggtggcagcagccaactcagctt | |
| | cctttcgggctttgttagcagccggatctcagtggtggtggtggtggtgctcccatctgacttgcaa | |
| | gaaaacagatggcaagcatgacaatcatttcgagtgcggccgcagcgacaaacaacagataaaacga | |
| | aaggcccagtctttcgactgagcctttcgttttatttgaagcttctttcagcaaaaaacccccgcagg | |
| | accccgaagaggcccccgcggggttatgctaggtcgactacgcagacgtaacaggaaacagctatga | |
| | cgggccccctaggtaagcagtatcttcgacagcttgtctctccagatgctcttgggccatcttccac | |
| | atcgtccgtagcagccttggcaatttgccatcactggcaaatacacataaatccaatgaatacggtt | |
| | accaccatcacattaccatgcaggtacacagcaagaattgacgttggcatatcacatggtgtaataa | |
| | ccccacttgtgaaacaacccagaataaggtacaaggcggaaatgtcgtcattctaaaataaaaggca | |
| | tggccaggaatttgtctaataccgggaacttaaattcagcttgaacaccagtcgcaaaaaattcaaa | |
| | gaaagtgattcaggttcgggttcgtggattggaacagcttctttttgtttcagtgatgagagaatcct | |
| | cctgtcactcgagaaagaatcaaagaggccaacaacgcagaacaggaaacagctatgacgggccccc | |
| | taggtaagcagtatcttcgacagcttgtctctccagatgctcttgggccatcttccacatcgtccgt | |
| | agcagccttggcaatttgccatcactggcaaatacacataaatccaatgaatacggttaccaccatc | |
| | acattaccatgcaggtacacagcaagaattgacgttggcatatcacatggtgtaataaccccacttg | |
| | tgaaacaacccagaataaggtacaaggcggaaatgtcgtcattctaaaataaaaggcatggccagga | |
| | atttgtctaataccgggaacttaaattcagcttgaacaccagtcgcaaaaaattcaaagaaagtgat | |
| | tcaggttcgggttcgtggattggaacagcttctttttgtttcagtgatgagagaatcctcctgtcact | |
| | cgagaaagaatcaaagaggccaacaacgacctgtagaggtcctcccttagtgagggttaattctcg | |
| | agtctccctatagtgagtcgtattaattccgtgtattctatagtgtcacctaaatcgttacgggttc | |
| | gtaaattctgcaggacttctagttattaatagtaatcaattacggggtcattagttcatagcccata | |
| | tatggagttccgcgttacataacttacggtaaatggcccgcctggctgaccgcccaacgacccccgc | |
| | ccattgacgtcaataatgacgtatgttcccatagtaacgccaatagggactttccattgacgtcaat | |
| | gggtggagtatttacggtaaactgcccacttggcagtacatcaagtgtatcatatgccaagtacgcc | |
| | ccctattgacgtcaatgacggtaaatggcccgcctggcattatgcccagtacatgaccttatgggac | |
| | tttcctacttggcagtacatctacgtattagtcatcgctattaccatggtcgaggtgagccccacgt | |
| | tctgcttcactctccccatctcccccccctccccacccccaattttgtatttatttatttttttaatt | |
| | attttgtgcagcgatgggggcgggggggggggggcgcgcgccaggcggggcggggcgggcgag | |
| | gggcgggcgggcgaggcggagaggtgcggcggcagccaatcagagcggcgcgctccgaaagtttc | |
| | cttttatggcgaggcggcggcggcggcggccctataaaaagcgaagcgcgcggcgggcgggagtcgc | |
| | tgcgcgctgccttcgccccgtgccccgctccgccgcgcctcggcgcgccgcccccggctctgactg | |
| | accgcgttactcccacaggtgagcgggcgggacggcccttctcctccgggctgtaattagcgcttgg | |
| | tttaatgacggcttgtttcttttctgtggctgcgtgaaagccttgaggggctccgggagggccctt | |
| | gtgcgggggggagcggctcgggggtgcgtgcgtgtgtgtgcgtggggagcgccgcgtgcggctcc | |
| | gcgctgcccggcggctgtgagcgctgcgggcgcggcgcggggctttgtgcgctccgcagtgtgcgcg | |
| | aggggagcgcggccgggggcggtgccccgcggtgcgggggggctgcgaggggaacaaaggctgcgtg | |
| | cggggtgtgtgcgtgggggggtgagcaggggtgtgggcgcgtcggtcgggctgcaacccccccctg | |
| | cacccccctccccgagttgctgagcacggcccggcttcgggtgcgggctccgtacggggcgtggcg | |
| | cggggctcgccgtgccgggcggggggtggcggcaggtggggtgccaggtgccggggcggggccgctcg | |
| | ggccggggagggctcggggagggggcgcggcggccccggagccgcggcggctgtcgaggcgcggcg | |
| | agccgcagccattgccttttatggtaatcgtgcgagagggcgcagggacttcctttgtcccaaatct | |
| | gtgcggagccgaaatctgggaggcgccgccgcacccctctagcgggcgcggggcgaagcggtgcgg | |
| | cgccggcaggaaggaaatgggcgggagggccttcgtgcgtcgccgcgccgccgtcccctttctccct | |
| | ctccagcctcggggctgtccgcgggggggacggctgccttcgggggggacgggcagggcggggttcg | |
| | gcttctggcgtgtgaccggcggctctagagcctctgctaaccatgttcatgccttcttctttttcct | |
| | acagctcctgggcaacgtgctggttattgtgctgtctcatcattttggcaaagaattgatttgatac | |
| | gcgggccgggatccctcgaggaattaccttttggccgtgccaccatgccagagcagcgaa | |
| | gtctgctcccgccccgaaaaagggctccaagaaggcggtgactaaggcgcagaagaaaggccgcaag | |
| | aagcgcaagcgcagccgcaaggagagctattccatctatgtgtacaaggttctgaagcaggtccacc | |
| | ctgacaccggcatttcgtccaaggccatgggcatcatgaattcgtttgtaacgacattttcgagcg | |
| | catcgctggtgaggcttcccgcctggcgcattacaacaagcgctcgaccatcacctccagggagatc | |
| | cagacggccgtgcgcctgctgctgcctggggagttggccaagcacgccgtgtccgagggtactaagg | |

TABLE 1B-continued

Sequences of the constructs, barcodes, and/or probes used in Example 1. See FIGS. 1C, 1D, 1F, 1G, and related figures for results.

| Name | Sequence | SEQ ID NO. |
|---|---|---|
| | ccatcaccaagtacaccagcgctaaggatccccgggtaccggtcgccaccatggtgagcaagggcga ggagctgttcaccggggtggtgcccatcctggtcgagctggacggcgacgtaaacggccacaagttc agcgtgtccggcgagggcgagggcgatgccacctacggcaagctgaccctgaagttcatctgcacca ccggcaagctgcccgtgcccggccaccctcgtgaccaccctgacctggggcgtgcagtgcttcgc ccgctaccccgaccacatgaagcagcacgacttcttcaagtccgccatgcccgaaggctacgtccag gagcgcaccatcttcttcaaggacgacggcaactacaagacccgcgccgaggtgaagttcgagggcg acaccctggtgaaccgcatcgagctgaagggcatcgacttcaaggaggacggcaacatcctgggca caagctggagtacaacgccatcagcgacaacgtctatatcaccgccgacaagcagaagaacggcatc aaggccaacttcaagatccgccacaacatcgaggacggcagcgtgcagctcgccgaccactaccagc agaacacccccatcggcgacggccccgtgctgctgcccgacaaccactacctgagcacccagtccaa gctgagcaaagaccccaacgagaagcgcgatcacatggtcctgctggagttcgtgaccgccgccggg atcactctcggcatggacgagctgtacaagtgaacctgagtcgtaacaggaaacagctatgacgggc cccctaggacgttcccatagctccttttgatgtcttaatgtaggttcaacagatatgcggcttcttc gcattctgatggcgtcagctacgataggcgagagctgaatagttgaaaattttagcagatgcctga gaaaattaaacttgatttgattccagtaatttaccaaaatacgcacagttgccttcttcgatgtaat cttttcaatcgtactatgtcgtatgcagttagcaaatgaaagtagcaacaccaatttgcgccagaat ttcacgtcgaaaatatccttaaaccttgcaagccaagttacggagttgaaatttccgtaagctacgg ttatcttccaatggcccatacttggctaaatcagagttcccttttcgtggaaactgcaatagccaaat tcctcgagaaagaatcaaagaggccaacaacgcagaacaggaaacagctatgacgggcccctagga cgttcccatagctccttttgatgtcttaatgtaggttcaacagatatgcggcttcttcgcattctga tggcgtcagctacgataggcgagagctgaatagttgaaaattttagcagatgcctgagaaaattaa acttgatttgattccagtaatttaccaaaatacgcacagttgccttcttcgatgtaatcttttcaat cgtactatgtcgtatgcagttagcaaatgaaagtagcaacaccaatttgcgccagaatttcacgtcg aaaatatccttaaaccttgcaagccaagttacggagttgaaatttccgtaagctacggttatcttcc aatggcccatacttggctaaatcagagttcccttcgtggaaactgcaatagccaaattcctcgaga aagaatcaaagaggccaacaacgacctgctaaggtctgtgccttctagttgccagccatctgttgtt tgcccctccccgtgccttccttgaccctggaagggccactcccactgtcctttcctaataaaatg aggaaattgcatcgcattgtctgagtaggtgtcattctattctggggggtggggtggggcaggacag caaggggggaggattgggaagagaatagcaggcatgctggggatgcggtgggctctatggtacg | |
| Control construct | agacacctcgagacccaataaaagatctttatttcattagatctgtgtgttggtttttgtgtgtc tagagtgtgggtgtgggcgttgtcctgcaggggaattgaacaggtgtaaaattggagggacaagact tcccacagattttcggttttgtcgggaagttttttaatagggggcaaataaggaaaatgggaggatag gtagtcatctggggttttatgcagcaaaactacaggttattattgcttgtgatccgcctcggagtat tttccatcgaggtagattaaagacatgctcacccgagttttatactctcctgcttgagatccttact acagtatgaaattacagtgtcgcgagttagactatgtaagcagaattttaatcattttttaaagagcc cagtacttcatatccatttctcccgctccttctgcagcttatcaaaaggtattttagaacactcat tttagccccattttcatttattatactggcttatccaaccctagacagagcattggcattttccct ttcctgatcttagaagtctgatgactcatgaaaccagacagattaccctgttatccctagaattcag cttgggataaaaagctatggcataggcggtaatacggttatccacagaatcagggggataacgcagga agaacatgtgagcaaaaggccagcaaaaggccaggaaccgtaaaaaggccgcgttgctggcgtttt tccataggctccgccccctgacgagcatcacaaaaatcgacgctcaagtcagaggtggcgaaaccc gacaggactataaagataccaggcgtttccccctggaagctccctcgtgcgctctcctgttccgacc ctgccgcttaccggatacctgtccgcctttctcccttcgggaagcgtggcgctttctcatagctcac gctgtaggtatctcagttcggtgtaggtcgttcgctccaagctgggctgtgtgcacgaaccccccgt tcagcccgaccgctgcgccttatccggtaactatcgtcttgagtccaacccggtaagacacgactta tcgccactggcagcagccactggtaacaggattagcagagcgaggtatgtaggcggtgctacagagt tcttgaagtggtggcctaactacggctacactagaagaacagtatttggtatctgcgctctgctgaa gccagttaccttcggaaaaagagttggtagctcttgatccggcaaacaaaccaccgctggtagcggt ggtttttttgtttgcaagcagcagattacgcgcagaaaaaaggatctcaagaagatcctttgatct tttctacggggtctgacgctcagtggaacgaaaactcacgttaagggattttggtcatgagattatc aaaaaggatcttcacctagatccttttaaattaaaaatgaagttttaaatcaatctaaagtatatat gagtaaacttggtctgacagttaccaatgcttaatcagtgaggcacctatctcagcgatctgtctat ttcgttcatccatagttgcctgactccccgtcgtgtagataactacgatacgggagggcttaccatc tggccccagtgctgcaatgataccgcgagatccacgctcaccggctccagatttatcagcaataaac cagccagccgaagggccgagccagaagtggtcctgcaacttatccgcctccatccagtctatta attgttgccgggaagctagagtaagtagttcgccagttaatagtttgcgcaacgttgttgccattgc tacaggcatcgtggtgtcacgctcgtcgtttggtatggcttcattcagctccggttcccaacgatca aggcgagttacatgatccccatgttgtgcaaaaagcggttagctccttcggtcctccgatcgttg tcagaagtaagttggccgcagtgttatcactcatggttatggcagcactgcataattctcttactgt catgccatccgtaagatgcttttctgtgactggtgagtactcaaccaagtcattctgagaatagtgt atgcggcgaccgagttgctcttgcccggcgtcaatacgggataataccgcgccacatagcagaactt taaaagtgctcatcattggaaaacgttcttcggggcgaaaactctcaaggatcttaccgctgttgag atccagttcgatgtaacccactcgtgcacccaactgatcttcagcatcttttactttcaccagcgtt tctgggtgagcaaaaacaggaaggcaaaatgccgcaaaaaagggaataagggcgacacggaaatgtt gaatactcatactcttcctttttcaatattattgaagcatttatcagggttattgtctcatgagcgg atacatatttgaatgtatttagaaaaataaacaaataggggtgatttaatctgtatcaggggcgtat agtggagcaaagcgaattctaactataacggtcctaaggtagcgaagccctccccctcggccccgcg ccgcagagtctggccgcgcgcccctgcgcaacgtggcaggaagcggcgcgctggggcgggacgggc agtagggctgagcggctgcggggcgggtgcaagcacgtttccgacttgagttgcctcaagagggcg tgctgagccagacctccatcgcgcactccggggagtggagggaaggagcgagggctcagttgggctg ttttggaggcaggaagcacttgctctcccaaagtcgctctgagttgttatcagtaagggagctgcag tggagtaggcggggagaaggccgcacccttctccgagggggggaggggagtgttgcaataccttctct | 7 |

TABLE 1B-continued

Sequences of the constructs, barcodes, and/or probes used in Example 1. See FIGS. 1C, 1D, 1F, 1G, and related figures for results.

| Name | Sequence | SEQ ID NO. |
|---|---|---|
| | gggagttctctgctgcctcctggcttctgaggaccgccctgggcctgggagaatcccttcccctct tccctcgtgatctgcaactccagtcttttctagaagatgggcgggagtcttttgggcaggcttaaagg ctaacctggttagggcgcagtagtccagggtttccttgatgatgtcatacttatcctgtcccttttt tttccacagctcgcggttgaggacaaactcttcgcggtcttttccagtgttgacaattaatcatcggc atagtatatcggcatagtataatacgacaaggtgaggaacgccaccatgattgaacaagatggattg cacgcaggttctccggccgcttgggtgggagaggctattcggctatgactgggcacaacagacaatcg gctgctctgatgccgccgtgttccggctgtcagcgcagggcgcccggttcttttttgtcaagaccga cctgtccggtgccctgaatgaactgcaagacgaggcagcgcggctatcgtggctggccacgacgggc gttccttgcgcagctgtgctcgacgttgtcactgaagcgggaagggactggctgctattgggcgaag tgccggggcaggatctcctgtcatctccaccttgctcctgccgagaaagtatccatcatggctgatgc aatgcggcggctgcatacgcttgatccggctacctgcccattcgaccaccaagcgaaacatcgcatc gagcgagcacgtactcggatggaagccggtcttgtcgatcaggatgatctggacgaagagcatcagg ggctcgcgccagccgaactgttcgccaggctcaaggcgagcatgcccgacggcgaggatctcgtcgt gaccatggcgatgcctgcttgccgaatatcatggtggaaaatggccgcttttctggattcatcgac tgtggccggctgggtgtggcggaccgctatcaggacatagcgttggctacccgtgatattgctgaag agctggcggcgaatgggctgaccgcttcctcgtgctttacggtatcgccgctcccgattcgcagcg catcgccttctatcgccttcttgacgagttcttctgatgtacaagtaaagcggccgcgactctagat cataatcagccataccacatttgtagaggttttacttgctttaaaaaacctcccacacctcccctg aacctgaaacataaaatgaatgcaattgttgttgttaacttgtttattgcagcttataatggttaca aataaagcaatagcatcacaaatttcacaaataaagcattttttcactgcattctagttgtggttt gtccaaactcatcaatgtatcttaggtctcgcgtactgtaggtcctttcagcaaaaaaccccctcaag acccgtttagaggccccaaggggttatgctagttattgctcaggtggcagcagccaactcagctt cctttcgggctttgttagcagccggatctcagtggtggtggtggtggtgctcccatctgacttgcaa gaaaacagatggcaagcatgacaatcatttcgagtgcggccgcagcgacaaacaacagataaaacga aaggcccagtctttcgactgagcctttcgttttatttgaagcttctttcagcaaaaaaccccgcagg accccgaagaggccccgcggggttatgctaggtcgactacgcagacgtaacaggaaacagctatga cgggcccctaggtaagcagtatcttcgacagcttgtctctccagatgctcttgggccatcttccac atcgtccgtagcagccttggcaatttgccatcactggcaaatacacataaatccaatgaatacggtt accaccatcacattaccatgcaggtacacagcaagaattgacgttggcatatcacatggtgtaataa ccccacttgtgaaacaacccagaataaggtacaaggcggaaatgtcgtcattctaaaataaaaggca tggccaggaatttgtctaataccgggaacttaaattcagcttgaacaccagtcgcaaaaaattcaaa gaaagtgattcaggttcgggttcgtggattggaacagcttcttttgtttcagtgatgagagaatcct cctgtcactcgagaaagaatcaaagaggccaacaacgcagaacaggaaacagctatgacgggcccc taggtaagcagtatcttcgacagcttgtctctccagatgctcttgggccatcttccacatcgtccgt agcagccttggcaatttgccatcactggcaaatacacataaatccaatgaatacggttaccaccatc acattaccatgcaggtacacagcaagaattgacgttggcatatcacatggtgtaataaccccacttg tgaaacaacccagaataaggtacaaggcggaaatgtcgtcattctaaaataaaaggcatggccagga atttgtctaataccgggaacttaaattcagcttgaacaccagtcgcaaaaaattcaaagaaagtgat tcaggttcgggttcgtggattggaacagcttcttttgtttcagtgatgagagaatcctcctgtcact cgagaaagaatcaaagaggccaacaacgacctgtagcgtaaattctgcaggacttctagttattaat agtaatcaattacggggtcattagttcatagcccatatatggagttccgcgttacataacttacggt aaatggcccgcctggctgaccgcccaacgacccccgcccattgacgtcaataatgacgtatgttccc atagtaacgccaatagggactttccattgacgtcaatgggtggagtatttacggtaaactgcccact tggcagtacatcaagtgtatcatatgccaagtacgccccctattgacgtcaatgacggtaaatggcc cgcctggcattatgcccagtacatgaccttatgggactttcctacttggcagtacatctacgtatta gtcatcgctattaccatggtcgaggtgagccccacgttctgcttcactctccccatctcccccccct ccccaccccaatttgtattttatttatttttaattatttgtgcagcgatggggcggggggggg gggggcgcgcgccaggcggggcgggcgggcgaggggcggggcgggcgaggcgagaggtgcg gcgcagccaatcagagcggcgcgctccgaaagttccttttatggcgaggcggcggcggcggc cctataaaaagcgaagcgcgcggcgggcgggagtcgctgcgcgctgccttcgccccgtgccccgctc cgccgccgcctcgcgccgcccgccccggctctgactgaccgcgttactccacaggtgagcgggcgg gacggcccttctcctccgggctgtaattagcgcttggtttaatgacggcttgtttcttttctgtggc tgcgtgaaagccttgaggggctccgggagggccctttgtgcggggggagcggctcggggggtgcgtg cgtgtgtgtgcgtggggagcgccgcgtgcggctccgcgctgccggcggctgtgagcgctgcggg cgcggcgcggggctttgtgcgctccgcagtgtgcgcgaggggagcgcggccgggggcggtgccccgc ggtgcgggggctgcgagggaacaaaggctgcgtgcggggtgtgtgcgtggggggtgagcaggg ggtgtgggcgcgtcggtcgggctgcaacccccccctgcaccccctccccgagttgctgagcacggc ccggcttcggggtgcgggctccgtacggggcgtggcgcggggctcgccgtgccgggcgggggtggc ggcaggtgggggtgccgggcgggcgggccgcctcgggccggggagggctcgggggagggcgcgg cggccccggagcgcgggcggctgcgaggcgcggcgagccgcagccattgccttttatggtaatcg tgcgagagggcgcagggacttcctttgtcccaaatctgtgcggagccgaaatctgggaggcgccgcc gcaccccctctagcgggcgcggggcgaagcggtgcggcgccggcaggaaggaaatgggcgggaggg ccttcgtgcgtcgccgcgccgccgtccccttctccctctccagcctcggggctgtccgcgggggac ggctgccttcgggggggacggggcgggttcggcttctggccgtgtgaccggcggctctagag cctctgctaaccatgttcatgccttcttctttttcctacagctcctgggcaacgtgctggttattgt gctgtctcatcatttggcaaagaattgatttgataccgcgggcccggatcccctcgagggaatta cctggttcgtagccgccaccatgccagagcagcgaagtctgctcccgccccgaaaaaggctccaa gaaggcggtgactaaggcgcagaagaaaggcggcaagagcgcaagcgcaaggaagagcgtat tccatctatgtgtacaaggttctgaagcaggtccaccctgacaccggcattctcgtccaaggccatg gcatcatgaattcgtttgtgaacgcacatttcgagcgcatcgctgttgaggcttccgcctggcgca ttacaacaagcgctcgaccatcacctccagggagatccagacggccgtgcgcctgctgctgcctggg gagttggccaagcacgccgtgtccgagggtactaaggccatcaccaagtacaccagcgctaaggatc cccgggtaccggtcgccaccatggtgagcaagggcgaggagctgttcaccggggtggtgcccatcct | |

TABLE 1B-continued

Sequences of the constructs, barcodes, and/or probes used in Example 1. See FIGS. 1C, 1D, 1F, 1G, and related figures for results.

| Name | Sequence | SEQ ID NO. |
|---|---|---|
| | ggtcgagctggacggcgacgtaaacggccacaagttcagcgtgtccggcgagggcgagggcgatgcc acctacggcaagctgaccctgaagttcatctgcaccaccggcaagctgcccgtgccctggcccaccc tcgtgaccaccctgacctggggcgtgcagtgcttcgcccgctaccccgaccacatgaagcagcacga cttcttcaagtccgccatgcccgaaggctacgtccaggagcgcaccatcttcttcaaggacgacggc aactacaagacccgcgccgaggtgaagttcgagggcgacaccctggtgaaccgcatcgagctgaagg gcatcgacttcaaggaggacggcaacatcctggggcacaagctggagtacaacgccatcagcgacaa cgtctatatcaccgccgacaagcagaagaacggcatcaaggccaacttcaagatccgccacaacatc gaggacggcagcgtgcagctcgccgaccactaccagcagaacacccccatcggcgacggccccgtgc tgctgcccgacaaccactacctgagcacccagtccaagctgagcaaagaccccaacgagaagcgcga tcacatggtcctgctggagttcgtgaccgccgcgggatcactctcggcatggacgagctgtacaag tgaacctttggcgtaacaggaaacagctatgacgggcccctaggacgttcccatagctccttttga tgtcttaatgtaggttcaacagatatgcggcttcttcgcattctgatggcgtcagctacgataggcg agagctgaatagttgaaaattttttagcagatgcctgagaaaattaaacttgatttgattccagtaat ttaccaaaatacgcacagttgccttcttcgatgtaatcttttcaatcgtactatgtcgtatgcagtt agcaaatgaaagtagcaacaccaatttgcgccagaatttcacgtcgaaaatatccttaaaccttgca agccaagttacggagttgaaatttccgtaagctacggttatcttccaatggcccatacttggctaaa tcagagttccctttcgtggaaactgcaatagccaaattcctcgagaaagaatcaaagaggccaacaa cgcagaacaggaaacagctatgacgggccccctaggacgttcccatagctccttttgatgtcttaat gtaggttcaacagatatgcggcttcttcgcattctgatggcgtcagctacgataggcgagagctgaa tagttgaaaattttttagcagatgcctgagaaaattaaacttgatttgattccagtaatttaccaaa tacgcacagttgccttcttcgatgtaatcttttcaatcgtactatgtcgtatgcagttagcaaatga aagtagcaacaccaatttgcgccagaatttcacgtcgaaaatatccttaaaccttgcagccaagttc acggagttgaaatttccgtaagctacggttatcttccaatggcccatacttggctaaatcagagttc cctttcgtggaaactgcaatagccaaattcctcgagaaagaatcaaagaggccaacaacgacctgag taggtctgtgccttctagttgccagccatctgttgtttgccctccccgtgccttccttgaccctg gaaggtgccactcccactgtcctttcctaataaaatgaggaaattgcatcgcattgtctgagtaggt gtcattctattctgggggtggggtgggcaggacagcaaggggaggattgggaagagaatagcag gcatgctggggatgcggtgggctctatggtacg | |
| Z3 construct | agacacctcgagacccaataaaagatctttattttcattagatctgtgtgttggttttttgtgtgtc tagagtgtgggtgtgggcgttgtcctgcagggggaattgaacaggtgtaaaattggagggacaagact tcccacagattttcggttttgtcgggaagttttttaataggggcaaataaggaaaatggggaggatag gtagtcatctggggttttatgcagcaaaactacaggttattattgcttgtgatccgcctcggagtat tttccatcgaggtagattaaagacatgctcacccgagttttatactctcctgcttgagatccttact acagtatgaaattacagtgtcgcgagttagactatgtaagtgaattttaatcattttttaaagagcc cagtacttcatatccatttctcccgctcctctctgcagccttatcaaaaggtattttagaacactcat tttagcccccattttcatttattatactggcttatccaaccccctagacagagcattggcattttccct ttcctgatcttagaagtctgatgactcatgaaaccagacagattaccctgttatccctagaattcag cttgggataaaaagctatgcataggcggtaatacggttatccacagaatcaggggataacgcagga aagaacatgtgagcaaaaggccagcaaaaggccaggaaccgtaaaaaaggccgcgttgctggcgtttt tccataggctccgccccctgacgagcatcacaaaaatcgacgctcaagtcagaggtggcgaaaccc gacaggactataaagataccaggcgttccccctggaagctccctcgtgcgctctcctgttccgacc ctgccgcttaccggatacctgtccgcctttctcccttcgggaagcgtggcgctttctcatagctcac gctgtaggtatctcagttcggtgtaggtcgttcgctccaagctgggctgtgtgcacgaaccccccgt tcagcccgaccgctgcgccttatccggtaactatcgtcttgagtccaacccggtaagacacgactta tcgccactggcagcagccactggtaacaggattagcagagcgaggtatgtaggcggtgctacagagt tcttgaagtggtggcctaactacggctacactagaagaacagtatttggtatctgcgctctgctgaa gccagttaccttcggaaaaagagttggtagctcttgatccggcaaacaaaccaccgctggtagcggt ggtttttttgtttgcaagcagcagattacgcgcagaaaaaaggatctcaagaagatcctttgatct tttctacggggtctgacgctcagtggaacgaaaactcacgttaagggattttggtcatgagattatc aaaaaggatcttcacctagatccttttaaattaaaaatgaagttttaaatcaatctaaagtatatat gagtaaacttggtctgacagttaccaatgcttaatcagtgaggcacctatctcagcgatctgtctat ttcgttcatccatagttgcctgactccccgtcgtgtagataactacgatacgggagggcttaccatc tggccccagtgctgcaatgataccgcgagatccacgctcaccggctccagatttatcagcaataaac cagccagccgaagggccgagcgcagaagtggtcctgcaactttatccgcctccatccagtctatta attgttgccgggaagctagaagtaagtagttcgccagttaatagtttgcgcaacgttgttgccattgc tacaggcatcgtggtgtcacgctcgtcgtttggtatggcttcattcagctccggttcccaacgatca aggcgagttacatgatccccccatgttgtgcaaaaaagcggttagctccttcggtcctccgatcgttg tcagaagtaagttggccgcagtgttatcactcatggttatggcagcactgcataattctcttactgt catgccatccgtaagatgcttttctgtgactggtgagtactcaaccaagtcattctgagaatagtgt atgcggcgaccgagttgctcttgcccggcgtcaatacgggataataccgcgccacatagcagaactt taaaagtgctcatcattggaaaacgttcttcggggcgaaaactctcaaggatcttaccgctgttgag atccagttcgatgtaacccactcgtgcacccaactgatcttcagcatcttttactttcaccagcgtt tctgggtgagcaaaaacaggaaggcaaaatgccgcaaaaaagggaataagggcgacacggaaatgtt gaatactcatactcttcctttttcaatattattgaagcatttatcagggttattgtctcatgagcgg atacatatttgaatgtatttagaaaaataaacaaataggggtgatttaatctgtatcaggggcgtat agtggagcaaagcgaattctaactataacggtcctaaggtagcgaaggccctcccctcggccccgcg ccgcagagtctggcgcgcgcccctgcgcaacgtggcaggaagcgcgctgtggggcgggagacgggc agtagggctgagcggctgcggggcgggtgcaagcacgtttccgacttgagttgcctcaagagggcg tgctgagccagacctccatcgcgcactccggggagtggaggggaaggagcgagggctcagttgggctg ttttggaggcaggaagcacttgctctcccaaagtgctctgagttgttatcagtaagggagctgcag tggagtaggcgggagaaggccgcacccttctccggagggggaggggagtgttgcaatacctttct gggagttctctgctgcctcctggcttctgaggaccgccctgggcctgggagaatcccttccccctct | 8 |

TABLE 1B-continued

Sequences of the constructs, barcodes, and/or probes used in Example 1. See FIGS. 1C, 1D, 1F, 1G, and related figures for results.

| Name | Sequence | SEQ ID NO. |
|---|---|---|
| | tccctcgtgatctgcaactccagtctttctagaagatgggcgggagtctttttgggcaggcttaaagg | |
| | ctaacctggttagggcgcagtagtccagggtttccttgatgatgtcatacttatcctgtcccttttt | |
| | tttccacagctcgccggttgaggacaaactcttcgcggtctttccagtgttgacaattaatcatcggc | |
| | atagtatatcggcatagtataatacgacaaggtgaggaacgccaccatgattgaacaagatggattg | |
| | cacgcaggttctccggccgcttgggtggagaggctattcggctatgactgggcacaacagacaatcg | |
| | gctgctctgatgccgccgtgttccggctgtcagcgcagggcgcccggttctttttgtcaagaccga | |
| | cctgtccggtgccctgaatgaactgcaagacgaggcagcgcggctatcgtggctggccacgacgggc | |
| | gttccttgcgcagctgtgctcgacgttgtcactgaagcgggaagggactggctgctattgggcgaag | |
| | tgccggggcaggatctcctgtcatctcaccttgctcctgccgagaaagtatccatcatggctgatgc | |
| | aatgcggcggctgcatacgcttgatccggctacctgcccattcgaccaccaagcgaaacatcgcatc | |
| | gagcgagcacgtactcggatggaagccggtcttgtcgatcaggatgatctggacgaagagcatcagg | |
| | ggctcgcgccagccgaactgttcgccaggctcaaggcgagcatgcccgacggcgaggatctcgtcgt | |
| | gacccatggcgatgcctgcttgccgaatatcatggtggaaaatggccgcttttctggattcatcgac | |
| | tgtggccggctgggtgtggcggaccgctatcaggacatagcgttggctacccgtgatattgctgaag | |
| | agcttggcggcgaatgggctgaccgcttcctcgtgctttacggtatcgccgctcccgattcgcagcg | |
| | catcgccttctatcgccttcttgacgagttcttctgatgtacaagtaaagcggccgcgactctagat | |
| | cataatcagccataccacatttgtagaggttttacttgctttaaaaaacctcccacacctcccctg | |
| | aacctgaaacataaaatgaatgcaattgttgttgttaacttgtttattgcagcttataatggttaca | |
| | aataaagcaatagcatcacaaatttcacaaataaagcatttttttcactgcattctagttgtggttt | |
| | gtccaaactcatcaatgtatcttaggtctcgcgtactgtcgtactgtcgtaggtttgtctggtcaac | |
| | caccgcgttctcagtggtgtacggtacaaaccacctcagaaggtggtttgtaccgtacaccactgag | |
| | aacgcggtggttgaccagacaaacctacggtagcgtaacaggaaacagctatgacgggcccctagg | |
| | cacattgcgtctttataaacttactaaaggttttggatagttttgaaccattgtttgacgaatatt | |
| | ccatattaaaaactctaaaataaaccccagccaccaacatttgaaccagcgttcccccatctccgc | |
| | tgtgatcattctagatctgtattatggcatcgactatgggaatacagggttattctcccatttatt | |
| | gaggtatatggccagttgcgcaacttctttgatgaaattttatttgtccgttgcatgattgaaatcc | |
| | taccagtagttatatatatgtcttttcattgttgtactttggataaagctgcttcttcagaacgct | |
| | ccctactatgctttaaacgcttattttcggaagaaatcatgtgggtcatattttttgcttctcgag | |
| | aaagaatcaaagaggccaacaacgcagaacaggaaacagctatgacgggcccctaggcacattgcg | |
| | tctttataaacttactaaaggttttggatagttttgaaccattgtttgacgaatattccatattaa | |
| | aaactctaaaataaaccccagccaccaacatttgaaccagcgttcccccatctccgctgtgatcat | |
| | tctagatctgtattatggcatcgactatgggaatacagggttattctcccatttattgaggtatat | |
| | ggccagttgcgcaacttctttgatgaaattttatttgtccgttgcatgattgaaatcctaccagtag | |
| | ttatatatatgtcttttcattgttgtactttggataaagctgcttcttcagaacgctccctactat | |
| | gctttaaacgcttattttcggaagaaatcatgtgggtcatattttttgcttctcgagaaagaatca | |
| | aagaggccaacaacgaccctggttcgtaggcttgtcgacgacggcgcttctccgtcgtcaggatcatac | |
| | ctagacacctcagaaggtcctcccctttagtgagggttaattctcgagtctccctatagtgagtcgta | |
| | ttaattccgtgtattctatagtgtcacctaaatcgttacggtagcgtactgtcgtaggtttgtctgg | |
| | tcaaccaccgcgctctcagtggtgtacggtacaaaccacctcagaaggtggtttgtaccgtacacca | |
| | ctgagagcgcggtggttgaccagacaaacctacggtagcgtaacaggaaacagctatgacgggcccc | |
| | ctaggggttctgacttcttacgaaaatgtggctagcattccattctctgacgttcaaagaatcgga | |
| | ataagtcatggtaatggtgggaaatctaatagaagcgactcccataacctccatatttcttggcaaa | |
| | taattctgtctggttaccgttcacgagccttcagagatctacgacgtgtagtgggtgggcttgccc | |
| | tccagggtgtagtttgtaattagaatgggatttcctgttttaagtacccaaatacgaaaattgctct | |
| | tgatgtttaacggctcacttttaagtaaagtttgtgccaataccgtgcatgggagtaagttattgcc | |
| | aatcttcgagaatttaggcaattttggtatactcaactgggtctaatatggtggacggaatgatttc | |
| | tcgagaaagaatcaaagaggccaacaacgcagaacaggaaacagctatgacgggcccctaggggggt | |
| | tctgacttcttacgaaaatgtggctagcattccattctctgacgttcaaagaatcggaataagtcat | |
| | ggtaatggtgggaaatctaatagaagcgactcccataacctccatatttcttggcaaataattctgt | |
| | ctgggttaccgttcacgagccttcagagatctacgacgtgtagtgggtgggcttgccctccaggtg | |
| | tagtttgtaattagaatgggatttcctgttttaagtacccaaatacgaaaattgctcttgatgttta | |
| | acggctcacttttaagtaaagtttgtgccaataccgtgcatgggagtaagttattgccaatcttcga | |
| | gaatttaggcaattttggtatactcaactgggtctaatatggtggacggaatgatttctcgagaaag | |
| | aatcaaagaggccaacaacgaccctggttcgtaggcttgtcgacgacggcgctctccgtcgtcaggat | |
| | catacctagacacctggttaggtcctcccctttagtgagggttaattctcgagtctccctatagtgag | |
| | tcgtattaattccgtgtattctatagtgtcacctaaatcgttacggtagcgtactgtcgtaggtttg | |
| | tctggtcaaccaccgcgcactcagtggtgtacggtacaaaccacctcagaaggtggtttgtaccgta | |
| | caccactgagtcgcggtggttgaccagacaaacctacggtagcgtaacaggaaacagctatgacgg | |
| | gcccctaggtaagcagtatcttcgacagcttgtctctccagatgctcttgggccatcttccacatc | |
| | gtccgtagcagccttggcaatttgccatcactggcaaatacacataaatccaatgaatacggttacc | |
| | accatcacattaccatgcaggtacacagcaagaattgacgttggcatatcacatggtgtaataaccc | |
| | cacttgtgaaacaacccagaataaggtacaaggcggaaatgtcgtcattctaaaataaaaggcatgg | |
| | ccaggaatttgtctaataccgggaacttaaattcagcttgaacaccagtcgcaaaaaattcaaagaa | |
| | agtgattcaggttcgggttcgtggattggaacagcttcttttgtttcagtgatgagagaatcctcct | |
| | gtcactcgagaaagaatcaaagaggccaacaacgcagaacaggaaacagctatgacgggcccctag | |
| | gtaagcagtatcttcgacagcttgtctctccagatgctcttgggccatcttccacatcgtccgtagc | |
| | agccttggcaatttgccatcactggcaaatacacataaatccaatgaatacggttaccaccatcaca | |
| | ttaccatgcaggtacacagcaagaattgacgttggcatatcacatggtgtaataaccccacttgtga | |
| | aacaacccagaataaggtacaaggcggaaatgtcgtcattctaaaataaaaggcatggccaggaatt | |
| | tgtctaataccgggaacttaaattcagcttgaacaccagtcgcaaaaaattcaaagaaagtgattca | |
| | ggttcgggttcgtggattggaacagcttcttttgtttcagtgatgagagaatcctcctgtcactcga | |
| | gaaagaatcaaagaggccaacaacgaccctggttcgtaggcttgtcgacgacggcgcactccgtcgtc | |
| | aggatcatacctagacacctgagtaggtcctcccctttagtgagggttaattctcgagtctccctata | |

TABLE 1B-continued

Sequences of the constructs, barcodes, and/or probes used in Example 1. See FIGS. 1C, 1D, 1F, 1G, and related figures for results.

| Name | Sequence | SEQ ID NO. |
|---|---|---|
| | gtgagtcgtattaattccgtgtattctatagtgtcacctaaatcgttacggctacgtaaattctgca ggacttctagttattaatagtaatcaattacggggtcattagttcatagcccatatatggagttccg cgttacataacttacggtaaatggcccgcctggctgaccgcccaacgaccccccgcccattgacgtca ataatgacgtatgttcccatagtaacgccaatagggactttccattgacgtcaatgggtggagtatt tacggtaaactgcccacttggcagtacatcaagtgtatcatatgccaagtacgccccctattgacgt caatgacggtaaatggcccgcctggcattatgcccagtacatgaccttatgggactttcctacttgg cagtacatctacgtattagtcatcgctattaccatggtcgaggtgagccccacgttctgcttcactc tccccatctcccccccctccccaccccccaattttgtatttatttttaattatttttgtgcagc gatggggcgggggggggggggggcgcgcgccaggcggggcggggcggggcgaggggcggggcggg gcgaggcggagaggtgcggcggcagccaatcagagcggcgcgctccgaaagtttccttttatggcga ggcggcggcggcggcggccctataaaaagcgaagcgcgcggcgggcgggagtcgctgcgcgctgcct tcgccccgtgcccgctccgccgccgcctcgccgccgcccgcccggctctgactgaccgcgttactc ccacaggtgagcgggcgggacggccccttctcctccgggctgtaattagcgcttggtttaatgacggc ttgtttcttttctgtggctgcgtgaaagccttgaggggctccgggagggcccttgtgcggggggag cggctcgggggtgcgtgcgtgtgtgtgcgtggggagcgccgcgtgcggctccgcgctgcccggc ggctgtgagcgctgcgggcgcggcgcggggcttttgtgcgctccgcagtgtgcgcgaggggagcgcgg ccggggcggtgcccgcggtgcgggggctgcgaggggaacaaaggctgcgtgcgggtgtgtgc gtgggggtgagcaggggtgtgggcgcgtcggtcgggctgcaaccccccctgcacccccctccc cgagttgctgagcacggcccggcttcgggtgcggggctccgtacggggcgtggcgcgggctcgccg tgccgggcgggggtggcggcaggtgggggtgccgggcggggcggggccgcctcgggccggggaggg ctcggggagggggcgcggcggccccggagcgccggcggctgtcgaggcgcggcgagccgcagccat tgccttttatggtaatcgtgcgagagggcgcagggacttccttttgtcccaaatctgtgcggagccga aatctgggaggcgccgccgcaccccctctagcgggcgcggggcgaagcggtgcggcgccggcaggaa ggaaatgggcggggagggccttcgtgcgtcgccgccgccgtcccctctccctctccagcctcgg ggctgtccgcgggggacggctgccttcgggggggacggggcagggcggggttcggcttctggcgtg tgaccggcggctctagagcctctgctaaccatgttcatgccttcttcttttcctacagctcctggg caacgtgctggttattgtgctgtctcatcattttggcaaagaattgatttgataccgcgggcccggg atccctcgagggaattacctgaaccgtagccgccaccatgccagagccagcgaagtctgctcccgc cccgaaaaagggctccaagaaggcggtgactaaggcgcagaagcggcaagaagcgcaagcgc agccgcaaggagagctattccatctatgtgtacaaggttctgaagcaggtccaccctgacaccggca tttcgtccaaggccatgggcatcatgaattcgtttgtgaacgacattttcgagcgcatcgctggtga ggcttcccgcctggcgcattacaacaagcgctcgaccatcacctccagggagatccagacggccgtg cgcctgctgctgcctggggagttggccaagcacgccgtgtccgagggtactaaggccatcaccaagt acaccagcgctaaggatccccgggtaccggtcgccaccatggtgagcaagggcgaggagctgttcac cggggtggtgcccatcctggtcgagctggacggcgacgtaaacggccacaagttcagcgtgtccggc gagggcgagggcgatgccacctacggcaagctgaccctgaagttcatctgcaccaccggcaagctgc ccgtgccctggcccaccctcgtgaccaccctgacctggggcgtgcagtgcttcgcccgctaccccga ccacatgaagcagcacgacttcttcaagtccgccatgcccgaaggctacgtccaggagcgcaccatc ttcttcaaggacgacggcaactacaagacccgcgccgaggtgaagttcgagggcgacaccctggtga accgcatcgagctgaagggcatcgacttcaaggaggacggcaacatcctggggcacaagctggagta caacgccatcagcgacaacgtctatatcaccgccgacaagcagaagaacggcatcaaggccaacttc aagatccgccacaacatcgaggacggcagcgtgcagctcgccgaccactaccagcagaacacccca tcggcgacggcccccgtgctgctgcccgacaaccactacctgagcacccagtccaagctgagcaaga ccccaacgagaagcgcgatcacatggtcctgctggagttcgtgaccgccgcgggatcactctcggc atggacgagctgtacaagtgaacctccttcgtaacaggaaacagctatgacgggcccctaggacgt tcccatagctcctttgatgtcttaatgtaggttcaacagatatgcggcttcttcgcattctgatgg cgtcagctacgataggcgagagctgaatagttgaaaatttttagcagatgcctgagaaaattaaact tgatttgattccagtaatttaccaaaatacgcacagttgccttcttcgatgtaatcttttcaatcgt actatgtcgtatgcagttagcaaatgaaagtagcaacaccaatttgcgccagaatttcacgtcgaaa atatccttaaaccttgcaagccaagttacggagttgaaatttccgtaagctacggttatcttccaat ggcccatacttggctaaatcagagttccctttcgtggaaactgcaatagccaaattcctcgagaaag aatcaaagaggccaacaacgcagaacaggaaacagctatgacgggcccctaggacgttcccatagc tcctttgatgtcttaatgtaggttcaacagatatgcggcttcttcgcattctgatggctcagctca cgataggcgagagctgaatagttgaaaattttagcagatgcctgagaaaattaaacttgatttgat tccagtaatttaccaaaatacgcacagttgccttcttcgatgtaatcttttcaatcgtactatgtcg tatgcagttagcaaatgaaagtagcaacaccaatttgcgccagaatttcacgtcgaaaatatcctta aaccttgcaagccaagttacggagttgaaatttccgtaagctacggttatcttccaatggcccatac ttggctaaatcagagttccctttcgtggaaactgcaatagccaaattcctcgagaaagaatcaaaga ggccaacaacgacctcttgaggtctgtgccttctagttgccagccatctgttgtttgcccctcccc gtgccttccttgaccctggaaggtgccactcccactgtcctttcctaataaaatgaggaaattgcat cgcattgtctgagtaggtgtcattctattctggggggtgggtgggcaggacagcaaggggagga ttgggaagagaatagcaggcatgctggggatgcggtgggctctatggtacg | |

TABLE 2

Sequences the constructs, barcodes, and/or probes used in Example 2. See FIGS. 2B-2H and related figures for results.

| Probe name | Probe sequence (probe-LINKER-INITIATOR) | HCR initiator | Fluoro-phore | SEQ ID NO. |
|---|---|---|---|---|
| smFISH Probe 1 | cgtggattggaacagcttct | N/A | Alexa 647 | 9 |
| smFISH Probe 2 | agcttgaacaccagtcgcaa | N/A | Alexa 488 | 10 |
| smFISH Probe 3 | gcatggccaggaatttgtct | N/A | Alexa 546 | 11 |
| HCR Probe 1 | cgtggattggaacagcttct-TATA-GCATTCTTTCTTGAGGAGGGCAGCAAACGGGAAGAG | B1 | Alexa 647 | 12 |
| HCR Probe 2 | agcttgaacaccagtcgcaa-ATATA-GCTCAGTCCATCCTCGTAAATCCTCATCAATCATC | B2 | Alexa 488 | 13 |
| HCR Probe 3 | gcatggccaggaatttgtct-TATA-AAAGTCTAATCCGTCCCTGCCTCTATATCTCCACTC | B3 | Alexa 546 | 14 |

TABLE 3A

Sequences the constructs, barcodes, and/or probes used in Example 3. See FIGS. 3C-3D and related figures for results.

| Color permutation | Probe name | Probe sequence (probe-LINKER-INITIATOR) | HCR initiator | Fluoro-phore | SEQ ID NO. |
|---|---|---|---|---|---|
| 1 | B1P2 | cgtggattggaacagcttct-TATA-GCATTCTTTCTTGAGGAGGGCAGCAAACGGGAAGAG | B1 | Alexa 594 | 15 |
| 1 | B2P2-TtoC | cgtggatcggaacagcttct-TATA-AGCTCAGTCCATCCTCGTAAATCCTCATCAATCATC | B2 | Alexa 546 | 16 |
| 1 | B3P2-TtoG | cgtggatgggaacagcttct-TATA-AAAGTCTAATCCGTCCCTGCCTCTATATCTCCACTC | B3 | Alexa 647 | 17 |
| 1 | B4P2-TtoA | cgtggataggaacagcttct-TATA-CACATTTACAGACCTCAACCTACCTCCAACTCTCAC | B4 | Alexa 488 | 18 |
| 2 | B2P2 | cgtggattggaacagcttct-TATA-AGCTCAGTCCATCCTCGTAAATCCTCATCAATCATC | B2 | Alexa 546 | 19 |
| 2 | B3P2-TtoC | cgtggatcggaacagcttct-TATA-AAAGTCTAATCCGTCCCTGCCTCTATATCTCCACTC | B3 | Alexa 647 | 20 |
| 2 | B4P2-TtoG | cgtggatgggaacagcttct-TATA-CACATTTACAGACCTCAACCTACCTCCAACTCTCAC | B4 | Alexa 488 | 21 |
| 2 | B1P2-TtoA | cgtggataggaacagcttct-TATA-GCATTCTTTCTTGAGGAGGGCAGCAAACGGGAAGAG | B1 | Alexa 594 | 22 |
| 3 | B3P2 | cgtggattggaacagcttct-TATA-AAAGTCTAATCCGTCCCTGCCTCTATATCTCCACTC | B3 | Alexa 647 | 23 |
| 3 | B4P2-TtoC | cgtggat cggaacagcttct-TATA-CACATTTACAGACCTCAACCTACCTCCAACTCTCAC | B4 | Alexa 488 | 24 |
| 3 | B1P2-TtoG | cgtggatgggaacagcttct-TATA-GCATTCTTTCTTGAGGAGGGCAGCAAACGGGAAGAG | B1 | Alexa 594 | 25 |
| 3 | B2P2-TtoA | cgtggataggaacagcttct-TATA-AGCTCAGTCCATCCTCGTAAATCCTCATCAATCATC | B2 | Alexa 546 | 26 |
| 4 | B4P2 | cgtggattggaacagcttct-TATA-CACATTTACAGACCTCAACCTACCTCCAACTCTCAC | B4 | Alexa 488 | 27 |
| 4 | B1P2-TtoC | cgtggat cggaacagcttct-TATA-GCATTCTTTCTTGAGGAGGGCAGCAAACGGGAAGAG | B1 | Alexa 594 | 28 |
| 4 | B2P2-TtoG | cgtggatgggaacagcttct-TATA-AGCTCAGTCCATCCTCGTAAATCCTCATCAATCATC | B2 | Alexa 546 | 29 |
| 4 | B3P2-TtoA | cgtggataggaacagcttct-TATA-AAAGTCTAATCCGTCCCTGCCTCTATATCTCCACTC | B3 | Alexa 647 | 30 |

TABLE 3A -continued

Sequences the constructs, barcodes, and/or probes used in Example 3. See FIGS. 3C-3D and related figures for results.

| Color permutation | Probe name | Probe sequence (probe-LINKER-INITIATOR) | HCR initiator | Fluorophore | SEQ ID NO. |
|---|---|---|---|---|---|
| 5 | B1P2 | cgtggattggaacagcttct-TATA-GCATTCTTTCTTGAGGAGGGCAGCAAACGGGAAGAG | B1 | Alexa 594 | 31 |
| 5 | B2P2-GtoC | cgtggattgcaacagcttct-TATA-AGCTCAGTCCATCCTCGTAAATCCTCATCAATCATC | B2 | Alexa 546 | 32 |
| 5 | B3P2-GtoT | cgtggattgtaacagcttct-TATA-AAAGTCTAATCCGTCCCTGCCTCTATATCTCCACTC | B3 | Alexa 647 | 33 |
| 5 | B4P2-GtoA | cgtggattgaaacagcttct-TATA-CACATTTACAGACCTCAACCTACCTCCAACTCTCAC | B4 | Alexa 488 | 34 |
| 6 | B2P2 | cgtggattggaacagcttct-TATA-AGCTCAGTCCATCCTCGTAAATCCTCATCAATCATC | B2 | Alexa 546 | 35 |
| 6 | B3P2-GtoC | cgtggattgcaacagcttct-TATA-AAAGTCTAATCCGTCCCTGCCTCTATATCTCCACTC | B3 | Alexa 647 | 36 |
| 6 | B4P2-GtoT | cgtggattgtaacagcttct-TATA-CACATTTACAGACCTCAACCTACCTCCAACTCTCAC | B4 | Alexa 488 | 37 |
| 6 | B1P2-GtoA | cgtggattgaaacagcttct-TATA-GCATTCTTTCTTGAGGAGGGCAGCAAACGGGAAGAG | B1 | Alexa 594 | 38 |
| 7 | B3P2 | cgtggattggaacagcttct-TATA-AAAGTCTAATCCGTCCCTGCCTCTATATCTCCACTC | B3 | Alexa 647 | 39 |
| 7 | B4P2-GtoC | cgtggattgcaacagcttct-TATA-CACATTTACAGACCTCAACCTACCTCCAACTCTCAC | B4 | Alexa 488 | 40 |
| 7 | B1P2-GtoT | cgtggattgtaacagcttct-TATA-GCATTCTTTCTTGAGGAGGGCAGCAAACGGGAAGAG | B1 | Alexa 594 | 41 |
| 7 | B2P2-GtoA | cgtggattgaaacagcttct-TATA-AGCTCAGTCCATCCTCGTAAATCCTCATCAATCATC | B2 | Alexa 546 | 42 |
| 8 | B4P2 | cgtggattggaacagcttct-TATA-CACATTTACAGACCTCAACCTACCTCCAACTCTCAC | B4 | Alexa 488 | 43 |
| 8 | B1P2-GtoC | cgtggattgcaacagcttct-TATA-GCATTCTTTCTTGAGGAGGGCAGCAAACGGGAAGAG | B1 | Alexa 594 | 44 |
| 8 | B2P2-GtoT | cgtggattgtaacagcttct-TATA-AGCTCAGTCCATCCTCGTAAATCCTCATCAATCATC | B2 | Alexa 546 | 45 |
| 8 | B3P2-GtoA | cgtggattgaaacagcttct-TATA-AAAGTCTAATCCGTCCCTGCCTCTATATCTCCACTC | B3 | Alexa 647 | 46 |
| 9 | B1P2 | cgtggattggaacagcttct-TATA-GCATTCTTTCTTGAGGAGGGCAGCAAACGGGAAGAG | B1 | Alexa 594 | 47 |
| 9 | B2P2-CtoA | cgtggattggaaaagcttct-TATA-AGCTCAGTCCATCCTCGTAAATCCTCATCAATCATC | B2 | Alexa 546 | 48 |
| 9 | B3P2-CtoG | cgtggattggaagagcttct-TATA-AAAGTCTAATCCGTCCCTGCCTCTATATCTCCACTC | B3 | Alexa 647 | 49 |
| 9 | B4P2-CtoT | cgtggattggaatagcttct-TATA-CACATTTACAGACCTCAACCTACCTCCAACTCTCAC | B4 | Alexa 488 | 50 |
| 10 | B2P2 | cgtggattggaacagcttct-TATA-AGCTCAGTCCATCCTCGTAAATCCTCATCAATCATC | B2 | Alexa 546 | 51 |
| 10 | B3P2-CtoA | cgtggattggaaaagcttct-TATA-AAAGTCTAATCCGTCCCTGCCTCTATATCTCCACTC | B3 | Alexa 647 | 52 |
| 10 | B4P2-CtoG | cgtggattggaagagcttct-TATA-CACATTTACAGACCTCAACCTACCTCCAACTCTCAC | B4 | Alexa 488 | 53 |
| 10 | B1P2-CtoT | cgtggattggaatagcttct-TATA-GCATTCTTTCTTGAGGAGGGCAGCAAACGGGAAGAG | B1 | Alexa 594 | 54 |

TABLE 3A -continued

Sequences the constructs, barcodes, and/or probes used in Example 3. See FIGS. 3C-3D and related figures for results.

| Color permuta-tion | Probe name | Probe sequence (probe-LINKER-INITIATOR) | HCR ini-tiator | Fluoro-phore | SEQ ID NO. |
|---|---|---|---|---|---|
| 11 | B3P2 | cgtggattggaacagcttct-TATA-AAAGTCTAATCCGTCCCTGCCTCTATATCTCCACTC | B3 | Alexa 647 | 55 |
| 11 | B4P2-CtoA | cgtggattggaaaagcttct-TATA-CACATTTACAGACCTCAACCTACCTCCAACTCTCAC | B4 | Alexa 488 | 56 |
| 11 | B1P2-CtoG | cgtggattggaagagcttct-TATA-GCATTCTTTCTTGAGGAGGGCAGCAAACGGGAAGAG | B1 | Alexa 594 | 57 |
| 11 | B2P2-CtoT | cgtggattggaatagcttct-TATA-AGCTCAGTCCATCCTCGTAAATCCTCATCAATCATC | B2 | Alexa 546 | 58 |
| 12 | B4P2 | cgtggattggaacagcttct-TATA-CACATTTACAGACCTCAACCTACCTCCAACTCTCAC | B4 | Alexa 488 | 59 |
| 12 | B1P2-CtoA | cgtggattggaaaagcttct-TATA-GCATTCTTTCTTGAGGAGGGCAGCAAACGGGAAGAG | B1 | Alexa 594 | 60 |
| 12 | B2P2-CtoG | cgtggattggaagagcttct-TATA-AGCTCAGTCCATCCTCGTAAATCCTCATCAATCATC | B2 | Alexa 546 | 61 |
| 12 | B3P2-CtoT | cgtggattggaatagcttct-TATA-AAAGTCTAATCCGTCCCTGCCTCTATATCTCCACTC | B3 | Alexa 647 | 62 |
| 13 | B1P2 | cgtggattggaacagcttct-TATA-GCATTCTTTCTTGAGGAGGGCAGCAAACGGGAAGAG | B1 | Alexa 594 | 63 |
| 13 | B2P2-AtoC | cgtggattggcacagcttct-TATA-AGCTCAGTCCATCCTCGTAAATCCTCATCAATCATC | B2 | Alexa 546 | 64 |
| 13 | B3P2-AtoG | cgtggattgggacagcttct-TATA-AAAGTCTAATCCGTCCCTGCCTCTATATCTCCACTC | B3 | Alexa 647 | 65 |
| 13 | B4P2-AtoT | cgtggattggtacagcttct-TATA-CACATTTACAGACCTCAACCTACCTCCAACTCTCAC | B4 | Alexa 488 | 66 |
| 14 | B2P2 | cgtggattggaacagcttct-TATA-AGCTCAGTCCATCCTCGTAAATCCTCATCAATCATC | B2 | Alexa 546 | 67 |
| 14 | B3P2-AtoC | cgtggattggcacagcttct-TATA-AAAGTCTAATCCGTCCCTGCCTCTATATCTCCACTC | B3 | Alexa 647 | 68 |
| 14 | B4P2-AtoG | cgtggattgggacagcttct-TATA-CACATTTACAGACCTCAACCTACCTCCAACTCTCAC | B4 | Alexa 488 | 69 |
| 14 | B1P2-AtoT | cgtggattggtacagcttct-TATA-GCATTCTTTCTTGAGGAGGGCAGCAAACGGGAAGAG | B1 | Alexa 594 | 70 |
| 15 | B3P2 | cgtggattggaacagcttct-TATA-AAAGTCTAATCCGTCCCTGCCTCTATATCTCCACTC | B3 | Alexa 647 | 71 |
| 15 | B4P2-AtoC | cgtggattggcacagcttct-TATA-CACATTTACAGACCTCAACCTACCTCCAACTCTCAC | B4 | Alexa 488 | 72 |
| 15 | B1P2-AtoG | cgtggattgggacagcttct-TATA-GCATTCTTTCTTGAGGAGGGCAGCAAACGGGAAGAG | B1 | Alexa 594 | 73 |
| 15 | B2P2-AtoT | cgtggattggtacagcttct-TATA-AGCTCAGTCCATCCTCGTAAATCCTCATCAATCATC | B2 | Alexa 546 | 74 |
| 16 | B4P2 | cgtggattggaacagcttct-TATA-CACATTTACAGACCTCAACCTACCTCCAACTCTCAC | B4 | Alexa 488 | 75 |
| 16 | B1P2-AtoC | cgtggattggcacagcttct-TATA-GCATTCTTTCTTGAGGAGGGCAGCAAACGGGAAGAG | B1 | Alexa 594 | 76 |
| 16 | B2P2-AtoG | cgtggattgggacagcttct-TATA-AGCTCAGTCCATCCTCGTAAATCCTCATCAATCATC | B2 | Alexa 546 | 77 |
| 16 | B3P2-AtoT | cgtggattggtacagcttct-TATA-AAAGTCTAATCCGTCCCTGCCTCTATATCTCCACTC | B3 | Alexa 647 | 78 |

TABLE 3B

Sequences the constructs, barcodes, and/or probes used in Example 3.
See FIG. 13 for results.

| Probe name | Probe sequence (probe-LINKER-INITIATOR) | HCR initiator | Fluoro-phore | Position | SNV | SEQ ID NO. |
|---|---|---|---|---|---|---|
| B2P2-C1toA | Agtggattggaacagcttct-TATA-AGCTCAGTCCATCCTCGTAAATCCTCATCAATCATC | B2 | 546 | 1 | A | 79 |
| B2P2-G2toC | cCtggattggaacagcttct-TATA-AGCTCAGTCCATCCTCGTAAATCCTCATCAATCATC | B2 | 546 | 2 | C | 80 |
| B2P2-T3toC | cgCggattggaacagcttct-TATA-AGCTCAGTCCATCCTCGTAAATCCTCATCAATCATC | B2 | 546 | 3 | C | 81 |
| B2P2-G4toC | cgtCgattggaacagcttct-TATA-AGCTCAGTCCATCCTCGTAAATCCTCATCAATCATC | B2 | 546 | 4 | C | 82 |
| B2P2-G5toC | cgtgCattggaacagcttct-TATA-AGCTCAGTCCATCCTCGTAAATCCTCATCAATCATC | B2 | 546 | 5 | C | 83 |
| B2P2-A6toC | cgtggCttggaacagcttct-TATA-AGCTCAGTCCATCCTCGTAAATCCTCATCAATCATC | B2 | 546 | 6 | C | 84 |
| B2P2-T7toC | cgtggaCtggaacagcttct-TATA-AGCTCAGTCCATCCTCGTAAATCCTCATCAATCATC | B2 | 546 | 7 | C | 85 |
| B3P2-C1toG | Ggtggattggaacagcttct-TATA-AAAGTCTAATCCGTCCCTGCCTCTATATCTCCACTC | B3 | 647 | 1 | G | 86 |
| B3P2-G2toT | cTtggattggaacagcttct-TATA-AAAGTCTAATCCGTCCCTGCCTCTATATCTCCACTC | B3 | 647 | 2 | T | 87 |
| B3P2-T3toG | cgGgattggaacagcttct-TATA-AAAGTCTAATCCGTCCCTGCCTCTATATCTCCACTC | B3 | 647 | 3 | G | 88 |
| B3P2-G4toT | cgtTgattggaacagcttct-TATA-AAAGTCTAATCCGTCCCTGCCTCTATATCTCCACTC | B3 | 647 | 4 | T | 89 |
| B3P2-G5toT | cgtgTattggaacagcttct-TATA-AAAGTCTAATCCGTCCCTGCCTCTATATCTCCACTC | B3 | 647 | 5 | T | 90 |
| B3P2-A6toT | cgtggTttggaacagcttct-TATA-AAAGTCTAATCCGTCCCTGCCTCTATATCTCCACTC | B3 | 647 | 6 | T | 91 |
| B3P2-T7toG | cgtggaGtggaacagcttct-TATA-AAAGTCTAATCCGTCCCTGCCTCTATATCTCCACTC | B3 | 647 | 7 | G | 92 |
| B4P2-C1toT | Tgtggattggaacagcttct-TATA-CACATTTACAGACCTCAACCTACCTCCAACTCTCAC | B4 | 488 | 1 | T | 93 |
| B4P2-G2toA | cAtggattggaacagcttct-TATA-CACATTTACAGACCTCAACCTACCTCCAACTCTCAC | B4 | 488 | 2 | A | 94 |
| B4P2-T3toA | cgAggattggaacagcttct-TATA-CACATTTACAGACCTCAACCTACCTCCAACTCTCAC | B4 | 488 | 3 | A | 95 |
| B4P2-G4toA | cgtAgattggaacagcttct-TATA-CACATTTACAGACCTCAACCTACCTCCAACTCTCAC | B4 | 488 | 4 | A | 96 |
| B4P2-G5toA | cgtgAattggaacagcttct-TATA-CACATTTACAGACCTCAACCTACCTCCAACTCTCAC | B4 | 488 | 5 | A | 97 |
| B4P2-A6toG | cgtggGttggaacagcttct-TATA-CACATTTACAGACCTCAACCTACCTCCAACTCTCAC | B4 | 488 | 6 | G | 98 |
| B4P2-T7toA | cgtggaAtggaacagcttct-TATA-CACATTTACAGACCTCAACCTACCTCCAACTCTCAC | B4 | 488 | 7 | A | 99 |
| B1P2-C1toT | Tgtggattggaacagcttct-TATA-GCATTCTTTCTTGAGGAGGGCAGCAAACGGGAAGAG | B1 | 594 | 1 | T | 100 |
| B1P2-G2toA | cAtggattggaacagcttct-TATA-GCATTCTTTCTTGAGGAGGGCAGCAAACGGGAAGAG | B1 | 594 | 2 | A | 101 |
| B1P2-T3toA | cgAggattggaacagcttct-TATA-GCATTCTTTCTTGAGGAGGGCAGCAAACGGGAAGAG | B1 | 594 | 3 | A | 102 |

TABLE 3B -continued

Sequences the constructs, barcodes, and/or probes used in Example 3.
See FIG. 13 for results.

| Probe name | Probe sequence (probe-LINKER-INITIATOR) | HCR initiator | Fluorophore | Position | SNV | SEQ ID NO. |
|---|---|---|---|---|---|---|
| B1P2-G4toA | cgtAgattggaacagcttct-TATA-GCATTCTTTCTTGAGGAGGGCAGCAAACGGGAAGAG | B1 | 594 | 4 | A | 103 |
| B1P2-G5toA | cgtgAattggaacagcttct-TATA-GCATTCTTTCTTGAGGAGGGCAGCAAACGGGAAGAG | B1 | 594 | 5 | A | 104 |
| B1P2-A6toG | cgtggGttggaacagcttct-TATA-GCATTCTTTCTTGAGGAGGGCAGCAAACGGGAAGAG | B1 | 594 | 6 | G | 105 |
| B1P2-T7toA | cgtggaAttggaacagcttct-TATA-GCATTCTTTCTTGAGGAGGGCAGCAAACGGGAAGAG | B1 | 594 | 7 | A | 106 |
| B3P2-C1toA | Agtggattggaacagcttct-TATA-AAAGTCTAATCCGTCCCTGCCTCTATATCTCCACTC | B3 | 647 | 1 | A | 107 |
| B3P2-G2toC | cCtggattggaacagcttct-TATA-AAAGTCTAATCCGTCCCTGCCTCTATATCTCCACTC | B3 | 647 | 2 | C | 108 |
| B3P2-T3toC | cgCggattggaacagcttct-TATA-AAAGTCTAATCCGTCCCTGCCTCTATATCTCCACTC | B3 | 647 | 3 | C | 109 |
| B3P2-G4toC | cgtCgattggaacagcttct-TATA-AAAGTCTAATCCGTCCCTGCCTCTATATCTCCACTC | B3 | 647 | 4 | C | 110 |
| B3P2-G5toC | cgtgCattggaacagcttct-TATA-AAAGTCTAATCCGTCCCTGCCTCTATATCTCCACTC | B3 | 647 | 5 | C | 111 |
| B3P2-A6toC | cgtggCttggaacagcttct-TATA-AAAGTCTAATCCGTCCCTGCCTCTATATCTCCACTC | B3 | 647 | 6 | C | 112 |
| B3P2-T7toC | cgtggaCtggaacagcttct-TATA-AAAGTCTAATCCGTCCCTGCCTCTATATCTCCACTC | B3 | 647 | 7 | C | 113 |
| B4P2-C1toG | Ggtggattggaacagcttct-TATA-CACATTTACAGACCTCAACCTACCTCCAACTCTCAC | B4 | 488 | 1 | G | 114 |
| B4P2-G2toT | cTtggattggaacagcttct-TATA-CACATTTACAGACCTCAACCTACCTCCAACTCTCAC | B4 | 488 | 2 | T | 115 |
| B4P2-T3toG | cgGggattggaacagcttct-TATA-CACATTTACAGACCTCAACCTACCTCCAACTCTCAC | B4 | 488 | 3 | G | 116 |
| B4P2-G4toT | cgtTgattggaacagcttct-TATA-CACATTTACAGACCTCAACCTACCTCCAACTCTCAC | B4 | 488 | 4 | T | 117 |
| B4P2-G5toT | cgtgTattggaacagcttct-TATA-CACATTTACAGACCTCAACCTACCTCCAACTCTCAC | B4 | 488 | 5 | T | 118 |
| B4P2-A6toT | cgtggTttggaacagcttct-TATA-CACATTTACAGACCTCAACCTACCTCCAACTCTCAC | B4 | 488 | 6 | T | 119 |
| B4P2-T7toG | cgtggaGtggaacagcttct-TATA-CACATTTACAGACCTCAACCTACCTCCAACTCTCAC | B4 | 488 | 7 | G | 120 |
| B1P2-C1toG | Ggtggattggaacagcttct-TATA-GCATTCTTTCTTGAGGAGGGCAGCAAACGGGAAGAG | B1 | 594 | 1 | G | 121 |
| B1P2-G2toT | cTtggattggaacagcttct-TATA-GCATTCTTTCTTGAGGAGGGCAGCAAACGGGAAGAG | B1 | 594 | 2 | T | 122 |
| B1P2-T3toG | cgGggattggaacagcttct-TATA-GCATTCTTTCTTGAGGAGGGCAGCAAACGGGAAGAG | B1 | 594 | 3 | G | 123 |
| B1P2-G4toT | cgtTgattggaacagcttct-TATA-GCATTCTTTCTTGAGGAGGGCAGCAAACGGGAAGAG | B1 | 594 | 4 | T | 124 |
| B1P2-G5toT | cgtgTattggaacagcttct-TATA-GCATTCTTTCTTGAGGAGGGCAGCAAACGGGAAGAG | B1 | 594 | 5 | T | 125 |
| B1P2-A6toT | cgtggTttggaacagcttct-TATA-GCATTCTTTCTTGAGGAGGGCAGCAAACGGGAAGAG | B1 | 594 | 6 | T | 126 |

TABLE 3B -continued

Sequences the constructs, barcodes, and/or probes used in Example 3.
See FIG. 13 for results.

| Probe name | Probe sequence (probe-LINKER-INITIATOR) | HCR initiator | Fluorophore | Position | SNV | SEQ ID NO. |
|---|---|---|---|---|---|---|
| B1P2-T7toG | cgtggaGtggaacagcttct-TATA-GCATTCTTTCTTGAGGAGGGCAGCAAACGGGAAGAG | B1 | 594 | 7 | G | 127 |
| B2P2-C1toT | Tgtggattggaacagcttct-TATA-AGCTCAGTCCATCCTCGTAAATCCTCATCAATCATC | B2 | 546 | 1 | T | 128 |
| B2P2-G2toA | cAtggattggaacagcttct-TATA-AGCTCAGTCCATCCTCGTAAATCCTCATCAATCATC | B2 | 546 | 2 | A | 129 |
| B2P2-T3toA | cgAggattggaacagcttct-TATA-AGCTCAGTCCATCCTCGTAAATCCTCATCAATCATC | B2 | 546 | 3 | A | 130 |
| B2P2-G4toA | cgtAgattggaacagcttct-TATA-AGCTCAGTCCATCCTCGTAAATCCTCATCAATCATC | B2 | 546 | 4 | A | 131 |
| B2P2-G5toA | cgtgAattggaacagcttct-TATA-AGCTCAGTCCATCCTCGTAAATCCTCATCAATCATC | B2 | 546 | 5 | A | 132 |
| B2P2-A6toG | cgtggGttggaacagcttct-TATA-AGCTCAGTCCATCCTCGTAAATCCTCATCAATCATC | B2 | 546 | 6 | G | 133 |
| B2P2-T7toA | cgtggaAtggaacagcttct-TATA-AGCTCAGTCCATCCTCGTAAATCCTCATCAATCATC | B2 | 546 | 7 | A | 134 |
| B4P2-C1toA | Agtggattggaacagcttct-TATA-CACATTTACAGACCTCAACCTACCTCCAACTCTCAC | B4 | 488 | 1 | A | 135 |
| B4P2-G2toC | cCtggattggaacagcttct-TATA-CACATTTACAGACCTCAACCTACCTCCAACTCTCAC | B4 | 488 | 2 | C | 136 |
| B4P2-T3toC | cgCggattggaacagcttct-TATA-CACATTTACAGACCTCAACCTACCTCCAACTCTCAC | B4 | 488 | 3 | C | 137 |
| B4P2-G4toC | cgtCgattggaacagcttct-TATA-CACATTTACAGACCTCAACCTACCTCCAACTCTCAC | B4 | 488 | 4 | C | 138 |
| B4P2-G5toC | cgtgCattggaacagcttct-TATA-CACATTTACAGACCTCAACCTACCTCCAACTCTCAC | B4 | 488 | 5 | C | 139 |
| B4P2-A6toC | cgtggCttggaacagcttct-TATA-CACATTTACAGACCTCAACCTACCTCCAACTCTCAC | B4 | 488 | 6 | C | 140 |
| B4P2-T7toC | cgtggaCtggaacagcttct-TATA-CACATTTACAGACCTCAACCTACCTCCAACTCTCAC | B4 | 488 | 7 | C | 141 |
| B1P2-C1toA | Agtggattggaacagcttct-TATA-GCATTCTTTCTTGAGGAGGGCAGCAAACGGGAAGAG | B1 | 594 | 1 | A | 142 |
| B1P2-G2toC | cCtggattggaacagcttct-TATA-GCATTCTTTCTTGAGGAGGGCAGCAAACGGGAAGAG | B1 | 594 | 2 | C | 143 |
| B1P2-T3toC | cgCggattggaacagcttct-TATA-GCATTCTTTCTTGAGGAGGGCAGCAAACGGGAAGAG | B1 | 594 | 3 | C | 144 |
| B1P2-G4toC | cgtCgattggaacagcttct-TATA-GCATTCTTTCTTGAGGAGGGCAGCAAACGGGAAGAG | B1 | 594 | 4 | C | 145 |
| B1P2-G5toC | cgtgCattggaacagcttct-TATA-GCATTCTTTCTTGAGGAGGGCAGCAAACGGGAAGAG | B1 | 594 | 5 | C | 146 |
| B1P2-A6toC | cgtggCttggaacagcttct-TATA-GCATTCTTTCTTGAGGAGGGCAGCAAACGGGAAGAG | B1 | 594 | 6 | C | 147 |
| B1P2-T7toC | cgtggaCtggaacagcttct-TATA-GCATTCTTTCTTGAGGAGGGCAGCAAACGGGAAGAG | B1 | 594 | 7 | C | 148 |
| B2P2-C1toG | Ggtggattggaacagcttct-TATA-AGCTCAGTCCATCCTCGTAAATCCTCATCAATCATC | B2 | 546 | 1 | G | 149 |
| B2P2-G2toT | cTtggattggaacagcttct-TATA-AGCTCAGTCCATCCTCGTAAATCCTCATCAATCATC | B2 | 546 | 2 | T | 150 |

TABLE 3B -continued

Sequences the constructs, barcodes, and/or probes used in Example 3.
See FIG. 13 for results.

| Probe name | Probe sequence (probe-LINKER-INITIATOR) | HCR initiator | Fluorophore | Position | SNV | SEQ ID NO. |
|---|---|---|---|---|---|---|
| B2P2-T3toG | cgGgattggaacagcttct-TATA-AGCTCAGTCCATCCTCGTAAATCCTCATCAATCATC | B2 | 546 | 3 | G | 151 |
| B2P2-G4toT | cgtTgattggaacagcttct-TATA-AGCTCAGTCCATCCTCGTAAATCCTCATCAATCATC | B2 | 546 | 4 | T | 152 |
| B2P2-G5toT | cgtgTattggaacagcttct-TATA-AGCTCAGTCCATCCTCGTAAATCCTCATCAATCATC | B2 | 546 | 5 | T | 153 |
| B2P2-A6toT | cgtggTttggaacagcttct-TATA-AGCTCAGTCCATCCTCGTAAATCCTCATCAATCATC | B2 | 546 | 6 | T | 154 |
| B2P2-T7toG | cgtggaGtggaacagcttct-TATA-AGCTCAGTCCATCCTCGTAAATCCTCATCAATCATC | B2 | 546 | 7 | G | 155 |
| B3P2-C1toT | Tgtggattggaacagcttct-TATA-AAAGTCTAATCCGTCCCTGCCTCTATATCTCCACTC | B3 | 647 | 1 | T | 156 |
| B3P2-G2toA | cAtggattggaacagcttct-TATA-AAAGTCTAATCCGTCCCTGCCTCTATATCTCCACTC | B3 | 647 | 2 | A | 157 |
| B3P2-T3toA | cgAggattggaacagcttct-TATA-AAAGTCTAATCCGTCCCTGCCTCTATATCTCCACTC | B3 | 647 | 3 | A | 158 |
| B3P2-G4toA | cgtAgattggaacagcttct-TATA-AAAGTCTAATCCGTCCCTGCCTCTATATCTCCACTC | B3 | 647 | 4 | A | 159 |
| B3P2-G5toA | cgtgAattggaacagcttct-TATA-AAAGTCTAATCCGTCCCTGCCTCTATATCTCCACTC | B3 | 647 | 5 | A | 160 |
| B3P2-A6toG | cgtggGttggaacagcttct-TATA-AAAGTCTAATCCGTCCCTGCCTCTATATCTCCACTC | B3 | 647 | 6 | G | 161 |
| B3P2-T7toA | cgtggaAtggaacagcttct-TATA-AAAGTCTAATCCGTCCCTGCCTCTATATCTCCACTC | B3 | 647 | 7 | A | 162 |
| B1P2 | cgtggattggaacagcttct-TATA-GCATTCTTTCTTGAGGAGGGCAGCAAACGGGAAGAG | B1 | 594 | All | Match | 163 |
| B2P2 | cgtggattggaacagcttct-TATA-AGCTCAGTCCATCCTCGTAAATCCTCATCAATCATC | B2 | 546 | All | Match | 164 |
| B3P2 | cgtggattggaacagcttct-TATA-AAAGTCTAATCCGTCCCTGCCTCTATATCTCCACTC | B3 | 647 | All | Match | 165 |
| B4P2 | Cgtggattggaacagcttct-TATA-CACATTTACAGACCTCAACCTACCTCCAACTCTCAC | B4 | 488 | All | Match | 166 |

TABLE 4A

Sequences the constructs, barcodes, and/or probes used in Example 4.
See FIGS. 4C-4F and related figures for results.
Design 1

| Target barcode | Control barcode | Probe name | Probe sequence (probe-LINKER-INITIATOR) | HCR initiator | Fluorophore | SEQ ID NO. |
|---|---|---|---|---|---|---|
| 1 | 2 | design1_probe1T-B1 | taaagaatgcgttggggcga-TATA-GCATTCTTTCTTGAGGAGGGCAGCAAACGGGAAGAG | B1 | Alexa 546 | 167 |
|   |   | design1_probe2T-B2 | ttccacatccctctgcgatt-TATA-AGCTCAGTCCATCCTCGTAAATCCTCATCAATCATC | B2 | Alexa 594 | 168 |
|   |   | design1_probe1C-B3 | taaagaacgcgttggggcga-TATA-AAAGTCTAATCCGTCCCTGCCTCTATATCTCCACTC | B3 | Alexa 647 | 169 |
|   |   | design1_probe2C-B4 | ttccacaccccctctgcgatt-TATA-CACATTTACAGACCTCAACCTACCTCCAACTCTCAC | B4 | Alexa 488 | 170 |
| 2 | 1 | design1_probe1T-B1 | taaagaatgcgttggggcga-TATA-GCATTCTTTCTTGAGGAGGGCAGCAAACGGGAAGAG | B1 | Alexa 594 | 171 |

TABLE 4A -continued

Sequences the constructs, barcodes, and/or probes used in Example 4.
See FIGS. 4C-4F and related figures for results.
Design 1

| Target barcode | Control barcode | Probe name | Probe sequence (probe-LINKER-INITIATOR) | HCR initiator | Fluoro- phore | SEQ ID NO. |
|---|---|---|---|---|---|---|
| | | design1_probe2T-B2 | ttccacatccctctgcgatt-TATA-AGCTCAGTCCATCCTCGTAAATCCTCATCAATCATC | B2 | Alexa 546 | 172 |
| | | design1_probe1C-B3 | taaagaacgcgttggggcga-TATA-AAAGTCTAATCCGTCCCTGCCTCTATATCTCCACTC | B3 | Alexa 488 | 173 |
| | | design1_probe2C-B4 | ttccacaccctctgcgatt-TATA-CACATTTACAGACCTCAACCTACCTCCAACTCTCAC | B4 | Alexa 647 | 174 |
| 3 | 4 | design1_probe3T-B3 | ataccaatcccttcggcgat-TATA-AAAGTCTAATCCGTCCCTGCCTCTATATCTCCACTC | B3 | Alexa 546 | 175 |
| | | design1_probe4T-B1 | ttagcgatacatccgaccca-TATA-GCATTCTTTCTTGAGGAGGGCAGCAAACGGGAAGAG | B1 | Alexa 594 | 176 |
| | | design1_probe3C-B2 | ataccaaccccttcggcgat-TATA-AGCTCAGTCCATCCTCGTAAATCCTCATCAATCATC | B2 | Alexa 647 | 177 |
| | | design1_probe4C-B4 | ttagcgacacatccgaccca-TATA-CACATTTACAGACCTCAACCTACCTCCAACTCTCAC | B4 | Alexa 488 | 178 |
| 4 | 3 | design1_probe3T-B3 | ataccaatcccttcggcgat-TATA-AAAGTCTAATCCGTCCCTGCCTCTATATCTCCACTC | B3 | Alexa 594 | 179 |
| | | design1_probe4T-B1 | ttagcgatacatccgaccca-TATA-GCATTCTTTCTTGAGGAGGGCAGCAAACGGGAAGAG | B1 | Alexa 546 | 180 |
| | | design1_probe3C-B2 | ataccaaccccttcggcgat-TATA-AGCTCAGTCCATCCTCGTAAATCCTCATCAATCATC | B2 | Alexa 488 | 181 |
| | | design1_probe4C-B4 | ttagcgacacatccgaccca-TATA-CACATTTACAGACCTCAACCTACCTCCAACTCTCAC | B4 | Alexa 647 | 182 |
| 5 | 6 | design1_probe5T-B2 | ctccaactgaatgaaggcga-TATA-AGCTCAGTCCATCCTCGTAAATCCTCATCAATCATC | B2 | Alexa 546 | 183 |
| | | design1_probe6T-B3 | ttcaacatacgccaatgcgg-TATA-AAAGTCTAATCCGTCCCTGCCTCTATATCTCCACTC | B3 | Alexa 594 | 184 |
| | | design1_probe5C-B1 | ctccaaccgaatgaaggcga-TATA-GCATTCTTTCTTGAGGAGGGCAGCAAACGGGAAGAG | B1 | Alexa 647 | 185 |
| | | design1_probe6C-B4 | ttcaacacacgccaatgcgg-TATA-CACATTTACAGACCTCAACCTACCTCCAACTCTCAC | B4 | Alexa 488 | 186 |
| 6 | 5 | design1_probe5T-B2 | ctccaactgaatgaaggcga-TATA-AGCTCAGTCCATCCTCGTAAATCCTCATCAATCATC | B2 | Alexa 594 | 187 |
| | | design1_probe6T-B3 | ttcaacatacgccaatgcgg-TATA-AAAGTCTAATCCGTCCCTGCCTCTATATCTCCACTC | B3 | Alexa 546 | 188 |
| | | design1_probe5C-B1 | ctccaaccgaatgaaggcga-TATA-GCATTCTTTCTTGAGGAGGGCAGCAAACGGGAAGAG | B1 | Alexa 488 | 189 |
| | | design1_probe6C-B4 | ttcaacacacgccaatgcgg-TATA-CACATTTACAGACCTCAACCTACCTCCAACTCTCAC | B4 | Alexa 647 | 190 |
| 7 | 8 | design1_probe7T-B1 | atcgcaatccaccaaagcag-TATA-GCATTCTTTCTTGAGGAGGGCAGCAAACGGGAAGAG | B1 | Alexa 546 | 191 |
| | | design1_probe8T-B2 | gtcaacatacacgccctgat-TATA-AGCTCAGTCCATCCTCGTAAATCCTCATCAATCATC | B2 | Alexa 594 | 192 |
| | | design1_probe7C-B3 | atcgcaacccaccaaagcag-TATA-AAAGTCTAATCCGTCCCTGCCTCTATATCTCCACTC | B3 | Alexa 647 | 193 |
| | | design1_probe8C-B4 | gtcaacacacacgccctgat-TATA-CACATTTACAGACCTCAACCTACCTCCAACTCTCAC | B4 | Alexa 488 | 194 |
| 8 | 7 | design1_probe7T-B1 | atcgcaatccaccaaagcag-TATA-GCATTCTTTCTTGAGGAGGGCAGCAAACGGGAAGAG | B1 | Alexa 594 | 195 |
| | | design1_probe8T-B2 | gtcaacatacacgccctgat-TATA-AGCTCAGTCCATCCTCGTAAATCCTCATCAATCATC | B2 | Alexa 546 | 196 |
| | | design1_probe7C-B3 | atcgcaacccaccaaagcag-TATA-AAAGTCTAATCCGTCCCTGCCTCTATATCTCCACTC | B3 | Alexa 488 | 197 |
| | | design1_probe8C-B4 | gtcaacacacacgccctgat-TATA-CACATTTACAGACCTCAACCTACCTCCAACTCTCAC | B4 | Alexa 647 | 198 |
| 9 | 10 | design1_probe9T-B3 | ttagagatgaacgccaacgc-TATA-AAAGTCTAATCCGTCCCTGCCTCTATATCTCCACTC | B3 | Alexa 546 | 199 |
| | | design1_probe10T-B1 | acacgactcaactccgaaga-TATA-GCATTCTTTCTTGAGGAGGGCAGCAAACGGGAAGAG | B1 | Alexa 594 | 200 |
| | | design1_probe9C-B2 | ttagagacgaacgccaacgc-TATA-AGCTCAGTCCATCCTCGTAAATCCTCATCAATCATC | B2 | Alexa 647 | 201 |
| | | design1_probe10C-B4 | acacgacccaactccgaaga-TATA-CACATTTACAGACCTCAACCTACCTCCAACTCTCAC | B4 | Alexa 488 | 202 |

TABLE 4A -continued

Sequences the constructs, barcodes, and/or probes used in Example 4.
See FIGS. 4C-4F and related figures for results.

Design 1

| Target barcode | Control barcode | Probe name | Probe sequence (probe-LINKER-INITIATOR) | HCR initiator | Fluorophore | SEQ ID NO. |
|---|---|---|---|---|---|---|
| 10 | 9 | design1_probe9T-B3 | ttagagatgaacgccaacgc-TATA-AAAGTCTAATCCGTCCCTGCCTCTATATCTCCACTC | B3 | Alexa 594 | 203 |
| | | design1_probe10T-B1 | acacgactcaactccgaaga-TATA-GCATTCTTTCTTGAGGAGGGCAGCAAACGGGAAGAG | B1 | Alexa 546 | 204 |
| | | design1_probe9C-B2 | ttagagacgaacgccaacgc-TATA-AGCTCAGTCCATCCTCGTAAATCCTCATCAATCATC | B2 | Alexa 488 | 205 |
| | | design1_probe10C-B4 | acacgacccaactccgaaga-TATA-CACATTTACAGACCTCAACCTACCTCCAACTCTCAC | B4 | Alexa 647 | 206 |
| 11 | 12 | design1_probe11T-B2 | atccgcatcaacggtagcaa-TATA-AGCTCAGTCCATCCTCGTAAATCCTCATCAATCATC | B2 | Alexa 546 | 207 |
| | | design1_probe12T-B3 | atcagcgtgacaactgtgct-TATA-AAAGTCTAATCCGTCCCTGCCTCTATATCTCCACTC | B3 | Alexa 594 | 208 |
| | | design1_probe11C-B1 | atccgcaccaacggtagcaa-TATA-GCATTCTTTCTTGAGGAGGGCAGCAAACGGGAAGAG | B1 | Alexa 647 | 209 |
| | | design1_probe12C-B4 | atcagcgcgacaactgtgct-TATA-CACATTTACAGACCTCAACCTACCTCCAACTCTCAC | B4 | Alexa 488 | 210 |
| 12 | 11 | design1_probe11T-B2 | atccgcatcaacggtagcaa-TATA-AGCTCAGTCCATCCTCGTAAATCCTCATCAATCATC | B2 | Alexa 594 | 211 |
| | | design1_probe12T-B3 | atcagcgtgacaactgtgct-TATA-AAAGTCTAATCCGTCCCTGCCTCTATATCTCCACTC | B3 | Alexa 546 | 212 |
| | | design1_probe11C-B1 | atccgcaccaacggtagcaa-TATA-GCATTCTTTCTTGAGGAGGGCAGCAAACGGGAAGAG | B1 | Alexa 488 | 213 |
| | | design1_probe12C-B4 | atcagcgcgacaactgtgct-TATA-CACATTTACAGACCTCAACCTACCTCCAACTCTCAC | B4 | Alexa 647 | 214 |

TABLE 4B

Sequences the constructs, barcodes, and/or probes used in Example 4.
See FIGS. 4C-4F and related figures for results.

Design 2*

| Target barcodes | Probe name | Probe sequence (probe-LINKER-INITIATOR) | HCR initiator | Fluorophore | SEQ ID NO. |
|---|---|---|---|---|---|
| 1 and 2 | design2_probe1T-B1 | ttacaactgactctccgtcc-TATA-GCATTCTTTCTTGAGGAGGGCAGCAAACGGGAAGAG | B1 | Alexa 546 | 215 |
| | design2_probe2T-B2 | ttacaactgactcctcctcg-TATA-AGCTCAGTCCATCCTCGTAAATCCTCATCAATCATC | B2 | Alexa 594 | 216 |
| | design2_probe1C-B3 | ttacaaccgactctccgtcc-TATA-AAAGTCTAATCCGTCCCTGCCTCTATATCTCCACTC | B3 | Alexa 647 | 217 |
| | design2_probe2C-B4 | ttacaaccgactcctcctcg-TATA-CACATTTACAGACCTCAACCTACCTCCAACTCTCAC | B4 | Alexa 488 | 218 |
| 3 and 4 | design2_probe3T-B3 | ttacaactgactcgtgcggt-TATA-AAAGTCTAATCCGTCCCTGCCTCTATATCTCCACTC | B3 | Alexa 546 | 219 |
| | design2_probe4T-B1 | ttacaactgactctggggtg-TATA-GCATTCTTTCTTGAGGAGGGCAGCAAACGGGAAGAg | B1 | Alexa 594 | 220 |
| | design2_probe3C-B2 | ttacaaccgactcgtgcggt-TATA-AGCTCAGTCCATCCTCGTAAATCCTCATCAATCATC | B2 | Alexa 647 | 221 |
| | design2_probe4C-B4 | ttacaaccgactctggggtg-TATA-CACATTTACAGACCTCAACCTACCTCCAACTCTCAC | B4 | Alexa 488 | 222 |
| 5 and 6 | design2_probe5T-B2 | ttacaactgacttgggcgtc-TATA-AGCTCAGTCCATCCTCGTAAATCCTCATCAATCATC | B2 | Alexa 546 | 223 |
| | design2_probe6T-B3 | ttacaactgactgcgtcctg-TATA-AAAGTCTAATCCGTCCCTGCCTCTATATCTCCACTC | B3 | Alexa 594 | 224 |
| | design2_probe5C-B1 | ttacaaccgacttgggcgtc-TATA-GCATTCTTTCTTGAGGAGGGCAGCAAACGGGAAGAg | B1 | Alexa 647 | 225 |
| | design2_probe6C-B4 | ttacaaccgactgcgtcctg-TATA-CACATTTACAGACCTCAACCTACCTCCAACTCTCAC | B4 | Alexa 488 | 226 |
| 7 and 8 | design2_probe7T-B1 | ttacaactgactgtcgccct-TATA-GCATTCTTTCTTGAGGAGGGCAGCAAACGGGAAGAg | B1 | Alexa 546 | 227 |
| | design2_probe8T-B2 | ttacaactgactgtgcctgc-TATA-AGCTCAGTCCATCCTCGTAAATCCTCATCAATCATC | B2 | Alexa 594 | 228 |

TABLE 4B -continued

Sequences the constructs, barcodes, and/or probes used in Example 4.
See FIGS. 4C-4F and related figures for results.
Design 2*

| Target barcodes | Probe name | Probe sequence (probe-LINKER-INITIATOR) | HCR initiator | Fluorophore | SEQ ID NO. |
|---|---|---|---|---|---|
| | design2_probe7C-B3 | ttacaaccgactgtcgccct-TATA-AAAGTCTAATCCGTCCCTGCCTCTATATCTCCACTC | B3 | Alexa 647 | 229 |
| | design2_probe8C-B4 | ttacaaccgactgtgcctgc-TATA-CACATTTACAGACCTCAACCTACCTCCAACTCTCAC | B4 | Alexa 488 | 230 |
| 9 and 10 | design2_probe9T-B3 | ttacaactgactggtcgctc-TATA-AAAGTCTAATCCGTCCCTGCCTCTATATCTCCACTC | B3 | Alexa 546 | 231 |
| | design2_probe10T-B1 | ttacaactgactgctgtccg-TATA-GCATTCTTTCTTGAGGAGGGCAGCAAACGGGAAGAg | B1 | Alexa 594 | 232 |
| | design2_probe9C-B2 | ttacaaccgactggtcgctc-TATA-AGCTCAGTCCATCCTCGTAAATCCTCATCAATCATC | B2 | Alexa 647 | 233 |
| | design2_probe10C-B4 | ttacaaccgactgctgtccg-TATA-CACATTTACAGACCTCAACCTACCTCCAACTCTCAC | B4 | Alexa 488 | 234 |
| 11 and 12 | design2_probe11T-B2 | ttacaactgactggctgtgg-TATA-AGCTCAGTCCATCCTCGTAAATCCTCATCAATCATC | B2 | Alexa 546 | 235 |
| | design2_probe12T-B3 | ttacaactgacttccctggc-TATA-AAAGTCTAATCCGTCCCTGCCTCTATATCTCCACTC | B3 | Alexa 594 | 236 |
| | design2_probe11C-B1 | ttacaaccgactggctgtgg-TATA-GCATTCTTTCTTGAGGAGGGCAGCAAACGGGAAGAg | B1 | Alexa 647 | 237 |
| | design2_probe12C-B4 | ttacaaccgacttccctggc-TATA-CACATTTACAGACCTCAACCTACCTCCAACTCTCAC | B4 | Alexa 488 | 238 |

*For design 2 experiments, in addition to the probes for barcodes being analyzed, all other probes targeting other barcodes of the array are also added, but in an orthogonal channel (i.e. B5 initiator), to reduce background.

TABLE 4C

Sequences the constructs, barcodes, and/or probes used in Example 4.
See FIGS. 4C-4F and 15-18 for results.

| Target barcode | gRNA name | gRNA sequence | SEQ ID NO. |
|---|---|---|---|
| 1 | design1_gRNA1 | ACGCATTCTTTATGACACGG | 239 |
| 2 | design1_gRNA2 | AGGGATGTGGAAACAGAACA | 240 |
| 3 | design1_gRNA3 | AGGGATTGGTATCTGAACAG | 241 |
| 4 | design1_gRNA4 | ATGTATCGCTAACAACCCAG | 242 |
| 5 | design1_gRNA5 | ATTCAGTTGGAGGATAACGG | 243 |
| 6 | design1_gRNA6 | GCGTATGTTGAATCACAGGG | 244 |
| 7 | design1_gRNA7 | GTGGATTGCGATACATACCG | 245 |
| 8 | design1_gRNA8 | GTGTATGTTGACGAATCACA | 246 |
| 9 | design1_gRNA9 | GTTCATCTCTAATAGCCGAG | 247 |
| 10 | design1_gRNA10 | GTTGAGTCGTGTAAGCAGAG | 248 |
| 11 | design1_gRNA11 | GTTGATGCGGATACAATGTG | 249 |
| 12 | design1_gRNA12 | TGTCACGCTGATGAATCTGG | 250 |
| 1 through 12 | design2_gRNA | AGTCAGTTGTAATCACAGGG | 251 |

TABLE 4D

Sequences the constructs, barcodes, and/or probes used in Example 4.
See FIGS. 4C-4F and related figures for results.

| Name | Sequence | SEQ ID NO. |
|---|---|---|
| Design 1 array | GCCTCCAGATTCATCAGCGTGACAACTGTGCTGTAGGACCCCACATTGTATCCGCATCAACGGTAGCAAGCAATCCCACTCTGCTTACACGACTCAACTCCGAAGAGTCGAACCGCTCGGCTATTAGAGATGAACGCCAACGCGTCGGCCCCTGTGATTCGTCAACATACACGCCCTGATAAATATCCTCGGTATGTATCGCAATCCACCAAAGCAGAGCGACCCACCCCTGTGATTCAACATACGCCAATGCGGACGCGGCCGCCGTTATCCTCCAACTGAATGAAGGCGACAACCACCCCTGGGTTGTTAGCGATACATCCGACCCAATCATACCGCTGTTCAGATACCAATCCCTTCGGCGATTTCCCGCCGTGTTCTGTTTCCACATCCCTCTGCGATTCGTGGCCCGCCGTGTCATAAAGAATGCGTTGGGGCGA | 252 |

TABLE 4D -continued

Sequences the constructs, barcodes, and/or probes used in Example 4.
See FIGS. 4C-4F and related figures for results.

| Name | Sequence | SEQ ID NO. |
|---|---|---|
| Design 1 lentiviral transfer plasmid | GTCGACGGATCGGGAGATCTCCCGATCCCCTATGGTGCACTCTCAGTACAATCTGCTCTGATGCCGC ATAGTTAAGCCAGTATCTGCTCCCTGCTTGTGTGTTGGAGGTCGCTGAGTAGTGCGCGAGCAAAATT TAAGCTACAACAAGGCAAGGCTTGACCGACAATTGCATGAAGAATCTGCTTAGGGTTAGGCGTTTTG CGCTGCTTCGCGATGTACGGGCCAGATATACGCGTTGACATTGATTATTGACTAGTTATTAATAGTA ATCAATTACGGGGTCATTAGTTCATAGCCCATATATGGAGTTCCGCGTTACATAACTTACGGTAAAT GGCCCGCCTGGCTGACCGCCCAACGACCCCCGCCCATTGACGTCAATAATGACGTATGTTCCCATAG TAACGCCAATAGGGACTTTCCATTGACGTCAATGGGTGGAGTATTTACGGTAAACTGCCCACTTGGC AGTACATCAAGTGTATCATATGCCAAGTACGCCCCCTATTGACGTCAATGACGGTAAATGGCCCGCC TGGCATTATGCCCAGTACATGACCTTATGGGACTTTCCTACTTGGCAGTACATCTACGTATTAGTCA TCGCTATTACCATGGTGATGCGGTTTTGGCAGTACATCAATGGGCGTGGATAGCGGTTTGACTCACG GGGATTTCCAAGTCTCCACCCCATTGACGTCAATGGGAGTTTGTTTTGGCACCAAAATCAACGGGAC TTTCCAAAATGTCGTAACAACTCCGCCCCATTGACGCAAATGGGCGGTAGGCGTGTACGGTGGGAGG TCTATATAAGCAGCGCGTTTTGCCTGTACTGGGTCTCTCTGGTTAGACCAGATCTGAGCCTGGGAGC TCTCTGGCTAACTAGGGAACCCACTGCTTAAGCCTCAATAAAGCTTGCCTTGAGTGCTTCAAGTAGT GTGTGCCCGTCTGTTGTGTGACTCTGGTAACTAGAGATCCCTCAGACCCTTTTAGTCAGTGTGGAAA ATCTCTAGCAGTGGCGCCCGAACAGGGACTTGAAAGCGAAAGGGAAACCAGAGGAGCTCTCTCGACG CAGGACTCGGCTTGCTGAAGCGCGCACGGCAAGAGGCGAGGGGCGGCGACTGGTGAGTACGCCAAAA ATTTTGACTAGCGGAGGCTAGAAGGAGAGAGATGGGTGCGAGAGCGTCAGTATTAAGCGGGGGAGAA TTAGATCGCGATGGGAAAAAATTCGGTTAAGGCCAGGGGGAAAGAAAAATATAAATTAAAACATAT AGTATGGGCAAGCAGGGAGCTAGAACGATTCGCAGTTAATCCTGGCCTGTTAGAAACATCAGAAGGC TGTAGACAAATACTGGGACAGCTACAACCATCCCTTCAGACAGGATCAGAAGAACTTAGATCATTAT ATAATACAGTAGCAACCCTCTATTGTGTGCATCAAAGGATAGAGATAAAAGACACCAAGGAAGCTTT AGACAAGATAGAGGAAGAGCAAAACAAAAGTAAGACCACCGCACAGCAAGCGGCCGCTGATCTTCAG ACCTGGAGGAGGAGATATGAGGGACAATTGGAGAAGTGAATTATATAAATATAAAGTAGTAAAAATT GAACCATTAGGAGTAGCACCCACCAAGGCAAAGAGAAGAGTGGTGCAGAGAGAAAAAAGAGCAGTGG GAATAGGAGCTTTGTTCCTTGGGTTCTTGGGAGCAGCAGGAAGCACTATGGGCGCAGCGTCAATGAC GCTGACGGTACAGGCCAGACAATTATTGTCTGGTATAGTGCAGCAGCAGAACAATTTGCTGAGGGCT ATTGAGGCGCAACAGCATCTGTTGCAACTCACAGTCTGGGGCATCAAGCAGCTCCAGGCAAGAATCC TGGCTGTGGAAAGATACCTAAAGGATCAACAGCTCCTGGGGATTTGGGGTTGCTCTGGAAAACTCAT TTGCACCACTGCTGTGCCTTGGAATGCTAGTTGGAGTAATAAATCTCTGGAACAGATTTGGAATCAC ACGACCTGGATGGAGTGGGACAGAGAAATTAACAATTACACAAGCTTAATACACTCCTTAATTGAAG AATCGCAAAACCAGCAAGAAAAGAATGAACAAGAATTATTGGAATTAGATAAATGGGCAAGTTTGTG GAATTGGTTTAACATAACAAATTGGCTGTGGTATATAAAATTATTCATAATGATAGTAGGAGGCTTG GTAGGTTTAAGAATAGTTTTTGCTGTACTTTCTATAGTGAATAGAGTTAGGCAGGGATATTCACCAT TATCGTTTCAGACCCACCTCCCAACCCCGAGGGGACCCGACAGGCCCGAAGGAATAGAAGAAGAAGG TGGAGAGAGAGACAGAGACAGATCCATTCGATTAGTGAACGGATCGGCACTGCGTGCGCCAATTCTG CAGACAAATGGCAGTATTCATCCACAATTTTAAAAGAAAAGGGGGGATTGGGGGGTACAGTGCAGGG GAAAGAATAGTAGACATAATAGCAACAGACATACAAACTAAAGAATTACAAAAACAAATTACAAAAA TTCAAAATTTTCGGGTTTATTACAGGGACAGCAGAGATCCAGTTTGGTTAATTTATAGCCTCCAGAT TCATCAGCGTGACAACTGTGCTGTAGGACCCCACATTGTATCCGCATCAACGGTAGCAAGCAATCCC ACTCTGCTTACACGACTCAACTCCGAAGAGTCGAACCGCTCGGCTATTAGAGATGAACGCCAACGCG TCGGCCCCTGTGATTCGTCAACATACACGCCCTGATAAATATCCTCGGTATGTATCGCAATCCACCA AAGCAGAGCGACCCACCCTGTGATTCAACATACGCCAATGCGGCACGGCCGCCGTTATCCTCCAAC TGAATGAAGGCGACAACCACCCCTGGGTTGTTAGCGATACATCCGACCCAATCATACCGCTGTTCAG ATACCAATCCCTTCGGCGATTTCCCGCCGTGTTCTGTTTCCACATCCCTCTGCGATTCGTGGCCCGC CGTGTCATAAAGAATGCGTTGGGGCGAccctttagtgagggttaattctcgagtctccctatagtga gtcgtattaattccgtgtattctatagtgtcacctaaatcgttacgggATTAACCCGTGTCGGCTCC AGATCTggcctccgcgccgggttttggcgcctcccgcgggcccccctttcctcacggcgagcgctgc cacgtcagacgaagggcgcagCgagcgtcctgatccttccgcccggacgctcaggacagcggcccgc tgctcataagactcggccttagaaccccagtatcagcagaaggacattttaggacgggacttgggtg actctagggcactggttttctttccagagagcggaacaggcgaggaaaagtagtccctctcggcga ttctgcggagggatctccgtgggcggtgaacgccgatgattatataaggacgcgccgggtgtggca cagctagttccgtcgcagccgggatttgggtcgcggttcttgtttgtggatcgctgtgatcgtcact tggtgagtAgcgggctgctggctggccggggctttcgtggccgccgggccgctcggtgggacggaa gcgtgtggagagaccgccaagggctgtagtctgggtccgcgagcaaggttgccctgaactgggggtt gggggagcgcaGcaaaatggcggctgttcccgagtcttgaagacgcttgtGaggcgggctg tgaggtcgttgaaacaaggtgggggcatggtgggcggcaagaacccaaggtcttgaggccttcgct aatgcgggaaagctcttattcgggtgagatgggctggggcaccatctggggaccctgacgtgaagtt tgtcactgactggagaactcggtttgtcgtctgttgcggggcggcagttatgGcggtgccgttggg cagtgcacccgtacctttgggagcgcgcgccCtcgtcgtgtcgtgacgtcacccgttctgttggctt ataatgcagggtggggccacctgccggtaggtgtgcggtaggcttttctccgtcgcaggacgcaggg ttcgggcctagggtaggctctcctgaatcgacaggcgccggacctctggtgaggggagggataagtg aggcgtcagtttctttggtcggttttatgtacctatcttcttaagtagctgaagctccggttttgaa ctatgcgctcggggttggcgagtgtgttttgtgaagtttttttaggcacccttttgaaatgtaatcatt tgggtcaatatgtaattttcagtgttagactagtaaattgtccgctaaattctggccgttttttggct tttttgttagacGAAGCTTGGGCTGCAGGTCGACTCTAGaGGATCCCGGGTAaggatccccgggta ccgtcgccaccatggtgagcaagggcgaggagctgttcaccggggtggtgcccatcctggtcgagc tggacggcgacgtaaacggccacaagttcagcgtgtccggcgagggcgagggcgatgccacctacgg caagctgaccctgaagttcatctgcaccaccggcaagctgcccgtgccctggcccaccctcgtgacc accctgacctggggcgtgcagtgcttcgcccgctaccccgaccacatgaagcagcacgacttcttca gtccgccatgcccgaaggctacgtccaggagcgcaccatcttcttcaaggacgacggcaactacaa gacccgcgccgaggtgaagttcgagggcgacaccctggtgaaccgcatcgagctgaagggcatcgac ttcaaggaggacggcaacatcctggggcacaagctggagtacaactacaacagccatcagcgacaacgtctata | 253 |

TABLE 4D -continued

Sequences the constructs, barcodes, and/or probes used in Example 4.
See FIGS. 4C-4F and related figures for results.

| Name | Sequence | SEQ ID NO. |
|------|----------|------------|
|  | tcaccgccgacaagcagaagaacggcatcaaggccaacttcaagatccgccacaacatcgaggacgg cagcgtgcagctcgccgaccactaccagcagaacaccccccatcggcgacggccccgtgctgctgccc gacaaccactacctgagcacccagtccaagctgagcaaagaccccaacgagaagcgcgatcacatgg tcctgctggagttcgtgaccgccgccgggatcactctcggcatggacgagctgtacaagtgaacctG AATTCGATATCAAGCTTATCGATAATCAACCTCTGGATTACAAAATTTGTGAAAGATTGACTGGTAT TCTTAACTATGTTGCTCCTTTTACGCTATGTGGATACGCTGCTTTAATGCCTTTGTATCATGCTATT GCTTCCCGTATGGCTTTCATTTTCTCCTCCTTGTATAAATCCTGGTTGCTGTCTCTTTATGAGGAGT TGTGGCCCGTTGTCAGGCAACGTGGCGTGGTGTGCACTGTGTTTGCTGACGCAACCCCCACTGGTTG GGGCATTGCCACCACCTGTCAGCTCCTTTCCGGGACTTTCGCTTTCCCCCTCCCTATTGCCACGGCG GAACTCATCGCCGCCTGCCTTGCCCGCTGCTGGACAGGGGCTCGGCTGTTGGGCACTGACAATTCCG TGGTGTTGTCGGGGAAATCATCGTCCTTTCCTTGGCTGCTCGCCTGTGTTGCCACCTGGATTCTGCG CGGGACGTCCTTCTGCTACGTCCCTTCGGCCCTCAATCCAGCGGACCTTCCTTCCCGCGGCCTGCTG CCGGCTCTGCGGCCTCTTCCGCGTCTTCGCCTTCGCCCTCAGACGAGTCGGATCTCCCTTTGGGCCG CCTCCCCGCATCGATACCGTCGAGACCTAGAAAAACATGGAGCAATCACAAGTAGCAATAC AGCAGCTACCAATGCTGATTGTGCCTGGCTAGAAGCACAAGAGGAGGAGGAGGTGGGTTTTCCAGTC ACACCTCAGGTACCTTTAAGACCAATGACTTACAAGGCAGCTGTAGATCTTAGCCACTTTTTAAAAG AAAAGGGGGGACTGGAAGGGCTAATTCACTCCCAACGAAGACAAGATATCCTTGATCTGTGGATCTA CCACACACAAGGCTACTTCCCTGATTGGCAGAACTACACACCAGGGCCAGGGATCAGATATCCACTG ACCTTTGGATGGTGCTACAAGCTAGTACCAGTTGAGCAAGAGAAGGTAGAAGAAGCCAATGAAGGAG AGAACACCCGCTTGTTACACCCTGTGAGCCTGCATGGGATGGATGACCCGGAGAGAGAAGTATTAGA GTGGAGGTTTGACAGCCGCCTAGCATTTCATCACATGGCCCGAGAGCTGCATCCGGACTGTACTGGG TCTCTCTGGTTAGACAGATCTGAGCCTGGGAGTCTCTGGCTAACTAGGGAACCCACTGCTTAAGC CTCAATAAAGCTTGCCTTGAGTGCTTCAAGTAGTGTGTGCCCGTCTGTTGTGTGACTCTGGTAACTA GAGATCCCTCAGACCCTTTTAGTCAGTGTGGAAAATCTCTAGCAGGGCCCGTTTAAACCCGCTGATC AGCCTCGACTGTGCCTTCTAGTTGCCAGCCATCTGTTGTTTGCCCCTCCCCCGTGCCTTCCTTGACC CTGGAAGGTGCCACTCCCACTGTCCTTTCCTAATAAAATGAGGAAATTGCATCGCATTGTCTGAGTA GGTGTCATTCTATTCTGGGGGGTGGGGTGGGGCAGGACAGCAAGGGGGAGGATTGGGAAGACAATAG CAGGCATGCTGGGGATGCGGTGGGCTCTATGGCTTCTGAGGCGGAAAGAACCAGCTGGGGCTCTAGG GGGTATCCCCACGCGCCCTGTAGCGGCGCATTAAGCGCGGCGGGTGTGGTGGTTACGCGCAGCGTGA CCGCTACACTTGCCAGCGCCCTAGCGCCCGCTCCTTTCGCTTTCTTCCCTTCCTTTCTCGCCACGTT CGCCGGCTTTCCCCGTCAAGCTCTAAATCGGGGGCTCCCTTTAGGGTTCCGATTTAGTGCTTTACGG CACCTCGACCCCAAAAAACTTGATTAGGGTGATGGTTCACGTAGTGGGCCATCGCCCTGATAGACGG TTTTTCGCCCTTTGACGTTGGAGTCCACGTTCTTTAATAGTGGACTCTTGTTCCAAACTGGAACAAC ACTCAACCCTATCTCGGTCTATTCTTTTGATTTATAAGGGATTTTGCCGATTTCGGCCTATTGGTTA AAAAATGAGCTGATTTAACAAAAATTTAACGCGAATTAATTCTGTGGAATGTGTGTCAGTTAGGGTG TGGAAAGTCCCCAGGCTCCCCAGCAGGCAGAAGTATGCAAAGCATGCATCTCAATTAGTCAGCAACC AGGTGTGGAAAGTCCCCAGGCTCCCCAGCAGGCAGAAGTATGCAAAGCATGCATCTCAATTAGTCAG CAACCATAGTCCCGCCCCTAACTCCGCCCATCCCGCCCCTAACTCCGCCCAGTTCCGCCCATTCTCC GCCCCATGGCTGACTAATTTTTTTTATTTATGCAGAGGCCGAGGCCGCCTCTGCCTCTGAGCTATTC CAGAAGTAGTGAGGAGGCTTTTTTGGAGGCCTAGGCTTTTGCAAAAAGCTCCCGGGAGCTTGTATAT CCATTTTCGGATCTGATCAGCACGTGTTGACAATTAATCATCGGCATAGTATATCGGCATAGTATAA TACGACAAGGTGAGGAACTAAACCATGGCCAAGTTGACCAGTGCCGTTCCGGTGCTCACCGCGCGCG ACGTCGCCGGAGCGGTCGAGTTCTGGACCGACCGGCTCGGGTTCTCCCGGGACTTCGTGGAGGACGA CTTCGCCGGTGTGGTCCGGGACGACGTGACCCTGTTCATCAGCGCGGTCCAGGACCAGGTGGTGCCG GACAACACCCTGGCCTGGGTGTGGGTGCGCGGCCTGGACGAGCTGTACGCCGAGTGGTCGGAGGTCG TGTCCACGAACTTCCGGGACGCCTCCGGGCCGGCCATGACCGAGATCGGCGAGCAGCCGTGGGGGCG GGAGTTCGCCCTGCGCGACCCGGCCGGCAACTGCGTGCACTTCGTGGCCGAGGAGCAGGACTGACAC GTGCTACGAGATTTCGATTCCACCGCCGCCTTCTATGAAAGGTTGGGCTTCGGAATCGTTTTCCGGG ACGCCGGCTGGATGATCCTCCAGCGCGGGGATCTCATGCTGGAGTTCTTCGCCCACCCCAACTTGTT TATTGCAGCTTATAATGGTTACAAATAAAGCAATAGCATCACAAATTTCACAAATAAAGCATTTTTT TCACTGCATTCTAGTTGTGGTTTGTCCAAACTCATCAATGTATCTTATCATGTCTGTATACCGTCGA CCTCTAGCTAGAGCTTGGCGTAATCATGGTCATAGCTGTTTCCTGTGTGAAATTGTTATCCGCTCAC AATTCCACACAACATACGAGCCGGAAGCATAAAGTGTAAAGCCTGGGGTGCCTAATGAGTGAGCTAA CTCACATTAATTGCGTTGCGCTCACTGCCCGCTTTCCAGTCGGGAAACCTGTCGTGCCAGCTGCATT AATGAATCGGCCAACGCGCGGGGAGAGGCGGTTTGCGTATTGGGCGCTCTTCCGCTTCCTCGCTCAC TGACTCGCTGCGCTCGGTCGTTCGGCTGCGGCGAGCGGTATCAGCTCACTCAAAGGCGGTAATACGG TTATCCACAGAATCAGGGGATAACGCAGGAAAGAACATGTGAGCAAAAGGCCAGCAAAAGGCCAGGA ACCGTAAAAAGGCCGCGTTGCTGGCGTTTTTCCATAGGCTCCGCCCCCTGACGAGCATCACAAAA TCGACGCTCAAGTCAGAGGTGGCGAAACCCGACAGGACTATAAAGATACCAGGCGTTTCCCCCTGGA AGCTCCCTCGTGCGCTCTCCTGTTCCGACCCTGCCGCTTACCGGATACCTGTCCGCCTTTCTCCCTT CGGGAAGCGTGGCGCTTTCTCATAGCTCACGCTGTAGGTATCTCAGTTCGGTGTAGGTCGTTCGCTC CAAGCTGGGCTGTGTGCACGAACCCCCCGTTCAGCCCGACCGCTGCGCCTTATCCGGTAACTATCGT CTTGAGTCCAACCCGGTAAGACACGACTTATCGCCACTGGCAGCAGCCACTGGTAACAGGATTAGCA GAGCGAGGTATGTAGGCGGTGCTACAGAGTTCTTGAAGTGGTGGCCTAACTACGGCTACACTAGAAG AACAGTATTTGGTATCTGCGCTCTGCTGAAGCCAGTTACCTTCGGAAAAAGAGTTGGTAGCTCTTGA TCCGGCAAACAAACCACCGCTGGTAGCGGTGGTTTTTTTGTTTGCAAGCAGCAGATTACGCGCAGAA AAAAAGGATCTCAAGAAGATCCTTTGATCTTTTCTACGGGGTCTGACGCTCAGTGGAACGAAAACTC ACGTTAAGGGATTTTGGTCATGAGATTATCAAAAAGGATCTTCACCTAGATCCTTTTAAATTAAAAA TGAAGTTTTAAATCAATCTAAAGTATATATGAGTAAACTTGGTCTGACAGTTACCAATGCTTAATCA GTGAGGCACCTATCTCAGCGATCTGTCTATTTCGTTCATCCATAGTTGCCTGACTCCCCGTCGTGTA GATAACTACGATACGGGAGGGCTTACCATCTGGCCCCAGTGCTGCAATGATACCGCGAGACCCACGC TCACCGGCTCCAGATTTATCAGCAATAAACCAGCCAGCCGGAAGGGCCGAGCGCAGAAGTGGTCCTG CAACTTTATCCGCCTCCATCCAGTCTATTAATTGTTGCCGGGAAGCTAGAGTAAGTAGTTCGCCAGT |  |

TABLE 4D -continued

Sequences the constructs, barcodes, and/or probes used in Example 4.
See FIGS. 4C-4F and related figures for results.

| Name | Sequence | SEQ ID NO. |
|---|---|---|
| | TAATAGTTTGCGCAACGTTGTTGCCATTGCTACAGGCATCGTGGTGTCACGCTCGTCGTTTGGTATG<br>GCTTCATTCAGCTCCGGTTCCCAACGATCAAGGCGAGTTACATGATCCCCCATGTTGTGCAAAAAAG<br>CGGTTAGCTCCTTCGGTCCTCCGATCGTTGTCAGAAGTAAGTTGGCCGCAGTGTTATCACTCATGGT<br>TATGGCAGCACTGCATAATTCTCTTACTGTCATGCCATCCGTAAGATGCTTTTCTGTGACTGGTGAG<br>TACTCAACCAAGTCATTCTGAGAATAGTGTATGCGGCGACCGAGTTGCTCTTGCCCGGCGTCAATAC<br>GGGATAATACCGCGCCACATAGCAGAACTTTAAAAGTGCTCATCATTGGAAAACGTTCTTCGGGGCG<br>AAAACTCTCAAGGATCTTACCGCTGTTGAGATCCAGTTCGATGTAACCCACTCGTGCACCCAACTGA<br>TCTTCAGCATCTTTTACTTTCACCAGCGTTTCTGGGTGAGCAAAAACAGGAAGGCAAAATGCCGCAA<br>AAAAGGGAATAAGGGCGACACGGAAATGTTGAATACTCATACTCTTCCTTTTTCAATATTATTGAAG<br>CATTTATCAGGGTTATTGTCTCATGAGCGGATACATATTTGAATGTATTTAGAAAAATAAACAAATA<br>GGGGTTCCGCGCACATTTCCCCGAAAAGTGCCACCTGAC | |
| Design 2 array | ctgtaggtTAGCAACCACCCTGTGATTACAACTGACTCCTCCTCGCGCAAGCCACCCTGTGATTACA<br>ACTGACTCTCCGTCCtacgcagaaggtCCTCTTCCACCCTGTGATTACAACTGACTCTGGGGTGGGT<br>GCTCCACCCTGTGATTACAACTGACTCGTGCGGTtacggtagaggtTTGACCCCACCCTGTGATTAC<br>AACTGACTGCGTCCTGTTGTATCCACCCTGTGATTACAACTGACTTGGGCGTCtacgggttaggtCT<br>GGGGCCACCCTGTGATTACAACTGACTGTGCCTGCCACTATCCACCCTGTGATTACAACTGACTGTC<br>GCCCTtacgttggaggtCCATGCCCACCCTGTGATTACAACTGACTGCTGTCCGTCCCTCCCACCCT<br>GTGATTACAACTGACTGGTCGCTctacggagtaggtGTCTCACCACCCTGTGATTACAACTGACTTC<br>CCTGGCCACTATCCACCCTGTGATTACAACTGACTGGCTGTGGtacggctaaggt | 254 |
| Design 2 lentiviral transfer plasmid | GTCGACGGATCGGGAGATCTCCCGATCCCCTATGGTGCACTCTCAGTACAATCTGCTCTGATGCCGC<br>ATAGTTAAGCCAGTATCTGCTCCCTGCTTGTGTGTTGGAGGTCGCTGAGTAGTGCGCGAGCAAAATT<br>TAAGCTACAACAAGGCAAGGCTTGACCGACAATTGCATGAAGAATCTGCTTAGGGTTAGGCGTTTTG<br>CGCTGCTTCGCGATGTACGGGCCAGATATACGCGTTGACATTGATTATTGACTAGTTATTAATAGTA<br>ATCAATTACGGGGTCATTAGTTCATAGCCCATATATGGAGTTCCGCGTTACATAACTTACGGTAAAT<br>GGCCCGCCTGGCTGACCGCCCAACGACCCCCGCCCATTGACGTCAATAATGACGTATGTTCCCATAG<br>TAACGCCAATAGGGACTTTCCATTGACGTCAATGGGTGGAGTATTTACGGTAAACTGCCCACTTGGC<br>AGTACATCAAGTGTATCATATGCCAAGTACGCCCCCTATTGACGTCAATGACGGTAAATGGCCCGCC<br>TGGCATTATGCCCAGTACATGACCTTATGGGACTTTCCTACTTGGCAGTACATCTACGTATTAGTCA<br>TCGCTATTACCATGGTGATGCGGTTTTGGCAGTACATCAATGGGCGTGGATAGCGGTTTGACTCACG<br>GGGATTTCCAAGTCTCCACCCCATTGACGTCAATGGGAGTTTGTTTTGGCACCAAAATCAACGGGAC<br>TTTCCAAAATGTCGTAACAACTCCGCCCCATTGACGCAAATGGGCGGTAGGCGTGTACGGTGGGAGG<br>TCTATATAAGCAGCGCGTTTTGCCTGTACTGGGTCTCTCTGGTTAGACCAGATCTGAGCCTGGGAGC<br>TCTCTGGCTAACTAGGGAACCCACTGCTTAAGCCTCAATAAAGCTTGCCTTGAGTGCTTCAAGTAGT<br>GTGTGCCCGTCTGTTGTGTGACTCTGGTAACTAGAGATCCCTCAGACCCTTTTAGTCAGTGTGGAAA<br>ATCTCTAGCAGTGGCGCCCGAACAGGGACTTGAAAGCGAAAGGGAAACCAGAGGAGCTCTCTCGACG<br>CAGGACTCGGCTTGCTGAAGCGCGCACGGCAAGAGGCGAGGGGCGGCGACTGGTGAGTACGCCAAAA<br>ATTTTGACTAGCGGAGGCTAGAAGGAGAGAGATGGGTGCGAGAGCGTCAGTATTAAGCGGGGGAGAA<br>TTAGATCGCGATGGGAAAAAATTCGGTTAAGGCCAGGGGGAAAGAAAAATATAAATTAAAACATAT<br>AGTATGGGCAAGCAGGGAGCTAGAACGATTCGCAGTTAATCCTGGCCTGTTAGAAACATCAGAAGGC<br>TGTAGACAAATACTGGGACAGCTACAACCATCCCTTCAGACAGGATCAGAAGAACTTAGATCATTAT<br>ATAATACAGTAGCAACCCTCTATTGTGTGCATCAAAGGATAGAGATAAAAGACACCAAGGAAGCTTT<br>AGACAAGATAGAGGAAGAGCAAAACAAAAGTAAGACCACCGCACAGCAAGCGGCCGCTGATCTTCAG<br>ACCTGGAGGAGGAGATATGAGGGACAATTGGAGAAGTGAATTATATAAATATAAAGTAGTAAAAATT<br>GAACCATTAGGAGTAGCACCCACCAAGGCAAAGAGAAGAGTGGTGCAGAGAGAAAAAAGAGCAGTGG<br>GAATAGGAGCTTTGTTCCTTGGGTTCTTGGGAGCAGCAGGAAGCACTATGGGCGCAGCGTCAATGAC<br>GCTGACGGTACAGGCCAGACAATTATTGTCTGGTATAGTGCAGCAGCAGAACAATTTGCTGAGGGCT<br>ATTGAGGCGCAACAGCATCTGTTGCAACTCACAGTCTGGGGCATCAAGCAGCTCCAGGCAAGAATCC<br>TGGCTGTGGAAAGATACCTAAAGGATCAACAGCTCCTGGGGATTTGGGGTTGCTCTGGAAAACTCAT<br>TTGCACCACTGCTGTGCCTTGGAATGCTAGTTGGAGTAATAAATCTCTGGAACAGATTTGGAATCAC<br>ACGACCTGGATGGAGTGGGACAGAGAAATTAACAATTACACAAGCTTAATACACTCCTTAATTGAAG<br>AATCGCAAAACCAGCAAGAAAAGAATGAACAAGAATTATTGGAATTAGATAAATGGGCAAGTTTGTG<br>GAATTGGTTTAACATAACAAATTGGCTGTGGTATATAAAATTATTCATAATGATAGTAGGAGGCTTG<br>GTAGGTTTAAGAATAGTTTTTGCTGTACTTTCTATAGTGAATAGAGTTAGGCAGGGATATTCACCAT<br>TATCGTTTCAGACCCACCTCCCAACCCCGAGGGGACCCGACAGGCCCGAAGGAATAGAAGAAGAAGG<br>TGGAGAGAGAGACAGAGACAGATCCATTCGATTAGTGAACGGATCGGCACTGCGTGCGCCAATTCTG<br>CAGACAAATGGCAGTATTCATCCACAATTTTAAAAGAAAAGGGGGATTGGGGGGTACAGTGCAGGG<br>GAAAGAATAGTAGACATAATAGCAACAGACATACAAACTAAAGAATTACAAAAACAAATTACAAAAA<br>TTCAAAATTTTCGGGTTTATTACAGGGACAGCAGAGATCCAGTTTGTTAATctgtaggtTAGCAAC<br>CACCCTGTGATTACAACTGACTCCTCCTCGCGCAAGCCACCCTGTGATTACAACTGACTCTCCGTCC<br>tacgcagaaggtCCTCTTCCACCCTGTGATTACAACTGACTCTGGGGTGGGTGCTCCACCCTGTGAT<br>TACAACTGACTCGTGCGGTtacggtagaggtTTGACCCCACCCTGTGATTACAACTGACTGCGTCCT<br>GTTGTATCCACCCTGTGATTACAACTGACTTGGGCGTCtacgggttaggtCTGGGGCCACCCTGTGA<br>TTACAACTGACTGTGCCTGCCACTATCCACCCTGTGATTACAACTGACTGTCGCCCTtacgttggag<br>gtCCATGCCCACCCTGTGATTACAACTGACTGCTGTCCGTCCCTCCCACCCTGTGATTACAACTGAC<br>TGGTCGCTctacggagtaggtGTCTCACCACCCTGTGATTACAACTGACTTCCCTGGCCACTATCCA<br>CCCTGTGATTACAACTGACTGGCTGTGGtacggctaaggtcctccctttagtgagggttaattctcg<br>agtctccctatagtgagtcgtattaattccgtgtattctatagtgtcacctaaatcgttacgagaca<br>cctATTAACCCGTGTCGGTCCCAGATCTggcctccgcgccgggttttggcgcctcccgcgggcgccc<br>cctcctcacggcgagcgctgccacgtcagacgaagggcgcagCgagcgtcctgatccttccgcccg<br>gacgctcaggacagcggcccgctgctcataagactcggccttagaacccagtatcagcagaaggac<br>attttaggacgggacttgggtgactctagggcactggttttctttccagagagcggaacaggcgagg | 255 |

TABLE 4D -continued

Sequences the constructs, barcodes, and/or probes used in Example 4.
See FIGS. 4C-4F and related figures for results.

| Name | Sequence | SEQ ID NO. |
|------|----------|------------|
|  | aaaagtagtcccttctcggcgattctgcggagggatctccgtggggcggtgaacgccgatgattata<br>taaggacgcgccgggtgtggcacagctagttccgtcgcagccgggatttgggtcgcggttcttgttt<br>gtggatcgctgtgatcgtcacttggtgagtAgcgggctgctgggctggccggggctttcgtggccgc<br>cgggccgctcggtgggacggaagcgtgtggagagaccgccaagggctgtagtctgggtccgcgagca<br>aggttgccctgaactgggggttggggggagcgcaGcaaaatggcggctgttcccgagtcttgaatgg<br>aagacgcttgtGaggcgggctgtgaggtcgttgaaacaaggtgggggcatggtgggcggcaagaac<br>ccaaggtcttgaggccttcgctaatgcgggaaagctcttattcgggtgagatgggctggggcaccat<br>ctggggaccctgacgtgaagtttgtcactgactggagaactcggtttgtcgtctgttgcggggcgg<br>cagttatgGcggtgccgttgggcagtgcaccgtaccttgggagcgcgcgccCtcgtcgtgtcgtg<br>acgtcacccgttctgttggcttataatgcagggtgggccacctgccggtaggtgtgcggtaggctt<br>ttctccgtcgcaggacgcagggttcgggcctagggtaggctctcctgaatcgacaggcgccggacct<br>ctggtgagggagggataagtgaggcgtcagtttcttggtcggttttatgtacctatcttcttaag<br>tagctgaagctccggttttgaactatgcgctcggggttggcgagtgtgttttgtgaagttttttagg<br>caccttttgaaatgtaatcatttggtcaatatgtaattttcagtgttagactagtaaattgtccgc<br>taaattctggccgttttttggcttttttgttagacGAAGCTTGGGCTGCAGGTCGACTCTAgAGGATC<br>CCCGGGTAaggatccccgggtaccggtcgccaccatggtgagcaagggcgaggagctgttcaccggg<br>gtggtgcccatcctggtcgagctggacggcgacgtaaacggccacaagttcagcgtgtccggcgagg<br>gcgagggcgatgccacctacggcaagctgaccctgaagttcatctgcaccaccggcaagctgcccgt<br>gccctggcccacccctcgtgaccaccctgacctggggcgtgcagtgcttcgcccgctaccccgaccac<br>atgaagcagcacgacttcttcaagtccgccatgcccgaaggctacgtccaggagcgcaccatcttct<br>tcaaggacgacggcaactacaagacccgcgccgaggtgaagttcgagggcgacaccctggtgaaccg<br>catcgagctgaagggcatcgacttcaaggaggacggcaacatcctggggcacaagctggagtacaac<br>gccatcagcgacaacgtctatatcaccgccgacaagcagaagaacggcatcaaggccaacttcaaga<br>tccgccacaacatcgaggacggcagcgtgcagctcgccgaccactaccagcagaacacccccatcgg<br>cgacggccccgtgctgctgcccgacaaccactacctgagcacccagtccaagctgagcaaagacccc<br>aacgagaagcgcgatcacatggtcctgctggagttcgtgaccgccgcgggatcactctcggcatgg<br>acgagctgtacaagtgaacctGAATTCGATATCAAGCTTATCGATAATCAACCTCTGGATTACAAAA<br>TTTGTGAAAGATTGACTGGTATTCTTAACTATGTTGCTCCTTTTACGCTATGTGGATACGCTGCTTT<br>AATGCCTTTGTATCATGCTATTGCTTCCCGTATGGCTTTCATTTTCTCCTCCTTGTATAAATCCTGG<br>TTGCTGTCTCTTTATGAGGAGTTGTGGCCCGTTGTCAGGCAACGTGGCGTGGTGTGCACTGTGTTTG<br>CTGACGCAACCCCCACTGGTTGGGGCATTGCCACCACCTGTCAGCTCCTTTCCGGGACTTTCGCTTT<br>CCCCCTCCCTATTGCCACGGCGGAACTCATCGCCGCCTGCCTTGCCCGCTGCTGGACAGGGGCTCGG<br>CTGTTGGGCACTGACAATTCCGTGGTGTTGTCGGGGAAATCATCGTCCTTTCCTTGGCTGCTCGCCT<br>GTGTTGCCACCTGGATTCTGCGCGGGACGTCCTTCTGCTACGTCCCTTCGGCCCTCAATCCAGCGGA<br>CCTTCCTTCCCGCGGCCTGCTGCCGGCTCTGCGGCCTCTTCCGCGTCTTCGCCTTCGCCCTCAGACG<br>AGTCGGATCTCCCTTTGGGCCGCCTCCCCGCATCGATACCGTCGACCTCGAGACCTAGAAAAACATG<br>GAGCAATCACAAGTAGCAATACAGCAGCTACCAATGCTGATTGTGCCTGGCTAGAAGCACAAGAGGA<br>GGAGGAGGTGGGTTTTCCAGTCACACCTCAGGTACCTTTAAGACCAATGACTTACAAGGCAGCTGTA<br>GATCTTAGCCACTTTTTAAAAGAAAAGGGGGGACTGGAAGGGCTAATTCACTCCCAACGAAGACAAG<br>ATATCCTTGATCTGTGGATCTACCACACACAAGGCTACTTCCCTGATTGGCAGAACTACACACCAGG<br>GCCAGGGATCAGATATCCACTGACCTTTGGATGGTGCTACAAGCTAGTACCAGTTGAGCAAGAGAAG<br>GTAGAAGAAGCCAATGAAGGAGAGAACACCCGCTTGTTACACCCTGTGAGCCTGCATGGGATGGATG<br>ACCCGGAGAGAGAAGTATTAGAGTGGAGGTTTGACAGCCGCCTAGCATTTCATCACATGGCCCGAGA<br>GCTGCATCCGGACTGTACTGGGTCTCTCTGGTTAGACCAGATCTGAGCCTGGGAGCTCTCTGGCTAA<br>CTAGGGAACCCACTGCTTAAGCCTCAATAAAGCTTGCCTTGAGTGCTTCAAGTAGTGTGTGCCCGTC<br>TGTTGTGTGACTCTGGTAACTAGAGATCCCTCAGACCCTTTTAGTCAGTGTGGAAAATCTCTAGCAG<br>GGCCCGTTTAAACCCGCTGATCAGCCTCGACTGTGCCTTCTAGTTGCCAGCCATCTGTTGTTTGCCC<br>CTCCCCCGTGCCTTCCTTGACCCTGGAAGGTGCCACTCCCACTGTCCTTTCCTAATAAAATGAGGAA<br>ATTGCATCGCATTGTCTGAGTAGGTGTCATTCTATTCTGGGGGGTGGGGTGGGGCAGGACAGCAAGG<br>GGGAGGATTGGGAAGACAATAGCAGGCATGCTGGGGATGCGGTGGGCTCTATGGCTTCTGAGGCGGA<br>AAGAACCAGCTGGGGCTCTAGGGGGTATCCCCACGCGCCCTGTAGCGGCGCATTAAGCGCGGCGGGT<br>GTGGTGGTTACGCGCAGCGTGACCGCTACACTTGCCAGCGCCCTAGCGCCCGCTCCTTTCGCTTTCT<br>TCCCTTCCTTTCTCGCCACGTTCGCCGGCTTTCCCCGTCAAGCTCTAAATCGGGGCTCCCTTTAGG<br>GTTCCGATTTAGTGCTTTACGGCACCTCGACCCCAAAAAACTTGATTAGGGTGATGGTTCACGTAGT<br>GGGCCATCGCCCTGATAGACGGTTTTTCGCCCTTTGACGTTGGAGTCCACGTTCTTTAATAGTGGAC<br>TCTTGTTCCAAACTGGAACAACACTCAACCCTATCTCGGTCTATTCTTTTGATTTATAAGGGATTTT<br>GCCGATTTCGGCCTATTGGTTAAAAAATGAGCTGATTTAACAAAAATTTAACGCGAATTAATTCTGT<br>GGAATGTGTGTCAGTTAGGGTGTGGAAAGTCCCCAGGCTCCCCAGCAGGCAGAAGTATGCAAAGCAT<br>GCATCTCAATTAGTCAGCAACCAGGTGTGGAAAGTCCCCAGGCTCCCCAGCAGGCAGAAGTATGCAA<br>AGCATGCATCTCAATTAGTCAGCAACCATAGTCCCGCCCCTAACTCCGCCCATCCCGCCCCTAACTC<br>CGCCCAGTTCCGCCCATTCTCCGCCCCATGGCTGACTAATTTTTTTTATTTATGCAGAGGCCGAGGC<br>CGCCTCTGCCTCTGAGCTATTCCAGAAGTAGTGAGGAGGCTTTTTTGGAGGCCTAGGCTTTTGCAAA<br>AAGCTCCCGGGAGCTTGTATATCCATTTTCGGATCTGATCAGCACGTGTTGACAATTAATCATCGGC<br>ATAGTATATCGGCATAGTATAATACGACAAGGTGAGGAACTAAACATGGCCAAGTTGACCAGTGCCG<br>GTTCCGGTGCTCACCGCGCGCGACGTCGCCGGAGCGGTCGAGTTCTGGACCGACCGGCTCGGGTTCT<br>CCCGGGACTTCGTGGAGGACGACTTCGCCGGTGTGGTCCGGGACGACGTGACCCTGTTCATCAGCGC<br>GGTCCAGGACCAGGTGGTGCCGGACAACACCCTGGCCTGGGTGTGGGTGCGCGGCCTGGACGAGCTG<br>TACGCCGAGTGGTCGGAGGTCGTGTCCACGAACTTCCGGGACCTGCCTCCGGGCCGGCCATGACCGAGA<br>TCGGCGAGCAGCCGTGGGGGCGGGAGTTCGCCCTGCGCGACCCGGCCGGCAACTGCGTGCACTTCGT<br>GGCCGAGGAGCAGGACTGACACGTGCTACGAGATTTCGATTCCACCGCCGCCTTCTATGAAAGGTTG<br>GGCTTCGGAATCGTTTTCCGGGACGCCGGCTGGATGATCCTCCAGCGCGGGGATCTCATGCTGGAGT<br>TCTTCGCCCACCCCAACTTGTTTATTGCAGCTTATAATGGTTACAAATAAAGCAATAGCATCACAAA<br>TTTCACAAATAAAGCATTTTTTTCACTGCATTCTAGTTGTGGTTTGTCCAAACTCATCAATGTATCT |  |

TABLE 4D -continued

Sequences the constructs, barcodes, and/or probes used in Example 4.
See FIGS. 4C-4F and related figures for results.

| Name | Sequence | SEQ ID NO. |
|---|---|---|
| | TATCATGTCTGTATACCGTCGACCTCTAGCTAGAGCTTGGCGTAATCATGGTCATAGCTGTTTCCTG TGTGAAATTGTTATCCGCTCACAATTCCACACAACATACGAGCCGGAAGCATAAAGTGTAAAGCCTG GGGTGCCTAATGAGTGAGCTAACTCACATTAATTGCGTTGCGCTCACTGCCCGCTTTCCAGTCGGGA AACCTGTCGTGCCAGCTGCATTAATGAATCGGCCAACGCGCGGGGAGAGGCGGTTTGCGTATTGGGC GCTCTTCCGCTTCCTCGCTCACTGACTCGCTGCGCTCGGTCGTTCGGCTGCGGCGAGCGGTATCAGC TCACTCAAAGGCGGTAATACGGTTATCCACAGAATCAGGGGATAACGCAGGAAAGAACATGTGAGCA AAAGGCCAGCAAAAGGCCAGGAACCGTAAAAAGGCCGCGTTGCTGGCGTTTTTCCATAGGCTCCGCC CCCCTGACGAGCATCACAAAAATCGACGCTCAAGTCAGAGGTGGCGAAACCCGACAGGACTATAAAG ATACCAGGCGTTTCCCCCTGGAAGCTCCCTCGTGCGCTCTCCTGTTCCGACCCTGCCGCTTACCGGA TACCTGTCCGCCTTTCTCCCTTCGGGAAGCGTGGCGCTTTCTCATAGCTCACGCTGTAGGTATCTCA GTTCGGTGTAGGTCGTTCGCTCCAAGCTGGGCTGTGTGCACGAACCCCCCGTTCAGCCCGACCGCTG CGCCTTATCCGGTAACTATCGTCTTGAGTCCAACCCGGTAAGACACGACTTATCGCCACTGGCAGCA GCCACTGGTAACAGGATTAGCAGAGCGAGGTATGTAGGCGGTGCTACAGAGTTCTTGAAGTGGTGGC CTAACTACGGCTACACTAGAAGAACAGTATTTGGTATCTGCGCTCTGCTGAAGCCAGTTACCTTCGG AAAAAGAGTTGGTAGCTCTTGATCCGGCAAACAAACCACCGCTGGTAGCGGTGGTTTTTTTGTTTGC AAGCAGCAGATTACGCGCAGAAAAAAAGGATCTCAAGAAGATCCTTTGATCTTTTCTACGGGGTCTG ACGCTCAGTGGAACGAAAACTCACGTTAAGGGATTTTGGTCATGAGATTATCAAAAAGGATCTTCAC CTAGATCCTTTTAAATTAAAAATGAAGTTTTAAATCAATCTAAAGTATATAGAGTAAACTTGGTCT GACAGTTACCAATGCTTAATCAGTGAGGCACCTATCTCAGCGATCTGTCTATTTCGTTCATCCATAG TTGCCTGACTCCCCGTCGTGTAGATAACTACGATACGGGAGGGCTTACCATCTGGCCCCAGTGCTGC AATGATACCGCGAGACCCACGCTCACCGGCTCCAGATTTATCAGCAATAAACCAGCCAGCCGGAAGG GCCGAGCGCAGAAGTGGTCCTGCAACTTTATCCGCCTCCATCCAGTCTATTAATTGTTGCCGGGAAG CTAGAGTAAGTAGTTCGCCAGTTAATAGTTTGCGCAACGTTGTTGCCATTGCTACAGGCATCGTGGT GTCACGCTCGTCGTTTGGTATGGCTTCATTCAGCTCCGGTTCCCAACGATCAAGGCGAGTTACATGA TCCCCCATGTTGTGCAAAAAAGCGGTTAGCTCCTTCGGTCCTCCGATCGTTGTCAGAAGTAAGTTGG CCGCAGTGTTATCACTCATGGTTATGGCAGCACTGCATAATTCTCTTACTGTCATGCCATCCGTAAG ATGCTTTTCTGTGACTGGTGAGTACTCAACCAAGTCATTCTGAGAATAGTGTATGCGGCGACCGAGT TGCTCTTGCCCGGCGTCAATACGGGATAATACCGCGCCACATAGCAGAACTTTAAAAGTGCTCATCA TTGGAAAACGTTCTTCGGGGCGAAAACTCTCAAGGATCTTACCGCTGTTGAGATCCAGTTCGATGTA ACCCACTCGTGCACCCAACTGATCTTCAGCATCTTTTACTTTCACCAGCGTTTCTGGGTGAGCAAAA ACAGGAAGGCAAAATGCCGCAAAAAAGGGAATAAGGGCGACACGGAAATGTTGAATACTCATACTCT TCCTTTTTCAATATTATTGAAGCATTTATCAGGGTTATTGTCTCATGAGCGGATACATATTTGAATG TATTTAGAAAAATAAACAAATAGGGGTTCCGCGCACATTTCCCCGAAAAGTGCCACCTGAC | |

TABLE 5A

Sequences the constructs, barcodes, and/or probes used in Example 5. See FIGS. 5B, 5D-5E, 5G-5H, and related figures for results.     40

| Probe target | HCR initiator | Fluorophore | Related figure(s) |
|---|---|---|---|
| ZL1-barcode | B1 | Alexa 594 | FIG. 5B (chick) |
| GFP | B3 | Alexa 647 | |
| ZL1-barcode | B1 | Alexa 594 | FIG. 5E (mouse) |
| GFP | B3 | Alexa 488 | |
| Tbx21 | B1 | Alexa 488 | FIGS. 22A-22 D(mouse) |
| Th | B4 | Alexa 647 | |

Pooled split initiator (v3.0) probes were purchased from Molecular Instruments and used according to their protocol.

TABLE 5B

Sequences the constructs, barcodes, and/or probes used in Example 5.
See FIGS. 5B, 5D-5E, 5G-5H, and related figures for results.

| Probe name | HCR initiator | Fluorophore | Related figure(s) | Probe sequence (probe-LINKER-INITIATOR) | SEQ ID NO. |
|---|---|---|---|---|---|
| P2B1 | B1 | Aelexa 594 | FIGS. 5D and | cgtggattggaacagcttct-TATA-GCATTCTTTCTTGAGGAGGGCAGCAAACGGGAAGAG | 256 |
| P2B3-TtoC | B3 | Alexa 488 | 5E, left panels | cgtggatcggaacagcttct-TATA-AAAGTCTAATCCGTCCCTGCCTCTATATCTCCACTC | 257 |
| P4B2 | B2 | Alexa 647 | | agcttgaacaccagtcgcaa-TATAAGCTCAGTCCATCCTCGTAAATCCTCATCAATCATC | 258 |
| P2B3 | B3 | Alexa 488 | FIGS. 5D and | cgtggattggaacagcttct-TATA-AAAGTCTAATCCGTCCCTGCCTCTATATCTCCACTC | 259 |

TABLE 5B -continued

Sequences the constructs, barcodes, and/or probes used in Example 5.
See FIGS. 5B, 5D-5E, 5G-5H, and related figures for results.

| Probe name | HCR initiator | Fluorophore | Related figure(s) | Probe sequence (probe-LINKER-INITIATOR) | SEQ ID NO. |
|---|---|---|---|---|---|
| P2B1-TtoC | B1 | Alexa 594 | 5E, right panels | cgtggatcggaacagcttct-TATA-GCATTCTTTCTTGAGGAGGGCAGCAAACGGGAAGAG | 260 |
| P4B2 | B2 | Alexa 647 | | agcttgaacaccagtcgcaa-TATA-AGCTCAGTCCATCCTCGTAAATCCTCATCAATCATC | 261 |

TABLE 5C

Sequences the constructs, barcodes, and/or probes used in Example 5.
See FIGS. 5B, 5D-5E, 5G-5H, and related figures for results.

| Probe name | HCR initiator | Fluorophore | Related figure panel(s) | probe sequence (probe-LINKER-INITIATOR) | SEQ ID NO. |
|---|---|---|---|---|---|
| LP1-1A | B1 | Alexa 594 | FIG. 5G | cgtggattggaacagcttct-TATA-GCATTCTTTCTTGAGGAGGGCAGCAAACGGGAAGAG | 262 |
| LP1-1G | B3 | Alexa 488 | | cgtggatcggaacagcttct-TATA-AAAGTCTAATCCGTCCCTGCCTCTATATCTCCACTC | 263 |
| LP1-2A | B2 | Alexa 647 | | ttccacatccctctgcgatt-TATA-AGCTCAGTCCATCCTCGTAAATCCTCATCAATCATC | 264 |
| LP1-2G | B4 | Alexa 546 | | Ttccacaccctctgcgatt-TATAC-ACATTTACAGACCTCAACCTACCTCCAACTCTCAC | 265 |
| LP3-2A | B3 | Alexa 647 | FIG. 19 (pair 2) | ataccaatcccttcggcgat-TATA-AAAGTCTAATCCGTCCCTGCCTCTATATCTCCACTC | 266 |
| LP3-2G | B2 | Alexa 546 | | ataccaacccttcggcgat-TATA-AGCTCAGTCCATCCTCGTAAATCCTCATCAATCATC | 267 |
| LP3-1A | B1 | Alexa 594 | | ttcaacatacgccaatgcgg-TATA-GCATTCTTTCTTGAGGAGGGCAGCAAACGGGAAGAg | 268 |
| LP3-1G | B4 | Alexa 488 | | ttcaacacacgccaatgcgg-TATA-CACATTTACAGACCTCAACCTACCTCCAACTCTCAC | 269 |
| LP3-1A | B2 | Alexa 594 | FIG. 19 (pair 3) | gtcaacatacacgccctgat-TATA-AGCTCAGTCCATCCTCGTAAATCCTCATCAATCATC | 270 |
| LP3-1G | B3 | Alexa 488 | | gtcaacacacacgccctgat-TATA-AAAGTCTAATCCGTCCCTGCCTCTATATCTCCACTC | 271 |
| LP3-2A | B1 | Alexa 647 | | ttagcgatacatccgaccca-TATA-GCATTCTTTCTTGAGGAGGGCAGCAAACGGGAAGAg | 272 |
| LP3-2G | B4 | Alexa 546 | | ttagcgacacatccgaccca-TATA-CACATTTACAGACCTCAACCTACCTCCAACTCTCAC | 273 |

TABLE 5D

Sequences the constructs, barcodes, and/or probes used in Example 5. See FIGS. 5B, 5D-5E, 5G-5H, and related figures for results.

| Barcode name | Barcode sequence | SEQ ID NO. |
|---|---|---|
| ZL1-barcode | cgacagcttgtctctccagatgctcttgggccatcttccacatcgtccgtagcagccttggcaatttgccatcactggcaaatacacataaatccaatgaatacggttaccaccatcacattaccatgcaggtacacagcaagaattgacgttggcatatcacatggtgtaataacccacttgtgaaacaacccagaataaggtacaaggcggaaatgtcgtcattctaaaataaaaggcatggccaggaatttgtctaatacgggaacttaaattcagcttgaacaccagtcgcaaaaaaattcaaagaaagtgattcaggttcgggttcgtggattggaacagcttcttttgtttcagtgatgagagaatcctcctgtca | 274 |
| pair 1-AA barcode | TTCCACATCCCTCTGCGATTCGTGGCatcgtggatTggaacagcttcttt | 275 |
| pair 1-GG barcode | TTCCACACCCCTCTGCGATTCGTGGCatcgtggatCggaacagcttcttt | 276 |
| pair 2-AA barcode | TTCAACATACGCCAATGCGGACGCGGCCGCTGTTCAGATACCAATCCCTTCGGCGATTTCCCG | 277 |
| pair 2-GG barcode | TTCAACACACGCCAATGCGGACGCGGCCGCTGTTCAGATACCAACCCCTTCGGCGATTTCCCG | 278 |
| pair 3-AA barcode | TTAGCGATACATCCGACCCAATCATACCCTGTGATTCGTCAACATACACGCCCTGATAAATAT | 279 |
| pair 3-GG barcode | TTAGCGACACATCCGACCCAATCATACCCTGTGATTCGTCAACACACACGCCCTGATAAATAT | 280 |

TABLE 6A

Sequences the constructs, barcodes, and/or probes used in Example 6. See FIGS. 6B-6D, and related figures for results.

| Barcode name | Barcode sequence | SEQ ID NO. |
|---|---|---|
| mL-1a | agatgctcctgagccatctt | 281 |
| mL-1b | cgtggattggaacagcttct | 282 |
| mL-1c | gaaagtgattcaggttcggg | 283 |
| mL-2a | agcttgaacaccagtcgcaa | 284 |
| mL-2b | gcatggccaggaatttgtct | 285 |
| mL-2c | ggcggaaatgtcgtcattct | 286 |
| mL-3a | ccacttgtgaaacaacccag | 287 |
| mL-3b | cgttggcatatcacatggtg | 288 |
| mL-3c | accatgcaggtacacagcaa | 289 |
| mL-4a | TTCCACATCCCTCTGCGATT | 290 |
| mL-4b | ATACCAATCCCTTCGGCGAT | 291 |
| mL-4c | ATCAGCGTGACAACTGTGCT | 292 |

TABLE 6B

Sequences the constructs, barcodes, and/or probes used in Example 6. See FIGS. 6B-6D, and related figures for results.

| Probe name | Probe sequence (probe-LINKER-INITIATOR) | HCR initiator | Fluorophore | Hybridization round | SEQ ID NO. |
|---|---|---|---|---|---|
| mL-1a-B1 | agatgctcctgagccatctt-TATA-GCATTCTTTCTTGAGGAGGGCAGCAAACGGGAAGAG | B1 | Alexa647 | 1 | 293 |
| mL-1b-B2 | cgtggattggaacagcttct-TATA-AGCTCAGTCCATCCTCGTAAATCCTCATCAATCATC | B2 | Alexa594 | | 294 |
| mL-1c-B4 | gaaagtgattcaggttcggg-TATA-CACATTTACAGACCTCAACCTACCTCCAACTCTCAC | B4 | Alexa546 | | 295 |
| mL-4a-B3 | ttccacatccctctgcgatt-TATA-AAAGTCTAATCCGTCCCTGCCTCTATATCTCCACTC | B3 | Alexa488 | | 296 |
| mL-2a-B1 | agcttgaacaccagtcgcaa-TATA-GCATTCTTTCTTGAGGAGGGCAGCAAACGGGAAGAG | B1 | Alexa647 | 2 | 297 |
| mL-2b-B2 | gcatggccaggaatttgtct-TATA-AGCTCAGTCCATCCTCGTAAATCCTCATCAATCATC | B2 | Alexa594 | | 298 |
| mL-2c-B4 | ggcggaaatgtcgtcattct-TATA-CACATTTACAGACCTCAACCTACCTCCAACTCTCAC | B4 | Alexa546 | | 299 |
| mL-4b-B3 | ataccaatcccttcggcgat-TATA-AAAGTCTAATCCGTCCCTGCCTCTATATCTCCACTC | B3 | Alexa488 | | 300 |
| mL-3a-B1 | ccacttgtgaaacaacccag-TATA-GCATTCTTTCTTGAGGAGGGCAGCAAACGGGAAGAG | B1 | Alexa647 | 3 | 301 |
| mL-3b-B2 | cgttggcatatcacatggtg-TATA-AGCTCAGTCCATCCTCGTAAATCCTCATCAATCATC | B2 | Alexa594 | | 302 |
| mL-3c-B4 | accatgcaggtacacagcaa-TATA-CACATTTACAGACCTCAACCTACCTCCAACTCTCAC | B4 | Alexa546 | | 303 |
| mL-4c-B3 | atcagcgtgacaactgtgct-TATA-AAAGTCTAATCCGTCCCTGCCTCTATATCTCCACTC | B3 | Alexa488 | | 304 |

To establish Z1 and Z3 monoclonal cultures, approximately 1000 cells from the polyclonal population were cultured on a 10 cm plate, from which individual colonies were picked and expanded. Clones were then genotyped by polymerase chain reaction (PCR) to ensure that: the transgene was inserted properly in one of the ROSA26 loci, the other ROSA26 locus was intact, and there was no other integration of the transgene or Cas9 elsewhere in the genome.

Zombie Procedure for Cell Culture Samples

Cells were washed with 1×PBS before fixation by 3:1 (v:v) mix of methanol and acetic acid (MAA) at room temperature for 20 minutes. Cross-linking fixation interferes with transcription by phage RNA polymerases, and therefore, should be avoided prior to the transcription step. Cells were then washed briefly first with 1× phosphate-buffered saline (PBS) and then with nuclease free water and subsequently were incubated with the transcription mix (MEGAscript Transcription Kit; Invitrogen, Carlsbad, Calif.) at 37° C. for 3 hours. All three RNA polymerases used in this study (T3, T7, and SP6) work at comparable levels. The choice of one polymerase over another in different experiments was mostly arbitrary. After transcription, cells were fixed with 4% formaldehyde solution in PBS for 20 minutes at room temperature followed by two washes with 5×SSC, for 5 minutes each, to remove traces of formaldehyde.

The samples were then pre-incubated in hybridization buffer at 37° C. for at least 10 minutes before overnight incubation, at 37° C., in hybridization buffer containing 4 nM of each probe. When the experiment involved probe competition or split initiator probes with 25 bp annealing region, 30% probe hybridization buffer (Molecular Technologies, Pasadena, Calif.) was used for hybridization and, the next day, samples were washed four times, 15 minutes each, at 37° C. with 30% probe wash buffer (Molecular Technologies, Pasadena, Calif.) to remove excess probes, as previously described. For probes with 20 bp annealing region, in the absence of competition, 10% hybridization buffer (composed of 10% formamide, 10% Dextran Sulfate and 2× saline-sodium citrate (SSC) in RNAse-Free water) was used for overnight hybridization as previously described. These samples were then washed with a wash buffer, composed of 30% formamide, 2×SSC, and 0.1%

Triton-X 100, at room temperature for 30 minutes, to remove excess probes, followed by a brief wash with 5×SSC.

HCR amplification was performed according to the manufacturer's instruction. Briefly, samples were first washed with 5×SSCT (5×SSC+0.1% Tween 20) for 5 minutes at room temperature and then incubated with amplification buffer (Molecular Technologies, Pasadena, Calif.) for at least 10 minutes at room temperature. Meanwhile, each fluorescently labeled hairpin was prepared by snap cooling (heating at 95° C. for 90 seconds and cooling to room temperature in a dark drawer for 30 minutes) in hairpin storage buffer. All the required hairpins were then added to the amplification buffer at the final concentration of 60 μM each. Cells were then incubated, in the dark, with amplification buffer containing the hairpins for 45 minutes at room temperature. Subsequently, excess hairpins were removed by five washes with 5×SSCT over one hour. 4',6-diamidino-2-phenylindole (DAPI) was added to the third wash to label nuclei. Nuclei could also be visualized using native fluorescent of Histone 2B protein-cyan fluorescent protein (H2B-CFP), when it was expressed in the cells (e.g. FIGS. 1C-1D). However, native fluorescence of cytoplasmically expressed fluorescent proteins could not be detected after the Zombie procedure. Samples were then kept in the dark at 4° C. until imaging.

When additional rounds of hybridization and imaging was required, samples were incubated first with 1× DNase I buffer (Roche (Basel, Switzerland) 4716728001) in nuclease free water at room temperature for 5 minutes and then with DNase I solution (2 U/μl of the enzyme in 1× buffer) at 37° C. for 3 hours, to digest probes and HCR hairpins from the previous round. Subsequently, samples were washed three times with pre-warmed 30% wash buffer at 37° C. (first two washes for 5 min each and the third wash for 15 min). Another round of hybridization and HCR was then performed as described above.

The procedure described above was the main protocol used in the cell culture experiments described herein. See Table 7 and FIGS. 23-25, for details regarding the variations to this main protocol.

TABLE 7

List of experimental conditions and their effect on barcode detection efficiency.

| Condition | Description | Result |
|---|---|---|
| PFA fixation | Fixed with 1, 2, and 4% formaldehyde solution in PBS, followed by permeabilization by either 3:1 (v/v) mix of methanol and acetic acid or 70% ethanol. | Fixation with PFA prior to transcription step drastically reduced the detection efficiency (see FIG. 10) |
| Methanol and acetic acid fixation | Fixed with 100% methanol as well as 5, 15, 25, 35, and 50% acetic acid in methanol solutions. | Mix of acetic acid in methanol provides the best results (see FIGS. 11-12). |
| Clarke's fluid fixation | Fixed with 3:1 (v/v) mix of ethanol:Acetic Acid for 15 minutes at room temperature. | Observed a decrease in detection efficiency compared to 3:1 MAA fixation. |
| Methanol and acetone fixation | Fixed with 1:1 (v/v) mix of methanol and acetone for 15 minutes at room temperature. | Observed a drastic decrease in the detection efficiency. |
| Proteinase K treatment | Permeablized the cells initially using 1, 5, and 10 ug/μl Proteinase K for 11 min at room temperature and in a subsequent experiment using 1 ug/μl of Proteinase K for 1, 2, 5, and 10 min at room temperature. | All of these treatments led to loss of most cells. |
| Triton X-100 | Washed the cells with 0.5% Triton X-100 for 10 minutes at room temperature after fixation by 3:1 MAA mix. | Observed no advantage over not washing the cells with this solution. |
| SDS | Washed with 0.1% SDS for 10 minutes at room temperature after fixation by 3:1 MAA mix. | It severely affected the cell morphology. |
| Histone wash | Washed with 2 mg/ml Dextran sulfate (MW 500,000), 0.2 mg/ml Heparin sodium salt, 0.1% IGEPAL CA-630, 10 mM EDTA, 10 mM Tris pH = 8.0 in nuclease free water for 10 minutes at room temperature after fixation by 3:1 MAA mix. | Observed a slight decrease in detection efficiency. |
| RNA polymerase concentration | Performed transcription with 2, 5, 10, 15, and 20 U/μl T7 RNA polymerase at 37° C. for 3 hours. | Observed no gain in efficiency for concentrations above 5 U/μl. |
| Duration of transcription reaction | Performed transcription with T7 RNA polymerase for 15, 30, 60, and 180 minutes at 37° C. | Duration of the transcription reaction only has a modest effect on detection efficiency (see FIG. 11) |

PFA, paraformaldehyde; MAA, mix of methanol and acetic acid (v/v).

Design of the Synthetic Memory Arrays

Each unit of the memory arrays included a 20 bp probe site that partially overlapped with a 20 bp gRNA target site. gRNA target sites were followed by PAM sequence (NGG). To limit the possible outcome of base editing by ABE, gRNAs were designed so that from their position 2 to 10 there was only one "A" nucleotide, which occurred at position 5. Azimuth 2.0 software was used to choose gRNA candidates with high on-target and low off-target scores. Each probe sequence was designed so that its GC content was 50% and its predicted Tm, calculated using nearest neighbor method, was between 56 and 60° C. Sequences that form hairpins or dimers and homopolymeric tracts of 5 bp or longer were avoided in the probes. Recognition sites of some restriction enzymes (BsaI, BsmBI, BpiI, AarI, and XbaI) were avoided within the memory arrays to facilitate cloning. For design 1 array, probe sequences were chosen to differ from each other in at least 7 positions, to ensure specificity. For design 2, since all memory units were targeted with the same gRNA, 12 out of 20 bp was shared among all probes. The remaining 8 bp were chosen so that all probes were different from each other in at least 2 positions of the first 4 nucleotides and at least another 2 positions among the second 4 nucleotides. Furthermore, to facilitate discrimination, probes targeting all 12 design 2 barcodes were mixed together, at equimolar ratio, with the ones not being analyzed in any given experiment at an orthogonal channel (e.g., B5 HCR initiator). See tables herein for full sequence of the arrays and their corresponding probes.

The Combinatorial Barcode Library

Synthetic gene fragments containing 81 barcode combinations were obtained from Twist Bioscience (San Francisco, Calif.) and cloned into a lentiviral transfer plasmid by golden gate cloning, using Esp3I and T7 DNA ligase (see tables herein for the sequence of plasmids and barcodes). After transformation into NEB 10-beta chemical competent *E. coli* (C3019I), more than 10,000 colonies were scraped off the plates and used to prepare DNA for lentiviral packaging.

Lentiviral Delivery of Barcodes

Lentiviral vectors were produced and stored as previously described using the plasmids described above. The viral titer was determined by serial dilution. Only viral preparations with at least $10^7$ infectious units/µl were used. To establish stable cell lines, HEK293T cells were resuspended in the culture media, at a density of 500,000 cells per mL. 3 µL of lentiviral prep was mixed in with 97 µL of cell suspension. 10 µL of this mix was then added to another 90 µL of cell suspension in a separate tube. After mixing, the cells of the second tube were cultured in a 96-well plate for 3 days, without change of media. Subsequently, the cells were expanded in fresh media and used for the experiments.

To deliver barcodes to chicken embryos, fertilized eggs of white leghorn chickens were obtained from McIntyre Poultry & Fertile Eggs (Lakeside, Calif.) and incubated in a humidified atmosphere at 38° C. for 35 to 40 hours. The lentiviral prep was then injected in the neural tube of embryos ranging between stages HH10 and HH11. After injection, the eggs were closed with Parafilm and kept at 38° C. The embryos were analyzed 3 days after injection, at 5 days of incubation (stage HH27).

In mice, lentiviral injections were carried out stereotactically into the olfactory bulb of 3-month old male BL6 mice (JAX). Mice were anesthetized by single intraperitoneal injection with Ketamine/Xylazine solution. The stereotaxic coordinates were 5.5 mm anterior from bregma, 1.2 mm lateral from the midline, and 0.40 mm ventral from the brain surface. A single injection per olfactory bulb was performed using 0.3 µl of the lentiviral prep. The mouse brains were analyzed either 3 or 12 days after injection, as described in the text.

In some instances, different viral integration sites or chromatin states could potentially vary in their accessibility to phage polymerases. All the experimental procedures performed on animal models was approved by the Institutional Animal Care and Use Committee of California Institute of Technology.

Next Generation Sequencing gDNA was extracted from cells using DNeasy Blood & Tissue kit (Qiagen, Hilden, Germany) according to manufacturer instructions. Amplicon libraries containing the regions of interest (i.e., memory arrays or library barcodes) were then generated, from gDNA, with a two-step PCR protocol to add Illumina adapters and Nextera i5 and i7 combinatorial indices. Indexed amplicons were pooled and sequenced on the Illumina MiSeq platform with a 600-cycle, v3 reagent kit (Illumina, MS-102-3003). To analyze next generation sequencing data, raw FASTQ files were aligned to a FASTA-format reference file containing the expected amplicon sequences. Alignment was performed using the Burrows-Wheeler Alignment Tool (bwa-mem). For the combinatorial viral library (FIG. 6E), the number of reads aligning to each possible reference sequence was computed using a custom script in R, available here. For the base editing samples (FIG. 18), base calls were extracted from each read at the base editor target sites, as well as the quality scores at these sites. Paired-end reads were merged, accepting the base call with the highest quality score in overlapping regions. Reads with the quality score of more than 10, at the target site position, were included in the analysis.

Histology

After harvesting, adult mouse brain and embryonic chicken tissues were washed with cold RNase free 0.1M phosphate-buffered saline solution (PBS, pH 7.4) at 4° C. Fresh tissues were then immersed into the Tissue-Tek O.C.T. Compound (#4583; Electron Microscopy Sciences, Hatfield, Pa.) and were frozen immediately for 3 minutes in isopentane cooled to −70° C. in dry ice. Samples were then stored at −80° C. until sectioning. 20 µm thick sections were obtained using a Leica Cryostat, mounted on SuperFrost slides or coverslips coated with 2% v/v solution of (3-Aminopropyl)triethoxysilane in acetone. Sections were then stored at −80° C. until use.

Zombie Procedure for Tissue Sections

The slides were first left to dry at room temperature for about 5 minutes and then fixed with MAA at room temperature in a glass staining jar for 3 hours. Subsequently, the slides were washed, by transfer to a new jar filled with PBS, three times for 5 minutes each. After a brief wash in nuclease free water, SecureSeal hybridization chambers (SKU: 621501; Grace Bio-Labs, Bend, Oreg.) were put on the slides and transcription mix (MEGAscript T7 or T3 Transcription Kit; Invitrogen) was added on the sections and incubated for 3 hours at 37° C. After transcription, samples were fixed with 4% formaldehyde in PBS overnight at 4° C. Formaldehyde was then removed by three washes with 5×SSC at room temperature for 10 minutes each.

Hybridization was performed similar to what is described above for cell culture samples. Sections were pre-hybridized with probe hybridization buffer for at least 30 minutes at 37° C., before overnight incubation with probe hybridization buffer containing 4 nM of each probe, at 37° C. When the experiment involved probe competition (e.g., FIGS. 5C-5H) or split initiator probes with 25 bp annealing region (e.g., FIGS. 5B and 22A-22D), 30% probe hybridization buffer (Molecular Technologies) was used for hybridization followed by 4×15 min wash at 37° C. with 30% probe wash buffer (Molecular Technologies). For probes with 20 bp annealing region, in the absence of competition (e.g., FIGS. 6A-6D), 10% hybridization buffer (composed of 10% formamide, 10% Dextran Sulfate and 2×SSC in RNAse-Free water) was used for overnight hybridization, followed by 2×30 min wash in 30% formamide, 2×SSC, and 0.1%

Triton-X 100, at room temperature. Then, after three brief washes with 5×SSCT at room temperature, sections were incubated with amplification buffer for 20 minutes, which was then replaced by amplification buffer containing snap cooled fluorescently labeled hairpins (Molecular Technologies, Pasadena, Calif.), each at 60 µM. After one hour incubation in the dark at room temperature, excess hairpins were removed by five washes with 5×SSCT over one hour. DAPI was added to the third wash to label nuclei.

For samples that required only one round of hybridization (e.g., FIGS. 5B-5E), hybridization chambers were removed at this point and sections were mounted in Aqua-mount (14-390-5; Thermo Scientific) and kept in the dark at 4° C. until imaging. For multiple rounds of hybridization, 5×SSCT was replaced with anti-bleaching buffer (50 mM Tris-HCl pH 8.0, 300 mM NaCl, 2×SSC, 3 mM Trolox (Sigma-Aldrich (St. Louis, Mo.) 238813), 0.8% D-glucose (Sigma-Aldrich (St. Louis, Mo.) G7528), 100-fold diluted Catalase (Sigma-Aldrich (St. Louis, Mo.) C3155), 0.5 mg/mL Glucose oxidase (Sigma-Aldrich (St. Louis, Mo.) G2133) and 0.02 U/mL SUPERase In RNase Inhibitor (Invitrogen (Carlsbad, Calif.) AM2694)) and samples were imaged as described below. After imaging, anti-bleaching buffer was washed first with 5×SSCT and then with 1× DNase I buffer (Roche 4716728001) in nuclease free water. Probes and HCR hairpins were then digested by 3 hours of incubation with DNase I solution (2 U/µl of the enzyme in 1× buffer) at 37° C. for 3 hours. Subsequently, the samples were washed three times with pre-warmed 30% wash buffer at 37° C. (first two washes for 5 min each and the third wash for 15 min). Another round of hybridization and HCR was then performed as described above.

Imaging

Cell culture samples were imaged on a Nikon Eclipse Ti inverted fluorescence microscope with a Zyla 4.2 scientific Complementary metal-oxide-semiconductor (sCMOS) camera (Andor, Belfast, Northern Ireland). A 60× oil objective (1.4 NA) were used and 20 z-stacks were acquired with 0.5 micron spacing between them for each position. Positions were chosen solely based on DAPI channel to avoid bias. Imaging settings, including the exposure times, were kept the same for all the experiments involving cultured cells. Tissue sections were imaged either, using ZEN 2.3 (blue edition), on a Zeiss (Oberkochen, Germany) LSM800 confocal microscope with a 40× (Zeiss 1.2 NA), water immersion objective (FIGS. 5B-5E), or, using MetaMorph, on a Nikon (Tokyo, Japan) Eclipse Ti inverted microscope, equipped with a Yokogawa CSU-W spinning disc unit (Andor) and an EMCCD camera (Andor iXon Ultra), using a 40× (Nikon 1.3 NA) oil objective (FIGS. 6A-6D and 22A-22D) or a 60× (Nikon 1.4 NA) oil objective (FIGS. 5F-5H). The same imaging setting was used for related samples to facilitate comparison between images.

Image Analysis

Images were processed and analyzed using MATLAB and Fiji, mainly by custom scripts. For cell culture experiments, maximum intensity projection of the raw images was used in all analyses.

Segmentation.

Segmentation of nuclei and dots was done automatically in MATLAB by filtering and thresholding of the images. However, the results were manually inspected to ensure accuracy. Segmentation of nuclei was done based on either CFP (FIGS. 1A-1G, 2A-2D, 3A-3D, 5A-5H, and their related figures) or DAPI (FIGS. 4A-4F, 6A-6D, 14, and 15-18) channel. When relevant to the analysis (e.g. for efficiency calculations) incorrectly segmented nuclei were manually identified and removed from the analysis. Active site dots were considered to belong to a cell if their center overlapped with the nuclear segmentation of that cell.

Intensity measurement.

An estimate of dot intensity, used for FIGS. 4E, 5G-5H, 8, 23-25, and 15-19 was obtained by integration of pixel intensities over each dot's segment. A more precise measure of dot intensity was used for FIGS. 3D and 13, which was based on fitting a 2D Gaussian to each dot's filtered pixel intensity values and calculating the volume under the surface of the Gaussian.

Colocalization.

Colocalization of dots was identified based on close proximity (less than 4 pixels) of the center of segmented dots in two or more channels.

Classification.

For single nucleotide detection, where four probes compete for the same target site (FIGS. 3D and 13), to assign a nucleotide to each dot, the natural log of intensity values for that dot in each channel were normalized linearly between 0 and 1, using the intensity values from all the dots detected in that channel across the experiment. The nucleotide associated with the channel that had the highest normalized intensity was then assigned to the dot. Calling the base edits (FIGS. 4A-4H and their related figures) as well as A and G classification in vivo (FIGS. 5G-5H and 19), was done by clustering natural log of intensity values in two groups using k-means clustering with cosine distance metric (kmeans function, MATLAB).

Registration.

Images of HEK293T cells transduced by the combinatorial viral library were registered initially based on CFP channel, using normalized cross-correlation method. A more refined registration was then achieved, using imregtform function in MATLAB, based on dots corresponding to different variant positions, regardless of their fluorescent channel, and using the CFP registration as the initial transformation.

Statistical Analysis

All experiments were performed in multiple distinct replicates, as indicated in the text and figure legends. Mutual information calculations in FIG. 9 were performed as previously described, by analyzing pairwise co-localization of barcodes in 564 cells across three replicates. Briefly, normalized mutual information (or uncertainty coefficient), U, between two barcodes, x and y, is defined as $$U(x \mid y) = \frac{H(x) - H(x \mid y)}{H(x)},$$

where H is the entropy calculated by the formula $H = -\Sigma_{i=}^{I} p_i \ln(p_i)$.

Example 1

Phage RNA Polymerases can Transcribe Synthetic DNA Barcodes in Fixed Cells

This example demonstrates transcription of synthetic DNA barcodes by phage RNA polymerases in fixed cells.

To develop a method for specifically amplifying and detecting barcodes integrated in the genome (FIG. 1A), a construct, labeled Z1 (FIG. 1B), containing a 900 bp barcode sequence downstream of tandem SP6, T7, and T3 phage promoters, along with an H2B-Cerulean fluorescent protein under the control of the constitutive mammalian CAG promoter for imaging of cell nuclei was designed. Z1 site was integrated specifically at the ROSA26 locus in mouse embryonic stem (mES) cells. A similar cell line was also made with a control construct that lacks the phage promoters (FIG. 1B).

To detect the barcode, polyclonal populations of cells were grown, fixed, added with the phage RNA polymerases in each, and performed HCR with a set of split initiator probes to detect RNA transcripts (see Methods for details). Fluorescence imaging revealed two types of dots: bright fluorescent dots within cell nuclei and more numerous, but considerably dimmer, diffraction-limited dots scattered throughout the nucleus and cytoplasm (FIG. 1C). Neither type of dot was observed when either the phage promoters or polymerase were omitted (FIG. 1C). Parental cells lacking a barcode exhibited no dots when cultured alone but showed some overlapping dimmer dots when co-cultured with engineered cells (FIGS. 7A-7D). These results indicate that the bright dots reflect phage polymerase-dependent transcription at the integration site, whereas the dimmer dots reflect individual transcripts that can diffuse away from the cell in which they were produced. Together, this barcode design and analysis protocol enable in situ expression and detection of genomically integrated barcodes at integration sites.

Next, to quantify the efficiency of detection, a monoclonal line with exactly one integration per diploid genome, termed mES-Z1, was selected. Within the clone, 1 or 2 bright dots were consistently detected in the majority of cells, likely due to cell cycle phase variation at the time of fixing, with a small fraction of cells missing any bright dots (FIGS. 1D and 8). While the transcription active sites were detected efficiently with all three phage RNA polymerases, the average detection efficiencies of T3 (88%) and T7 (85%) were higher than that of SP6 (75%) (FIG. 1D). Variations in efficiencies may reflect the relative positions of the promoters in the construct, relative amounts of active enzymes, as well as intrinsic differences between the polymerases.

A lack of barcode detection could result if certain cells were impermeable to polymerases or otherwise do not permit in situ transcription. Alternatively, it could reflect intrinsic stochasticity in the polymerization reaction. To distinguish these possibilities, a second line containing a single integration of a construct termed Z3, in which three barcodes were each controlled by a separate set of phage promoters and can be detected using distinct fluorescence channels was engineered (FIG. 1E). If non-detection was a property of the individual cells, it was expected to predominantly detect either all three barcodes or no barcodes (strong correlation). By contrast, in a stochastic transcription model, it was expected that detection of one barcode would not affect the probability of detecting another barcode (weak correlation).

Analysis of active site co-localization in 564 cells revealed no significant correlation or pairwise mutual information between any pair of barcodes (chi-squared test, p-values 0.7970, 0.1917, and 0.1256 for the three pairs; FIG. 9). The chance of detecting each barcode in a cell was independent of detection of the other barcodes (FIG. 1F). Consistent with this observation, the fraction of cells with no detected active sites declined exponentially with the number of barcodes analyzed in the same cell at the rate expected from the single barcode detection frequencies (FIG. 1G). Together, these data suggest that detection was a stochastic event that occurred independently at each barcode. Therefore, although a fraction of barcodes failed to produce detectable signal, the false negative rate per cell can be reduced by increasing the barcode copy number. This property is valuable in the study of rare cell types, where capturing information from majority of cells is essential.

Altogether, these data indicate that phage RNA polymerases can transcribe synthetic DNA barcodes in fixed cells.

Example 2

Zombie Enables Reliable In Situ Detection of 20 bp DNA Barcodes

This example demonstrates reliable detection of short DNA barcodes using the Zombie method and system described herein.

Barcode transcription produces multiple RNA molecules from the same template in close proximity, which effectively amplifies the barcode target and could facilitate robust detection of short barcodes. To test this, fixed mES-Z1 cells after the in vitro transcription step were hybridized with three orthogonal 20 bp probes targeting regions downstream of the phage promoters (FIG. 2A). The binding of these probes, by both smFISH and HCR were then analyzed. In both analyses, easily detectable transcription active sites were observed in all three channels (FIGS. 2B and 10). For all three phage RNA polymerases, the active sites could be detected in a large fraction of cells (FIG. 2C), and most dots were redundantly detected in multiple channels (FIG. 2D).

RNA transcription sites contain multiple RNA molecules transcribed from the same template in close proximity, potentially reducing the number of probes required for detectable signal (FIG. 2A). To test this, fixed mES-Z1 cells after the in vitro transcription step were hybridized with 20 bp probes targeting regions downstream of the phage promoters. Three different probes each with a distinct (orthogonal) HCR initiator were designed, allowing simultaneous detection of each probe in a different fluorescent channel. Following HCR amplification, bright, easily detectable dots were observed at the transcription active sites in all three channels (FIG. 2E). Despite some differences in their efficiency, all three phage RNA polymerases showed high barcode detection rates ranging from 65 to 84 percent of cells (FIG. 2G). Because the monoclonal Z1 cell line contains one construct per diploid genome, one or two active sites per cell were expected to be observed, and cells without apparent active sites thereby represented false negative detection events. Analysis revealed that most dots were detected in multiple channels, suggesting that detection was reliable (FIG. 2H). Furthermore, HCR amplification was not necessary for in situ detection of short (20 bp) barcodes. The procedure was repeated but included only one of the two hairpins required for HCR amplification. This hairpin can bind to the initiator of the corresponding probes and generate a fluorescent signal, but cannot initiate a chain reaction. Nevertheless, individual transcription active sites were observed as distinct dots (FIG. 2F) and the detection was at rates similar to those obtained with HCR amplification (FIG. 2G; exact Wilcoxon rank sum test, p>0.5). However, co-localization of the detected active sites in three fluorescent channels was reduced in the absence of HCR amplification (FIG. 2H). Thus, HCR amplification increased detection reliability, but was not strictly necessary for analysis.

These results show that barcodes as short as 20 bp can be efficiently and reliably detected in situ.

Example 3

Zombie Enables In Situ Detection of Single Nucleotide Mismatches

This example demonstrates in situ detection of single nucleotide mismatches using the Zombie method and system disclosed herein.

Discrimination of small sequence differences could facilitate imaging-based barcoding applications. While structured and toehold probes can be used to detect single nucleotide variations by leveraging base pairing within the probe, traditional probes can bind to target sequences even when they contain a single nucleotide mismatch (FIG. 11). it was expected that simultaneously competing multiple probes, each containing a distinct nucleotide at a single site, for binding to the many transcripts present in an active site could lead to preferential binding of exact match probes over mismatch probes, and thereby enable nucleotide identification (FIG. 3A).

To test this idea, mES-Z1 cells, performed in vitro transcription were fixed with T7 RNA polymerase, and targeted a 20 bp region of the Z1 barcode with four probes, each containing a distinct nucleotide at a single position, and each detectable with orthogonal HCR initiators in different fluorescence channels (FIG. 3B). To control for systematic differences among fluorescent dyes, each analysis was performed with four different fluorescence channel permutations (FIGS. 3C and 12, columns) and quantified the relative fluorescence intensities of each channel for each active site. This analysis was performed four times, once for each possible nucleotide at the variable position (FIGS. 3C-3D and 12).

When targeting A, C, or G, a strong preference for the correct target nucleotide (FIG. 3D) across different color-HCR initiator permutations was observed, ranging between 92 to 96% for A, 79 to 93% for C, and 93 to 99% for G (percentages indicate the fraction of fluorescent dots that were 'called' correctly by the algorithm). Without being bound by any particular theory, it was believed that some inaccurate calls can be explained by non-specific background HCR amplification in a region that overlaps with the cell nuclei but was not a true active site. However, when targeting U, in addition to the matched A probes, detectable signal was also observed from the mismatched G probes (FIG. 12), consistent with wobble base pairing between U and G. Nevertheless, the base calling algorithm detected the correct match probe in three out of four permutations tested, with 90%, 97%, and 85% accuracy (FIG. 3D).

To investigate the dependence of single nucleotide variant (SNV) discrimination on the position of variant nucleotide within the probe, a similar analysis was performed with SNVs in positions 1 through 7 of the probes (FIG. 13). Positions 2 through 7 provided accurate SNV discrimination. Further, this analysis provided additional examples of accurate discrimination when U was the target (FIG. 13, position 6).

These results indicate that probe competition can enable accurate in situ identification of SNVs.

Example 4

Zombie Reads Out In Vivo Barcode Base Edits

This example demonstrates that the Zombie method and system disclosed herein are capable of reading out in vivo barcode base edits.

CRISPR base editors have recently emerged as powerful tools for precise and predictable genome editing. They can target and edit genomic DNA with single base pair resolution in a multiplexable manner. Heritable somatic mutations created by base editors could enable subsequent reconstruction of cell lineage and event histories. The ability to read out base edits by imaging, rather than sequencing, can enable lineage and event history recording approaches that preserve spatial information, operate in individual cells, and allow accurate recovery of sequence information from a high fraction of cells. As demonstrated herein, the Zombie method and system disclosed herein allow in situ detection of single nucleotide mismatches, this example shows that the Zombie method and system disclosed herein can be combined with base editors to read out single base pair changes in a synthetic memory unit.

A set of 12 memory units (FIG. 4B, left panel) that can each be edited by Adenine Base Editor (ABE) together with a unique gRNA was engineered. These units also incorporated phage promoters to enable readout. These 12 memory units were concatenated into a single ~500 bp cassette and inserted into a lentivirus, and the viruses were integrated into the genome of HEK293 cells to create the ZMEM cell line (FIG. 4A). Plasmids expressing ABE, a gRNA targeting one recording site, and a GFP transfection reporter were transiently co-transfected into Z-MEM cells, and the cells were cultured for five days. To analyze editing, cells were fixed, added with T3 polymerase to transcribe the barcodes, and analyzed for barcodes by HCR using competing probes with distinct HCR initiators, containing either a T or a C to probe the unedited A or edited G state, respectively. As a negative control, a second barcode that was not targeted by the gRNA was also probed. This procedure was then repeated, individually targeting each of the 12 units.

These experiments revealed that editing could be targeted to distinct memory units and read out with high fidelity. Individual memory units showed a binary response in imaging, appearing either in the A channel or in the G channel, but not both (left panel in FIGS. 4C-4E, and FIG. 14). Across ten memory units, the median edit rate was 12.7%. However, different units showed varying edit rates, ranging from 1.7% to 21.7% (The two remaining units each had one probe that failed to generate signal, and were not considered further). A broad range of edit rates, achieved here by using gRNAs with different efficiency to edit different memory units, has been shown to be advantageous for recording applications. Memory units that were not targeted by gRNA showed apparent edit rates close to 0 (FIG. 4F, left panel), consistent with both strong targeting specificity by ABE and accurate amplification and readout by Zombie. Together, these results show that Zombie can enable in situ readout of base edits in engineered memory elements.

31 bp barcodes that could be edited by the Adenine Base Editor (ABE) https://paperpile.com/c/kLgtra/XdWgp and a corresponding gRNA were engineered (FIG. 4A). These barcodes were concatenated into ~500 bp arrays, and preceded by phage promoters. Using lentiviral vectors, multiple array copies were incorporated into the genome of HEK293T cells to create the Z-MEM cell lines (FIG. 4A). Plasmids expressing the ABE (ABE7.10), the gRNA, and a fluorescent co-transfection marker (e.g., GFP) were transiently co-transfected into Z-MEM cells, and cells were cultured for five days. To analyze editing, cells were fixed, added with T3 RNA polymerase, and detected for transcribed barcodes using competing probes with distinct HCR initiators for edited and unedited states. This analysis was performed pair-wise, on adjacent barcodes. As a negative control, the analysis on cells that did not receive ABE or gRNA was also performed.

A key parameter for recording is the edit rate, defined as the probability of an edit occurring at a given unedited target site per unit time. To estimate the relative edit rates of different barcodes, the percentage of dots that were edited for each barcode in each design was tabulated (FIG. 4F). These values varied widely across ten distinct design 1 barcodes, from 1.6% to 19.7% with a median of 12.9% (Probes for the two remaining units failed to generate signal and were not considered in the analysis). A broad range of edit rates, such as that observed here, has been shown to be advantageous in recording applications. Similarly, design 2 units were edited at rates ranging from 15.5% to 51.5% with a median 31.3%. By contrast, memory units that were not targeted showed apparent edit rates close to 0 (FIG. 4F), consistent with both strong targeting specificity by ABE and accurate amplification and readout by Zombie. In a separate experiment, it was observed that the edit rates measured by Zombie were similar to those measured by next generation sequencing for the same set of barcodes, further validating the accuracy of Zombie in situ readout (FIG. 18).

Two types of synthetic memory arrays were designed (FIG. 4B). Design 1 enables independent addressing of different barcodes by distinct gRNAs, facilitating multi-channel recording. By contrast, design 2 uses one gRNA to edit all 12 barcodes, allowing a single gRNA to generate greater sequence diversity. In both cases, editing should result in single base pair changes in corresponding barcodes.

In both designs, individual barcodes showed an approximately binary response in imaging, appearing in either the edited or unedited channel, but not both (FIG. 4C). Moreover, pairwise analysis of the adjacent barcodes verified independent addressing in design 1 and multiplexed addressing in design 2 (FIG. 4D). The signal intensity was quantified for each dot, in the edited and unedited channels, with or without co-transfection of ABE and gRNA (FIGS. 4E, 15, 16A-16B, and 17A-17B). Without ABE or gRNA most dots clustered in a single region (FIG. 4E, blue points). By contrast, when ABE and gRNA were both present a second cluster appeared, with a larger mean ratio of edited to unedited probe intensity (FIG. 4E, orange points), reflecting successful editing in a substantial fraction of cells (FIG. 4F). Similar behavior was observed with the other analyzed barcodes (FIGS. 16A-16B and 17A-17B). k-means clustering was then used to classify the active sites as edited or unedited, with bootstrap resampling allowing determination of confidence for each assignment (FIGS. 15, 16A-16B, and 17A-17B). In both designs, except for a small subpopulation (yellow dots in FIGS. 16A-16B and 17A-17B), active sites could be robustly classified based on their relative signal intensity.

Together, these results show that base editing can be targeted to distinct memory units and read out quantitatively in situ with high fidelity by Zombie.

Example 5

Zombie Identifies Compact Barcodes in Embryonic and Adult Tissues

This example demonstrates identification of compact barcodes in embryonic and adult animal tissues using the Zombie method and system disclosed herein.

Reconstructing lineage information in embryos, brains, and tumors requires the ability to discriminate among a set of distinct barcodes or barcode edits in complex spatially organized contexts. To test Zombie readout within tissues, a lentivirus, termed ZL1, containing probe target sequences downstream of phage promoters, along with a divergently oriented, constitutively expressed fluorescent protein reporter was engineered to enable identification of transduced cells (FIG. 5A). The lentivirus was first injected into the lumen of the developing chick neural tube at stage HH10, and embryos were analyzed 3 days later at stage HH27 (FIG. 5A, left). In a parallel study, Zombie readout was analyzed in adult mouse brain tissues, focusing on the olfactory bulb, which incorporates newly generated neurons in the adult stage. The ZL1 lentivirus was injected into the granular cell layer of the olfactory bulb and sacrificed the mice for analysis 3 days later (FIG. 5A, right). In both cases, robust, T7 polymerase-dependent in situ barcode transcription was observed within the transduced regions (FIG. 5B). Together, these results show that Zombie can be used to detect viral barcodes in embryonic and adult tissues.

The ability to discriminate single base pair mismatches in the same chick and mouse contexts was tested next. Tissues with an equimolar mixture of perfect match and single base mismatch probes, along with a third reference probe targeting a distinct downstream region, each in a distinct color channel were tested (FIG. 5C). As a control, color channels were also swapped for the match and mismatch probes. Match probes strongly outcompeted mismatch probes, regardless of the color channel, in both organisms (FIGS. 5D-5E). Further, matching probes co-localized with reference probes, indicating that match-mismatch probe competition does not hinder detection efficiency (FIGS. 5D-5E). Taken together, these results demonstrate that Zombie can discriminate between single base pair mismatches in chick embryos and adult mouse brains.

Many in vivo barcoding and recording applications require simultaneous analysis of multiple barcode variants. To assess this capability, three pairs of distinctly barcoded lentiviruses were designed. Each virus contained two distinct 20 bp barcodes, each containing an A or a G at a designated variable position. These viruses were designed such that the identity of the variable base in one barcode matched that of the other barcode in the same virus (FIG. 5F). With this design, two barcodes on the same virus should appear strongly correlated in the variable base, while barcodes on different viruses should vary independently. A and G were selected to mimic possible base editing outcomes (FIG. 4A).

Mouse olfactory bulbs were co-injected with a mix of these three viral pairs. 12 days later, Zombie was used with three consecutive rounds of hybridization and imaging to read out all pairs of viral barcodes. Single nucleotide differences between barcodes were readily identifiable based on the relative signal intensity of competing probes (FIGS. 5G and 19). Further, as expected, a strong correlation between the state of two barcodes appearing on the same virus was observed, at each Zombie active site (FIGS. 5G-5H). Overall, 92% of sites were classified correctly as either A or G for both barcodes (FIG. 5H). Some of the remaining sites, classified as A for one barcode and G for another, might be explained by integration of both members of a lentivirus pair at sites too close to be spatially resolved (FIGS. 20A-20D). Together, these results indicate that Zombie permits multiplexed barcode readout with single base discrimination in brain tissue.

Combinatorial barcode libraries (FIG. 6A) can provide an exponentially increasing number of distinct barcodes with only a linear increase in the number of hybridization and imaging cycles needed to read them out. The ability to detect short (20 bp) DNA barcodes in situ should facilitate construction and delivery of such libraries. As a proof of principle, a lentiviral library containing 81 distinct combinations of 12 barcode sequences was constructed, each 20 bp long (FIG. 6A). HEK293T cells were transduced with this library and read out the library in 3 rounds of hybridization and imaging, each one probing 4 out of 12 barcodes with orthogonal color channels (FIG. 21). In this analysis, barcode combinations were detected at frequencies consistent with those measured by next generation sequencing (FIG. 6B), corroborating the accuracy of in situ readout.

In a parallel, in vivo study, the combinatorial library was injected into the lumen of the developing neural tube at stage HH11 chick embryos. Three days later (stage HH27), the embryos were frozen, performed with the Zombie procedure, and analyzed in three rounds of hybridization, as with the HEK293T cells (FIG. 6C). Cells with distinct combinations of barcodes were detected in both neural tube and retina of chick embryos (FIG. 6D). In many instances, cells labeled with the same barcode combination were observed close to each other and organized in a way that suggests clonal relationship (FIG. 6D, middle panel, clone 13). In other cases, despite relatively sparse labeling, cells with different barcode combinations were intermixed, indicating the necessity for high barcode diversity in establishing clonal relationships (FIG. 6D, left panel, clones 13, 16, and 11). These results demonstrate how Zombie can facilitate the use of combinatorial barcode libraries with imaging readout both in vitro and in vivo.

Finally, an ideal barcode readout system would be compatible with analysis of endogenous gene expression. To test this, gene expression was analyzed alongside barcode detection in the olfactory bulb of mice injected with the paired viruses (FIG. 5F). Using HCR, it was confirmed that Tbx21 (expressed by projection neurons) and Tyrosine hydroxylase (Th; expressed by periglomerular cells) could be detected alongside barcodes, in the mitral and glomerular layers, respectively, as expected (FIGS. 22A-22D).

This analysis demonstrates the suitability of Zombie for barcoding and recording applications that require readout of endogenous gene expression as well as barcodes in tissue samples.

Terminology

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. As used in this specification and the appended claims, the singular forms "a," "an," and "the" include plural references unless the context clearly dictates otherwise. Any reference to "or" herein is intended to encompass "and/or" unless otherwise stated.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method of determining barcode sequences in situ, comprising:
providing a plurality of cells each comprising a barcode polynucleotide with a barcode sequence;
fixing the plurality of cells using a fixative to generate a plurality of fixed cells;
generating a plurality of barcode molecules comprising the barcode sequence of the barcode polynucleotide in each of the plurality of fixed cells;
contacting the plurality of fixed cells with a plurality of detection probes each comprising a barcode binding sequence and an initiator sequence, thereby each of the plurality of barcode molecules comprising the barcode sequence of the barcode polynucleotide in the fixed cell hybridizes to a detection probe, of the plurality of detection probes, comprising the barcode binding sequence reverse complementary to the barcode sequence, or a portion thereof;
contacting the plurality of fixed cells with pairs of amplifier probes, wherein the amplifier probes of each pair of the pairs of amplifier probes comprise an identical fluorophore, thereby a first amplifier probe of a pair of amplifier probes of the pairs of amplifier probes hybridizes to (i) the initiator sequence of a detection probe of the plurality of detection probes hybridized to a barcode molecule in a fixed cell of the plurality of fixed cells and (ii) a second amplifier probe of the pair of amplifier probes;
detecting the fluorophore, or fluorescence thereof, of the pair of amplifier probes with the first amplifier probe hybridized to the detection probe hybridized to the barcode molecules in each of the plurality of fixed cells using fluorescence imaging; and
determining the barcode sequence in each of the plurality of fixed cells using the fluorophore detected, wherein the fluorophore detected indicates the barcode sequence of the barcode polynucleotide in the one or more fixed cells.

2. A method of determining barcode sequences in situ, comprising:
providing a plurality of cells each comprising a barcode polynucleotide with a barcode sequence;
fixing the plurality of cells using a fixative to generate a plurality of fixed cells;
generating a plurality of barcode molecules comprising the barcode sequence of the barcode polynucleotide in each of the plurality of fixed cells by transcribing the barcode polynucleotide;
contacting the plurality of fixed cells with a plurality of detection probes each comprising a barcode binding sequence and a fluorophore, thereby each of the plurality of barcode molecules comprising the barcode sequence of the barcode oligonucleotide in the fixed cell hybridizes to a detection probe, of the plurality of detection probes, comprising the barcode binding sequence reverse complementary to the barcode sequence of the barcode polynucleotide;
detecting the fluorophore, or fluorescence thereof, of the detection probe hybridized to the barcode molecules in each of the plurality of fixed cells using in situ fluorescence imaging; and
determining the barcode sequence in each of the plurality of fixed cells using the fluorophore detected, wherein the fluorophore detected indicates the barcode sequence of the barcode polynucleotide in the one or more fixed cells.

3. A method of determining barcode sequences in situ, comprising:
providing a plurality of cells each comprising a barcode polynucleotide with a barcode sequence;
fixing cells of the plurality of cells using a fixative to obtain a plurality of fixed cells;
generating, for each of one or more fixed cells of the plurality of fixed cells, a plurality of barcode molecules comprising the barcode sequence of the barcode polynucleotide in the fixed cell by transcribing the barcode polynucleotide;

contacting each of the one or more fixed cells with a plurality of detection probes each comprising a barcode binding sequence, thereby (i) one, at least one, or each of the plurality of barcode molecules comprising the barcode sequence of the oligonucleotide in the fixed cell hybridizes to a detection probe of the plurality of detection probes comprising the barcode binding sequence reverse complementary to the barcode sequence, or a portion thereof, and (ii) the detection probe is associated with a fluorophore; and detecting the fluorophore, or fluorescence thereof, associated with the detection probe hybridized to the one, at least one, or each barcode molecule in each of the one or more fixed cells using in situ fluorescence imaging, wherein the fluorophore, associated with the detection probe hybridized to the barcode molecule comprising the barcode sequence of the barcode polynucleotide in the fixed cell, detected indicates the barcode sequence of the barcode polynucleotide in the fixed cell.

4. The method of claim 3, wherein contacting each of the one or more fixed cells with the plurality of detection probes comprises:

contacting each of the one or more fixed cells with the plurality of detection probes each comprising the barcode binding sequence and an initiator sequence, thereby one, at least one, or each of the plurality of barcode molecules comprising the barcode sequence of the oligonucleotide in the fixed cell hybridizes to a detection probe of the plurality of detection probes comprising the barcode binding sequence reverse complementary to the barcode sequence, or a portion thereof; and contacting each of the one or more fixed cells with pairs of amplifier probes, wherein the amplifier probes of each pair of amplifier probes comprise an identical fluorophore, thereby a first amplifier probe of a pair of amplifier probes hybridizes to (i) the initiator sequence of a detection probe of the plurality of detection probes hybridized to a barcode molecule in the fixed cell and (ii) a second amplifier probe of the pair of amplifier probes.

5. The method of claim 4,
wherein (1) a first amplifier probe of the pair of amplifier probes comprises: (1a) a first amplifier probe subsequence of the first amplifier probe reverse complementary to a first subsequence of the initiator sequence of the detection probe of the plurality of detection probes, (1b) a second amplifier probe subsequence of the first amplifier probe reverse complementary to a second subsequence of the initiator sequence, (1c) a third amplifier probe subsequence of the first amplifier probe, and (1d) a fourth amplifier probe subsequence of the first amplifier probe comprising the second subsequence of the initiator sequence, and wherein (2) a second amplifier probe of the pair of amplifier probes comprises: (2a) a first amplifier probe subsequence of the second amplifier probe comprising a reverse complementary sequence of the third amplifier probe subsequence of the first amplifier probe, (2b) a second amplifier probe subsequence of the second amplifier probe comprising the second amplifier probe subsequence of the first amplifier probe, (2c) a third amplifier probe subsequence of the second amplifier probe comprising the first subsequence of the initiator sequence, and (2d) a fourth amplifier probe subsequence of the second amplifier probe comprising the second subsequence of the initiator sequence.

6. The method of claim 4, wherein said detecting comprises detecting the fluorophore of the first amplifier probe hybridized to the initiator sequence of the detection probe hybridized to the barcode molecule in the fixed cell and the fluorophore of the second amplifier probe of the pair of amplifier probes comprising the first amplifier probe.

7. The method of claim 3, wherein the contacting each of the one or more fixed cells with the plurality of detection probes comprises:

contacting each of the one or more fixed cells with the plurality of detection probes each comprising the barcode binding sequence and an initiator sequence, thereby one, at least one, or each of the plurality of barcode molecules comprising the barcode sequence of the oligonucleotide in the fixed cell hybridizes to a detection probe of the plurality of detection probes comprising the barcode binding sequence reverse complementary to the barcode sequence, or a portion thereof; and contacting each of the one or more fixed cells with a plurality of first amplifier probes each comprising a different fluorophore, thereby a first amplifier probe of the plurality of first amplifier probes hybridizes to the initiator sequence of a detection probe of the plurality of detection probes hybridized to a barcode molecule in the fixed cell.

8. The method of claim 7, wherein two, or different, first amplifier probes of the plurality of first amplifier probes comprise different fluorophores.

9. The method of claim 7, wherein said detecting comprises detecting the fluorophore of the first amplifier probe hybridized to the initiator sequence of the detection probe hybridized to the barcode molecule in the fixed cell.

10. The method of claim 3, wherein the contacting each of the one or more fixed cells with the plurality of detection probes comprises:

contacting each of the one or more fixed cells with the plurality of detection probes each comprising the barcode binding sequence and a fluorophore, thereby one, at least one, or each of the plurality of barcode molecules comprising the barcode sequence of the oligonucleotide in the fixed cell hybridizes to a detection probe of the plurality of detection probes comprising the barcode binding sequence reverse complementary to the barcode sequence, or a portion thereof, and the fluorophore.

11. The method of claim 10, wherein said detecting comprises detecting the fluorophore of the detection probe hybridized to the barcode molecule in the fixed cell.

12. The method of claim 3, wherein a genome of one, at least one, or each cell of the plurality of cell comprises the barcode polynucleotide with the barcode sequence.

13. The method of claim 3, wherein the barcode polynucleotide comprises at least one promoter upstream of the barcode sequence.

14. The method of claim 3, wherein the barcode polynucleotide of one, at least one, or each of the plurality of cells comprises two or more barcode sequences.

15. The method of claim 13, wherein the polynucleotide comprises a constitutively active promoter upstream of a marker gene, wherein the at least one promoter and the constitutively active promoter have divergent orientations.

16. The method of claim 3, wherein the fixative comprises a non-cross-linking fixative, a precipitating fixative, a denaturing fixative or a combination thereof.

17. The method of claim 3, comprising: fixing fixed cells of the plurality of fixed cells using a second fixative to obtain a plurality of second fixed cells, wherein contacting each of the one or more fixed cells comprises: contacting each of the one or more second fixed cells with a plurality of detection probes each comprising a barcode binding sequence, thereby (i) one, at least one, or each of the plurality of barcode molecules comprising the barcode sequence of the oligonucleotide in the second fixed cell hybridizes to a detection probe of the plurality of detection probes comprising the barcode binding sequence reverse complementary to the barcode sequence, or a portion thereof, and (ii) the detection probe is associated with a fluorophore, wherein detecting the fluorophore, or fluorescence thereof comprises: detecting the fluorophore, or fluorescence thereof, associated with the detection probe hybridized to the one, at least one, or each barcode molecule in each of the one or more second fixed cells using fluorescence imaging, and wherein the fluorophore, associated with the detection probe hybridized to the barcode molecule comprising the barcode sequence of the barcode polynucleotide in the second fixed cell, detected indicates the barcode sequence of the barcode polynucleotide in the second fixed cell, optionally wherein the second fixative comprises a cross-linking fixative.

18. The method of claim 3, wherein one, at least one, or each of the plurality of cells comprises no barcode molecule.

19. The method of claim 3, wherein the contacting each of the one or more fixed cells with the plurality of detection probes comprises: contacting each of the one or more fixed cells with detection probe molecules of each of the plurality of detection probes, thereby (i) one, at least one, or each of the plurality of barcode molecules comprising the barcode sequence of the oligonucleotide in the fixed cell hybridizes to a detection probe molecule of the detection probe of the plurality of detection probes comprising the barcode binding sequence reverse complementary to the barcode sequence, or a portion thereof, and (ii) the detection probe molecule of the detection probe is associated with a fluorophore.

20. The method of claim 3, comprising:
    determining the barcode sequence in each of the one or more fixed cells using the fluorophore, associated with the detection probe hybridized to the barcode molecule comprising the barcode sequence of the barcode polynucleotide in the fixed cell, detected,
    determining lineages of, and/or a clonal relationship between, two or more fixed cells of the plurality of fixed cells using the barcode sequence of the barcode polynucleotide in each of the two or more fixed cells, and/or
    determining a spatial relationship of two or more fixed cells of the plurality of fixed cells; and correlating the barcode sequences of the barcode polynucleotide in each of the two or more fixed cells with a spatial relationship of the two or more fixed cells.

21. The method of claim 20, comprising: staining nuclei of the plurality of fixed cells; and identifying nuclei of the plurality of fixed cells based on the nuclei stained, wherein said detecting comprises: detecting the fluorescence of the fluorophore, associated with the detection probe hybridized to the barcode molecule comprising the barcode sequence of the barcode polynucleotide in the fixed cell, in the nucleus of the cell identified.

22. The method of claim 3, comprising: base editing the barcode sequence of the barcode polynucleotide in one, at least one, or each of the plurality of cells.

23. The method of claim 22,
    wherein said base editing comprises: base editing the barcode sequence of the barcode polynucleotide in one, at least one, or each of the plurality of cells at the one position that the possible barcode sequences from the set of possible barcode sequences are different,
    wherein said base editing comprises base editing the barcode sequence of the barcode polynucleotide in one, at least one, or each of the plurality of cells at one or more predetermined time points, and/or
    wherein said base editing comprises base editing the barcode sequence of the barcode polynucleotide in one, at least one, or each of the plurality of cells at an edit rate, optionally wherein the edit rate is predetermined, optionally wherein the edit rate is about 1% to about 100% edit per unit time, and optionally wherein the edit rate is about 1% to 100% edit per cell per cell division cycle.

24. The method of claim 3, comprising: determining gene expression in one, at least one, or each of the plurality of cells, and/or correlating gene expressions of two or more fixed cells of the plurality of fixed cells with the lineages of, the clonal relationship between, and/or the spatial relationship of, the two or more fixed cells.

25. The method of claim 3, wherein two, at least two, or each of the plurality of cells are cultured under different conditions, wherein each of the different conditions comprises a genetic perturbation, an environmental perturbation, or a combination thereof.

26. The method of claim 1, wherein the generating the plurality of barcode molecules comprises transcribing the barcode polynucleotide in each of the plurality of fixed cells to generate the plurality of barcode molecules comprising the barcode sequence of the barcode polynucleotide using a phage RNA polymerase.

27. The method of claim 2, wherein the transcribing the barcode polynucleotide comprises using a phage RNA polymerase.

28. The method of claim 2, wherein the detecting the fluorophore, or fluorescence thereof, of the detection probe hybridized to the barcode molecules in each of the plurality of fixed cells does not comprise sequencing.

29. The method of claim 3, wherein the transcribing the barcode polynucleotide comprises a phage RNA polymerase.

30. The method of claim 3, wherein the detecting the fluorophore, or fluorescence thereof, associated with the detection probe hybridized to the one, at least one, or each barcode molecule in each of the one or more fixed cells does not comprise sequencing.

* * * * *

SEQUENCE LISTING

<160> NUMBER OF SEQ ID NOS: 304

<210> SEQ ID NO 1
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 1
caggacaacg cccacacacc                                                 20

<210> SEQ ID NO 2
<211> LENGTH: 916
<212> TYPE: DNA
<213> ORGANISM: Artificial Sequence
<220> FEATURE:
<223> OTHER INFORMATION: Synthetic Polynucleotide

<400> SEQUENCE: 2
taacaggaaa cagctatgac gggcccccta ggtaagcagt atcttcgaca gcttgtctct      60
ccagatgctc ttgggccatc ttccacatcg tccgtagcag ccttggcaat ttgccatcac    120
tggcaaatac acataaatcc aatgaatacg gttaccacca tcacattacc atgcaggtac    180
acagcaagaa ttgacgttgg catatcacat ggtgtaataa ccccacttgt gaaacaaccc    240
agaataaggt acaaggcgga aatgtcgtca ttctaaaata aaaggcatgg ccaggaattt    300
gtctaatacc gggaacttaa attcagcttg aacaccagtc gcaaaaaatt caagaaaagt    360
gattcaggtt cgggttcgtg gattggaaca gcttcttttg tttcagtgat gagagaatcc    420
tcctgtcact cgagaaagaa tcaaagaggc aacaacgca gaacaggaaa cagctatgac     480
gggcccccta ggtaagcagt atcttcgaca gcttgtctct ccagatgctc ttgggccatc    540
ttccacatcg tccgtagcag ccttggcaat ttgccatcac tggcaaatac acataaatcc    600
aatgaatacg gttaccacca tcacattacc atgcaggtac acagcaagaa ttgacgttgg    660
catatcacat ggtgtaataa ccccacttgt gaaacaaccc agaataaggt acaaggcgga    720
aatgtcgtca ttctaaaata aaaggcatgg ccaggaattt gtctaatacc gggaacttaa    780
attcagcttg aacaccagtc gcaaaaaatt caagaaaagt gattcaggtt cgggttcgtg    840
gattggaaca gcttcttttg tttcagtgat gagagaatcc tcctgtcact cgagaaagaa    900
tcaaagaggc aacaa                                                     916

<210> SEQ ID NO 3
<211> LENGTH: 916
<212> TYPE: DNA
<213> ORGANISM: Artificial Sequence
<220> FEATURE:
<223> OTHER INFORMATION: Synthetic Polynucleotide

<400> SEQUENCE: 3
taacaggaaa cagctatgac gggcccccta ggtaagcagt atcttcgaca gcttgtctct      60
ccagatgctc ttgggccatc ttccacatcg tccgtagcag ccttggcaat ttgccatcac    120
tggcaaatac acataaatcc aatgaatacg gttaccacca tcacattacc atgcaggtac    180
acagcaagaa ttgacgttgg catatcacat ggtgtaataa ccccacttgt gaaacaaccc    240
agaataaggt acaaggcgga aatgtcgtca ttctaaaata aaaggcatgg ccaggaattt    300
gtctaatacc gggaacttaa attcagcttg aacaccagtc gcaaaaaatt caagaaaagt    360
gattcaggtt cgggttcgtg gattggaaca gcttcttttg tttcagtgat gagagaatcc    420

```
tcctgtcact cgagaaagaa tcaaagaggc caacaacgca gaacaggaaa cagctatgac      480
gggcccccta ggtaagcagt atcttcgaca gcttgtctct ccagatgctc ttgggccatc      540
ttccacatcg tccgtagcag ccttggcaat tgccatcac tggcaaatac acataaatcc       600
aatgaatacg gttaccacca tcacattacc atgcaggtac acagcaagaa ttgacgttgg      660
catatcacat ggtgtaataa ccccacttgt gaaacaaccc agaataaggt acaaggcgga      720
aatgtcgtca ttctaaaata aaaggcatgg ccaggaattt gtctaatacc gggaacttaa      780
attcagcttg aacaccagtc gcaaaaaatt caaagaaagt gattcaggtt cgggttcgtg      840
gattggaaca gcttcttttg tttcagtgat gagagaatcc tcctgtcact cgagaaagaa      900
tcaaagaggc caacaa                                                     916

<210> SEQ ID NO 4
<211> LENGTH: 916
<212> TYPE: DNA
<213> ORGANISM: Artificial Sequence
<220> FEATURE:
<223> OTHER INFORMATION: Synthetic Polynucleotide

<400> SEQUENCE: 4
taacaggaaa cagctatgac gggcccccta gggggttctg acttcttacg aaaatgtggc       60
tagcattcca ttctctgacg ttcaaagaat cggaataagt catggtaatg gtgggaaatc      120
taatagaagc gactcccata acctccatat ttcttggcaa ataattctgt ctgggttacc      180
gttcacgagc cttcagagat ctacgacgtg tagtgggtgg gcttgccctc cagggtgtag      240
tttgtaatta gaatgggatt tcctgtttta agtacccaaa tacgaaaatt gctcttgatg      300
tttaacggct cacttttaag taaagtttgt gccaataccg tgcatgggag taagttattg      360
ccaatcttcg agaatttagg caattttggt atactcaact gggtctaata tggtggacgg      420
aatgatttct cgagaaagaa tcaaagaggc caacaacgca gaacaggaaa cagctatgac      480
gggcccccta gggggttctg acttcttacg aaaatgtggc tagcattcca ttctctgacg      540
ttcaaagaat cggaataagt catggtaatg gtgggaaatc taatagaagc gactcccata      600
acctccatat ttcttggcaa ataattctgt ctgggttacc gttcacgagc cttcagagat      660
ctacgacgtg tagtgggtgg gcttgccctc cagggtgtag tttgtaatta gaatgggatt      720
tcctgtttta agtacccaaa tacgaaaatt gctcttgatg tttaacggct cacttttaag      780
taaagtttgt gccaataccg tgcatgggag taagttattg ccaatcttcg agaatttagg      840
caattttggt atactcaact gggtctaata tggtggacgg aatgatttct cgagaaagaa      900
tcaaagaggc caacaa                                                     916

<210> SEQ ID NO 5
<211> LENGTH: 916
<212> TYPE: DNA
<213> ORGANISM: Artificial Sequence
<220> FEATURE:
<223> OTHER INFORMATION: Synthetic Polynucleotide

<400> SEQUENCE: 5
taacaggaaa cagctatgac gggcccccta ggcacattgc gtctttataa acttactaaa       60
ggttttggat agttttgaac ccattgtttg acgaatattc catattaaaa actctaaaat      120 aaacccccagc caccaacatt tgaaccagcg ttcccccat ctccgctgtg atcattctag      180
atctgtatta tggcatcgac tatgggaata cagggttatt ctcccatttt attgaggtat      240
```

-continued

| | |
|---|---|
| atggccagtt gcgcaacttc tttgatgaaa ttttatttgt ccgttgcatg attgaaatcc | 300 |
| taccagtagt tatatatatg tctttttcat tgttgtactt tggataaagc tgcttcttca | 360 |
| gaacgctccc tactatgctt taaacgctta ttttcggaag aaatcatgtg ggtcatattt | 420 |
| ttttgcttct cgagaaagaa tcaaagaggc caacaacgca aacaggaaa cagctatgac | 480 |
| gggcccccta ggcacattgc gtctttataa acttactaaa ggttttggat agttttgaac | 540 |
| ccattgtttg acgaatattc catattaaaa actctaaaat aaaccccagc caccaacatt | 600 |
| tgaaccagcg ttcccccat ctccgctgtg atcattctag atctgtatta tggcatcgac | 660 |
| tatgggaata cagggttatt ctcccatttt attgaggtat atggccagtt gcgcaacttc | 720 |
| tttgatgaaa ttttatttgt ccgttgcatg attgaaatcc taccagtagt tatatatatg | 780 |
| tctttttcat tgttgtactt tggataaagc tgcttcttca gaacgctccc tactatgctt | 840 |
| taaacgctta ttttcggaag aaatcatgtg ggtcatattt ttttgcttct cgagaaagaa | 900 |
| tcaaagaggc caacaa | 916 |

<210> SEQ ID NO 6
<211> LENGTH: 9711
<212> TYPE: DNA
<213> ORGANISM: Artificial Sequence
<220> FEATURE:
<223> OTHER INFORMATION: Synthetic Polynucleotide

<400> SEQUENCE: 6

| | |
|---|---|
| agacacctcg agacccaata aaagatcttt attttcatta gatctgtgtg ttggtttttt | 60 |
| gtgtgtctag agtgtgggtg tgggcgttgt cctgcagggg aattgaacag gtgtaaaatt | 120 |
| ggagggacaa gacttcccac agattttcgg ttttgtcggg aagtttttta ataggggcaa | 180 |
| ataaggaaaa tgggaggata ggtagtcatc tggggtttta tgcagcaaaa ctacaggtta | 240 |
| ttattgcttg tgatccgcct cggagtattt tccatcgagg tagattaaag acatgctcac | 300 |
| ccgagtttta tactctcctg cttgagatcc ttactacagt atgaaattac agtgtcgcga | 360 |
| gttagactat gtaagcagaa ttttaatcat ttttaaagag cccagtactt catatccatt | 420 |
| tctcccgctc cttctgcagc cttatcaaaa ggtattttag aacactcatt ttagccccat | 480 |
| tttcatttat tatactggct tatccaaccc ctagacagag cattggcatt ttccctttcc | 540 |
| tgatcttaga agtctgatga ctcatgaaac cagacagatt accctgttat ccctagaatt | 600 |
| cagcttggga taaaaagcta tggcataggc ggtaatacgg ttatccacag aatcagggga | 660 |
| taacgcagga agaacatgt gagcaaaagg ccagcaaaag gccaggaacc gtaaaaaggc | 720 |
| cgcgttgctg gcgttttcc ataggctccg ccccctgac gagcatcaca aaaatcgacg | 780 |
| ctcaagtcag aggtggcgaa acccgacagg actataaaga taccaggcgt ttccccctgg | 840 |
| aagctccctc gtgcgctctc ctgttccgac cctgccgctt accggatacc tgtccgcctt | 900 |
| tctcccttcg ggaagcgtgg cgctttctca tagctcacgc tgtaggtatc tcagttcggt | 960 |
| gtaggtcgtt cgctccaagc tgggctgtgt gcacgaaccc cccgttcagc ccgaccgctg | 1020 |
| cgccttatcc ggtaactatc gtcttgagtc aacccggta agacacgact tatcgccact | 1080 |
| ggcagcagcc actggtaaca ggattagcag agcgaggtat gtaggcggtg ctacagagtt | 1140 |
| cttgaagtgg tggcctaact acggctacac tagaagaaca gtatttggta tctgcgctct | 1200 |
| gctgaagcca gttaccttcg gaaaaagagt tggtagctct tgatccggca aacaaaccac | 1260 |
| cgctggtagc ggtggttttt ttgtttgcaa gcagcagatt acgcgcagaa aaaaaggatc | 1320 |
| tcaagaagat cctttgatct tttctacggg gtctgacgct cagtggaacg aaaactcacg | 1380 |

```
ttaagggatt ttggtcatga gattatcaaa aaggatcttc acctagatcc ttttaaatta   1440
aaaatgaagt tttaaatcaa tctaaagtat atatgagtaa acttggtctg acagttacca   1500
atgcttaatc agtgaggcac ctatctcagc gatctgtcta tttcgttcat ccatagttgc   1560
ctgactcccc gtcgtgtaga taactacgat acgggagggc ttaccatctg gccccagtgc   1620
tgcaatgata ccgcgagatc cacgctcacc ggctccagat ttatcagcaa taaaccagcc   1680
agccggaagg gccgagcgca gaagtggtcc tgcaacttta ccgcctcca tccagtctat    1740 taattgttgc cgggaagcta gagtaagtag ttcgccagtt aatagtttgc gcaacgttgt   1800
tgccattgct acaggcatcg tggtgtcacg ctcgtcgttt ggtatggctt cattcagctc   1860
cggttcccaa cgatcaaggc gagttacatg atccccatg ttgtgcaaaa aagcggttag    1920
ctccttcggt cctccgatcg ttgtcagaag taagttggcc gcagtgttat cactcatggt   1980
tatggcagca ctgcataatt ctcttactgt catgccatcc gtaagatgct tttctgtgac   2040
tggtgagtac tcaaccaagt cattctgaga atagtgtatg cggcgaccga gttgctcttg   2100
cccggcgtca atacgggata ataccgcgcc acatagcaga actttaaaag tgctcatcat   2160
tggaaaacgt tcttcgggc gaaaactctc aaggatctta ccgctgttga gatccagttc    2220
gatgtaaccc actcgtgcac ccaactgatc ttcagcatct tttactttca ccagcgtttc   2280
tgggtgagca aaaacaggaa ggcaaaatgc cgcaaaaaag ggaataaggg cgacacggaa   2340
atgttgaata ctcatactct ccttttttca atattattga agcatttatc agggttattg   2400
tctcatgagc ggatacatat ttgaatgtat ttagaaaaat aaacaaatag gggtgattta   2460
atctgtatca ggggcgtata gtggagcaaa gcgaattcta actataacgg tcctaaggta   2520
gcgaaggccc tcccctcggc cccgcgccgc agagtctggc cgcgcgcccc tgcgcaacgt   2580
ggcaggaagc gcgcgctggg ggcggggacg ggcagtaggg ctgagcggct gcggggcggg   2640
tgcaagcacg tttccgactt gagttgcctc aagagggcg tgctgagcca gacctccatc    2700
gcgcactccg gggagtggag ggaaggagcg agggctcagt tgggctgttt tggaggcagg   2760
aagcacttgc tctcccaaag tcgctctgag ttgttatcag taaggagct gcagtggagt    2820 aggcggggag aaggccgcac ccttctccgg aggggggagg ggagtgttgc aatacctttc   2880
tgggagttct ctgctgcctc ctggcttctg aggaccgccc tgggcctggg agaatccctt   2940 cccccctcttc cctcgtgatc tgcaactcca gtctttctag aagatgggcg ggagtctttt   3000
gggcaggctt aaaggctaac ctggttaggg cgcagtagtc cagggtttcc ttgatgatgt   3060
catacttatc ctgtcccttt ttttttccaca gctcgcggtt gaggacaaac tcttcgcggt   3120
ctttccagtg ttgacaatta atcatcggca tagtatatcg gcatagtata atacgacaag   3180
gtgaggaacg ccaccatgat tgaacaagat ggattgcacg caggttctcc ggccgcttgg   3240
gtggagaggc tattcggcta tgactgggca caacagacaa tcggctgctc tgatgccgcc   3300
gtgttccggc tgtcagcgca ggggcgcccg gttcttttg tcaagaccga cctgtccggt    3360
gccctgaatg aactgcaaga cgaggcagcg cggctatcgt ggctggccac gacgggcgtt   3420
ccttgcgcag ctgtgctcga cgttgtcact gaagcgggaa gggactggct gctattgggc   3480
gaagtgccgg ggcaggatct cctgtcatct caccttgctc ctgccgagaa agtatccatc   3540
atggctgatg caatgcggcg gctgcatacg cttgatccgg ctacctgccc attcgaccac   3600
caagcgaaac atcgcatcga gcgagcacgt actcggatgg aagccggtct tgtcgatcag   3660
gatgatctgg acgaagagca tcaggggctc gcgccagccg aactgttcgc caggctcaag   3720
```

```
gcgagcatgc ccgacggcga ggatctcgtc gtgacccatg gcgatgcctg cttgccgaat    3780
atcatggtgg aaaatggccg cttttctgga ttcatcgact gtggccggct gggtgtggcg    3840
gaccgctatc aggacatagc gttggctacc cgtgatattg ctgaagagct tggcggcgaa    3900
tgggctgacc gcttcctcgt gctttacggt atcgccgctc ccgattcgca gcgcatcgcc    3960
ttctatcgcc ttcttgacga gttcttctga tgtacaagta aagcggccgc gactctagat    4020
cataatcagc cataccacat ttgtagaggt tttacttgct ttaaaaaacc tcccacacct    4080
ccccctgaac ctgaaacata aaatgaatgc aattgttgtt gttaacttgt ttattgcagc    4140
ttataatggt tacaaataaa gcaatagcat cacaaatttc acaaataaag cattttttc    4200
actgcattct agttgtggtt tgtccaaact catcaatgta tcttaggtct cgcgtactgt    4260
aggtcctttc agcaaaaaac ccctcaagac ccgtttagag gccccaaggg gttatgctag    4320
ttattgctca gcggtggcag cagccaactc agcttccttt cgggctttgt tagcagccgg    4380
atctcagtgg tggtggtggt ggtgctccca tctgacttgc aagaaaacag atggcaagca    4440
tgacaatcat ttcgagtgcg gccgcagcga caaacaacag ataaaacgaa aggcccagtc    4500
tttcgactga gcctttcgtt ttatttgaag cttctttcag caaaaaaccc cgcaggaccc    4560
ccgaagaggc ccgcggggt tatgctaggt cgactacgca gacgtaacag gaaacagcta    4620
tgacgggccc cctaggtaag cagtatcttc gacagcttgt ctctccagat gctcttgggc    4680
catcttccac atcgtccgta gcagccttgg caatttgcca tcactggcaa atacacataa    4740
atccaatgaa tacggttacc accatcacat taccatgcag gtacacagca agaattgacg    4800
ttggcatatc acatggtgta ataacccccac ttgtgaaaca acccagaata aggtacaagg    4860
cggaaatgtc gtcattctaa aataaaaggc atggccagga atttgtctaa taccgggaac    4920
ttaaattcag cttgaacacc agtcgcaaaa aattcaaaga aagtgattca ggttcgggtt    4980
cgtggattgg aacagcttct tttgtttcag tgatgagaga atcctcctgt cactcgagaa    5040
agaatcaaag aggccaacaa cgcagaacag gaaacagcta tgacgggccc cctaggtaag    5100
cagtatcttc gacagcttgt ctctccagat gctcttgggc catcttccac atcgtccgta    5160
gcagccttgg caatttgcca tcactggcaa atacacataa atccaatgaa tacggttacc    5220
accatcacat taccatgcag gtacacagca agaattgacg ttggcatatc acatggtgta    5280
ataacccccac ttgtgaaaca acccagaata aggtacaagg cggaaatgtc gtcattctaa    5340
aataaaaggc atggccagga atttgtctaa taccgggaac ttaaattcag cttgaacacc    5400
agtcgcaaaa aattcaaaga aagtgattca ggttcgggtt cgtggattgg aacagcttct    5460
tttgtttcag tgatgagaga atcctcctgt cactcgagaa agaatcaaag aggccaacaa    5520
cgacctgtag aggtcctccc tttagtgagg gttaattctc gagtctccct atagtgagtc    5580
gtattaattc cgtgtattct atagtgtcac ctaaatcgtt acgggttcgt aaattctgca    5640
ggacttctag ttattaatag taatcaatta cggggtcatt agttcatagc ccatatatgg    5700
agttccgcgt tacataactt acggtaaatg gcccgcctgg ctgaccgccc aacgaccccc    5760
gcccattgac gtcaataatg acgtatgttc ccatagtaac gccaataggg actttccatt    5820
gacgtcaatg ggtggagtat ttacggtaaa ctgcccactt ggcagtacat caagtgtatc    5880
atatgccaag tacgccccct attgacgtca atgacggtaa atggcccgcc tggcattatg    5940
cccagtacat gaccttatgg gactttccta cttggcagta catctacgta ttagtcatcg    6000
ctattaccat ggtcgaggtg agccccacgt tctgcttcac tctccccatc tccccccct    6060
ccccaccccc aattttgtat ttatttattt ttaattatt ttgtgcagcg atggggcgg    6120
```

```
ggggggggggg ggggcgcgcg ccaggcgggg cggggcgggg cgaggggcgg ggcggggcga    6180
ggcggagagg tgcggcggca gccaatcaga gcggcgcgct ccgaaagttt cctttttatgg    6240 cgaggcggcg gcggcggcgg ccctataaaa agcgaagcgc gcggcgggcg ggagtcgctg    6300
cgcgctgcct tcgccccgtg ccccgctccg ccgccgcctc gcgccgcccg ccccggctct    6360
gactgaccgc gttactccca caggtgagcg ggcgggacgg cccttctcct ccgggctgta    6420
attagcgctt ggtttaatga cggcttgttt ctttttctgtg gctgcgtgaa agccttgagg    6480
ggctccggga gggccctttg tgcgggggga gcggctcggg gggtgcgtgc gtgtgtgtgt    6540
gcgtggggag cgccgcgtgc ggctccgcgc tgcccggcgg ctgtgagcgc tgcgggcgcg    6600
gcgcggggct ttgtgcgctc cgcagtgtgc gcgaggggag cgcggccggg ggcggtgccc    6660
cgcggtgcgg gggggctgcg aggggaacaa aggctgcgtg cggggtgtgt gcgtgggggg    6720
gtgagcaggg ggtgtgggcg cgtcggtcgg gctgcaaccc ccccctgcac ccccctcccc    6780
gagttgctga gcacgcccg gcttcgggtg cgggctccg tacgggcgt ggcgcggggc       6840 tcgccgtgcc gggcggggg tggcggcagg tgggggtgcc gggcggggcg gggccgcctc    6900
gggccgggga gggctcgggg gagggcgcg gcggcccccg gagcgccggc ggctgtcgag    6960
gcgcggcgag ccgcagccat tgccttttat ggtaatcgtg cgagagggcg cagggacttc    7020 cttttgtccca aatctgtgcg gagccgaaat ctgggaggcg ccgccgcacc ccctctagcg    7080
ggcgcggggc gaagcggtgc ggcgccggca ggaaggaaat gggcggggag ggccttcgtg    7140
cgtcgccgcg ccgccgtccc cttctccctc tccagcctcg gggctgtccg cgggggacg    7200 gctgccttcg ggggggacgg ggcagggcgg ggttcggctt ctggcgtgtg accggcggct    7260
ctagagcctc tgctaaccat gttcatgcct tcttcttttt cctacagctc ctgggcaacg    7320
tgctggttat tgtgctgtct catcattttg gcaaagaatt gatttgatac cgcgggcccg    7380 ggatccctc gagggaatta cctttggcgt agccgccacc atgccagagc cagcgaagtc    7440
tgctcccgcc ccgaaaaagg gctccaagaa ggcggtgact aaggcgcaga agaaaggcgg    7500
caagaagcgc aagcgcagcc gcaaggagag ctattccatc tatgtgtaca aggttctgaa    7560
gcaggtccac cctgacaccg gcatttcgtc caaggccatg ggcatcatga attcgttgt    7620 gaacgacatt ttcgagcgca tcgctggtga ggcttcccgc ctggcgcatt acaacaagcg    7680
ctcgaccatc acctccaggg agatccgac ggccgtgcgc ctgctgctgc ctggggagtt    7740
ggccaagcac gccgtgtccg agggtactaa ggccatcacc aagtacacca gcgctaagga    7800
tccccgggta ccggtcgcca ccatggtgag caagggcgag gagctgttca ccggggtggt    7860
gcccatcctg gtcgagctgg acggcgacgt aaacggccac aagttcagcg tgtccggcga    7920
gggcgagggc gatgccacct acggcaagct gaccctgaag ttcatctgca ccaccggcaa    7980
gctgcccgtg ccctggccca ccctcgtgac caccctgacc tggggcgtgc agtgcttcgc    8040
ccgctacccc gaccacatga agcagcacga cttcttcaag tccgccatgc ccgaaggcta    8100
cgtccaggag cgcaccatct tcttcaagga cgacggcaac tacaagaccc gcgccgaggt    8160
gaagttcgag ggcgacaccc tggtgaaccg catcgagctg aagggcatcg acttcaagga    8220
ggacggcaac atcctggggc acaagctgga gtacaacgcc atcagcgaca acgtctatat    8280
caccgccgac aagcagaaga acggcatcaa ggccaacttc aagatccgcc acaacatcga    8340
ggacggcagc gtgcagctcg ccgaccacta ccagcagaac accccatcg gcgacggccc    8400 cgtgctgctg cccgacaacc actacctgag cacccagtcc aagctgagca agacccaa     8460
```

```
cgagaagcgc gatcacatgg tcctgctgga gttcgtgacc gccgccggga tcactctcgg    8520
catggacgag ctgtacaagt gaacctgagt cgtaacagga acagctatg acgggccccc     8580
taggacgttc ccatagctcc ttttgatgtc ttaatgtagg ttcaacagat atgcggcttc    8640
ttcgcattct gatggcgtca gctacgatag gcgagagctg aatagttgaa aattttttagc   8700
agatgcctga gaaaattaaa cttgatttga ttccagtaat ttaccaaaat acgcacagtt    8760
gccttcttcg atgtaatctt ttcaatcgta ctatgtcgta tgcagttagc aaatgaaagt    8820
agcaacacca atttgcgcca gaatttcacg tcgaaaatat ccttaaacct tgcaagccaa    8880
gttacggagt tgaaatttcc gtaagctacg gttatcttcc aatggcccat acttggctaa    8940
atcagagttc cctttcgtgg aaactgcaat agccaaattc ctcgagaaag aatcaaagag    9000
gccaacaacg cagaacagga acagctatg acgggccccc taggacgttc ccatagctcc     9060
ttttgatgtc ttaatgtagg ttcaacagat atgcggcttc ttcgcattct gatggcgtca    9120
gctacgatag gcgagagctg aatagttgaa aattttttagc agatgcctga gaaaattaaa   9180
cttgatttga ttccagtaat ttaccaaaat acgcacagtt gccttcttcg atgtaatctt    9240
ttcaatcgta ctatgtcgta tgcagttagc aaatgaaagt agcaacacca atttgcgcca    9300
gaatttcacg tcgaaaatat ccttaaacct tgcaagccaa gttacggagt tgaaatttcc    9360
gtaagctacg gttatcttcc aatggcccat acttggctaa atcagagttc cctttcgtgg    9420
aaactgcaat agccaaattc ctcgagaaag aatcaaagag gccaacaacg acctgctaag    9480
gtctgtgcct tctagttgcc agccatctgt tgtttgcccc tccccgtgc cttccttgac      9540
cctggaaggt gccactccca ctgtcctttc ctaataaaat gaggaaattg catcgcattg    9600
tctgagtagg tgtcattcta ttctgggggg tgggtgggg caggacagca aggggggagga    9660
ttgggaagag aatagcaggc atgctgggga tgcggtgggc tctatggtac g              9711

<210> SEQ ID NO 7
<211> LENGTH: 9614
<212> TYPE: DNA
<213> ORGANISM: Artificial Sequence
<220> FEATURE:
<223> OTHER INFORMATION: Synthetic Polynucleotide

<400> SEQUENCE: 7
agacacctcg agacccaata aaagatcttt attttcatta gatctgtgtg ttggtttttt      60
gtgtgtctag agtgtgggtg tgggcgttgt cctgcagggg aattgaacag gtgtaaaatt     120
ggagggacaa gacttcccac agattttcgg ttttgtcggg aagttttta ataggggcaa      180
ataaggaaaa tgggaggata ggtagtcatc tggggtttta tgcagcaaaa ctacaggtta     240
ttattgcttg tgatccgcct cggagtattt tccatcgagg tagattaaag acatgctcac     300
ccgagtttta tactctcctg cttgagatcc ttactacagt atgaaattac agtgtcgcga     360
gttagactat gtaagcagaa ttttaatcat ttttaaagag cccagtactt catatccatt     420
tctcccgctc cttctgcagc cttatcaaaa ggtattttag aacactcatt ttagccccat    480
tttcatttat tatactggct tatccaaccc ctagacagag cattggcatt ttcccttttcc   540
tgatcttaga agtctgatga ctcatgaaac cagacagatt accctgttat ccctagaatt    600
cagcttggga taaaaagcta tggcataggc ggtaatacgg ttatccacag aatcagggga    660
taacgcagga agaacatgt gagcaaaagg ccagcaaaag gccaggaacc gtaaaaaggc      720
cgcgttgctg gcgttttttcc ataggctccg ccccccctgac gagcatcaca aaaatcgacg   780
ctcaagtcag aggtggcgaa acccgacagg actataaaga taccaggcgt ttccccctgg    840
```

```
aagctccctc gtgcgctctc ctgttccgac cctgccgctt accggatacc tgtccgcctt    900
tctcccttcg ggaagcgtgg cgctttctca tagctcacgc tgtaggtatc tcagttcggt    960
gtaggtcgtt cgctccaagc tgggctgtgt gcacgaaccc cccgttcagc ccgaccgctg   1020
cgccttatcc ggtaactatc gtcttgagtc aacccggta  agacacgact tatcgccact   1080
ggcagcagcc actggtaaca ggattagcag agcgaggtat gtaggcggtg ctacagagtt   1140
cttgaagtgg tggcctaact acggctacac tagaagaaca gtatttggta tctgcgctct   1200
gctgaagcca gttaccttcg gaaaagagt  tggtagctct tgatccggca aacaaaccac   1260
cgctggtagc ggtggttttt tgtttgcaa  gcagcagatt acgcgcagaa aaaaggatc    1320
tcaagaagat cctttgatct tttctacggg gtctgacgct cagtggaacg aaaactcacg   1380
ttaagggatt ttggtcatga gattatcaaa aaggatcttc acctagatcc ttttaaatta   1440
aaaatgaagt tttaaatcaa tctaaagtat atatgagtaa acttggtctg acagttacca   1500
atgcttaatc agtgaggcac ctatctcagc gatctgtcta tttcgttcat ccatagttgc   1560
ctgactcccc gtcgtgtaga taactacgat acgggagggc ttaccatctg gccccagtgc   1620
tgcaatgata ccgcgagatc cacgctcacc ggctccagat ttatcagcaa taaaccagcc   1680
agccggaagg gccgagcgca gaagtggtcc tgcaacttta tccgcctcca tccagtctat   1740
taattgttgc cgggaagcta gagtaagtag ttcgccagtt aatagtttgc gcaacgttgt   1800
tgccattgct acaggcatcg tggtgtcacg ctcgtcgttt ggtatggctt cattcagctc   1860
cggttcccaa cgatcaaggc gagttacatg atcccccatg ttgtgcaaaa aagcggttag   1920
ctccttcggt cctccgatcg ttgtcagaag taagttggcc gcagtgttat cactcatggt   1980
tatggcagca ctgcataatt ctcttactgt catgccatcc gtaagatgct tttctgtgac   2040
tggtgagtac tcaaccaagt cattctgaga atagtgtatg cggcgaccga gttgctcttg   2100
cccggcgtca atacgggata ataccgcgcc acatagcaga actttaaaag tgctcatcat   2160
tggaaaacgt tcttcggggc gaaaactctc aaggatctta ccgctgttga tccagttc    2220
gatgtaaccc actcgtgcac ccaactgatc ttcagcatct tttactttca ccagcgtttc   2280
tgggtgagca aaaacaggaa ggcaaaatgc cgcaaaaaag gaataagggc gacacggaa    2340
atgttgaata ctcatactct ccttttttca atattattga agcatttatc agggttattg   2400
tctcatgagc ggatacatat ttgaatgtat ttagaaaaat aaacaaatag gggtgattta   2460
atctgtatca ggggcgtata gtggagcaaa gcgaattcta actataacgg tcctaaggta   2520
gcgaaggccc tcccctcggc cccgcgccgc agagtctggc cgcgcgcccc tgcgcaacgt   2580
ggcaggaagc gcgcgctggg ggcggggacg ggcagtaggg ctgagcggct gcggggcggg   2640
tgcaagcacg tttccgactt gagttgcctc aagaggggcg tgctgagcca gacctccatc   2700
gcgcactccg gggagtggag ggaaggagcg agggctcagt tgggctgttt tggaggcagg   2760
aagcacttgc tctcccaaag tcgctctgag ttgttatcag taagggagct gcagtggagt   2820
aggcggggag aaggccgcac ccttctccgg agggggggagg ggagtgttgc aatacctttc   2880
tgggagttct ctgctgcctc ctggcttctg aggaccgccc tgggcctggg agaatccctt   2940
cccctcttc  cctcgtgatc tgcaactcca gtctttctag aagatgggcg ggagtctttt   3000
gggcaggctt aaaggctaac ctggttaggg cgcagtagtc cagggtttcc ttgatgatgt   3060
catacttatc ctgtccctt  tttttccaca gctcgcggtt gaggacaaac tcttcgcggt   3120
ctttccagtg ttgacaatta atcatcggca tagtatatcg gcatagtata atacgacaag   3180
```

```
gtgaggaacg ccaccatgat tgaacaagat ggattgcacg caggttctcc ggccgcttgg   3240
gtggagaggc tattcggcta tgactgggca caacagacaa tcggctgctc tgatgccgcc   3300
gtgttccggc tgtcagcgca ggggcgcccg gttcttttg tcaagaccga cctgtccggt   3360
gccctgaatg aactgcaaga cgaggcagcg cggctatcgt ggctggccac gacgggcgtt   3420
ccttgcgcag ctgtgctcga cgttgtcact gaagcgggaa gggactggct gctattgggc   3480
gaagtgccgg ggcaggatct cctgtcatct caccttgctc ctgccgagaa agtatccatc   3540
atggctgatg caatgcggcg gctgcatacg cttgatccgg ctacctgccc attcgaccac   3600
caagcgaaac atcgcatcga gcgagcacgt actcggatgg aagccggtct tgtcgatcag   3660
gatgatctgg acgaagagca tcaggggctc gcgccagccg aactgttcgc caggctcaag   3720
gcgagcatgc ccgacggcga ggatctcgtc gtgacccatg gcgatgcctg cttgccgaat   3780
atcatggtgg aaaatggccg cttttctgga ttcatcgact gtggccggct gggtgtggcg   3840
gaccgctatc aggacatagc gttggctacc cgtgatattg ctgaagagct ggcggcgaa   3900 tgggctgacc gcttcctcgt gctttacggt atcgccgctc ccgattcgca gcgcatcgcc   3960
ttctatcgcc ttcttgacga gttcttctga tgtacaagta aagcggccgc gactctagat   4020
cataatcagc cataccacat ttgtagaggt tttacttgct ttaaaaaacc tcccacacct   4080
ccccctgaac ctgaaacata aaatgaatgc aattgttgtt gttaacttgt ttattgcagc   4140
ttataatggt tacaaataaa gcaatagcat cacaaatttc acaaataaag catttttttc   4200
actgcattct agttgtggtt tgtccaaact catcaatgta tcttaggtct cgcgtactgt   4260
aggtcctttc agcaaaaaac ccctcaagac ccgtttagag gccccaaggg gttatgctag   4320
ttattgctca gcggtggcag cagccaactc agcttccttt cgggctttgt tagcagccgg   4380
atctcagtgg tggtggtggt ggtgctccca tctgacttgc aagaaaacag atggcaagca   4440
tgacaatcat ttcgagtgcg gccgcagcga caaacaacag ataaaacgaa aggcccagtc   4500
tttcgactga gcctttcgtt ttatttgaag cttcttcag caaaaaaccc cgcaggaccc   4560
ccgaagaggc ccgcggggt tatgctaggt cgactacgca gacgtaacag gaaacagcta   4620
tgacgggccc cctaggtaag cagtatcttc gacagcttgt ctctccagat gctcttgggc   4680
catcttccac atcgtccgta gcagccttgg caatttgcca tcactggcaa atacacataa   4740
atccaatgaa tacggttacc accatcacat taccatgcag gtacacagca agaattgacg   4800
ttggcatatc acatggtgta ataaccccac ttgtgaaaca acccagaata aggtacaagg   4860
cggaaatgtc gtcattctaa aataaaaggc atggccagga atttgtctaa taccgggaac   4920
ttaaattcag cttgaacacc agtcgcaaaa aattcaaaga aagtgattca ggttcgggtt   4980
cgtggattgg aacagcttct tttgtttcag tgatgagaga atcctcctgt cactcgagaa   5040
agaatcaaag aggccaacaa cgcagaacag gaaacagcta tgacgggccc cctaggtaag   5100
cagtatcttc gacagcttgt ctctccagat gctcttgggc catcttccac atcgtccgta   5160
gcagccttgg caatttgcca tcactggcaa atacacataa atccaatgaa tacggttacc   5220
accatcacat taccatgcag gtacacagca agaattgacg ttggcatatc acatggtgta   5280
ataaccccac ttgtgaaaca acccagaata aggtacaagg cggaaatgtc gtcattctaa   5340
aataaaaggc atggccagga atttgtctaa taccgggaac ttaaattcag cttgaacacc   5400
agtcgcaaaa aattcaaaga aagtgattca ggttcgggtt cgtggattgg aacagcttct   5460
tttgtttcag tgatgagaga atcctcctgt cactcgagaa agaatcaaag aggccaacaa   5520
cgacctgtag cgtaaattct gcaggacttc tagttattaa tagtaatcaa ttacggggtc   5580
```

```
attagttcat agcccatata tggagttccg cgttacataa cttacggtaa atggcccgcc    5640
tggctgaccg cccaacgacc cccgcccatt gacgtcaata atgacgtatg ttcccatagt   5700
aacgccaata gggactttcc attgacgtca atgggtggag tatttacggt aaactgccca   5760
cttggcagta catcaagtgt atcatatgcc aagtacgccc cctattgacg tcaatgacgg   5820
taaatggccc gcctggcatt atgcccagta catgacctta tgggactttc ctacttggca   5880
gtacatctac gtattagtca tcgctattac catggtcgag gtgagcccca cgttctgctt   5940
cactctcccc atctccccccc cctccccacc cccaattttg tatttattta ttttttaatt   6000
attttgtgca gcgatggggg cggggggggg ggggggcgc gcgccaggcg gggcggggcg   6060
gggcgagggg cggggcgggg cgaggcggag aggtgcggcg gcagccaatc agagcggcgc   6120
gctccgaaag tttccttttta tggcgaggcg gcggcggcgg cggccctata aaaagcgaag   6180
cgcgcggcgg gcgggagtcg ctgcgcgctg ccttcgcccc gtgccccgct ccgccgccgc   6240
ctcgcgccgc ccgccccggc tctgactgac cgcgttactc ccacaggtga gcgggcggga   6300
cggcccttct cctccgggct gtaattagcg cttggtttaa tgacggcttg tttcttttct   6360
gtggctgcgt gaaagccttg aggggctccg gagggccct ttgtgcgggg ggagcggctc    6420 gggggggtgcg tgcgtgtgtg tgtgcgtggg gagcgccgcg tgcggctccg cgctgcccgg   6480
cggctgtgag cgctgcggc gcggcgcggg gctttgtgcg ctccgcagtg tgcgcgaggg    6540
gagcgcggcc ggggcggtg ccccgcggtg cggggggct gcgaggggaa caaaggctgc    6600 gtgcggggt tgtgcgtggg ggggtgagca ggggggtgtgg gcgcgtcggt cgggctgcaa   6660
cccccccctg caccccctc cccgagttgc tgagcacggc ccggcttcgg gtgcggggct    6720
ccgtacgggg cgtggcgcgg ggctcgccgt gccgggcggg gggtggcggc aggtgggggt   6780
gccgggcggg gcggggccgc ctcgggccgg ggagggctcg ggggagggc gcggcggccc    6840 ccggagcgcc ggcggctgtc gaggcgcggc gagccgcagc cattgccttt tatggtaatc   6900
gtgcgagagg gcgcagggac ttcctttgtc ccaaatctgt gcggagccga aatctgggag   6960
gcgccgccgc accccctcta gcgggcgcgg ggcgaagcgg tgcggcgccg gcaggaagga   7020
aatgggcggg gagggccttc gtgcgtcgcc gcgccgccgt cccctcctcc ctctccagcc   7080
tcggggctgt ccgcgggggg acggctgcct tcgggggga cggggcaggg cggggttcgg   7140
cttctggcgt gtgaccggcg gctctagagc ctctgctaac catgttcatg ccttcttctt   7200
tttcctacag ctcctgggca acgtgctggt tattgtgctg tctcatcatt ttggcaaaga   7260
attgatttga taccgcgggc ccgggatccc ctcgaggaa ttacctggtt cgtagccgcc    7320
accatgccag agccagcgaa gtctgctccc gccccgaaaa agggctccaa gaaggcggtg   7380
actaaggcgc agaagaaagg cggcaagaag cgcaagcgca gccgcaagga gagctattcc   7440
atctatgtgt acaaggttct gaagcaggtc caccctgaca ccggcatttc gtccaaggcc   7500
atgggcatca tgaattcgtt tgtgaacgac attttcgagc gcatcgctgg tgaggcttcc   7560
cgcctggcgc attacaacaa gcgctcgacc atcacctcca gggagatcca gacggccgtg   7620
cgcctgctgc tgcctgggga gttgccaag cacgccgtgt ccgagggtac taaggccatc    7680
accaagtaca ccagcgctaa ggatccccgg gtaccggtcg ccaccatggt gagcaagggc   7740
gaggagctgt tcaccggggt ggtgcccatc ctggtcgagc tggacggcga cgtaaacggc   7800
cacaagttca gcgtgtccgg cgagggcgag ggcgatgcca cctacggcaa gctgaccctg   7860
aagttcatct gcaccaccgg caagctgccc gtgccctggc ccaccctcgt gaccaccctg   7920
```

-continued

```
acctggggcg tgcagtgctt cgcccgctac cccgaccaca tgaagcagca cgacttcttc    7980
aagtccgcca tgcccgaagg ctacgtccag gagcgcacca tcttcttcaa ggacgacggc    8040
aactacaaga cccgcgccga ggtgaagttc gagggcgaca ccctggtgaa ccgcatcgag    8100
ctgaagggca tcgacttcaa ggaggacggc aacatcctgg gcacaagct ggagtacaac    8160
gccatcagcg acaacgtcta tatcaccgcc gacaagcaga gaacggcat caaggccaac    8220
ttcaagatcc gccacaacat cgaggacggc agcgtgcagc tcgccgacca ctaccagcag    8280
aacacccca tcggcgacgg ccccgtgctg ctgcccgaca ccactacct gagcacccag    8340
tccaagctga gcaaagaccc caacgagaag cgcgatcaca tggtcctgct ggagttcgtg    8400
accgccgccg ggatcactct cggcatggac gagctgtaca agtgaacctt tggcgtaaca    8460
ggaaacagct atgacgggcc ccctaggacg ttcccatagc tccttttgat gtcttaatgt    8520
aggttcaaca gatatgcggc ttcttcgcat tctgatggcg tcagctacga taggcgagag    8580
ctgaatagtt gaaattttt agcagatgcc tgagaaaatt aaacttgatt tgattccagt    8640
aatttaccaa aatacgcaca gttgccttct tcgatgtaat cttttcaatc gtactatgtc    8700
gtatgcagtt agcaaatgaa agtagcaaca ccaatttgcg ccagaatttc acgtcgaaaa    8760
tatccttaaa ccttgcaagc caagttacgg agttgaaatt ccgtaagct acggttatct    8820
tccaatggcc catacttggc taaatcagag ttccctttcg tggaaactgc aatagccaaa    8880
ttcctcgaga aagaatcaaa gaggccaaca acgcagaaca ggaaacagct atgacgggcc    8940
ccctaggacg ttcccatagc tccttttgat gtcttaatgt aggttcaaca gatatgcggc    9000
ttcttcgcat tctgatggcg tcagctacga taggcgagag ctgaatagtt gaaattttt    9060
agcagatgcc tgagaaaatt aaacttgatt tgattccagt aatttaccaa aatacgcaca    9120
gttgccttct tcgatgtaat cttttcaatc gtactatgtc gtatgcagtt agcaaatgaa    9180
agtagcaaca ccaatttgcg ccagaatttc acgtcgaaaa tatccttaaa ccttgcaagc    9240
caagttacgg agttgaaatt ccgtaagct acggttatct tccaatggcc catacttggc    9300
taaatcagag ttccctttcg tggaaactgc aatagccaaa ttcctcgaga aagaatcaaa    9360
gaggccaaca acgacctgag taggtctgtg ccttctagtt gccagccatc tgttgtttgc    9420
ccctccccg tgccttcctt gaccctggaa ggtgccactc ccactgtcct ttcctaataa    9480
aatgaggaaa ttgcatcgca ttgtctgagt aggtgtcatt ctattctggg gggtggggtg    9540
gggcaggaca gcaagggga ggattgggaa gagaatagca ggcatgctgg ggatgcggtg    9600
ggctctatgg tacg                                                     9614
```

<210> SEQ ID NO 8
<211> LENGTH: 11977
<212> TYPE: DNA
<213> ORGANISM: Artificial Sequence
<220> FEATURE:
<223> OTHER INFORMATION: Synthetic Polynucleotide

<400> SEQUENCE: 8

```
agacacctcg agacccaata aaagatcttt attttcatta gatctgtgtg ttggtttttt     60
gtgtgtctag agtgtgggtg tgggcgttgt cctgcagggg aattgaacag gtgtaaaatt    120
ggagggacaa gacttcccac agattttcgg ttttgtcggg aagttttta atagggggcaa    180
ataaggaaaa tgggaggata ggtagtcatc tggggtttta tgcagcaaaa ctacaggtta    240
ttattgcttg tgatccgcct cggagtattt tccatcgagg tagattaaag acatgctcac    300
ccgagttta tactctcctg cttgagatcc ttactacagt atgaaattac agtgtcgcga    360
```

```
gttagactat gtaagcagaa ttttaatcat ttttaaagag cccagtactt catatccatt    420
tctcccgctc cttctgcagc cttatcaaaa ggtattttag aacactcatt ttagccccat    480
tttcatttat tatactggct tatccaaccc ctagacagag cattggcatt ttcccttttcc   540 tgatcttaga agtctgatga ctcatgaaac cagacagatt accctgttat ccctagaatt    600
cagcttggga taaaaagcta tggcataggc ggtaatacgg ttatccacag aatcagggga    660
taacgcagga aagaacatgt gagcaaaagg ccagcaaaag gccaggaacc gtaaaaaggc    720
cgcgttgctg gcgttttttcc ataggctccg cccccctgac gagcatcaca aaaatcgacg    780
ctcaagtcag aggtggcgaa acccgacagg actataaaga taccaggcgt ttccccctgg    840
aagctccctc gtgcgctctc ctgttccgac cctgccgctt accggatacc tgtccgcctt    900
tctcccttcg ggaagcgtgg cgctttctca tagctcacgc tgtaggtatc tcagttcggt    960
gtaggtcgtt cgctccaagc tgggctgtgt gcacgaaccc cccgttcagc ccgaccgctg   1020
cgccttatcc ggtaactatc gtcttgagtc aacccggta  agacgact atcgccact  1080 ggcagcagcc actggtaaca ggattagcag agcgaggtat gtaggcggtg ctacagagtt   1140
cttgaagtgg tggcctaact acggctacac tagaagaaca gtatttggta tctgcgctct   1200
gctgaagcca gttaccttcg gaaaaagagt tggtagctct tgatccggca aacaaaccac   1260
cgctggtagc ggtggttttt ttgtttgcaa gcagcagatt acgcgcagaa aaaaaggatc   1320
tcaagaagat cctttgatct tttctacggg gtctgacgct cagtggaacg aaaactcacg   1380
ttaagggatt ttggtcatga gattatcaaa aaggatcttc acctagatcc ttttaaatta   1440
aaaatgaagt tttaaatcaa tctaaagtat atatgagtaa acttggtctg acagttacca   1500
atgcttaatc agtgaggcac ctatctcagc gatctgtcta tttcgttcat ccatagttgc   1560
ctgactcccc gtcgtgtaga taactacgat acgggagggc ttaccatctg gccccagtgc   1620
tgcaatgata ccgcgagatc cacgctcacc ggctccagat ttatcagcaa taaaccagcc   1680
agccggaagg gccgagcgca gaagtggtcc tgcaacttta tccgcctcca tccagtctat   1740
taattgttgc cgggaagcta gagtaagtag ttcgccagtt aatagtttgc gcaacgttgt   1800
tgccattgct acaggcatcg tggtgtcacg ctcgtcgttt ggtatggctt cattcagctc   1860
cggttcccaa cgatcaaggc gagttacatg atcccccatg ttgtgcaaaa aagcggttag   1920
ctccttcggt cctccgatcg ttgtcagaag taagttggcc gcagtgttat cactcatggt   1980
tatggcagca ctgcataatt ctcttactgt catgccatcc gtaagatgct tttctgtgac   2040
tggtgagtac tcaaccaagt cattctgaga atagtgtatg cggcgaccga gttgctcttg   2100
cccggcgtca atacgggata ataccgcgcc acatagcaga actttaaaag tgctcatcat   2160
tggaaaacgt tcttcgggc gaaaactctc aaggatctta ccgctgttga tccagttc    2220 gatgtaaccc actcgtgcac ccaactgatc ttcagcatct tttactttca ccagcgtttc   2280
tgggtgagca aaaacaggaa ggcaaaatgc cgcaaaaaag gaataagggc gacacggaa    2340 atgttgaata ctcatactct tcctttttca atattattga agcatttatc agggttattg   2400
tctcatgagc ggatacatat ttgaatgtat ttagaaaaat aaacaaatag gggtgattta   2460
atctgtatca ggggcgtata gtggagcaaa gcgaattcta actataacgg tcctaaggta   2520
gcgaaggccc tcccctcggc cccgcgccgc agagtctggc cgcgcgcccc tgcgcaacgt   2580
ggcaggaagc gcgcgctggg ggcggggacg ggcagtaggg ctgagcggct gcggggcggg   2640
tgcaagcacg tttccgactt gagttgcctc aagagggggcg tgctgagcca gacctccatc   2700
```

```
gcgcactccg gggagtggag ggaaggagcg agggctcagt tgggctgttt tggaggcagg    2760
aagcacttgc tctcccaaag tcgctctgag ttgttatcag taaggagct gcagtggagt    2820 aggcggggag aaggccgcac ccttctccgg agggggagg ggagtgttgc aatacctttc    2880
tgggagttct ctgctgcctc ctggcttctg aggaccgccc tgggcctggg agaatccctt    2940 cccctcttc cctcgtgatc tgcaactcca gtctttctag aagatgggcg ggagtctttt    3000
gggcaggctt aaaggctaac ctggttaggg cgcagtagtc cagggtttcc ttgatgatgt    3060
catacttatc ctgtcccttt ttttttccaca gctcgcggtt gaggacaaac tcttcgcggt    3120
ctttccagtg ttgacaatta atcatcggca tagtatatcg gcatagtata atacgacaag    3180
gtgaggaacg ccaccatgat tgaacaagat ggattgcacg caggttctcc ggccgcttgg    3240
gtggagaggc tattcggcta tgactgggca acagacaa tcggctgctc tgatgccgcc    3300
gtgttccggc tgtcagcgca ggggcgcccg gttcttttg tcaagaccga cctgtccggt    3360
gccctgaatg aactgcaaga cgaggcagcg cggctatcgt ggctggccac gacgggcgtt    3420
ccttgcgcag ctgtgctcga cgttgtcact gaagcgggaa gggactggct gctattgggc    3480
gaagtgccgg ggcaggatct cctgtcatct caccttgctc ctgccgagaa agtatccatc    3540
atggctgatg caatgcggcg gctgcatacg cttgatccgg ctacctgccc attcgaccac    3600
caagcgaaac atcgcatcga gcgagcacgt actcggatgg aagccggtct tgtcgatcag    3660
gatgatctgg acgaagagca tcaggggctc gcgccagccg aactgttcgc caggctcaag    3720
gcgagcatgc ccgacggcga ggatctcgtc gtgacccatg gcgatgcctg cttgccgaat    3780
atcatggtgg aaaatggccg cttttctgga ttcatcgact gtggccggct gggtgtggcg    3840
gaccgctatc aggacatagc gttggctacc cgtgatattg ctgaagagct tggcggcgaa    3900
tgggctgacc gcttcctcgt gctttacggt atcgccgctc ccgattcgca gcgcatcgcc    3960
ttctatcgcc ttcttgacga gttcttctga tgtacaagta aagcggccgc gactctagat    4020
cataatcagc cataccacat ttgtagaggt tttacttgct ttaaaaaacc tcccacacct    4080
ccccctgaac ctgaaacata aaatgaatgc aattgttgtt gttaacttgt ttattgcagc    4140
ttataatggt tacaaataaa gcaatagcat cacaaatttc acaaataaag catttttttc    4200
actgcattct agttgtggtt tgtccaaact catcaatgta tcttaggtct cgcgtactgt    4260
cgtactgtcg taggtttgtc tggtcaacca ccgcgttctc agtggtgtac ggtacaaacc    4320
acctcagaag gtggtttgta ccgtacacca ctgagaacgc ggtggttgac cagacaaacc    4380
tacggtagcg taacaggaaa cagctatgac gggccccta ggcacattgc gtctttataa    4440
acttactaaa ggttttggat agttttgaac ccattgtttg acgaatattc catattaaaa    4500
actctaaaat aaaccccagc caccaacatt tgaaccagcg ttccccccat ctccgctgtg    4560
atcattctag atctgtatta tggcatcgac tatgggaata cagggttatt ctcccatttt    4620
attgaggtat atggccagtt gcgcaacttc tttgatgaaa ttttatttgt ccgttgcatg    4680
attgaaatcc taccagtagt tatatatatg tcttttcat tgttgtactt tggataaagc    4740
tgcttcttca gaacgctccc tactatgctt taaacgctta ttttcggaag aaatcatgtg    4800
ggtcatattt ttttgcttct cgagaaagaa tcaaagaggc caacaacgca gaacaggaaa    4860
cagctatgac gggccccta ggcacattgc gtctttataa acttactaaa ggttttggat    4920
agttttgaac ccattgtttg acgaatattc catattaaaa actctaaaat aaaccccagc    4980
caccaacatt tgaaccagcg ttccccccat ctccgctgtg atcattctag atctgtatta    5040
tggcatcgac tatgggaata cagggttatt ctcccatttt attgaggtat atggccagtt    5100
```

```
gcgcaacttc tttgatgaaa ttttatttgt ccgttgcatg attgaaatcc taccagtagt    5160
tatatatatg tcttttttcat tgttgtactt tggataaagc tgcttcttca gaacgctccc    5220
tactatgctt taaacgctta ttttcggaag aaatcatgtg ggtcatattt ttttgcttct    5280
cgagaaagaa tcaaagaggc caacaacgac ctggttcgta ggcttgtcga cgacggcgtt    5340
ctccgtcgtc aggatcatac ctagacacct cagaaggtcc tccctttagt gagggttaat    5400
tctcgagtct ccctatagtg agtcgtatta attccgtgta ttctatagtg tcacctaaat    5460
cgttacggta gcgtactgtc gtaggtttgt ctggtcaacc accgcgctct cagtggtgta    5520
cggtacaaac cacctcagaa ggtggtttgt accgtacacc actgagagcg cggtggttga    5580
ccagacaaac ctacggtagc gtaacaggaa acagctatga cgggccccct aggggggttct    5640 gacttcttac gaaaatgtgg ctagcattcc attctctgac gttcaaagaa tcggaataag    5700
tcatggtaat ggtgggaaat ctaatagaag cgactcccat aacctccata tttcttggca    5760
aataattctg tctgggttac cgttcacgag ccttcagaga tctacgacgt gtagtgggtg    5820
ggcttgccct ccagggtgta gtttgtaatt agaatgggat ttcctgtttt aagtacccaa    5880
atacgaaaat tgctcttgat gtttaacggc tcacttttaa gtaaagtttg tgccaatacc    5940
gtgcatggga gtaagttatt gccaatcttc gagaatttag gcaattttgg tatactcaac    6000
tgggtctaat atggtggacg gaatgatttc tcgagaaaga atcaaagagg ccaacaacgc    6060
agaacaggaa acagctatga cgggccccct aggggggttct gacttcttac gaaaatgtgg    6120
ctagcattcc attctctgac gttcaaagaa tcggaataag tcatggtaat ggtgggaaat    6180
ctaatagaag cgactcccat aacctccata tttcttggca aataattctg tctgggttac    6240
cgttcacgag ccttcagaga tctacgacgt gtagtgggtg ggcttgccct ccagggtgta    6300
gtttgtaatt agaatgggat ttcctgtttt aagtacccaa atacgaaaat tgctcttgat    6360
gtttaacggc tcacttttaa gtaaagtttg tgccaatacc gtgcatggga gtaagttatt    6420
gccaatcttc gagaatttag gcaattttgg tatactcaac tgggtctaat atggtggacg    6480
gaatgatttc tcgagaaaga atcaaagagg ccaacaacga cctggttcgt aggcttgtcg    6540
acgacggcgc tctccgtcgt caggatcata cctagacacc tggttaggtc ctccctttag    6600
tgagggttaa ttctcgagtc tccctatagt gagtcgtatt aattccgtgt attctatagt    6660
gtcacctaaa tcgttacgtt ggcgtactgt cgtaggtttg tctggtcaac caccgcgcac    6720
tcagtggtgt acggtacaaa ccacctcaga aggtggtttg taccgtacac cactgagtgc    6780
gcggtggttg accagacaaa cctacggtag cgtaacagga acagctatg acgggccccc    6840 taggtaagca gtatcttcga cagcttgtct ctccagatgc tcttgggcca tcttccacat    6900
cgtccgtagc agccttggca atttgccatc actggcaaat acacataaat ccaatgaata    6960
cggttaccac catcacatta ccatgcaggt acacagcaag aattgacgtt ggcatatcac    7020
atggtgtaat aaccccactt gtgaaacaac ccagaataag gtacaaggcg gaaatgtcgt    7080
cattctaaaa taaaggcat ggccaggaat ttgtctaata ccgggaactt aaattcagct    7140
tgaacaccag tcgcaaaaaa ttcaaagaaa gtgattcagg ttcgggttcg tggattggaa    7200
cagcttcttt tgtttcagtg atgagagaat cctcctgtca ctcgagaaag aatcaaagag    7260
gccaacaacg cagaacagga acagctatg acgggccccc taggtaagca gtatcttcga    7320
cagcttgtct ctccagatgc tcttgggcca tcttccacat cgtccgtagc agccttggca    7380
atttgccatc actggcaaat acacataaat ccaatgaata cggttaccac catcacatta    7440
```

```
ccatgcaggt acacagcaag aattgacgtt ggcatatcac atggtgtaat aaccccactt    7500
gtgaaacaac ccagaataag gtacaaggcg gaaatgtcgt cattctaaaa taaaaggcat    7560
ggccaggaat tgtctaata ccgggaactt aaattcagct tgaacaccag tcgcaaaaaa     7620
ttcaaagaaa gtgattcagg ttcgggttcg tggattggaa cagcttcttt tgtttcagtg    7680
atgagagaat cctcctgtca ctcgagaaag aatcaaagag gccaacaacg acctggttcg    7740
taggcttgtc gacgacggcg cactccgtcg tcaggatcat acctagacac ctgagtaggt    7800
cctcccttta gtgagggtta attctcgagt ctccctatag tgagtcgtat taattccgtg    7860
tattctatag tgtcacctaa atcgttacgg ctacgtaaat tctgcaggac ttctagttat    7920
taatagtaat caattacggg gtcattagtt catagcccat atatggagtt ccgcgttaca    7980
taacttacgg taaatggccc gcctggctga ccgcccaacg acccccgccc attgacgtca    8040
ataatgacgt atgttcccat agtaacgcca atagggactt tccattgacg tcaatgggtg    8100
gagtatttac ggtaaactgc ccacttggca gtacatcaag tgtatcatat gccaagtacg    8160
ccccctattg acgtcaatga cggtaaatgg cccgcctggc attatgccca gtacatgacc    8220
ttatgggact ttcctacttg gcagtacatc tacgtattag tcatcgctat taccatggtc    8280
gaggtgagcc ccacgttctg cttcactctc cccatctccc cccctccccc accccaatt     8340 ttgtatttat ttattttta attattttgt gcagcgatgg gggcgggggg gggggggggg    8400
cgcgcgccag gcggggcggg gcggggcgag gggcggggcg gggcgaggcg gagaggtgcg    8460
gcggcagcca atcagagcgg cgcgctccga aagtttcctt ttatggcgag gcggcggcgg    8520
cggcggccct ataaaaagcg aagcgcgcgg cgggcgggag tcgctgcgcg ctgccttcgc    8580
cccgtgcccc gctccgccgc cgcctcgcgc cgcccgcccc ggctctgact gaccgcgtta    8640
ctcccacagg tgagcgggcg ggacggccct tctcctccgg gctgtaatta gcgcttggtt    8700
taatgacggc ttgtttcttt tctgtggctg cgtgaaagcc ttgaggggct ccgggagggc    8760
cctttgtgcg gggggagcgg ctcggggggt gcgtgcgtgt gtgtgtgcgt ggggagcgcc    8820
gcgtgcggct ccgcgctgcc cggcggctgt gagcgctgcg ggcgcggcgc ggggctttgt    8880
gcgctccgca gtgtgcgcga ggggagcgcg gccgggggcg gtgccccgcg gtgcgggggg    8940
gctgcgaggg gaacaaaggc tgcgtgcggg gtgtgtgcgt gggggggtga gcaggggtg     9000 tgggcgcgtc ggtcgggctg caacccccc ctgcaccccc ctccccgagt tgctgagcac     9060
ggcccggctt cgggtgcggg gctccgtacg gggcgtggcg cggggctcgc cgtgccgggc    9120
ggggggtggc ggcaggtggg ggtgccggc ggggcgggc cgcctcgggc cggggagggc     9180 tcggggagg ggcgcggcgg ccccccggagc gccggcggct gtcgaggcgc ggcgagccgc    9240
agccattgcc ttttatggta atcgtgcgag agggcgcagg gacttccttt gtcccaaatc    9300
tgtgcggagc cgaaatctgg gaggcgccgc cgcacccccct ctagcgggcg cggggcgaag   9360
cggtgcggcg ccggcaggaa ggaaatgggc ggggagggcc ttcgtgcgtc gccgcgccgc    9420
cgtccccttc tccctctcca gcctcgggcc tgtccgcggg gggacggctg ccttcggggg   9480
ggacggggca gggcggggtt cggcttctgg cgtgtgaccg gcggctctag agcctctgct    9540
aaccatgttc atgccttctt cttttttccta cagctcctgg gcaacgtgct ggttattgtg    9600
ctgtctcatc attttggcaa agaattgatt tgataccgcg ggcccgggat cccctcgagg    9660
gaattacctg aaccgtagcc gccaccatgc cagagccagc gaagtctgct cccgccccga    9720 aaagggctc caagaaggcg gtgactaagg cgcagaagaa aggcggcaag aagcgcaagc    9780
gcagccgcaa ggagagctat tccatctatg tgtacaaggt tctgaagcag gtccacccetg    9840
```

```
acaccggcat tcgtccaag gccatgggca tcatgaattc gtttgtgaac gacattttcg    9900
agcgcatcgc tggtgaggct tcccgcctgg cgcattacaa caagcgctcg accatcacct    9960
ccagggagat ccagacggcc gtgcgcctgc tgctgcctgg ggagttggcc aagcacgccg   10020
tgtccgaggg tactaaggcc atcaccaagt acaccagcgc taaggatccc cgggtaccgg   10080
tcgccaccat ggtgagcaag ggcgaggagc tgttcaccgg ggtggtgccc atcctggtcg   10140
agctggacgg cgacgtaaac ggccacaagt tcagcgtgtc cggcgagggc gagggcgatg   10200
ccacctacgg caagctgacc ctgaagttca tctgcaccac cggcaagctg cccgtgccct   10260
ggcccaccct cgtgaccacc ctgacctggg gcgtgcagtg cttcgcccgc taccccgacc   10320
acatgaagca gcacgacttc ttcaagtccg ccatgcccga aggctacgtc caggagcgca   10380
ccatcttctt caaggacgac ggcaactaca agacccgcgc cgaggtgaag ttcgagggcg   10440
acaccctggt gaaccgcatc gagctgaagg gcatcgactt caaggaggac ggcaacatcc   10500
tggggcacaa gctggagtac aacgccatca gcgacaacgt ctatatcacc gccgacaagc   10560
agaagaacgg catcaaggcc aacttcaaga tccgccacaa catcgaggac ggcagcgtgc   10620
agctcgccga ccactaccag cagaacaccc ccatcggcga cggccccgtg ctgctgcccg   10680
acaaccacta cctgagcacc cagtccaagc tgagcaaaga ccccaacgag aagcgcgatc   10740
acatggtcct gctggagttc gtgaccgccg ccgggatcac tctcggcatg gacgagctgt   10800
acaagtgaac ctccttcgta acaggaaaca gctatgacgg gccccctagg acgttcccat   10860
agctcctttt gatgtcttaa tgtaggttca acagatatgc ggcttcttcg cattctgatg   10920
gcgtcagcta cgataggcga gagctgaata gttgaaaatt tttagcagat gcctgagaaa   10980
attaaacttg atttgattcc agtaatttac caaaatacgc acagttgcct tcttcgatgt   11040
aatcttttca atcgtactat gtcgtatgca gttagcaaat gaaagtagca acaccaattt   11100
gcgccagaat ttcacgtcga aaatatcctt aaaccttgca agccaagtta cggagttgaa   11160
atttccgtaa gctacggtta tcttccaatg gcccatactt ggctaaatca gagttccctt   11220
tcgtggaaac tgcaatagcc aaattcctcg agaaagaatc aaagaggcca acaacgcaga   11280
acaggaaaca gctatgacgg gccccctagg acgttcccat agctcctttt gatgtcttaa   11340
tgtaggttca acagatatgc ggcttcttcg cattctgatg gcgtcagcta cgataggcga   11400
gagctgaata gttgaaaatt tttagcagat gcctgagaaa attaaacttg atttgattcc   11460
agtaatttac caaaatacgc acagttgcct tcttcgatgt aatcttttca atcgtactat   11520
gtcgtatgca gttagcaaat gaaagtagca acaccaattt gcgccagaat ttcacgtcga   11580
aaatatcctt aaaccttgca agccaagtta cggagttgaa atttccgtaa gctacggtta   11640
tcttccaatg gcccatactt ggctaaatca gagttccctt tcgtggaaac tgcaatagcc   11700
aaattcctcg agaaagaatc aaagaggcca acaacgacct cttgaggtct gtgccttcta   11760
gttgccagcc atctgttgtt tgcccctccc ccgtgccttc cttgaccctg aaggtgcca   11820
ctcccactgt cctttcctaa taaaatgagg aaattgcatc gcattgtctg agtaggtgtc   11880
attctattct gggggtggg gtggggcagg acagcaaggg ggaggattgg gaagagaata   11940
gcaggcatgc tggggatgcg gtgggctcta tggtacg                           11977
```

<210> SEQ ID NO 9
<211> LENGTH: 20
<212> TYPE: DNA
<213> ORGANISM: Artificial Sequence
<220> FEATURE:

<223> OTHER INFORMATION: Synthetic Oligonucleotide

<400> SEQUENCE: 9
cgtggattgg aacagcttct                                        20

<210> SEQ ID NO 10
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 10
agcttgaaca ccagtcgcaa                                        20

<210> SEQ ID NO 11
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 11
gcatggccag gaatttgtct                                        20

<210> SEQ ID NO 12
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 12
cgtggattgg aacagcttct tatagcattc tttcttgagg agggcagcaa acgggaagag    60

<210> SEQ ID NO 13
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 13
agcttgaaca ccagtcgcaa tataagctca gtccatcctc gtaaatcctc atcaatcatc    60

<210> SEQ ID NO 14
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 14
gcatggccag gaatttgtct tataaaagtc taatccgtcc ctgcctctat atctccactc    60

<210> SEQ ID NO 15
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 15
cgtggattgg aacagcttct tatagcattc tttcttgagg agggcagcaa acgggaagag    60

```
<210> SEQ ID NO 16
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 16
cgtggatcgg aacagcttct tataagctca gtccatcctc gtaaatcctc atcaatcatc    60

<210> SEQ ID NO 17
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 17
cgtggatggg aacagcttct tataaaagtc taatccgtcc ctgcctctat atctccactc    60

<210> SEQ ID NO 18
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 18
cgtggatagg aacagcttct tatacacatt tacagacctc aacctacctc caactctcac    60

<210> SEQ ID NO 19
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 19
cgtggattgg aacagcttct tataagctca gtccatcctc gtaaatcctc atcaatcatc    60

<210> SEQ ID NO 20
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 20
cgtggatcgg aacagcttct tataaaagtc taatccgtcc ctgcctctat atctccactc    60

<210> SEQ ID NO 21
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 21
cgtggatggg aacagcttct tatacacatt tacagacctc aacctacctc caactctcac    60

<210> SEQ ID NO 22
<211> LENGTH: 60
<212> TYPE: DNA
<213> ORGANISM: Artificial Sequence
<220> FEATURE:
<223> OTHER INFORMATION: Synthetic Polynucleotide
```

<400> SEQUENCE: 22
cgtggatagg aacagcttct tatagcattc tttcttgagg agggcagcaa acgggaagag    60

<210> SEQ ID NO 23
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 23
cgtggattgg aacagcttct tataaaagtc taatccgtcc ctgcctctat atctccactc    60

<210> SEQ ID NO 24
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 24
cgtggatcgg aacagcttct tatacacatt tacagacctc aacctacctc caactctcac    60

<210> SEQ ID NO 25
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 25
cgtggatggg aacagcttct tatagcattc tttcttgagg agggcagcaa acgggaagag    60

<210> SEQ ID NO 26
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 26
cgtggatagg aacagcttct tataagctca gtccatcctc gtaaatcctc atcaatcatc    60

<210> SEQ ID NO 27
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 27
cgtggattgg aacagcttct tatacacatt tacagacctc aacctacctc caactctcac    60

<210> SEQ ID NO 28
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 28
cgtggatcgg aacagcttct tatagcattc tttcttgagg agggcagcaa acgggaagag    60

<210> SEQ ID NO 29
<211> LENGTH: 60

```
<212> TYPE: DNA
<213> ORGANISM: Artificial Sequence
<220> FEATURE:
<223> OTHER INFORMATION: Synthetic Polynucleotide

<400> SEQUENCE: 29
cgtggatggg aacagcttct tataagctca gtccatcctc gtaaatcctc atcaatcatc        60

<210> SEQ ID NO 30
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 30
cgtggatagg aacagcttct tataaaagtc taatccgtcc ctgcctctat atctccactc        60

<210> SEQ ID NO 31
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 31
cgtggattgg aacagcttct tatagcattc tttcttgagg agggcagcaa acgggaagag        60

<210> SEQ ID NO 32
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 32
cgtggattgc aacagcttct tataagctca gtccatcctc gtaaatcctc atcaatcatc        60

<210> SEQ ID NO 33
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 33
cgtggattgt aacagcttct tataaaagtc taatccgtcc ctgcctctat atctccactc        60

<210> SEQ ID NO 34
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 34
cgtggattga aacagcttct tatacacatt tacagacctc aacctacctc caactctcac        60

<210> SEQ ID NO 35
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 35
```
cgtggattgg aacagcttct tataagctca gtccatcctc gtaaatcctc atcaatcatc    60

<210> SEQ ID NO 36
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 36
cgtggattgc aacagcttct tataaaagtc taatccgtcc ctgcctctat atctccactc    60

<210> SEQ ID NO 37
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 37
cgtggattgt aacagcttct tatacacatt tacagacctc aacctacctc caactctcac    60

<210> SEQ ID NO 38
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 38
cgtggattga aacagcttct tatagcattc tttcttgagg agggcagcaa acgggaagag    60

<210> SEQ ID NO 39
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 39
cgtggattgg aacagcttct tataaaagtc taatccgtcc ctgcctctat atctccactc    60

<210> SEQ ID NO 40
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 40
cgtggattgc aacagcttct tatacacatt tacagacctc aacctacctc caactctcac    60

<210> SEQ ID NO 41
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 41
cgtggattgt aacagcttct tatagcattc tttcttgagg agggcagcaa acgggaagag    60

<210> SEQ ID NO 42
<211> LENGTH: 60
<212> TYPE: DNA
<213> ORGANISM: Artificial Sequence

```
<220> FEATURE:
<223> OTHER INFORMATION: Synthetic Polynucleotide

<400> SEQUENCE: 42
cgtggattga aacagcttct tataagctca gtccatcctc gtaaatcctc atcaatcatc    60

<210> SEQ ID NO 43
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 43
cgtggattgg aacagcttct tatacacatt tacagacctc aacctacctc caactctcac    60

<210> SEQ ID NO 44
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 44
cgtggattgc aacagcttct tatagcattc tttcttgagg agggcagcaa acgggaagag    60

<210> SEQ ID NO 45
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 45
cgtggattgt aacagcttct tataagctca gtccatcctc gtaaatcctc atcaatcatc    60

<210> SEQ ID NO 46
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 46
cgtggattga aacagcttct tataaaagtc taatccgtcc ctgcctctat atctccactc    60

<210> SEQ ID NO 47
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 47
cgtggattgg aacagcttct tatagcattc tttcttgagg agggcagcaa acgggaagag    60

<210> SEQ ID NO 48
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 48
cgtggattgg aaaagcttct tataagctca gtccatcctc gtaaatcctc atcaatcatc    60
```

```
<210> SEQ ID NO 49
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 49
cgtggattgg aagagcttct tataaaagtc taatccgtcc ctgcctctat atctccactc    60

<210> SEQ ID NO 50
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 50
cgtggattgg aatagcttct tatacacatt tacagacctc aacctacctc caactctcac    60

<210> SEQ ID NO 51
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 51
cgtggattgg aacagcttct tataagctca gtccatcctc gtaaatcctc atcaatcatc    60

<210> SEQ ID NO 52
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 52
cgtggattgg aaaagcttct tataaaagtc taatccgtcc ctgcctctat atctccactc    60

<210> SEQ ID NO 53
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 53
cgtggattgg aagagcttct tatacacatt tacagacctc aacctacctc caactctcac    60

<210> SEQ ID NO 54
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 54
cgtggattgg aatagcttct tatagcattc tttcttgagg agggcagcaa acgggaagag    60

<210> SEQ ID NO 55
<211> LENGTH: 60
<212> TYPE: DNA
<213> ORGANISM: Artificial Sequence
<220> FEATURE:
<223> OTHER INFORMATION: Synthetic Polynucleotide
```

<400> SEQUENCE: 55
cgtggattgg aacagcttct tataaaagtc taatccgtcc ctgcctctat atctccactc    60

<210> SEQ ID NO 56
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 56
cgtggattgg aaaagcttct tatacacatt tacagacctc aacctacctc caactctcac    60

<210> SEQ ID NO 57
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 57
cgtggattgg aagagcttct tatagcattc tttcttgagg agggcagcaa acgggaagag    60

<210> SEQ ID NO 58
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 58
cgtggattgg aatagcttct tataagctca gtccatcctc gtaaatcctc atcaatcatc    60

<210> SEQ ID NO 59
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 59
cgtggattgg aacagcttct tatacacatt tacagacctc aacctacctc caactctcac    60

<210> SEQ ID NO 60
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 60
cgtggattgg aaaagcttct tatagcattc tttcttgagg agggcagcaa acgggaagag    60

<210> SEQ ID NO 61
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 61
cgtggattgg aagagcttct tataagctca gtccatcctc gtaaatcctc atcaatcatc    60

<210> SEQ ID NO 62

```
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 62
cgtggattgg aatagcttct tataaaagtc taatccgtcc ctgcctctat atctccactc    60

<210> SEQ ID NO 63
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 63
cgtggattgg aacagcttct tatagcattc tttcttgagg agggcagcaa acgggaagag    60

<210> SEQ ID NO 64
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 64
cgtggattgg cacagcttct tataagctca gtccatcctc gtaaatcctc atcaatcatc    60

<210> SEQ ID NO 65
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 65
cgtggattgg gacagcttct tataaaagtc taatccgtcc ctgcctctat atctccactc    60

<210> SEQ ID NO 66
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 66
cgtggattgg tacagcttct tatacacatt tacagacctc aacctacctc caactctcac    60

<210> SEQ ID NO 67
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 67
cgtggattgg aacagcttct tataagctca gtccatcctc gtaaatcctc atcaatcatc    60

<210> SEQ ID NO 68
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 68
```

```
cgtggattgg cacagcttct tataaaagtc taatccgtcc ctgcctctat atctccactc    60

<210> SEQ ID NO 69
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 69
cgtggattgg gacagcttct tatacacatt tacagacctc aacctacctc caactctcac    60

<210> SEQ ID NO 70
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 70
cgtggattgg tacagcttct tatagcattc tttcttgagg agggcagcaa acgggaagag    60

<210> SEQ ID NO 71
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 71
cgtggattgg aacagcttct tataaaagtc taatccgtcc ctgcctctat atctccactc    60

<210> SEQ ID NO 72
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 72
cgtggattgg cacagcttct tatacacatt tacagacctc aacctacctc caactctcac    60

<210> SEQ ID NO 73
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 73
cgtggattgg gacagcttct tatagcattc tttcttgagg agggcagcaa acgggaagag    60

<210> SEQ ID NO 74
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 74
cgtggattgg tacagcttct tataagctca gtccatcctc gtaaatcctc atcaatcatc    60

<210> SEQ ID NO 75
<211> LENGTH: 60
<212> TYPE: DNA
```

<213> ORGANISM: Artificial Sequence
<220> FEATURE:
<223> OTHER INFORMATION: Synthetic Polynucleotide

<400> SEQUENCE: 75
cgtggattgg aacagcttct tatacacatt tacagacctc aacctacctc caactctcac    60

<210> SEQ ID NO 76
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 76
cgtggattgg cacagcttct tatagcattc tttcttgagg agggcagcaa acgggaagag    60

<210> SEQ ID NO 77
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 77
cgtggattgg gacagcttct tataagctca gtccatcctc gtaaatcctc atcaatcatc    60

<210> SEQ ID NO 78
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 78
cgtggattgg tacagcttct tataaaagtc taatccgtcc ctgcctctat atctccactc    60

<210> SEQ ID NO 79
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 79
agtggattgg aacagcttct tataagctca gtccatcctc gtaaatcctc atcaatcatc    60

<210> SEQ ID NO 80
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 80
cctggattgg aacagcttct tataagctca gtccatcctc gtaaatcctc atcaatcatc    60

<210> SEQ ID NO 81
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 81
cgcggattgg aacagcttct tataagctca gtccatcctc gtaaatcctc atcaatcatc    60

<210> SEQ ID NO 82
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 82
cgtcgattgg aacagcttct tataagctca gtccatcctc gtaaatcctc atcaatcatc    60

<210> SEQ ID NO 83
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 83
cgtgcattgg aacagcttct tataagctca gtccatcctc gtaaatcctc atcaatcatc    60

<210> SEQ ID NO 84
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 84
cgtggcttgg aacagcttct tataagctca gtccatcctc gtaaatcctc atcaatcatc    60

<210> SEQ ID NO 85
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 85
cgtggactgg aacagcttct tataagctca gtccatcctc gtaaatcctc atcaatcatc    60

<210> SEQ ID NO 86
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 86
ggtggattgg aacagcttct tataaaagtc taatccgtcc ctgcctctat atctccactc    60

<210> SEQ ID NO 87
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 87
cttggattgg aacagcttct tataaaagtc taatccgtcc ctgcctctat atctccactc    60

<210> SEQ ID NO 88
<211> LENGTH: 60
<212> TYPE: DNA
<213> ORGANISM: Artificial Sequence
<220> FEATURE:

<223> OTHER INFORMATION: Synthetic Polynucleotide

<400> SEQUENCE: 88
cggggattgg aacagcttct tataaaagtc taatccgtcc ctgcctctat atctccactc    60

<210> SEQ ID NO 89
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 89
cgttgattgg aacagcttct tataaaagtc taatccgtcc ctgcctctat atctccactc    60

<210> SEQ ID NO 90
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 90
cgtgtattgg aacagcttct tataaaagtc taatccgtcc ctgcctctat atctccactc    60

<210> SEQ ID NO 91
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 91
cgtggtttgg aacagcttct tataaaagtc taatccgtcc ctgcctctat atctccactc    60

<210> SEQ ID NO 92
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 92
cgtggagtgg aacagcttct tataaaagtc taatccgtcc ctgcctctat atctccactc    60

<210> SEQ ID NO 93
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 93
tgtggattgg aacagcttct tatacacatt tacagacctc aacctacctc caactctcac    60

<210> SEQ ID NO 94
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 94
catggattgg aacagcttct tatacacatt tacagacctc aacctacctc caactctcac    60

```
<210> SEQ ID NO 95
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 95
cgaggattgg aacagcttct tatacacatt tacagacctc aacctacctc caactctcac    60

<210> SEQ ID NO 96
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 96
cgtagattgg aacagcttct tatacacatt tacagacctc aacctacctc caactctcac    60

<210> SEQ ID NO 97
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 97
cgtgaattgg aacagcttct tatacacatt tacagacctc aacctacctc caactctcac    60

<210> SEQ ID NO 98
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 98
cgtgggttgg aacagcttct tatacacatt tacagacctc aacctacctc caactctcac    60

<210> SEQ ID NO 99
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 99
cgtggaatgg aacagcttct tatacacatt tacagacctc aacctacctc caactctcac    60

<210> SEQ ID NO 100
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 100
tgtggattgg aacagcttct tatagcattc tttcttgagg agggcagcaa acgggaagag    60

<210> SEQ ID NO 101
<211> LENGTH: 60
<212> TYPE: DNA
<213> ORGANISM: Artificial Sequence
<220> FEATURE:
<223> OTHER INFORMATION: Synthetic Polynucleotide
```

<400> SEQUENCE: 101
catggattgg aacagcttct tatagcattc tttcttgagg agggcagcaa acgggaagag    60

<210> SEQ ID NO 102
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 102
cgaggattgg aacagcttct tatagcattc tttcttgagg agggcagcaa acgggaagag    60

<210> SEQ ID NO 103
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 103
cgtagattgg aacagcttct tatagcattc tttcttgagg agggcagcaa acgggaagag    60

<210> SEQ ID NO 104
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 104
cgtgaattgg aacagcttct tatagcattc tttcttgagg agggcagcaa acgggaagag    60

<210> SEQ ID NO 105
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 105
cgtgggttgg aacagcttct tatagcattc tttcttgagg agggcagcaa acgggaagag    60

<210> SEQ ID NO 106
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 106
cgtggaatgg aacagcttct tatagcattc tttcttgagg agggcagcaa acgggaagag    60

<210> SEQ ID NO 107
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 107
agtggattgg aacagcttct tataaaagtc taatccgtcc ctgcctctat atctccactc    60

<210> SEQ ID NO 108
<211> LENGTH: 60

```
<212> TYPE: DNA
<213> ORGANISM: Artificial Sequence
<220> FEATURE:
<223> OTHER INFORMATION: Synthetic Polynucleotide

<400> SEQUENCE: 108
cctggattgg aacagcttct tataaaagtc taatccgtcc ctgcctctat atctccactc    60

<210> SEQ ID NO 109
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 109
cgcggattgg aacagcttct tataaaagtc taatccgtcc ctgcctctat atctccactc    60

<210> SEQ ID NO 110
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 110
cgtcgattgg aacagcttct tataaaagtc taatccgtcc ctgcctctat atctccactc    60

<210> SEQ ID NO 111
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 111
cgtgcattgg aacagcttct tataaaagtc taatccgtcc ctgcctctat atctccactc    60

<210> SEQ ID NO 112
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 112
cgtggcttgg aacagcttct tataaaagtc taatccgtcc ctgcctctat atctccactc    60

<210> SEQ ID NO 113
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 113
cgtggactgg aacagcttct tataaaagtc taatccgtcc ctgcctctat atctccactc    60

<210> SEQ ID NO 114
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 114
```
ggtggattgg aacagcttct tatacacatt tacagacctc aacctacctc caactctcac    60

<210> SEQ ID NO 115
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 115
cttggattgg aacagcttct tatacacatt tacagacctc aacctacctc caactctcac    60

<210> SEQ ID NO 116
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 116
cggggattgg aacagcttct tatacacatt tacagacctc aacctacctc caactctcac    60

<210> SEQ ID NO 117
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 117
cgttgattgg aacagcttct tatacacatt tacagacctc aacctacctc caactctcac    60

<210> SEQ ID NO 118
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 118
cgtgtattgg aacagcttct tatacacatt tacagacctc aacctacctc caactctcac    60

<210> SEQ ID NO 119
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 119
cgtggtttgg aacagcttct tatacacatt tacagacctc aacctacctc caactctcac    60

<210> SEQ ID NO 120
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 120
cgtggagtgg aacagcttct tatacacatt tacagacctc aacctacctc caactctcac    60

<210> SEQ ID NO 121
<211> LENGTH: 60
<212> TYPE: DNA
<213> ORGANISM: Artificial Sequence

```
<220> FEATURE:
<223> OTHER INFORMATION: Synthetic Polynucleotide

<400> SEQUENCE: 121
ggtggattgg aacagcttct tatagcattc tttcttgagg agggcagcaa acgggaagag      60

<210> SEQ ID NO 122
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 122
cttggattgg aacagcttct tatagcattc tttcttgagg agggcagcaa acgggaagag      60

<210> SEQ ID NO 123
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 123
cggggattgg aacagcttct tatagcattc tttcttgagg agggcagcaa acgggaagag      60

<210> SEQ ID NO 124
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 124
cgttgattgg aacagcttct tatagcattc tttcttgagg agggcagcaa acgggaagag      60

<210> SEQ ID NO 125
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 125
cgtgtattgg aacagcttct tatagcattc tttcttgagg agggcagcaa acgggaagag      60

<210> SEQ ID NO 126
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 126
cgtggtttgg aacagcttct tatagcattc tttcttgagg agggcagcaa acgggaagag      60

<210> SEQ ID NO 127
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 127
cgtggagtgg aacagcttct tatagcattc tttcttgagg agggcagcaa acgggaagag      60
```

<210> SEQ ID NO 128
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 128
tgtggattgg aacagcttct tataagctca gtccatcctc gtaaatcctc atcaatcatc    60

<210> SEQ ID NO 129
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 129
catggattgg aacagcttct tataagctca gtccatcctc gtaaatcctc atcaatcatc    60

<210> SEQ ID NO 130
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 130
cgaggattgg aacagcttct tataagctca gtccatcctc gtaaatcctc atcaatcatc    60

<210> SEQ ID NO 131
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 131
cgtagattgg aacagcttct tataagctca gtccatcctc gtaaatcctc atcaatcatc    60

<210> SEQ ID NO 132
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 132
cgtgaattgg aacagcttct tataagctca gtccatcctc gtaaatcctc atcaatcatc    60

<210> SEQ ID NO 133
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 133
cgtgggttgg aacagcttct tataagctca gtccatcctc gtaaatcctc atcaatcatc    60

<210> SEQ ID NO 134
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 134
cgtggaatgg aacagcttct tataagctca gtccatcctc gtaaatcctc atcaatcatc    60

<210> SEQ ID NO 135
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 135
agtggattgg aacagcttct tatacacatt tacagacctc aacctacctc caactctcac    60

<210> SEQ ID NO 136
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 136
cctggattgg aacagcttct tatacacatt tacagacctc aacctacctc caactctcac    60

<210> SEQ ID NO 137
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 137
cgcggattgg aacagcttct tatacacatt tacagacctc aacctacctc caactctcac    60

<210> SEQ ID NO 138
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 138
cgtcgattgg aacagcttct tatacacatt tacagacctc aacctacctc caactctcac    60

<210> SEQ ID NO 139
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 139
cgtgcattgg aacagcttct tatacacatt tacagacctc aacctacctc caactctcac    60

<210> SEQ ID NO 140
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 140
cgtggcttgg aacagcttct tatacacatt tacagacctc aacctacctc caactctcac    60

<210> SEQ ID NO 141

```
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 141
cgtggactgg aacagcttct tatacacatt tacagacctc aacctacctc caactctcac    60

<210> SEQ ID NO 142
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 142
agtggattgg aacagcttct tatagcattc tttcttgagg agggcagcaa acgggaagag    60

<210> SEQ ID NO 143
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 143
cctggattgg aacagcttct tatagcattc tttcttgagg agggcagcaa acgggaagag    60

<210> SEQ ID NO 144
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 144
cgcggattgg aacagcttct tatagcattc tttcttgagg agggcagcaa acgggaagag    60

<210> SEQ ID NO 145
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 145
cgtcgattgg aacagcttct tatagcattc tttcttgagg agggcagcaa acgggaagag    60

<210> SEQ ID NO 146
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 146
cgtgcattgg aacagcttct tatagcattc tttcttgagg agggcagcaa acgggaagag    60

<210> SEQ ID NO 147
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 147
```
cgtggcttgg aacagcttct tatagcattc tttcttgagg agggcagcaa acgggaagag    60

<210> SEQ ID NO 148
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 148
cgtggactgg aacagcttct tatagcattc tttcttgagg agggcagcaa acgggaagag    60

<210> SEQ ID NO 149
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 149
ggtggattgg aacagcttct tataagctca gtccatcctc gtaaatcctc atcaatcatc    60

<210> SEQ ID NO 150
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 150
cttggattgg aacagcttct tataagctca gtccatcctc gtaaatcctc atcaatcatc    60

<210> SEQ ID NO 151
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 151
cggggattgg aacagcttct tataagctca gtccatcctc gtaaatcctc atcaatcatc    60

<210> SEQ ID NO 152
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 152
cgttgattgg aacagcttct tataagctca gtccatcctc gtaaatcctc atcaatcatc    60

<210> SEQ ID NO 153
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 153
cgtgtattgg aacagcttct tataagctca gtccatcctc gtaaatcctc atcaatcatc    60

<210> SEQ ID NO 154
<211> LENGTH: 60
<212> TYPE: DNA

<213> ORGANISM: Artificial Sequence
<220> FEATURE:
<223> OTHER INFORMATION: Synthetic Polynucleotide

<400> SEQUENCE: 154
cgtggtttgg aacagcttct tataagctca gtccatcctc gtaaatcctc atcaatcatc    60

<210> SEQ ID NO 155
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 155
cgtggagtgg aacagcttct tataagctca gtccatcctc gtaaatcctc atcaatcatc    60

<210> SEQ ID NO 156
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 156
tgtggattgg aacagcttct tataaaagtc taatccgtcc ctgcctctat atctccactc    60

<210> SEQ ID NO 157
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 157
catggattgg aacagcttct tataaaagtc taatccgtcc ctgcctctat atctccactc    60

<210> SEQ ID NO 158
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 158
cgaggattgg aacagcttct tataaaagtc taatccgtcc ctgcctctat atctccactc    60

<210> SEQ ID NO 159
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 159
cgtagattgg aacagcttct tataaaagtc taatccgtcc ctgcctctat atctccactc    60

<210> SEQ ID NO 160
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 160
cgtgaattgg aacagcttct tataaaagtc taatccgtcc ctgcctctat atctccactc    60

<210> SEQ ID NO 161
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 161
cgtgggttgg aacagcttct tataaaagtc taatccgtcc ctgcctctat atctccactc    60

<210> SEQ ID NO 162
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 162
cgtggaatgg aacagcttct tataaaagtc taatccgtcc ctgcctctat atctccactc    60

<210> SEQ ID NO 163
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 163
cgtggattgg aacagcttct tatagcattc tttcttgagg agggcagcaa acgggaagag    60

<210> SEQ ID NO 164
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 164
cgtggattgg aacagcttct tataagctca gtccatcctc gtaaatcctc atcaatcatc    60

<210> SEQ ID NO 165
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 165
cgtggattgg aacagcttct tataaaagtc taatccgtcc ctgcctctat atctccactc    60

<210> SEQ ID NO 166
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 166
cgtggattgg aacagcttct tatacacatt tacagacctc aacctacctc caactctcac    60

<210> SEQ ID NO 167
<211> LENGTH: 60
<212> TYPE: DNA
<213> ORGANISM: Artificial Sequence
<220> FEATURE:

<223> OTHER INFORMATION: Synthetic Polynucleotide

<400> SEQUENCE: 167
taaagaatgc gttggggcga tatagcattc tttcttgagg agggcagcaa acgggaagag    60

<210> SEQ ID NO 168
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 168
ttccacatcc ctctgcgatt tataagctca gtccatcctc gtaaatcctc atcaatcatc    60

<210> SEQ ID NO 169
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 169
taaagaacgc gttggggcga tataaaagtc taatccgtcc ctgcctctat atctccactc    60

<210> SEQ ID NO 170
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 170
ttccacaccc ctctgcgatt tatacacatt tacagacctc aacctacctc caactctcac    60

<210> SEQ ID NO 171
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 171
taaagaatgc gttggggcga tatagcattc tttcttgagg agggcagcaa acgggaagag    60

<210> SEQ ID NO 172
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 172
ttccacatcc ctctgcgatt tataagctca gtccatcctc gtaaatcctc atcaatcatc    60

<210> SEQ ID NO 173
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 173
taaagaacgc gttggggcga tataaaagtc taatccgtcc ctgcctctat atctccactc    60

<210> SEQ ID NO 174
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 174
ttccacaccc ctctgcgatt tatacacatt tacagacctc aacctacctc caactctcac    60

<210> SEQ ID NO 175
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 175
ataccaatcc cttcggcgat tataaaagtc taatccgtcc ctgcctctat atctccactc    60

<210> SEQ ID NO 176
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 176
ttagcgatac atccgaccca tatagcattc tttcttgagg agggcagcaa acgggaagag    60

<210> SEQ ID NO 177
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 177
ataccaaccc cttcggcgat tataagctca gtccatcctc gtaaatcctc atcaatcatc    60

<210> SEQ ID NO 178
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 178
ttagcgacac atccgaccca tatacacatt tacagacctc aacctacctc caactctcac    60

<210> SEQ ID NO 179
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 179
ataccaatcc cttcggcgat tataaaagtc taatccgtcc ctgcctctat atctccactc    60

<210> SEQ ID NO 180
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 180
ttagcgatac atccgaccca tatagcattc tttcttgagg agggcagcaa acgggaagag    60

<210> SEQ ID NO 181
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 181
ataccaaccc cttcggcgat tataagctca gtccatcctc gtaaatcctc atcaatcatc    60

<210> SEQ ID NO 182
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 182
ttagcgacac atccgaccca tatacacatt tacagacctc aacctacctc caactctcac    60

<210> SEQ ID NO 183
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 183
ctccaactga atgaaggcga tataagctca gtccatcctc gtaaatcctc atcaatcatc    60

<210> SEQ ID NO 184
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 184
ttcaacatac gccaatgcgg tataaaagtc taatccgtcc ctgcctctat atctccactc    60

<210> SEQ ID NO 185
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 185
ctccaaccga atgaaggcga tatagcattc tttcttgagg agggcagcaa acgggaagag    60

<210> SEQ ID NO 186
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 186
ttcaacacac gccaatgcgg tatacacatt tacagacctc aacctacctc caactctcac    60

<210> SEQ ID NO 187
<211> LENGTH: 60

-continued

<212> TYPE: DNA
<213> ORGANISM: Artificial Sequence
<220> FEATURE:
<223> OTHER INFORMATION: Synthetic Polynucleotide

<400> SEQUENCE: 187
ctccaactga atgaaggcga tataagctca gtccatcctc gtaaatcctc atcaatcatc    60

<210> SEQ ID NO 188
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 188
ttcaacatac gccaatgcgg tataaaagtc taatccgtcc ctgcctctat atctccactc    60

<210> SEQ ID NO 189
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 189
ctccaaccga atgaaggcga tatagcattc tttcttgagg agggcagcaa acgggaagag    60

<210> SEQ ID NO 190
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 190
ttcaacacac gccaatgcgg tatacacatt tacagacctc aacctacctc caactctcac    60

<210> SEQ ID NO 191
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 191
atcgcaatcc accaaagcag tatagcattc tttcttgagg agggcagcaa acgggaagag    60

<210> SEQ ID NO 192
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 192
gtcaacatac acgccctgat tataagctca gtccatcctc gtaaatcctc atcaatcatc    60

<210> SEQ ID NO 193
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 193

```
atcgcaaccc accaaagcag tataaaagtc taatccgtcc ctgcctctat atctccactc    60

<210> SEQ ID NO 194
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 194
gtcaacacac acgccctgat tatacacatt tacagacctc aacctacctc caactctcac    60

<210> SEQ ID NO 195
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 195
atcgcaatcc accaaagcag tatagcattc tttcttgagg agggcagcaa acgggaagag    60

<210> SEQ ID NO 196
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 196
gtcaacatac acgccctgat tataagctca gtccatcctc gtaaatcctc atcaatcatc    60

<210> SEQ ID NO 197
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 197
atcgcaaccc accaaagcag tataaaagtc taatccgtcc ctgcctctat atctccactc    60

<210> SEQ ID NO 198
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 198
gtcaacacac acgccctgat tatacacatt tacagacctc aacctacctc caactctcac    60

<210> SEQ ID NO 199
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 199
ttagagatga acgccaacgc tataaaagtc taatccgtcc ctgcctctat atctccactc    60

<210> SEQ ID NO 200
<211> LENGTH: 60
<212> TYPE: DNA
<213> ORGANISM: Artificial Sequence
```

```
<220> FEATURE:
<223> OTHER INFORMATION: Synthetic Polynucleotide

<400> SEQUENCE: 200
acacgactca actccgaaga tatagcattc tttcttgagg agggcagcaa acgggaagag    60

<210> SEQ ID NO 201
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 201
ttagagacga acgccaacgc tataagctca gtccatcctc gtaaatcctc atcaatcatc    60

<210> SEQ ID NO 202
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 202
acacgaccca actccgaaga tatacacatt tacagacctc aacctacctc caactctcac    60

<210> SEQ ID NO 203
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 203
ttagagatga acgccaacgc tataaaagtc taatccgtcc ctgcctctat atctccactc    60

<210> SEQ ID NO 204
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 204
acacgactca actccgaaga tatagcattc tttcttgagg agggcagcaa acgggaagag    60

<210> SEQ ID NO 205
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 205
ttagagacga acgccaacgc tataagctca gtccatcctc gtaaatcctc atcaatcatc    60

<210> SEQ ID NO 206
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 206
acacgaccca actccgaaga tatacacatt tacagacctc aacctacctc caactctcac    60
```

<210> SEQ ID NO 207
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 207
atccgcatca acggtagcaa tataagctca gtccatcctc gtaaatcctc atcaatcatc    60

<210> SEQ ID NO 208
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 208
atcagcgtga caactgtgct tataaaagtc taatccgtcc ctgcctctat atctccactc    60

<210> SEQ ID NO 209
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 209
atccgcacca acggtagcaa tatagcattc tttcttgagg agggcagcaa acgggaagag    60

<210> SEQ ID NO 210
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 210
atcagcgcga caactgtgct tatacacatt tacagacctc aacctacctc caactctcac    60

<210> SEQ ID NO 211
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 211
atccgcatca acggtagcaa tataagctca gtccatcctc gtaaatcctc atcaatcatc    60

<210> SEQ ID NO 212
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 212
atcagcgtga caactgtgct tataaaagtc taatccgtcc ctgcctctat atctccactc    60

<210> SEQ ID NO 213
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 213
atccgcacca acggtagcaa tatagcattc tttcttgagg agggcagcaa acgggaagag    60

<210> SEQ ID NO 214
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 214
atcagcgcga caactgtgct tatacacatt tacagacctc aacctacctc caactctcac    60

<210> SEQ ID NO 215
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 215
ttacaactga ctctccgtcc tatagcattc tttcttgagg agggcagcaa acgggaagag    60

<210> SEQ ID NO 216
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 216
ttacaactga ctcctcctcg tataagctca gtccatcctc gtaaatcctc atcaatcatc    60

<210> SEQ ID NO 217
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 217
ttacaaccga ctctccgtcc tataaaagtc taatccgtcc ctgcctctat atctccactc    60

<210> SEQ ID NO 218
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 218
ttacaaccga ctcctcctcg tatacacatt tacagacctc aacctacctc caactctcac    60

<210> SEQ ID NO 219
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 219
ttacaactga ctcgtgcggt tataaaagtc taatccgtcc ctgcctctat atctccactc    60

<210> SEQ ID NO 220

```
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 220
ttacaactga ctctggggtg tatagcattc tttcttgagg agggcagcaa acgggaagag      60

<210> SEQ ID NO 221
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 221
ttacaaccga ctcgtgcggt tataagctca gtccatcctc gtaaatcctc atcaatcatc      60

<210> SEQ ID NO 222
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 222
ttacaaccga ctctggggtg tatacacatt tacagacctc aacctacctc caactctcac      60

<210> SEQ ID NO 223
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 223
ttacaactga cttgggcgtc tataagctca gtccatcctc gtaaatcctc atcaatcatc      60

<210> SEQ ID NO 224
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 224
ttacaactga ctgcgtcctg tataaaagtc taatccgtcc ctgcctctat atctccactc      60

<210> SEQ ID NO 225
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 225
ttacaaccga cttgggcgtc tatagcattc tttcttgagg agggcagcaa acgggaagag      60

<210> SEQ ID NO 226
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 226
```

```
ttacaaccga ctgcgtcctg tatacacatt tacagacctc aacctacctc caactctcac    60

<210> SEQ ID NO 227
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 227
ttacaactga ctgtcgccct tatagcattc tttcttgagg agggcagcaa acgggaagag    60

<210> SEQ ID NO 228
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 228
ttacaactga ctgtgcctgc tataagctca gtccatcctc gtaaatcctc atcaatcatc    60

<210> SEQ ID NO 229
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 229
ttacaaccga ctgtcgccct tataaaagtc taatccgtcc ctgcctctat atctccactc    60

<210> SEQ ID NO 230
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 230
ttacaaccga ctgtgcctgc tatacacatt tacagacctc aacctacctc caactctcac    60

<210> SEQ ID NO 231
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 231
ttacaactga ctggtcgctc tataaaagtc taatccgtcc ctgcctctat atctccactc    60

<210> SEQ ID NO 232
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 232
ttacaactga ctgctgtccg tatagcattc tttcttgagg agggcagcaa acgggaagag    60

<210> SEQ ID NO 233
<211> LENGTH: 60
<212> TYPE: DNA
```

```
<213> ORGANISM: Artificial Sequence
<220> FEATURE:
<223> OTHER INFORMATION: Synthetic Polynucleotide

<400> SEQUENCE: 233
ttacaaccga ctggtcgctc tataagctca gtccatcctc gtaaatcctc atcaatcatc    60

<210> SEQ ID NO 234
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 234
ttacaaccga ctgctgtccg tatacacatt tacagacctc aacctacctc caactctcac    60

<210> SEQ ID NO 235
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 235
ttacaactga ctggctgtgg tataagctca gtccatcctc gtaaatcctc atcaatcatc    60

<210> SEQ ID NO 236
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 236
ttacaactga cttccctggc tataaaagtc taatccgtcc ctgcctctat atctccactc    60

<210> SEQ ID NO 237
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 237
ttacaaccga ctggctgtgg tatagcattc tttcttgagg agggcagcaa acgggaagag    60

<210> SEQ ID NO 238
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 238
ttacaaccga cttccctggc tatacacatt tacagacctc aacctacctc caactctcac    60

<210> SEQ ID NO 239
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 239
acgcattctt tatgacacgg                                                20
```

```
<210> SEQ ID NO 240
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 240
agggatgtgg aaacagaaca                                                20

<210> SEQ ID NO 241
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 241
agggattggt atctgaacag                                                20

<210> SEQ ID NO 242
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 242
atgtatcgct aacaacccag                                                20

<210> SEQ ID NO 243
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 243
attcagttgg aggataacgg                                                20

<210> SEQ ID NO 244
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 244
gcgtatgttg aatcacaggg                                                20

<210> SEQ ID NO 245
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 245
gtggattgcg atacataccg                                                20

<210> SEQ ID NO 246
<211> LENGTH: 20
<212> TYPE: DNA
<213> ORGANISM: Artificial Sequence
<220> FEATURE:
```

<223> OTHER INFORMATION: Synthetic Oligonucleotide

<400> SEQUENCE: 246
gtgtatgttg acgaatcaca                                          20

<210> SEQ ID NO 247
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 247
gttcatctct aatagccgag                                          20

<210> SEQ ID NO 248
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 248
gttgagtcgt gtaagcagag                                          20

<210> SEQ ID NO 249
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 249
gttgatgcgg atacaatgtg                                          20

<210> SEQ ID NO 250
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 250
tgtcacgctg atgaatctgg                                          20

<210> SEQ ID NO 251
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 251
agtcagttgt aatcacaggg                                          20

<210> SEQ ID NO 252
<211> LENGTH: 439
<212> TYPE: DNA
<213> ORGANISM: Artificial Sequence
<220> FEATURE:
<223> OTHER INFORMATION: Synthetic Polynucleotide

<400> SEQUENCE: 252
gcctccagat tcatcagcgt gacaactgtg ctgtaggacc ccacattgta tccgcatcaa    60
cggtagcaag caatcccact ctgcttacac gactcaactc cgaagagtcg aaccgctcgg   120

```
ctattagaga tgaacgccaa cgcgtcggcc cctgtgattc gtcaacatac acgccctgat    180
aaatatcctc ggtatgtatc gcaatccacc aaagcagagc gacccaccct gtgattcaac    240
atacgccaat gcggacgcgg ccgccgttat cctccaactg aatgaaggcg acaaccaccc    300
ctgggttgtt agcgatacat ccgacccaat cataccgctg ttcagatacc aatcccttcg    360
gcgatttccc gccgtgttct gtttccacat ccctctgcga ttcgtggccc gccgtgtcat    420
aaagaatgcg ttggggcga                                                 439

<210> SEQ ID NO 253
<211> LENGTH: 10491
<212> TYPE: DNA
<213> ORGANISM: Artificial Sequence
<220> FEATURE:
<223> OTHER INFORMATION: Synthetic Polynucleotide

<400> SEQUENCE: 253
gtcgacggat cgggagatct cccgatcccc tatggtgcac tctcagtaca atctgctctg     60
atgccgcata gttaagccag tatctgctcc ctgcttgtgt gttggaggtc gctgagtagt    120
gcgcgagcaa aatttaagct acaacaaggc aaggcttgac cgacaattgc atgaagaatc    180
tgcttagggt taggcgtttt gcgctgcttc gcgatgtacg ggccagatat acgcgttgac    240
attgattatt gactagttat taatagtaat caattacggg gtcattagtt catagcccat    300
atatggagtt ccgcgttaca taacttacgg taaatggccc gcctggctga ccgcccaacg    360
acccccgccc attgacgtca ataatgacgt atgttcccat agtaacgcca atagggactt    420
tccattgacg tcaatgggtg gagtatttac ggtaaactgc ccacttggca gtacatcaag    480
tgtatcatat gccaagtacg ccccctattg acgtcaatga cggtaaatgg cccgcctggc    540
attatgccca gtacatgacc ttatgggact ttcctacttg gcagtacatc tacgtattag    600
tcatcgctat taccatggtg atgcggtttt ggcagtacat caatgggcgt ggatagcggt    660
ttgactcacg gggatttcca agtctccacc ccattgacgt caatgggagt ttgttttggc    720
accaaaatca acgggacttt ccaaaatgtc gtaacaactc cgccccattg acgcaaatgg    780
gcggtaggcg tgtacggtgg gaggtctata taagcagcgc gttttgcctg tactgggtct    840
ctctggttag accagatctg agcctgggag ctctctggct aactagggaa cccactgctt    900
aagcctcaat aaagcttgcc ttgagtgctt caagtagtgt gtgcccgtct gttgtgtgac    960
tctggtaact agagatccct cagacccttt tagtcagtgt ggaaaatctc tagcagtggc   1020
gcccgaacag ggacttgaaa gcgaaaggga accagagga gctctctcga cgcaggactc   1080
ggcttgctga agcgcgcacg gcaagaggcg aggggcggcg actggtgagt acgccaaaaa   1140
ttttgactag cggaggctag aaggagagag atgggtgcga gagcgtcagt attaagcggg   1200
ggagaattag atcgcgatgg gaaaaaattc ggttaaggcc agggggaaag aaaaaatata   1260
aattaaaaca tatagtatgg gcaagcaggg agctagaacg attcgcagtt aatcctggcc   1320
tgttagaaac atcagaaggc tgtagacaaa tactgggaca gctacaacca tcccttcaga   1380
caggatcaga agaacttaga tcattatata atacagtagc aaccctctat tgtgtgcatc   1440
aaaggataga gataaaagac accaaggaag ctttagacaa gatagaggaa gagcaaaaca   1500
aaagtaagac caccgcacag caagcggccg ctgatcttca gacctggagg aggagatatg   1560
agggacaatt ggagaagtga attatataaa tataaagtag taaaaattga accattagga   1620
gtagcaccca ccaaggcaaa gagaagagtg gtgcagagag aaaaaagagc agtgggaata   1680
```

```
ggagctttgt tccttgggtt cttgggagca gcaggaagca ctatgggcgc agcgtcaatg    1740
acgctgacgg tacaggccag acaattattg tctggtatag tgcagcagca gaacaatttg    1800
ctgagggcta ttgaggcgca acagcatctg ttgcaactca cagtctgggg catcaagcag    1860
ctccaggcaa gaatcctggc tgtggaaaga tacctaaagg atcaacagct cctggggatt    1920
tggggttgct ctggaaaact catttgcacc actgctgtgc cttggaatgc tagttggagt    1980
aataaatctc tggaacagat ttggaatcac acgacctgga tggagtggga cagagaaatt    2040
aacaattaca caagcttaat acactcctta attgaagaat cgcaaaacca gcaagaaaag    2100
aatgaacaag aattattgga attagataaa tgggcaagtt tgtggaattg gtttaacata    2160
acaaattggc tgtggtatat aaaattattc ataatgatag taggaggctt ggtaggttta    2220
agaatagttt ttgctgtact ttctatagtg aatagagtta ggcagggata ttcaccatta    2280
tcgtttcaga cccacctccc aaccccgagg ggacccgaca ggcccgaagg aatagaagaa    2340
gaaggtggag agagagacag agacagatcc attcgattag tgaacggatc ggcactgcgt    2400
gcgccaattc tgcagacaaa tggcagtatt catccacaat tttaaaagaa aagggggat    2460
tgggggtac agtgcagggg aaagaatagt agacataata gcaacagaca tacaaactaa    2520
agaattacaa aaacaaatta caaaaattca aaattttcgg gtttattaca gggacagcag    2580
agatccagtt tggttaattt atagcctcca gattcatcag cgtgacaact gtgctgtagg    2640
accccacatt gtatccgcat caacggtagc aagcaatccc actctgctta cacgactcaa    2700
ctccgaagag tcgaaccgct cggctattag agatgaacgc caacgcgtcg gccctgtga    2760
ttcgtcaaca tacacgccct gataaatatc ctcggtatgt atcgcaatcc accaaagcag    2820
agcgacccac cctgtgattc aacatacgcc aatgcggacg cggccgccgt tatcctccaa    2880
ctgaatgaag cgacaaccca ccctgggtt gttagcgata catccgaccc aatcataccg    2940
ctgttcagat accaatccct tcggcgattt ccgccgtgt tctgtttcca catccctctg    3000
cgattcgtgg cccgccgtgt cataaagaat gcgttgggc gacccttag tgagggttaa    3060
ttctcgagtc tccctatagt gagtcgtatt aattccgtgt attctatagt gtcacctaaa    3120
tcgttacggg attaacccgt gtcggctcca gatctggcct ccgcgccggg ttttggcgcc    3180
tcccgcgggc gcccccctcc tcacggcgag cgctgccacg tcagacgaag ggcgcagcga    3240
gcgtcctgat ccttccgccc ggacgctcag gacagcggcc cgctgctcat aagactcggc    3300
cttagaaccc cagtatcagc agaaggacat tttaggacgg gacttgggtg actctagggc    3360
actggttttc tttccagaga gcggaacagg cgaggaaaag tagtcccttc tcggcgattc    3420
tgcggaggga tctccgtggg gcggtgaacg ccgatgatta tataaggacg cgccgggtgt    3480
ggcacagcta gttccgtcgc agccgggatt tgggtcgcgg ttcttgtttg tggatcgctg    3540
tgatcgtcac ttggtgagta gcgggctgct gggctggccg gggctttcgt ggccgccggg    3600
ccgctcggtg ggacggaagc gtgtggagag accgccaagg gctgtagtct gggtccgcga    3660
gcaaggttgc cctgaactgg gggttggggg agcgcagca aaatggcggc tgttcccgag    3720
tcttgaatgg aagacgcttg tgaggcgggc tgtgaggtcg ttgaaacaag gtgggggca    3780
tggtgggcgc caagaaccca aggtcttgag gccttcgcta atgcgggaaa gctcttattc    3840
gggtgagatg ggctggggca ccatctgggg accctgacgt gaagtttgtc actgactgga    3900
gaactcggtt tgtcgtctgt tgcggggcg gcagttatgg cggtgccgtt ggcagtgca    3960
cccgtacctt tgggagcgcg cgccctcgtc gtgtcgtgac gtcacccgtt ctgttggctt    4020
ataatgcagg gtggggccac ctgccggtag gtgtgcggta ggcttttctc cgtcgcagga    4080
```

```
cgcagggttc gggcctaggg taggctctcc tgaatcgaca ggcgccggac ctctggtgag    4140
gggagggata agtgaggcgt cagtttcttt ggtcggtttt atgtacctat cttcttaagt    4200
agctgaagct ccggttttga actatgcgct cggggttggc gagtgtgttt tgtgaagttt    4260
tttaggcacc ttttgaaatg taatcatttg ggtcaatatg taattttcag tgttagacta    4320
gtaaattgtc cgctaaattc tggccgtttt tggctttttt gttagacgaa gcttgggctg    4380
caggtcgact ctagaggatc cccgggtaag gatccccggg taccggtcgc caccatggtg    4440
agcaagggcg aggagctgtt caccggggtg gtgcccatcc tggtcgagct ggacggcgac    4500
gtaaacggcc acaagttcag cgtgtccggc gagggcgagg gcgatgccac ctacggcaag    4560
ctgaccctga agttcatctg caccaccggc aagctgcccg tgccctggcc caccctcgtg    4620
accaccctga cctggggcgt gcagtgcttc gcccgctacc ccgaccacat gaagcagcac    4680
gacttcttca gtccgccat gcccgaaggc tacgtccagg agcgcaccat cttcttcaag    4740
gacgacggca actacaagac ccgcgccgag gtgaagttcg agggcgacac cctggtgaac    4800
cgcatcgagc tgaagggcat cgacttcaag gaggacggca acatcctggg gcacaagctg    4860
gagtacaacg ccatcagcga caacgtctat atcaccgccg acaagcagaa gaacggcatc    4920
aaggccaact tcaagatccg ccacaacatc gaggacggca gcgtgcagct cgccgaccac    4980
taccagcaga cacccccat cggcgacggc cccgtgctgc tgcccgacaa ccactacctg    5040
agcacccagt ccaagctgag caaagacccc aacgagaagc gcgatcacat ggtcctgctg    5100
gagttcgtga ccgccgccgg gatcactctc ggcatggacg agctgtacaa gtgaacctga    5160
attcgatatc aagcttatcg ataatcaacc tctggattac aaaatttgtg aaagattgac    5220
tggtattctt aactatgttg ctccttttac gctatgtgga tacgctgctt taatgccttt    5280
gtatcatgct attgcttccc gtatggcttt cattttctcc tccttgtata aatcctggtt    5340
gctgtctctt tatgaggagt tgtggcccgt tgtcaggcaa cgtggcgtgg tgtgcactgt    5400
gtttgctgac gcaaccccca ctggttgggg cattgccacc acctgtcagc tcctttccgg    5460
gactttcgct ttccccctcc ctattgccac ggcggaactc atcgccgcct gccttgcccg    5520
ctgctggaca ggggctcggc tgttgggcac tgacaattcc gtggtgttgt cggggaaatc    5580
atcgtccttt ccttggctgc tcgcctgtgt tgccacctgg attctgcgcg gacgtccttc    5640 tgctacgtc ccttcggccc tcaatccagc ggaccttcct tcccgcggcc tgctgccggc    5700
tctgcggcct cttccgcgtc ttcgccttcg ccctcagacg agtcggatct cccttttgggc    5760 cgcctccccg catcgatacc gtcgacctcg agacctagaa aaacatggag caatcacaag    5820
tagcaataca gcagctacca atgctgattg tgcctggcta aagcacaag aggaggagga    5880 ggtgggtttt ccagtcacac ctcaggtacc tttaagacca atgacttaca aggcagctgt    5940
agatcttagc cacttttttaa aagaaaaggg gggactggaa gggctaattc actcccaacg    6000
aagacaagat atccttgatc tgtggatcta ccacacacaa ggctacttcc ctgattggca    6060
gaactacaca ccagggccag ggatcagata tccactgacc tttggatggt gctacaagct    6120
agtaccagtt gagcaagaga aggtagaaga agccaatgaa ggagagaaca cccgcttgtt    6180
acaccctgtg agcctgcatg gaatggatga cccggagaga gaagtattag agtggaggtt    6240
tgacagccgc ctagcatttc atcacatggc ccgagagctg catccggact gtactgggtc    6300
tctctggtta gaccagatct gagcctggga gctctctggc taactaggga acccactgct    6360
taagcctcaa taaagcttgc cttgagtgct tcaagtagtg tgtgcccgtc tgttgtgtga    6420
```

| | |
|---|---|
| ctctggtaac tagagatccc tcagacccett ttagtcagtg tggaaaatct ctagcagggc | 6480 |
| ccgtttaaac ccgctgatca gcctcgactg tgccttctag ttgccagcca tctgttgttt | 6540 |
| gcccctcccc cgtgccttcc ttgaccctgg aaggtgccac tcccactgtc ctttcctaat | 6600 |
| aaaatgagga aattgcatcg cattgtctga gtaggtgtca ttctattctg ggggtgggg | 6660 |
| tggggcagga cagcaagggg gaggattggg aagacaatag caggcatgct ggggatgcgg | 6720 |
| tgggctctat ggcttctgag gcggaaagaa ccagctgggg ctctagggg tatccccacg | 6780 |
| cgccctgtag cggcgcatta agcgcggcgg gtgtggtggt tacgcgcagc gtgaccgcta | 6840 |
| cacttgccag cgccctagcg cccgctcctt tcgctttctt ccttcctttt ctcgccacgt | 6900 |
| tcgccggctt tccccgtcaa gctctaaatc gggggctccc tttagggttc cgatttagtg | 6960 |
| ctttacggca cctcgacccc aaaaaacttg attagggtga tggttcacgt agtgggccat | 7020 |
| cgccctgata cacggttttt cgccctttga cgttggagtc cacgttcttt aatagtggac | 7080 |
| tcttgttcca aactgaaaca acactcaacc ctatctcggt ctattctttt gatttataag | 7140 |
| ggattttgcc gatttcggcc tattggttaa aaaatgagct gatttaacaa aaatttaacg | 7200 |
| cgaattaatt ctgtggaatg tgtgtcagtt agggtgtgga aagtcccag gctcccagc | 7260 |
| aggcagaagt atgcaaagca tgcatctcaa ttagtcagca accaggtgtg gaaagtcccc | 7320 |
| aggctcccca gcaggcagaa gtatgcaaag catgcatctc aattagtcag caaccatagt | 7380 |
| cccgccccta actccgccca tcccgcccct aactccgccc agttccgccc attctccgcc | 7440 |
| ccatggctga ctaattttt ttatttatgc agaggccgag gccgcctctg cctctgagct | 7500 |
| attccagaag tagtgaggag gcttttttgg aggcctaggc ttttgcaaaa agctcccggg | 7560 |
| agcttgtata tccatttcg gatctgatca gcacgtgttg acaattaatc atcggcatag | 7620 |
| tatatcggca tagtataata cgacaaggtg aggaactaaa ccatgccaa gttgaccagt | 7680 |
| gccgttccgg tgctcaccgc gcgcgacgtc gccggagcgg tcgagttctg gaccgaccgg | 7740 |
| ctcgggttct cccgggactt cgtggaggac gacttcgccg gtgtggtccg ggacgacgtg | 7800 |
| accctgttca tcagcgcggt ccaggaccag gtggtgccgg acaacaccct ggcctgggtg | 7860 |
| tgggtgcgcg gcctggacga gctgtacgcc gagtggtcgg aggtcgtgtc cacgaacttc | 7920 |
| cgggacgcct ccgggccggc catgaccgag atcggcgagc agccgtgggg cgggagttc | 7980 |
| gccctgcgcg accggccgg caactgcgtg cacttcgtgg ccgaggagca ggactgacac | 8040 |
| gtgctacgag atttcgattc caccgccgcc ttctatgaaa ggttgggctt cggaatcgtt | 8100 |
| ttccgggacg ccggctggat gatcctccag cgcggggatc tcatgctgga gttcttcgcc | 8160 |
| cacccccaact tgtttattgc agcttataat ggttacaaat aaagcaatag catcacaaat | 8220 |
| ttcacaaata aagcattttt ttcactgcat tctagttgtg gtttgtccaa actcatcaat | 8280 |
| gtatcttatc atgtctgtat accgtcgacc tctagctaga gcttggcgta atcatggtca | 8340 |
| tagctgtttc ctgtgtgaaa ttgttatccg ctcacaattc cacacaacat acgagccgga | 8400 |
| agcataaagt gtaaagcctg gggtgcctaa tgagtgagct aactcacatt aattgcgttg | 8460 |
| cgctcactgc ccgctttcca gtcgggaaac ctgtcgtgcc agctgcatta atgaatcggc | 8520 |
| caacgcgcgg ggagaggcgg tttgcgtatt gggcgctctt ccgcttcctc gctcactgac | 8580 |
| tcgctgcgct cggtcgttcg gctgcggcga gcggtatcag ctcactcaaa ggcggtaata | 8640 |
| cggttatcca cagaatcagg ggataacgca ggaaagaaca tgtgagcaaa aggccagcaa | 8700 |
| aaggccagga accgtaaaaa ggccgcgttg ctggcgtttt tccataggct ccgcccccct | 8760 |
| gacgagcatc acaaaaatcg acgctcaagt cagaggtggc gaaacccgac aggactataa | 8820 |

```
agataccagg cgtttccccc tggaagctcc ctcgtgcgct ctcctgttcc gaccctgccg    8880
cttaccggat acctgtccgc ctttctccct tcgggaagcg tggcgctttc tcatagctca    8940
cgctgtaggt atctcagttc ggtgtaggtc gttcgctcca agctgggctg tgtgcacgaa    9000
ccccccgttc agcccgaccg ctgcgcctta tccggtaact atcgtcttga gtccaacccg    9060
gtaagacacg acttatcgcc actggcagca gccactggta acaggattag cagagcgagg    9120
tatgtaggcg gtgctacaga gttcttgaag tggtggccta actacggcta cactagaaga    9180
acagtatttg gtatctgcgc tctgctgaag ccagttacct tcggaaaaag agttggtagc    9240
tcttgatccg gcaaacaaac caccgctggt agcggtggtt ttttgtttg caagcagcag    9300 attacgcgca gaaaaaagg atctcaagaa gatcctttga tcttttctac ggggtctgac    9360
gctcagtgga acgaaaactc acgttaaggg attttggtca tgagattatc aaaaaggatc    9420
ttcacctaga tccttttaaa ttaaaaatga agttttaaat caatctaaag tatatatgag    9480
taaacttggt ctgacagtta ccaatgctta atcagtgagg cacctatctc agcgatctgt    9540
ctatttcgtt catccatagt tgcctgactc cccgtcgtgt agataactac gatacgggag    9600
ggcttaccat ctggccccag tgctgcaatg ataccgcgag acccacgctc accggctcca    9660
gatttatcag caataaacca gccagccgga agggccgagc gcagaagtgg tcctgcaact    9720
ttatccgcct ccatccagtc tattaattgt tgccgggaag ctagagtaag tagttcgcca    9780
gttaatagtt tgcgcaacgt tgttgccatt gctacaggca tcgtggtgtc acgctcgtcg    9840
tttggtatgg cttcattcag ctccggttcc caacgatcaa ggcgagttac atgatccccc    9900
atgttgtgca aaaaagcggt tagctccttc ggtcctccga tcgttgtcag aagtaagttg    9960
gccgcagtgt tatcactcat ggttatggca gcactgcata attctcttac tgtcatgcca   10020
tccgtaagat gcttttctgt gactggtgag tactcaacca agtcattctg agaatagtgt   10080
atgcggcgac cgagttgctc ttgcccggcg tcaatacggg ataataccgc gccacatagc   10140
agaactttaa aagtgctcat cattggaaaa cgttcttcgg ggcgaaaact ctcaaggatc   10200
ttaccgctgt tgagatccag ttcgatgtaa cccactcgtg cacccaactg atcttcagca   10260
tcttttactt tcaccagcgt ttctgggtga gcaaaaacag gaaggcaaaa tgccgcaaaa   10320
aagggaataa gggcgacacg gaaatgttga atactcatac tcttcctttt tcaatattat   10380
tgaagcattt atcagggtta ttgtctcatg agcggataca tatttgaatg tatttagaaa   10440
aataaacaaa taggggttcc gcgcacattt ccccgaaaag tgccacctga c            10491
```

<210> SEQ ID NO 254
<211> LENGTH: 524
<212> TYPE: DNA
<213> ORGANISM: Artificial Sequence
<220> FEATURE:
<223> OTHER INFORMATION: Synthetic Polynucleotide

<400> SEQUENCE: 254

```
ctgtaggtta gcaaccaccc tgtgattaca actgactcct cctcgcgcaa gccaccctgt      60
gattacaact gactctccgt cctacgcaga aggtcctctt ccaccctgtg attacaactg     120
actctggggt gggtgctcca ccctgtgatt acaactgact cgtgcggtta cggtagaggt     180
ttgaccccac cctgtgatta caactgactg cgtcctgttg tatccaccct gtgattacaa     240
ctgacttggg cgtctacggg ttaggtctgg ggccaccctg tgattacaac tgactgtgcc     300
tgccactatc caccctgtga ttacaactga ctgtcgccct tacgttggag gtccatgccc     360
```

| | |
|---|---|
| accctgtgat tacaactgac tgctgtccgt ccctcccacc ctgtgattac aactgactgg | 420 |
| tcgctctacg gagtaggtgt ctcaccaccc tgtgattaca actgacttcc ctggccacta | 480 |
| tccaccctgt gattacaact gactggctgt ggtacggcta aggt | 524 |

<210> SEQ ID NO 255
<211> LENGTH: 10580
<212> TYPE: DNA
<213> ORGANISM: Artificial Sequence
<220> FEATURE:
<223> OTHER INFORMATION: Synthetic Polynucleotide

<400> SEQUENCE: 255

| | |
|---|---|
| gtcgacggat cgggagatct cccgatcccc tatggtgcac tctcagtaca atctgctctg | 60 |
| atgccgcata gttaagccag tatctgctcc ctgcttgtgt gttggaggtc gctgagtagt | 120 |
| gcgcgagcaa aatttaagct acaacaaggc aaggcttgac cgacaattgc atgaagaatc | 180 |
| tgcttagggt taggcgtttt cgctgcttc gcgatgtacg ggccagatat acgcgttgac | 240 |
| attgattatt gactagttat taatagtaat caattacggg gtcattagtt catagcccat | 300 |
| atatggagtt ccgcgttaca taacttacgg taaatggccc gcctggctga ccgcccaacg | 360 |
| acccccgccc attgacgtca ataatgacgt atgttcccat agtaacgcca atagggactt | 420 |
| tccattgacg tcaatgggtg gagtatttac ggtaaactgc ccacttggca gtacatcaag | 480 |
| tgtatcatat gccaagtacg ccccctattg acgtcaatga cggtaaatgg cccgcctggc | 540 |
| attatgccca gtacatgacc ttatgggact ttcctacttg gcagtacatc tacgtattag | 600 |
| tcatcgctat taccatggtg atgcggtttt ggcagtacat caatgggcgt ggatagcggt | 660 |
| ttgactcacg gggatttcca agtctccacc ccattgacgt caatgggagt ttgttttggc | 720 |
| accaaaatca acgggacttt ccaaaatgtc gtaacaactc cgccccattg acgcaaatgg | 780 |
| gcggtaggcg tgtacggtgg gaggtctata taagcagcgc gttttgcctg tactgggtct | 840 |
| ctctggttag accagatctg agcctgggag ctctctggct aactagggaa cccactgctt | 900 |
| aagcctcaat aaagcttgcc ttgagtgctt caagtagtgt gtgcccgtct gttgtgtgac | 960 |
| tctggtaact agagatccct cagacccttt tagtcagtgt ggaaaatctc tagcagtggc | 1020 |
| gcccgaacag ggacttgaaa gcgaaaggga accagagga gctctctcga cgcaggactc | 1080 |
| ggcttgctga agcgcgcacg gcaagaggcg aggggcggcg actggtgagt acgccaaaaa | 1140 |
| ttttgactag cggaggctag aaggagagag atgggtgcga gagcgtcagt attaagcggg | 1200 |
| ggagaattag atcgcgatgg gaaaaaattc ggttaaggcc agggggaaag aaaaaatata | 1260 |
| aattaaaaca tatagtatgg gcaagcaggg agctagaacg attcgcagtt aatcctggcc | 1320 |
| tgttagaaac atcagaaggc tgtagacaaa tactgggaca gctacaacca tcccttcaga | 1380 |
| caggatcaga agaacttaga tcattatata atacagtagc aaccctctat tgtgtgcatc | 1440 |
| aaaggataga gataaaagac accaaggaag ctttagacaa gatagaggaa gagcaaaaca | 1500 |
| aaagtaagac caccgcacag caagcggccg ctgatcttca gacctggagg aggagatatg | 1560 |
| agggacaatt ggagaagtga attatataaa tataaagtag taaaaattga accattagga | 1620 |
| gtagcaccca ccaaggcaaa gagaagagtg gtgcagagag aaaaaagagc agtgggaata | 1680 |
| ggagctttgt tccttgggtt cttgggagca gcaggaagca ctatgggcgc agcgtcaatg | 1740 |
| acgctgacgg tacaggccag acaattattg tctggtatag tgcagcagca gaacaatttg | 1800 |
| ctgagggcta ttgaggcgca acagcatctg ttgcaactca cagtctgggg catcaagcag | 1860 |
| ctccaggcaa gaatcctggc tgtggaaaga tacctaaagg atcaacagct cctggggatt | 1920 |

```
tggggttgct ctggaaaact catttgcacc actgctgtgc cttggaatgc tagttggagt    1980
aataaatctc tggaacagat ttggaatcac acgacctgga tggagtggga cagagaaatt    2040
aacaattaca caagcttaat acactcctta attgaagaat cgcaaaacca gcaagaaaag    2100
aatgaacaag aattattgga attagataaa tgggcaagtt tgtggaattg gtttaacata    2160
acaaattggc tgtggtatat aaaattattc ataatgatag taggaggctt ggtaggttta    2220
agaatagttt ttgctgtact ttctatagtg aatagagtta ggcagggata ttcaccatta    2280
tcgtttcaga cccacctccc aaccccgagg ggacccgaca ggcccgaagg aatagaagaa    2340
gaaggtggag agagagacag agacagatcc attcgattag tgaacggatc ggcactgcgt    2400
gcgccaattc tgcagacaaa tggcagtatt catccacaat tttaaaagaa aaggggggat    2460
tggggggtac agtgcagggg aaagaatagt agacataata gcaacagaca tacaaactaa    2520
agaattacaa aaacaaatta caaaaattca aaattttcgg gtttattaca gggacagcag    2580
agatccagtt tggttaatct gtaggttagc aaccaccctg tgattacaac tgactcctcc    2640
tcgcgcaagc caccctgtga ttacaactga ctctccgtcc tacgcagaag gtcctcttcc    2700
accctgtgat tacaactgac tctggggtgg gtgctccacc ctgtgattac aactgactcg    2760
tgcggttacg gtagaggttt gaccccaccc tgtgattaca actgactgcg tcctgttgta    2820
tccaccctgt gattacaact gacttgggcg tctacgggtt aggtctgggg ccaccctgtg    2880
attacaactg actgtgcctg ccactatcca ccctgtgatt acaactgact gtcgccctta    2940
cgttggaggt ccatgcccac cctgtgatta caactgactg ctgtccgtcc ctcccaccct    3000
gtgattacaa ctgactggtc gctctacgga gtaggtgtct caccaccctg tgattacaac    3060
tgacttccct ggccactatc caccctgtga ttacaactga ctggctgtgg tacggctaag    3120
gtcctccctt tagtgagggt taattctcga gtctccctat agtgagtcgt attaattccg    3180
tgtattctat agtgtcacct aaatcgttac gagacaccta ttaacccgtg tcggctccag    3240
atctggcctc cgcgccgggt tttggcgcct cccgcgggcg ccccctcct cacggcgagc    3300 gctgccacgt cagacgaagg gcgcagcgag cgtcctgatc cttccgcccg gacgctcagg    3360
acagcggccc gctgctcata agactcggcc ttagaacccc agtatcagca gaaggacatt    3420
ttaggacggg acttgggtga ctctagggca ctggtttttct ttccagagag cggaacaggc    3480
gaggaaaagt agtcccttct cggcgattct gcggagggat ctccgtgggg cggtgaacgc    3540
cgatgattat ataaggacgc gccgggtgtg gcacagctag ttccgtcgca gccgggattt    3600
gggtcgcggt tcttgtttgt ggatcgctgt gatcgtcact tggtgagtag cgggctgctg    3660
ggctggccgg ggctttcgtg gccgccgggc cgctcggtgg gacggaagcg tgtggagaga    3720
ccgccaaggg ctgtagtctg ggtccgcgag caaggttgcc ctgaactggg ggttgggggg    3780
agcgcagcaa aatggcggct gttcccgagt cttgaatgga agacgcttgt gaggcgggct    3840
gtgaggtcgt tgaaacaagg tgggggggcat ggtgggcggc aagaacccaa ggtcttgagg    3900
ccttcgctaa tgcgggaaag ctcttattcg ggtgagatgg gctggggcac catctgggga    3960
ccctgacgtg aagtttgtca ctgactggag aactcggttt gtcgtctgtt gcggggggcgg    4020 cagttatggc ggtgccgttg ggcagtgcac ccgtacccttt gggagcgcgc gccctcgtcg    4080
tgtcgtgacg tcacccgttc tgttggctta taatgcaggg tggggccacc tgccggtagg    4140
tgtgcggtag gcttttctcc gtcgcaggac gcagggttcg ggcctagggt aggctctcct    4200
gaatcgacag gcgccggacc tctggtgagg ggagggataa gtgaggcgtc agtttctttg    4260
```

```
gtcggtttta tgtacctatc ttcttaagta gctgaagctc cggttttgaa ctatgcgctc    4320
ggggttggcg agtgtgtttt gtgaagtttt ttaggcacct tttgaaatgt aatcatttgg    4380
gtcaatatgt aattttcagt gttagactag taaattgtcc gctaaattct ggccgttttt    4440
ggcttttttg ttagacgaag cttgggctgc aggtcgactc tagaggatcc ccgggtaagg    4500
atccccgggt accggtcgcc accatggtga gcaagggcga ggagctgttc accggggtgg    4560
tgcccatcct ggtcgagctg gacggcgacg taaacggcca caagttcagc gtgtccggcg    4620
agggcgaggg cgatgccacc tacggcaagc tgaccctgaa gttcatctgc accaccggca    4680
agctgcccgt gccctggccc accctcgtga ccaccctgac ctggggcgtg cagtgcttcg    4740
cccgctaccc cgaccacatg aagcagcacg acttcttcaa gtccgccatg cccgaaggct    4800
acgtccagga gcgcaccatc ttcttcaagg acgacggcaa ctacaagacc cgcgccgagg    4860
tgaagttcga gggcgacacc ctggtgaacc gcatcgagct gaagggcatc gacttcaagg    4920
aggacggcaa catcctgggg cacaagctgg agtacaacgc catcagcgac aacgtctata    4980
tcaccgccga caagcagaag aacggcatca aggccaactt caagatccgc cacaacatcg    5040
aggacggcag cgtgcagctc gccgaccact accagcagaa caccccatc ggcgacggcc    5100
ccgtgctgct gcccgacaac cactacctga gcacccagtc caagctgagc aaagacccca    5160
acgagaagcg cgatcacatg gtcctgctgg agttcgtgac cgccgccggg atcactctcg    5220
gcatggacga gctgtacaag tgaacctgaa ttcgatatca agcttatcga taatcaacct    5280
ctggattaca aaatttgtga agattgact ggtattctta actatgttgc tccttttacg    5340
ctatgtggat acgctgcttt aatgcctttg tatcatgcta ttgcttcccg tatggctttc    5400
attttctcct ccttgtataa atcctggttg ctgtctcttt atgaggagtt gtggcccgtt    5460
gtcaggcaac gtggcgtggt gtgcactgtg tttgctgacg caaccccac tggttggggc    5520
attgccacca cctgtcagct ccttttcggg actttcgctt tccccctccc tattgccacg    5580
gcggaactca tcgccgcctg ccttgcccgc tgctggacag gggctcggct gttgggcact    5640
gacaattccg tggtgttgtc ggggaaatca tcgtcctttc cttggctgct cgcctgtgtt    5700
gccacctgga ttctgcgcgg gacgtccttc tgctacgtcc cttcggccct caatccagcg    5760
gaccttcctt cccgcggcct gctgccggct ctgcggcctc ttccgcgtct tcgccttcgc    5820
cctcagacga gtcggatctc cctttgggcc gcctccccgc atcgataccg tcgacctcga    5880
gacctagaaa acatggagc aatcacaagt agcaatacag cagctaccaa tgctgattgt    5940
gcctggctag aagcacaaga ggaggaggag gtgggttttc cagtcacacc tcaggtacct    6000
ttaagaccaa tgacttacaa ggcagctgta gatcttagcc actttttaaa agaaaagggg    6060
ggactggaag ggctaattca ctcccaacga agacaagata tccttgatct gtggatctac    6120
cacacacaag gctacttccc tgattggcag aactacacac cagggccagg gatcagatat    6180
ccactgacct ttggatggtg ctacaagcta gtaccagttg agcaagagaa ggtagaagaa    6240
gccaatgaag gagagaacac ccgcttgtta caccctgtga gcctgcatgg gatggatgac    6300
ccggagagag aagtattaga gtggaggttt gacagccgcc tagcatttca tcacatggcc    6360
cgagagctgc atccggactg tactgggtct ctctggttag accagatctg agcctgggag    6420
ctctctggct aactagggaa cccactgctt aagcctcaat aaagcttgcc ttgagtgctt    6480
caagtagtgt gtgcccgtct gttgtgtgac tctggtaact agagatccct cagacccttt    6540
tagtcagtgt ggaaaatctc tagcagggcc cgtttaaacc cgctgatcag cctcgactgt    6600
gccttctagt tgccagccat ctgttgtttg cccctccccc gtgccttcct tgaccctgga    6660
```

```
aggtgccact cccactgtcc tttcctaata aaatgaggaa attgcatcgc attgtctgag    6720
taggtgtcat tctattctgg ggggtggggt ggggcaggac agcaaggggg aggattggga    6780
agacaatagc aggcatgctg gggatgcggt gggctctatg gcttctgagg cggaaagaac    6840
cagctggggc tctaggggt atccccacgc gccctgtagc ggcgcattaa gcgcggcggg     6900
tgtggtggtt acgcgcagcg tgaccgctac acttgccagc gccctagcgc ccgctccttt    6960
cgctttcttc ccttcctttc tcgccacgtt cgccggcttt ccccgtcaag ctctaaatcg    7020
ggggctccct ttagggttcc gatttagtgc tttacggcac ctcgacccca aaaaacttga    7080
ttagggtgat ggttcacgta gtgggccatc gccctgatag acggttttc gccctttgac     7140
gttggagtcc acgttcttta atagtggact cttgttccaa actggaacaa cactcaaccc    7200
tatctcggtc tattcttttg atttataagg gattttgccg atttcggcct attggttaaa    7260
aaatgagctg atttaacaaa aatttaacgc gaattaattc tgtggaatgt gtgtcagtta    7320
gggtgtggaa agtccccagg ctccccagca ggcagaagta tgcaaagcat gcatctcaat    7380
tagtcagcaa ccaggtgtgg aaagtcccca ggctccccag caggcagaag tatgcaaagc    7440
atgcatctca attagtcagc aaccatagtc ccgcccctaa ctccgcccat cccgccccta    7500
actccgccca gttccgccca ttctccgccc catggctgac taatttttt tatttatgca     7560
gaggccgagg ccgcctctgc ctctgagcta ttccagaagt agtgaggagg cttttttgga    7620
ggcctaggct tttgcaaaaa gctcccggga gcttgtatat ccatttcgg atctgatcag     7680
cacgtgttga caattaatca tcggcatagt atatcggcat agtataatac gacaaggtga    7740
ggaactaaac catggccaag ttgaccagtg ccgttccggt gctcaccgcg cgcgacgtcg    7800
ccggagcggt cgagttctgg accgaccggc tcgggttctc ccgggacttc gtggaggacg    7860
acttcgccgg tgtggtccgg gacgacgtga ccctgttcat cagcgcggtc caggaccagg    7920
tggtgccgga caacccctg gcctgggtgt gggtgcgcgg cctggacgag ctgtacgccg     7980
agtggtcgga ggtcgtgtcc acgaacttcc gggacgcctc cgggccggcc atgaccgaga    8040
tcggcgagca gccgtggggg cgggagttcg ccctgcgcga cccggccggc aactgcgtgc    8100
acttcgtggc cgaggagcag gactgacacg tgctacgaga tttcgattcc accgccgcct    8160
tctatgaaag gttgggcttc ggaatcgttt tccggacgc cggctggatg atcctccagc     8220
gcggggatct catgctggag ttcttcgccc accccaactt gtttattgca gcttataatg    8280
gttacaaata aagcaatagc atcacaaatt tcacaaataa agcatttttt tcactgcatt    8340
ctagttgtgg tttgtccaaa ctcatcaatg tatcttatca tgtctgtata ccgtcgacct    8400
ctagctagag cttggcgtaa tcatggtcat agctgtttcc tgtgtgaaat tgttatccgc    8460
tcacaattcc acacaacata cgagccgaa gcataaagtg taaagcctgg ggtgcctaat     8520
gagtgagcta actcacatta attgcgttgc gctcactgcc cgctttccag tcgggaaacc    8580
tgtcgtgcca gctgcattaa tgaatcggcc aacgcgcggg gagaggcggt ttgcgtattg    8640
ggcgctcttc cgcttcctcg ctcactgact cgctgcgctc ggtcgttcgg ctgcggcgag    8700
cggtatcagc tcactcaaag gcggtaatac ggttatccac agaatcaggg gataacgcag    8760
gaaagaacat gtgagcaaaa ggccagcaaa aggccaggaa ccgtaaaaag gccgcgttgc    8820
tggcgttttt ccataggctc cgcccccctg acgagcatca caaaaatcga cgctcaagtc    8880
agaggtggcg aaacccgaca ggactataaa gataccaggc gtttccccct ggaagctccc    8940
tcgtgcgctc tcctgttccg accctgccgc ttaccggata cctgtccgcc tttctccctt    9000
```

```
cgggaagcgt ggcgctttct catagctcac gctgtaggta tctcagttcg gtgtaggtcg      9060
ttcgctccaa gctgggctgt gtgcacgaac cccccgttca gcccgaccgc tgcgccttat      9120
ccggtaacta tcgtcttgag tccaacccgg taagacacga cttatcgcca ctggcagcag      9180
ccactggtaa caggattagc agagcgaggt atgtaggcgg tgctacagag ttcttgaagt      9240
ggtggcctaa ctacggctac actagaagaa cagtatttgg tatctgcgct ctgctgaagc      9300
cagttacctt cggaaaaaga gttggtagct cttgatccgg caaacaaacc accgctggta      9360
gcggtggttt ttttgtttgc aagcagcaga ttacgcgcag aaaaaaagga tctcaagaag      9420
atcctttgat cttttctacg gggtctgacg ctcagtggaa cgaaaactca cgttaaggga      9480
ttttggtcat gagattatca aaaaggatct tcacctagat ccttttaaat taaaaatgaa      9540
gttttaaatc aatctaaagt atatatgagt aaacttggtc tgacagttac caatgcttaa      9600
tcagtgaggc acctatctca gcgatctgtc tatttcgttc atccatagtt gcctgactcc      9660
ccgtcgtgta gataactacg atacgggagg gcttaccatc tggccccagt gctgcaatga      9720
taccgcgaga cccacgctca ccggctccag atttatcagc aataaaccag ccagccggaa      9780
gggccgagcg cagaagtggt cctgcaactt tatccgcctc catccagtct attaattgtt      9840
gccgggaagc tagagtaagt agttcgccag ttaatagttt gcgcaacgtt gttgccattg      9900
ctacaggcat cgtggtgtca cgctcgtcgt ttggtatggc ttcattcagc tccggttccc      9960
aacgatcaag gcgagttaca tgatccccca tgttgtgcaa aaaagcggtt agctccttcg     10020
gtcctccgat cgttgtcaga agtaagttgg ccgcagtgtt atcactcatg gttatggcag     10080
cactgcataa ttctcttact gtcatgccat ccgtaagatg cttttctgtg actggtgagt     10140
actcaaccaa gtcattctga gaatagtgta tgcggcgacc gagttgctct tgcccggcgt     10200
caatacggga taataccgcg ccacatagca gaactttaaa agtgctcatc attggaaaac     10260
gttcttcggg gcgaaaactc tcaaggatct taccgctgtt gagatccagt tcgatgtaac     10320
ccactcgtgc acccaactga tcttcagcat cttttacttt caccagcgtt tctgggtgag     10380
caaaaacagg aaggcaaaat gccgcaaaaa agggaataag ggcgacacgg aaatgttgaa     10440
tactcatact cttcctttt caatattatt gaagcattta tcagggttat tgtctcatga     10500
gcggatacat atttgaatgt atttagaaaa ataaacaaat agggggttccg cgcacatttc     10560 cccgaaaagt gccacctgac                                                 10580

<210> SEQ ID NO 256
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 256
cgtggattgg aacagcttct tatagcattc tttcttgagg agggcagcaa acgggaagag       60

<210> SEQ ID NO 257
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 257
cgtggatcgg aacagcttct tataaaagtc taatccgtcc ctgcctctat atctccactc       60
```

```
<210> SEQ ID NO 258
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 258
agcttgaaca ccagtcgcaa tataagctca gtccatcctc gtaaatcctc atcaatcatc      60

<210> SEQ ID NO 259
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 259
cgtggattgg aacagcttct tataaaagtc taatccgtcc ctgcctctat atctccactc      60

<210> SEQ ID NO 260
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 260
cgtggatcgg aacagcttct tatagcattc tttcttgagg agggcagcaa acgggaagag      60

<210> SEQ ID NO 261
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 261
agcttgaaca ccagtcgcaa tataagctca gtccatcctc gtaaatcctc atcaatcatc      60

<210> SEQ ID NO 262
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 262
cgtggattgg aacagcttct tatagcattc tttcttgagg agggcagcaa acgggaagag      60

<210> SEQ ID NO 263
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 263
cgtggatcgg aacagcttct tataaaagtc taatccgtcc ctgcctctat atctccactc      60

<210> SEQ ID NO 264
<211> LENGTH: 60
<212> TYPE: DNA
<213> ORGANISM: Artificial Sequence
<220> FEATURE:
<223> OTHER INFORMATION: Synthetic Polynucleotide
```

<400> SEQUENCE: 264
ttccacatcc ctctgcgatt tataagctca gtccatcctc gtaaatcctc atcaatcatc    60

<210> SEQ ID NO 265
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 265
ttccacaccc ctctgcgatt tatacacatt tacagacctc aacctacctc caactctcac    60

<210> SEQ ID NO 266
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 266
ataccaatcc cttcggcgat tataaaagtc taatccgtcc ctgcctctat atctccactc    60

<210> SEQ ID NO 267
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 267
ataccaaccc cttcggcgat tataagctca gtccatcctc gtaaatcctc atcaatcatc    60

<210> SEQ ID NO 268
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 268
ttcaacatac gccaatgcgg tatagcattc tttcttgagg agggcagcaa acgggaagag    60

<210> SEQ ID NO 269
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 269
ttcaacacac gccaatgcgg tatacacatt tacagacctc aacctacctc caactctcac    60

<210> SEQ ID NO 270
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 270
gtcaacatac acgccctgat tataagctca gtccatcctc gtaaatcctc atcaatcatc    60

<210> SEQ ID NO 271
<211> LENGTH: 60

```
<212> TYPE: DNA
<213> ORGANISM: Artificial Sequence
<220> FEATURE:
<223> OTHER INFORMATION: Synthetic Polynucleotide

<400> SEQUENCE: 271
gtcaacacac acgccctgat tataaaagtc taatccgtcc ctgcctctat atctccactc      60

<210> SEQ ID NO 272
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 272
ttagcgatac atccgaccca tatagcattc tttcttgagg agggcagcaa acgggaagag      60

<210> SEQ ID NO 273
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 273
ttagcgacac atccgaccca tatacacatt tacagacctc aacctacctc caactctcac      60

<210> SEQ ID NO 274
<211> LENGTH: 383
<212> TYPE: DNA
<213> ORGANISM: Artificial Sequence
<220> FEATURE:
<223> OTHER INFORMATION: Synthetic Polynucleotide

<400> SEQUENCE: 274
cgacagcttg tctctccaga tgctcttggg ccatcttcca catcgtccgt agcagccttg      60
gcaatttgcc atcactggca atacacata aatccaatga atacggttac caccatcaca    120
ttaccatgca ggtacacagc aagaattgac gttggcatat cacatggtgt aataacccca    180
cttgtgaaac aacccagaat aaggtacaag gcggaaatgt cgtcattcta aaataaaagg    240
catggccagg aatttgtcta ataccgggaa cttaaattca gcttgaacac cagtcgcaaa    300
aaattcaaag aaagtgattc aggttcgggt tcgtggattg aacagcttc ttttgtttca    360 gtgatgagag aatcctcctg tca                                             383

<210> SEQ ID NO 275
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 275
ttccacatcc ctctgcgatt cgtggcatcg tggattggaa cagcttcttt                50

<210> SEQ ID NO 276
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 276
```
ttccacaccc ctctgcgatt cgtggcatcg tggatcggaa cagcttcttt    50

<210> SEQ ID NO 277
<211> LENGTH: 63
<212> TYPE: DNA
<213> ORGANISM: Artificial Sequence
<220> FEATURE:
<223> OTHER INFORMATION: Synthetic Polynucleotide

<400> SEQUENCE: 277
ttcaacatac gccaatgcgg acgcggccgc tgttcagata ccaatcccctt cggcgatttc    60 ccg    63

<210> SEQ ID NO 278
<211> LENGTH: 63
<212> TYPE: DNA
<213> ORGANISM: Artificial Sequence
<220> FEATURE:
<223> OTHER INFORMATION: Synthetic Polynucleotide

<400> SEQUENCE: 278
ttcaacacac gccaatgcgg acgcggccgc tgttcagata ccaacccctt cggcgatttc    60
ccg    63

<210> SEQ ID NO 279
<211> LENGTH: 63
<212> TYPE: DNA
<213> ORGANISM: Artificial Sequence
<220> FEATURE:
<223> OTHER INFORMATION: Synthetic Polynucleotide

<400> SEQUENCE: 279
ttagcgatac atccgaccca atcataccct gtgattcgtc aacatacacg ccctgataaa    60
tat    63

<210> SEQ ID NO 280
<211> LENGTH: 63
<212> TYPE: DNA
<213> ORGANISM: Artificial Sequence
<220> FEATURE:
<223> OTHER INFORMATION: Synthetic Polynucleotide

<400> SEQUENCE: 280
ttagcgacac atccgaccca atcataccct gtgattcgtc aacacacacg ccctgataaa    60
tat    63

<210> SEQ ID NO 281
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 281
agatgctcct gagccatctt    20

<210> SEQ ID NO 282
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 282
cgtggattgg aacagcttct                                               20

<210> SEQ ID NO 283
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 283
gaaagtgatt caggttcggg                                               20

<210> SEQ ID NO 284
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 284
agcttgaaca ccagtcgcaa                                               20

<210> SEQ ID NO 285
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 285
gcatggccag gaatttgtct                                               20

<210> SEQ ID NO 286
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 286
ggcggaaatg tcgtcattct                                               20

<210> SEQ ID NO 287
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 287
ccacttgtga acaacccag                                                20

<210> SEQ ID NO 288
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 288
cgttggcata tcacatggtg                                               20

<210> SEQ ID NO 289
<211> LENGTH: 20
<212> TYPE: DNA

```
<213> ORGANISM: Artificial Sequence
<220> FEATURE:
<223> OTHER INFORMATION: Synthetic Oligonucleotide

<400> SEQUENCE: 289
accatgcagg tacacagcaa                                               20

<210> SEQ ID NO 290
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 290
ttccacatcc ctctgcgatt                                               20

<210> SEQ ID NO 291
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 291
ataccaatcc cttcggcgat                                               20

<210> SEQ ID NO 292
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 292
atcagcgtga caactgtgct                                               20

<210> SEQ ID NO 293
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 293
agatgctcct gagccatctt tatagcattc tttcttgagg agggcagcaa acgggaagag     60

<210> SEQ ID NO 294
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 294
cgtggattgg aacagcttct tataagctca gtccatcctc gtaaatcctc atcaatcatc     60

<210> SEQ ID NO 295
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 295
gaaagtgatt caggttcggg tatacacatt tacagacctc aacctacctc caactctcac     60
```

<210> SEQ ID NO 296
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 296
ttccacatcc ctctgcgatt tataaaagtc taatccgtcc ctgcctctat atctccactc    60

<210> SEQ ID NO 297
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 297
agcttgaaca ccagtcgcaa tatagcattc tttcttgagg agggcagcaa acgggaagag    60

<210> SEQ ID NO 298
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 298
gcatggccag gaatttgtct tataagctca gtccatcctc gtaaatcctc atcaatcatc    60

<210> SEQ ID NO 299
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 299
ggcggaaatg tcgtcattct tatacacatt tacagacctc aacctacctc caactctcac    60

<210> SEQ ID NO 300
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 300
ataccaatcc cttcggcgat tataaaagtc taatccgtcc ctgcctctat atctccactc    60

<210> SEQ ID NO 301
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 301
ccacttgtga acaacccag tatagcattc tttcttgagg agggcagcaa acgggaagag    60

<210> SEQ ID NO 302
<211> LENGTH: 60
<212> TYPE: DNA
<213> ORGANISM: Artificial Sequence
<220> FEATURE:

```
<223> OTHER INFORMATION: Synthetic Polynucleotide

<400> SEQUENCE: 302
cgttggcata tcacatggtg tataagctca gtccatcctc gtaaatcctc atcaatcatc    60

<210> SEQ ID NO 303
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 303
accatgcagg tacacagcaa tatacacatt tacagacctc aacctacctc caactctcac    60

<210> SEQ ID NO 304
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 304
atcagcgtga caactgtgct tataaaagtc taatccgtcc ctgcctctat atctccactc    60
```